(12) United States Patent
Dota

(10) Patent No.: US 9,826,741 B2
(45) Date of Patent: *Nov. 28, 2017

(54) TETRAZOLINONE COMPOUND AND APPLICATION THEREOF

(71) Applicant: SUMITOMO CHEMICAL COMPANY, LIMITED, Tokyo (JP)

(72) Inventor: Koichiro Dota, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/128,619

(22) PCT Filed: Mar. 25, 2015

(86) PCT No.: PCT/JP2015/060305
§ 371 (c)(1),
(2) Date: Sep. 23, 2016

(87) PCT Pub. No.: WO2015/147332
PCT Pub. Date: Oct. 1, 2015

(65) Prior Publication Data
US 2017/0105415 A1   Apr. 20, 2017

(30) Foreign Application Priority Data

Mar. 28, 2014   (JP) ................. 2014-067944

(51) Int. Cl.
*A01N 43/713* (2006.01)
*C07D 403/12* (2006.01)

(52) U.S. Cl.
CPC ......... *A01N 43/713* (2013.01); *C07D 403/12* (2013.01)

(58) Field of Classification Search
None
See application file for complete search history.

(56) References Cited

U.S. PATENT DOCUMENTS 5,589,439 A   12/1996   Goto et al.
5,641,727 A   6/1997   Goto et al.
(Continued)

FOREIGN PATENT DOCUMENTS

CN   102875540 A   1/2013
EP   0 902 028 A1   3/1999
(Continued)

OTHER PUBLICATIONS

International Search Report, issued in PCT/JP2015/060305, PCT/ISA/210, dated May 26, 2015.
(Continued)

*Primary Examiner* — Alicia L Otton
(74) *Attorney, Agent, or Firm* — Birch, Stewart, Kolasch & Birch, LLP

(57) ABSTRACT

A tetrazolinone compound represented by formula (1):

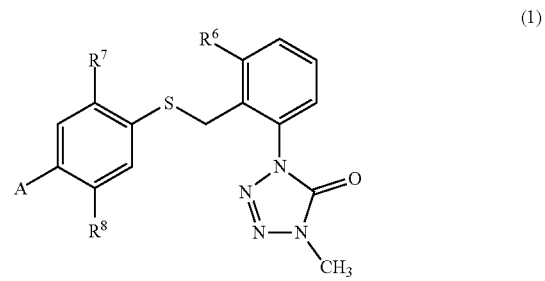

wherein A represents the following group A1, A2, A3, or A4; A;

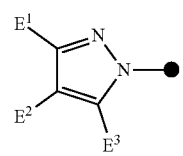

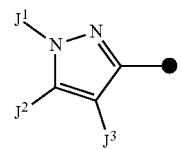

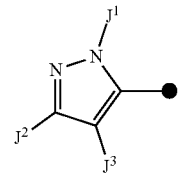

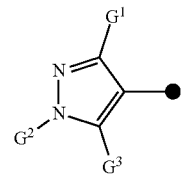

in which $R^6$ represents a hydrogen atom, a C1-C4 alkyl group optionally having one or more halogen atoms, etc.; $R^7$ and $R^8$ each represents a hydrogen atom, a C1-C4 alkyl group optionally having one or more halogen atoms, etc.; $E^1$, $E^2$, $E^3$, $J^1$, $J^2$, $J^3$, $J^4$, $G^1$, $G^2$, and $G^3$ each represents a hydrogen atom, etc.; has excellent control activity against pests.

6 Claims, No Drawings

(56) References Cited

U.S. PATENT DOCUMENTS

| | | | |
|---|---|---|---|
| 5,861,359 A | 1/1999 | Theodoridis | |
| 6,294,503 B1 | 9/2001 | Gupta et al. | |
| 6,583,090 B1 | 6/2003 | Gewehr et al. | |
| 2014/0323305 A1 | 10/2014 | Rheinheimer et al. | |
| 2015/0031733 A1 | 1/2015 | Yoshimoto et al. | |
| 2015/0051171 A1 | 2/2015 | Yoshimoto et al. | |
| 2015/0203511 A1 | 7/2015 | Arimori et al. | |
| 2015/0223460 A1 | 8/2015 | Arimori et al. | |
| 2015/0299146 A1 | 10/2015 | Hasegawa et al. | |
| 2015/0336908 A1 | 11/2015 | Shioda et al. | |
| 2016/0081339 A1 | 3/2016 | Yoshimoto et al. | |
| 2016/0081340 A1 | 3/2016 | Arimori et al. | |
| 2016/0150787 A1 | 6/2016 | Azuma et al. | |
| 2016/0157489 A1 | 6/2016 | Shioda et al. | |
| 2016/0159755 A1 | 6/2016 | Shioda et al. | |
| 2016/0174558 A1 | 6/2016 | Hou et al. | |
| 2016/0205935 A1 | 7/2016 | Akioka et al. | |
| 2016/0249617 A1 | 9/2016 | Dota | |
| 2016/0272622 A1 | 9/2016 | Azuma et al. | |
| 2016/0311775 A1 | 10/2016 | Shioda et al. | |

FOREIGN PATENT DOCUMENTS

| | | |
|---|---|---|
| JP | 8-81459 A | 3/1996 |
| JP | 8-99975 A | 4/1996 |
| JP | 9-87281 A | 3/1997 |
| JP | 9-100272 A | 4/1997 |
| JP | 9-100277 A | 4/1997 |
| JP | 9-110863 A | 4/1997 |
| JP | 9-208565 A | 8/1997 |
| JP | 11-152278 A | 6/1999 |
| JP | 2001-512460 A | 8/2001 |
| JP | 2002-506060 A | 2/2002 |
| WO | WO 96/36229 A1 | 11/1996 |
| WO | WO 98/25912 A1 | 6/1998 |
| WO | WO 98/35961 A1 | 8/1998 |
| WO | WO 98/51683 A1 | 11/1998 |
| WO | WO 99/46246 A1 | 9/1999 |
| WO | WO 99/48890 A1 | 9/1999 |
| WO | WO 2013/092224 A1 | 6/2013 |
| WO | WO 2013/162072 A1 | 10/2013 |
| WO | WO 2013/162077 A1 | 10/2013 |
| WO | WO 2014/051161 A1 | 4/2014 |
| WO | WO 2014/051165 A1 | 4/2014 |
| WO | WO 2014/084223 A1 | 6/2014 |
| WO | WO 2014/104268 A1 | 7/2014 |
| WO | WO 2014/104382 A1 | 7/2014 |
| WO | WO 2014/104384 A1 | 7/2014 |
| WO | WO 2014/175465 A1 | 10/2014 |
| WO | WO 2014/192953 A1 | 12/2014 |
| WO | WO 2015/005499 A1 | 1/2015 |
| WO | WO 2015/016335 A1 | 2/2015 |
| WO | WO 2015/016372 A1 | 2/2015 |
| WO | WO 2015/016373 A1 | 2/2015 |
| WO | WO 2015/030217 A1 | 3/2015 |
| WO | WO 2015/041360 A1 | 3/2015 |
| WO | WO 2015/046480 A1 | 4/2015 |
| WO | WO 2015/050039 A1 | 4/2015 |
| WO | WO 2015/050040 A1 | 4/2015 |
| WO | WO 2015/056806 A1 | 4/2015 |
| WO | WO 2015/060461 A1 | 4/2015 |
| WO | WO 2015/088038 A1 | 6/2015 |
| WO | WO 2015/147314 A1 | 10/2015 |
| WO | WO 2015/147336 A1 | 10/2015 |

OTHER PUBLICATIONS

English translation of the Written Opinion of the International Searching Authority (Form PCT/ISA/237) for International Application No. PCT/JP2014/078005, dated Nov. 25, 2014.

European Patent Office Communication and extended search report issued in the corresponding European Patent Application No. 15769758.2 dated Aug. 7, 2017.

TETRAZOLINONE COMPOUND AND APPLICATION THEREOF

TECHNICAL FIELD

The present invention relates to a tetrazolinone compound and application thereof.

BACKGROUND ART

Heretofore, various chemicals have been developed so as to control pests and provided in practice use, but in some cases, these chemicals may not exert enough activity.

Meanwhile, there have been known, as agents for controlling pests, 1-{2-[2-chloro-4-(pyrazol-1-yl)-phenoxymethyl]-phenyl}-4-meth yl-1,4-dihydrotetrazol-5-one having a tetrazolinone ring (compounds represented by the following formula (A):

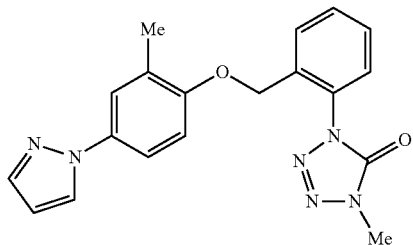

(A)

(see WO 99/46246 A)).

The present invention provides compounds having excellent control activity against pests.

DISCLOSURE OF THE INVENTION

The present inventors have intensively studied so as to find compounds having excellent control activity against pests, and found that a tetrazolinone compound represented by the following formula (1) has excellent control activity against pests, thus completing the present invention.

The present invention includes the followings [1] to [8].

[1] A tetrazolinone compound represented by formula (1):

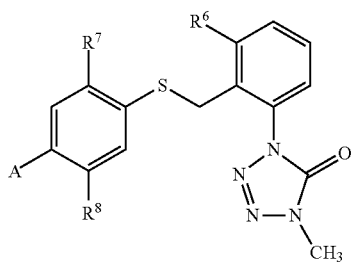

(1)

wherein A represents the following group A1, A2, A3, or A4; A;

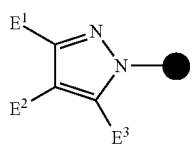

A1

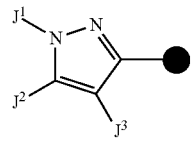

A2

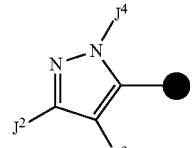

A3

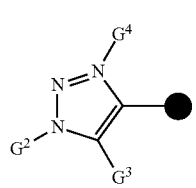

A4 in which $R^6$, $R^7$, and $R^8$ each represents a hydrogen atom, a halogen atom, a C1-C4 alkyl group optionally having one or more halogen atoms, a C3-C4 cycloalkyl group optionally having one or more halogen atoms, or a C1-C4 alkoxy group optionally having one or more halogen atoms, $G^1$ and $G^3$ each represents a hydrogen atom, a halogen atom, a C1-C4 alkoxy group optionally having one or more halogen atoms, or a C1-C4 alkyl group optionally having one or more halogen atoms, $G^2$, $J^1$, and $J^4$ each represents a hydrogen atom, a C1-C4 alkyl group optionally having one or more halogen atoms, or a C3-C4 cycloalkyl group optionally having one or more halogen atoms, and $E^1$, $E^2$, $E^3$, $J^2$, and $J^3$ each represents a hydrogen atom, a halogen atom, a cyano group, an aldehyde group, a C1-C4 alkoxy group optionally having one or more halogen atoms, a C1-C4 alkyl group optionally having one or more halogen atoms, or a C3-C4 cycloalkyl group optionally having one or more halogen atoms.

[2] The tetrazolinone compound according to [1], wherein A is A1.

[3] The tetrazolinone compound according to [1], wherein A is A2.

[4] The tetrazolinone compound according to [1], wherein A is A3.

[5] The tetrazolinone compound according to [1], wherein A is A4.

[6] A pest control agent comprising the tetrazolinone compound according to any one of [1] to [5].

[7] A method for control pests, which comprises applying an effective amount of the tetrazolinone compound according to any one of [1] to [5] to plants or soil.

[8] Use of the tetrazolinone compound according to any one of [1] to [5] for controlling pests.

According to the present invention, pests can be controlled.

MODE FOR CARRYING OUT THE INVENTION

In the present invention, a tetrazolinone compound represented by formula (1) is referred to as the present compound, and a pest control agent containing the present compound is referred to as the present control agent.

Substituents as used herein will be mentioned below.

The halogen atom represents a fluorine atom, a chlorine atom, a bromine atom, and an iodine atom.

Examples of the C1-C4 alkyl group optionally having one or more halogen atoms include a methyl group, an ethyl group, a propyl group, an isopropyl group, a butyl group, an isobutyl group, a sec-butyl group, a tert-butyl group, a fluoromethyl group, a chloromethyl group, a dichloromethyl group, a difluoromethyl group, a trifluoromethyl group, a trichloromethyl group, a 2-fluoroethyl group, a 2,2,2-trifluoroethyl group, and a 1-trifluoromethyl-2,2,2-trifluoroethyl group.

Examples of the C3-C4 cycloalkyl group optionally having one or more halogen atoms include a cyclopropyl group, a cyclobutyl group, a 2,2-dichlorocyclopropyl group, and a 2,2-difluorocyclopropyl group.

Examples of the C1-C4 alkoxy group optionally having one or more halogen atoms include a methoxy group, an ethoxy group, a propyloxy group, an isopropyloxy group, a butyloxy group, a trifluoromethoxy group, a difluoromethoxy group, a 2-fluoroethoxy group, a 2,2,2-trifluoroethoxy group, a 3-chloropropoxy group, and a 3-chlorobutyloxy group.

Examples of Aspect of the present compound include the following compounds.

A tetrazolinone compound in which $R^6$ is a hydrogen atom in formula (1).

A tetrazolinone compound in which $R^6$ is a halogen atom in formula (1).

A tetrazolinone compound in which $R^6$ is a C1-C4 alkyl group optionally having one or more halogen atoms in formula (1).

A tetrazolinone compound in which $R^6$ is a C3-C4 cycloalkyl group optionally having one or more halogen atoms in formula (1).

A tetrazolinone compound in which $R^6$ is a C1-C4 alkoxy group optionally having one or more halogen atoms in formula (1).

A tetrazolinone compound in which $R^7$ is a hydrogen atom in formula (1).

A tetrazolinone compound in which $R^7$ is a halogen atom in formula (1).

A tetrazolinone compound in which $R^7$ is a C1-C4 alkyl group optionally having one or more halogen atoms in formula (1).

A tetrazolinone compound in which $R^7$ is a C3-C4 cycloalkyl group optionally having one or more halogen atoms in formula (1).

A tetrazolinone compound in which $R^7$ is a C1-C4 alkoxy group optionally having one or more halogen atoms in formula (1).

A tetrazolinone compound in which $R^8$ is a hydrogen atom in formula (1).

A tetrazolinone compound in which $R^8$ is a halogen atom in formula (1).

A tetrazolinone compound in which $R^8$ is a C1-C4 alkyl group optionally having one or more halogen atoms in formula (1).

A tetrazolinone compound in which $R^8$ is a C3-C4 cycloalkyl group optionally having one or more halogen atoms in formula (1).

A tetrazolinone compound in which $R^8$ is a C1-C4 alkoxy group optionally having one or more halogen atoms in formula (1). A tetrazolinone compound in which $R^6$ is a C1-C4 alkyl group optionally having one or more halogen atoms, $R^7$ is a C1-C4 alkyl group optionally having one or more halogen atoms, or a halogen atom, $R^8$ is a hydrogen atom, a C1-C4 alkyl group optionally having one or more halogen atoms, or a halogen atom, $G^1$ and $G^3$ are hydrogen atoms, $G^2$, $J^1$, and $J^4$ are each a C1-C4 alkyl group optionally having one or more halogen atoms, each of $E^1$, $E^2$, $E^3$, $J^2$, and $J^3$ is a hydrogen atom or a C1-C4 alkyl group optionally having one or more halogen atoms.

A tetrazolinone compound in which $R^6$ is a C1-C4 alkyl group optionally having one or more halogen atoms, $R^7$ is a C1-C4 alkyl group optionally having one or more halogen atoms, or a halogen atom, $R^8$ is a hydrogen atom, $G^1$ and $G^3$ are hydrogen atoms, each of $G^2$, $J^1$, and $J^4$ is a C1-C4 alkyl group optionally having one or more halogen atoms, and each of $E^1$, $E^2$, $E^3$, $J^2$, and $J^3$ is a hydrogen atom or a C1-C4 alkyl group optionally having one or more halogen atoms.

[Aspect 1]

A tetrazolinone compound represented by formula (1a):

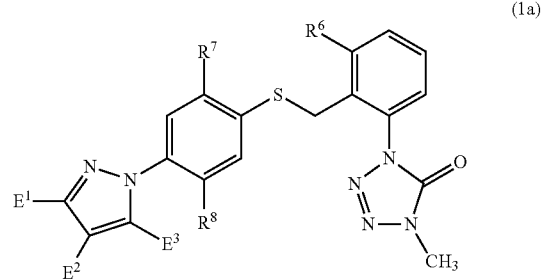

wherein symbols are the same as defined above.

A tetrazolinone compound in which $R^6$ is a C1-C4 alkyl group optionally having one or more halogen atoms, or a hydrogen atom in [Aspect 1].

A tetrazolinone compound in which $R^6$ is a C1-C4 alkyl group optionally having one or more halogen atoms, or a halogen atom, or a C1-C4 alkoxy group optionally having one or more halogen atoms in [Aspect 1].

A tetrazolinone compound in which $R^6$ is a C3-C4 cycloalkyl group optionally having one or more halogen atoms in [Aspect 1].

A tetrazolinone compound in which $R^6$ is a hydrogen atom or a halogen atom in [Aspect 1].

A tetrazolinone compound in which $R^6$ is a hydrogen atom in [Aspect 1].

A tetrazolinone compound in which $R^6$ is a halogen atom in [Aspect 1].

A tetrazolinone compound in which $R^6$ is a methyl group in [Aspect 1].

A tetrazolinone compound in which $R^6$ is an ethyl group in [Aspect 1].

A tetrazolinone compound in which $R^6$ is a methoxy group in [Aspect 1].

A tetrazolinone compound in which $R^6$ is a cyclopropyl group in [Aspect 1].

A tetrazolinone compound in which $R^6$ is a C1-C4 alkyl group optionally having one or more halogen atoms, a halogen atom, a C3-C4 cycloalkyl group optionally having one or more halogen atoms, or a C1-C4 alkoxy group optionally having one or more halogen atoms, $R^7$ is a C1-C4 alkyl group optionally having one or more halogen atoms, or a halogen atom, $R^8$ is a hydrogen atom, a C1-C4 alkyl group optionally having one or more halogen atoms, or a halogen atom, and each of $E^1$, $E^2$, and $E^3$ is a hydrogen atom, a halogen atom, a cyano group, an aldehyde group, a C1-C4 alkoxy group optionally having one or more halogen atoms, or a C1-C4 alkyl group optionally having one or more halogen atoms in [Aspect 1].

A tetrazolinone compound in which $R^6$ is a C1-C4 alkyl group optionally having one or more halogen atoms, or a halogen atom, $R^7$ is a C1-C4 alkyl group optionally having one or more halogen atoms, $R^8$ is a hydrogen atom or a C1-C4 alkyl group optionally having one or more halogen atoms, and each of $E^1$, $E^2$, and $E^3$ is a hydrogen atom, a halogen atom, a cyano group, an aldehyde group, or a C1-C4 alkyl group optionally having one or more halogen atoms in [Aspect 1].

A tetrazolinone compound in which $R^6$ is a C1-C4 alkyl group optionally having one or more halogen atoms, or a halogen atom, each of $R^7$ and $R^8$ is a C1-C4 alkyl group optionally having one or more halogen atoms, or a halogen atom, $R^8$ is a hydrogen atom or a C1-C4 alkyl group optionally having one or more halogen atoms, and each of $E^1$, $E^2$, and $E^3$ is a hydrogen atom or a C1-C4 alkyl group optionally having one or more halogen atoms in [Aspect 1].

A tetrazolinone compound in which $R^6$ is a C1-C4 alkyl group optionally having one or more halogen atoms, $R^7$ is a C1-C4 alkyl group optionally having one or more halogen atoms, or a halogen atom, $R^8$ is a hydrogen atom or a C1-C4 alkyl group optionally having one or more halogen atoms, and each of $E^1$, $E^2$, and $E^3$ is a hydrogen atom or a C1-C4 alkyl group optionally having one or more halogen atoms in [Aspect 1].

[Aspect 2]

A tetrazolinone compound represented by formula (1b):

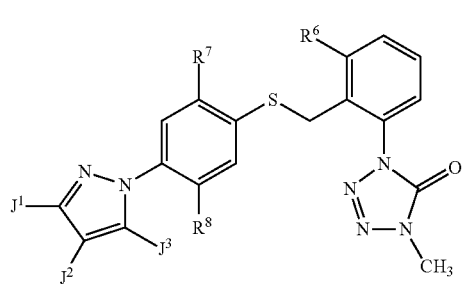

(1b)

wherein symbols are the same as defined above.

A tetrazolinone compound in which $R^6$ is a C1-C4 alkyl group optionally having one or more halogen atoms, or a hydrogen atom in [Aspect 2].

A tetrazolinone compound in which $R^6$ is a C1-C4 alkyl group optionally having one or more halogen atoms, a halogen atom, or a C1-C4 alkoxy group optionally having one or more halogen atoms in [Aspect 2].

A tetrazolinone compound in which $R^6$ is a C3-C4 cycloalkyl group optionally having one or more halogen atoms in [Aspect 2].

A tetrazolinone compound in which $R^6$ is a hydrogen atom or a halogen atom in [Aspect 2].

A tetrazolinone compound in which $R^6$ is a hydrogen atom in [Aspect 2].

A tetrazolinone compound in which $R^6$ is a halogen atom in [Aspect 2].

A tetrazolinone compound in which $R^6$ is a methyl group in [Aspect 2].

A tetrazolinone compound in which $R^6$ is an ethyl group in [Aspect 2].

A tetrazolinone compound in which $R^6$ is a methoxy group in [Aspect 2].

A tetrazolinone compound in which $R^6$ is a cyclopropyl group in [Aspect 2].

A tetrazolinone compound in which $R^6$ is a C1-C4 alkyl group optionally having one or more halogen atoms, a halogen atom, a C3-C4 cycloalkyl group optionally having one or more halogen atoms, or a C1-C4 alkoxy group optionally having one or more halogen atoms, $R^7$ is a C1-C4 alkyl group optionally having one or more halogen atoms, or a halogen atom, $R^8$ is a hydrogen atom, a C1-C4 alkyl group optionally having one or more halogen atoms, or a halogen atom, $J^1$ is a C1-C4 alkyl group optionally having one or more halogen atoms, and $J^2$ and $J^3$ are hydrogen atoms, halogen atoms, cyano groups, aldehyde groups, C1-C4 alkoxy groups optionally having one or more halogen atoms, or C1-C4 alkyl groups optionally having one or more halogen atoms in [Aspect 2].

A tetrazolinone compound in which $R^6$ is a C1-C4 alkyl group optionally having one or more halogen atoms, or a halogen atom, $R^7$ is a C1-C4 alkyl group optionally having one or more halogen atoms, $R^8$ is a hydrogen atom or a C1-C4 alkyl group optionally having one or more halogen atoms, $J^1$ is a C1-C4 alkyl group optionally having one or more halogen atoms, and $J^2$ and $J^3$ are halogen atoms, cyano groups, aldehyde groups, C1-C4 alkoxy groups optionally having one or more halogen atoms, or C1-C4 alkyl groups optionally having one or more halogen atoms in [Aspect 2].

A tetrazolinone compound in which $R^6$ is a C1-C4 alkyl group optionally having one or more halogen atoms, or a halogen atom, $R^7$ is a C1-C4 alkyl group optionally having one or more halogen atoms, or a halogen atom, $R^8$ is a hydrogen atom or a C1-C4 alkyl group optionally having one or more halogen atoms, $J^1$ is a C1-C4 alkyl group optionally having one or more halogen atoms, and $J^2$ and $J^3$ are halogen atoms, or a C1-C4 alkyl group optionally having one or more halogen atoms in [Aspect 2].

A tetrazolinone compound in which $R^6$ is a C1-C4 alkyl group optionally having one or more halogen atoms, $R^7$ is a C1-C4 alkyl group optionally having one or more halogen atoms, $R^8$ is a hydrogen atom, $J^1$ is a C1-C4 alkyl group optionally having one or more halogen atoms, $J^2$ is a hydrogen atom, a C1-C4 alkyl group optionally having one or more halogen atoms, or a halogen atom, and $J^3$ is a hydrogen atom or a C1-C4 alkyl group optionally having one or more halogen atoms in [Aspect 2].

[Aspect 3]

A tetrazolinone compound represented by formula (1c):

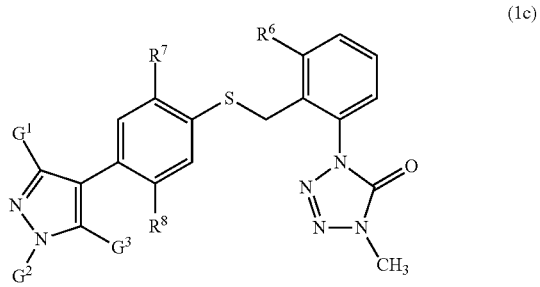

(1c)

wherein symbols are the same as defined above.

A tetrazolinone compound in which $R^6$ is a C1-C4 alkyl group optionally having one or more halogen atoms, or a hydrogen atom in [Aspect 3].

A tetrazolinone compound in which $R^6$ is a C1-C4 alkyl group optionally having one or more halogen atoms, a halogen atom, or a C1-C4 alkoxy group optionally having one or more halogen atoms in [Aspect 3].

A tetrazolinone compound in which $R^6$ is a C3-C4 cycloalkyl group optionally having one or more halogen atoms in [Aspect 3].

A tetrazolinone compound in which $R^6$ is a hydrogen atom or a halogen atom in [Aspect 3].

A tetrazolinone compound in which $R^6$ is a hydrogen atom in [Aspect 3].

A tetrazolinone compound in which $R^6$ is a halogen atom in [Aspect 3].

A tetrazolinone compound in which $R^6$ is a methyl group in [Aspect 3].

A tetrazolinone compound in which $R^6$ is an ethyl group in [Aspect 3].

A tetrazolinone compound in which $R^6$ is a methoxy group in [Aspect 3].

A tetrazolinone compound in which $R^6$ is a cyclopropyl group in [Aspect 3].

A tetrazolinone compound in which $R^6$ is a C1-C4 alkyl group optionally having one or more halogen atoms, a halogen atom, a C3-C4 cycloalkyl group optionally having one or more halogen atoms, or a C1-C4 alkoxy group optionally having one or more halogen atoms, $R^7$ is a C1-C4 alkyl group optionally having one or more halogen atoms, or a halogen atom, $R^8$ is a hydrogen atom, a C1-C4 alkyl group optionally having one or more halogen atoms, or a halogen atom, $G^1$ and $G^3$ are hydrogen atoms, halogen atoms, or C1-C4 alkyl groups optionally having one or more halogen atoms, and $G^2$ is a hydrogen atom, a C1-C4 alkyl group optionally having one or more halogen atoms, or a C3-C4 cycloalkyl group optionally having one or more halogen atoms in [Aspect 3].

A tetrazolinone compound in which $R^6$ is a C1-C4 alkyl group optionally having one or more halogen atoms, or a halogen atom, $R^7$ is a C1-C4 alkyl group optionally having one or more halogen atoms, $R^8$ is a hydrogen atom or a C1-C4 alkyl group optionally having one or more halogen atoms, $G^1$ and $G^3$ are hydrogen atoms, and $G^2$ is a C1-C4 alkyl group optionally having one or more halogen atoms in [Aspect 3].

A tetrazolinone compound in which $R^6$ is a C1-C4 alkyl group optionally having one or more halogen atoms, $R^7$ is a C1-C4 alkyl group optionally having one or more halogen atoms, $R^8$ is a hydrogen atom, $G^1$ and $G^3$ are hydrogen atoms, $G^2$ is a C1-C4 alkyl group optionally having one or more halogen atoms [Aspect 3].

[Aspect 4]

A tetrazolinone compound represented by formula (1d):

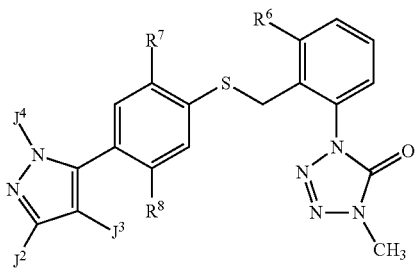

(1d)

wherein symbols are the same as defined above.

A tetrazolinone compound in which $R^6$ is a C1-C4 alkyl group optionally having one or more halogen atoms, or a hydrogen atom in [Aspect 4].

A tetrazolinone compound in which $R^6$ is a C1-C4 alkyl group optionally having one or more halogen atoms, a halogen atom, or a C1-C4 alkoxy group optionally having one or more halogen atoms in [Aspect 4].

A tetrazolinone compound in which $R^6$ is a C3-C4 cycloalkyl group optionally having one or more halogen atoms in [Aspect 4].

A tetrazolinone compound in which $R^6$ is a hydrogen atom or a halogen atom in [Aspect 4].

A tetrazolinone compound in which $R^6$ is a hydrogen atom in [Aspect 4].

A tetrazolinone compound in which $R^6$ is a halogen atom in [Aspect 4].

A tetrazolinone compound in which $R^6$ is a methyl group in [Aspect 4].

A tetrazolinone compound in which $R^6$ is an ethyl group in [Aspect 4].

A tetrazolinone compound in which $R^6$ is a methoxy group in [Aspect 4].

A tetrazolinone compound in which $R^6$ is a cyclopropyl group in [Aspect 4].

A tetrazolinone compound in which $R^6$ is a C1-C4 alkyl group optionally having one or more halogen atoms, a halogen atom, a C3-C4 cycloalkyl group optionally having one or more halogen atoms, or a C1-C4 alkoxy group optionally having one or more halogen atoms, $R^7$ is a C1-C4 alkyl group optionally having one or more halogen atoms, or a halogen atom, $R^8$ is a C1-C4 alkyl group optionally having one or more halogen atoms, or a halogen atom, and $J^2$, $J^3$, and $J^4$ are hydrogen atoms or C1-C4 alkyl groups optionally having one or more halogen atoms in [Aspect 4].

Next, a process for producing the present compound will be described.

The present compound can be produced, for example, by the following Production Processes.

(Production Process A)

The present compound can be produced by reacting a compound represented by formula (A-1) (hereinafter referred to as the compound (A-1)) with a compound represented by formula (A-2) (hereinafter referred to as the compound (A-2)) in the presence of a base:

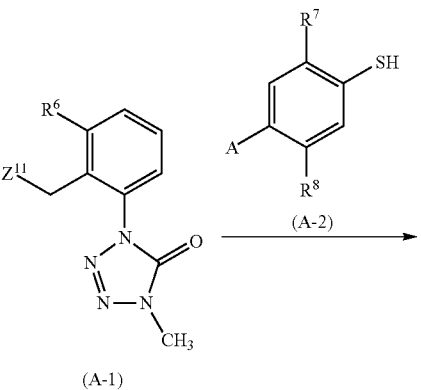

(A-1)
(A-2)

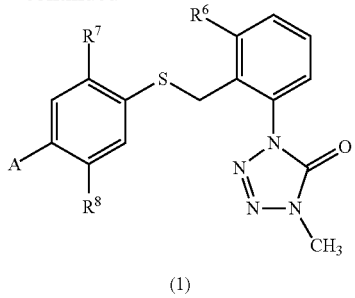

(1)

wherein $R^6$, $R^7$, $R^8$, and A are the same as defined above, and $Z^{11}$ represents a leaving group such as a chlorine atom, a bromine atom, an iodine atom, a methanesulfonyloxy group, a trifluoromethanesulfonyloxy group, and a p-toluenesulfonyloxy group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; mixtures thereof, and mixtures of water and these solvents.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

The compound (A-1) is produced in accordance with Synthesis Example 33 mentioned in WO 2013/162072 A.

In the reaction, the compound (A-2) is usually used in the proportion within a range of 1 to 10 mols, and the base is usually used in the proportion within a range of 1 to 10 mols, based on 1 mol of the compound (A-1).

The reaction temperature of the reaction is usually within a range of −20 to 150° C. The reaction time of the reaction is usually within a range of 0.1 to 24 hours.

In the reaction, if necessary, sodium iodide, tetrabutylammonium iodide, and the like may be added, and these compounds are usually used in the proportion within a range of 0.001 to 1.2 mols based on 1 mol of the compound (A-1).

After completion of the reaction, the present compound can be isolated by performing post-treatment operations such as extraction of the reaction mixture with an organic solvent, and drying and concentration of the organic layer. The isolated present compound can also be purified by chromatography, recrystallization, and the like.

(Production Process B)

Among the present compounds, a compound represented by formula (1-4) in which A is A2, and $J^1$ and $J^2$ are hydrogen atoms (hereinafter referred to as the compound (1-4)) can be produced by reacting a compound represented by formula (B-1) (hereinafter referred to as the compound (B-1)) with a hydrazine compound:

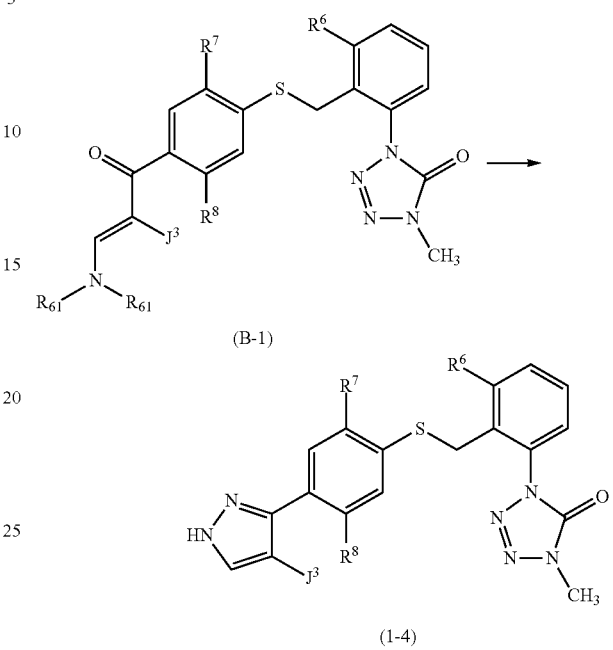

wherein $R^6$, $R^7$, $R^8$, and $J^3$ are the same as defined above, $R^{61}$ represents a methyl group or an ethyl group, and two $R^{61}$(s) may be the same or different to each other.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; halogenated hydrocarbons such as chloroform, 1,2-dichloroetane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; alcohols such as methanol, ethanol, propanol, and butanol; mixtures thereof, and mixtures of water and these solvents.

Examples of the hydrazine compound to be used in the reaction include hydrazine monohydrate, hydrazine hydrochloride, hydrazine sulfate, and anhydrous hydrazine.

In the reaction, the hydrazine compound is usually used in the proportion within a range of 1 to 100 mols based on 1 mol of the compound (B-1).

The reaction temperature of the reaction is usually within a range of −20 to 150° C. The reaction time of the reaction is usually within a range of 0.1 to 24 hours.

After completion of the reaction, the compound (1-4) can be isolated by performing post-treatment operations such as extraction of the reaction mixture with an organic solvent, and drying and concentration of the organic layer. After completion of the reaction, the compound (1-4) can also be isolated by performing post-treatment operations such as concentration of the reaction mixture after completion of the reaction. The compound may also be purified by operations such as chromatography and recrystallization.

(Production Process C)

Among the present compounds, a compound represented by formula (1-5) in which A is A2 and $J^1$ is a hydrogen atom (hereinafter referred to as the compound (1-5)) can be produced by reacting a compound represented by formula (C-1) (hereinafter referred to as the compound (C-1)) with a hydrazine compound:

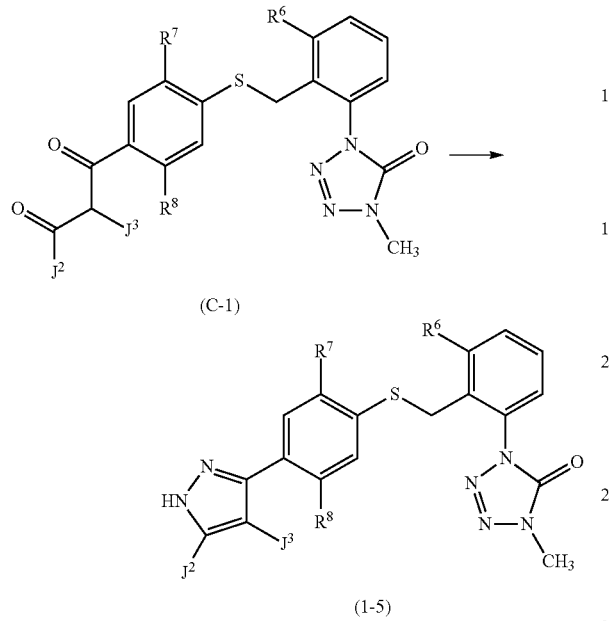

(C-1)

(1-5)

wherein symbols are the same as defined above.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; halogenated hydrocarbons such as chloroform, 1,2-dichloroetane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; alcohols such as methanol, ethanol, propanol, and butanol; mixtures thereof, and mixtures of water and these solvents.

Examples of the hydrazine compound to be used in the reaction include hydrazine monohydrate, hydrazine hydrochloride, hydrazine sulfate, and anhydrous hydrazine.

In the reaction, the hydrazine compound is usually used in the proportion within a range of 1 to 100 mols based on 1 mol of the compound (C-1).

The reaction temperature of the reaction is usually within a range of −20 to 150° C. The reaction time of the reaction is usually within a range of 0.1 to 24 hours.

After completion of the reaction, the compound (1-5) can be isolated by performing post-treatment operations such as extraction of the reaction mixture with an organic solvent, and drying and concentration of the organic layer. The isolated compound may also be purified by operations such as chromatography and recrystallization.

(Production Process D)

Among the present compounds, a compound represented by formula (1-6) in which A is A2 (hereinafter referred to as the compound (1-6)) can be produced by reacting the compound (1-5) with a compound represented by formula (1-7) (hereinafter referred to as the compound (1-7)) in the presence of a base:

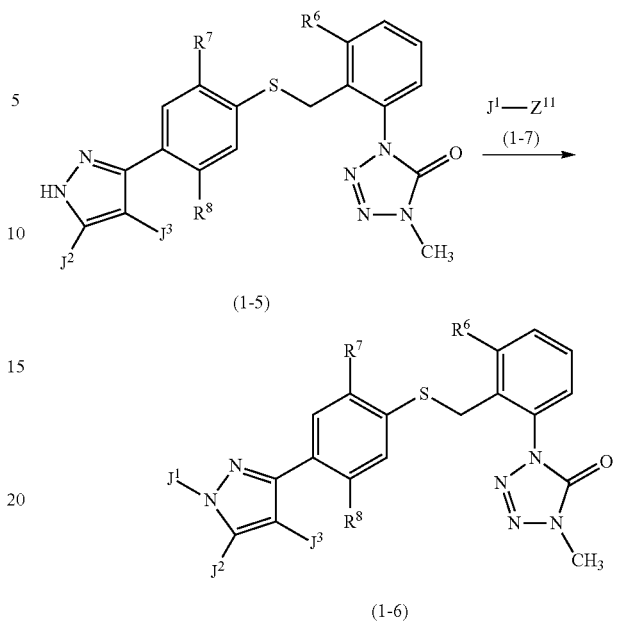

(1-5)

(1-6)

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; mixtures thereof, and mixtures of water and these solvents.

Commercially available products can be usually used as the compound (1-7) to be used in the reaction.

Examples thereof include alkyl halides such as chlorodifluoromethane, methyl bromide, ethyl bromide, propyl bromide, butyl bromide, methyl iodide, ethyl iodide, propyl iodide, isopropyl iodide, isobutyl iodide, cyclopropyl bromide, 1,1-difluoro-2-iodoethane, and 1,1,1-trifluoro-2-iodoethane; dimethyl sulfate, methyl p-toluenesulfonate, ethyl p-toluenesulfonate, propyl p-toluenesulfonate, methyl methanesulfonate, ethyl methanesulfonate, propyl methanesulfonate, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; alkali metal hydrides such as lithium hydride, sodium hydride, and potassium hydride; and alkali metal alkoxides such as sodium tert-butoxide and potassium tert-butoxide.

In the reaction, the compound (1-7) is usually used in the proportion within a range of 1 to 10 mols, and the base is usually used in the proportion within a range of 1 to 10 mols, based on 1 mol of the compound (1-5).

The reaction temperature of the reaction is usually within a range of −20 to 150° C. The reaction time of the reaction is usually within a range of 0.1 to 24 hours.

After completion of the reaction, the present compound represented by formula (1-6) can be isolated by performing post-treatment operations such as extraction of the reaction mixture with an organic solvent, and drying and concentration of the organic layer. The isolated present compound can also be purified by chromatography, recrystallization, and the like.

(Production Process E)

Among the present compounds, a compound represented by formula (1-9) in which A is A1 (hereinafter referred to as the compound (1-9)) can be produced by reacting a compound represented by formula (1-8) (hereinafter referred to as the compound (1-8)) with a compound represented by formula (YD2) (hereinafter referred to as the compound (YD2)) in the presence of a copper reagent and a base:

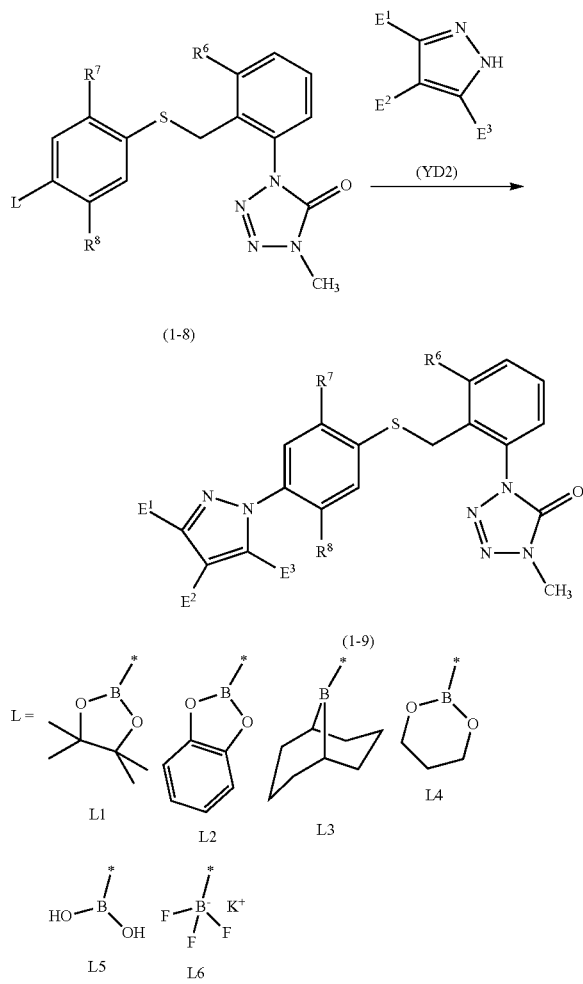

wherein $R^6$, $R^7$, $R^8$, $E^1$, $E^2$, and $E^3$ are the same as defined above, and L represents the above-mentioned group L1, L2, L3, L4, L5, or L6.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as N,N-dimethylformamide, 1, 3-dimethyl-2-imidazolidinone, and N-methylpyrrolidone; esters such as ethyl acetate and methyl acetate; sulfoxides such as dimethyl sulfoxide; nitriles such as acetonitrile; alcohols such as methanol, ethanol, propanol, and butanol; water and mixtures thereof.

Examples of the copper reagent to be used in the reaction include copper(II) acetate, copper(I) oxide, copper(I) iodide, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal fluorides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, usually, the compound (YD2) is used in the proportion within a range of 1 to 10 mols, the copper reagent is used in the proportion within a range of 1 to 10 mols, and the base is used in the proportion within a range of 1 to 10 mols, based on 1 mol of the compound (1-8).

In the reaction, a dehydrating agent such as a molecular sieve is used in the proportion within a range of 100 to 500% by mass based on the compound (1-8).

The reaction temperature of the reaction is usually within a range of −20 to 150° C. The reaction time of the reaction is usually within a range of 0.1 to 120 hours.

After completion of the reaction, the compound (1-9) can be isolated by performing post-treatment operations such as extraction of the reaction mixture with an organic solvent, and drying and concentration of the organic layer. The isolated compound can also be purified by chromatography, recrystallization, and the like.

A method for synthesizing an intermediate compound will be shown below.

(Reference Production Process AA)

The compound (A-2) can be produced by mixing a compound represented by formula (A-3) (hereinafter referred to as the compound (A-3)) with a base:

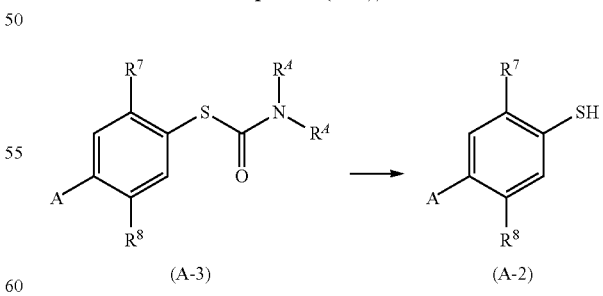

wherein $R^7$, $R^8$, and A are the same as defined above, $R^A$ represents a C1-C6 alkyl group, and two $R^A$(s) may be the same or different to each other.

The reaction is usually performed in a solvent.

Examples of the solvent to be used in the reaction include alcohols such as methanol, ethanol, isopropanol, and butanol; hydrocarbons such as toluene and xylene; ethers such as tetrahydrofuran, 1,4-dioxane, ethylene glycol dimethyl ether, and anisole; acid amides such as N,N-dimethylformamide, 1,3-dimethyl-2-imidazolidinone, and N-methylpyrrolidone; sulfoxides such as dimethyl sulfoxide; nitriles such as acetonitrile; mixtures thereof, and mixtures of water and these solvents.

Examples of the base to be used in the reaction include alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

In the reaction, the base is usually used in the proportion within a range of 1 to 10 mols based on 1 mol of the compound (A-3).

The reaction temperature of the reaction is usually within a range of −20 to 150° C. The reaction time of the reaction is usually within a range of 0.1 to 24 hours.

After completion of the reaction, the compound (A-2) can be isolated by performing post-treatment operations such as extraction of the reaction mixture with an organic solvent, and drying and concentration of the organic layer. The isolated compound (A-2) can also be purified by chromatography, recrystallization, and the like.

(Reference Production Process AB)

The compound (A-3) can be produced by heating a compound represented by formula (A-4) (hereinafter referred to as the compound (A-4)) in the presence of a solvent:

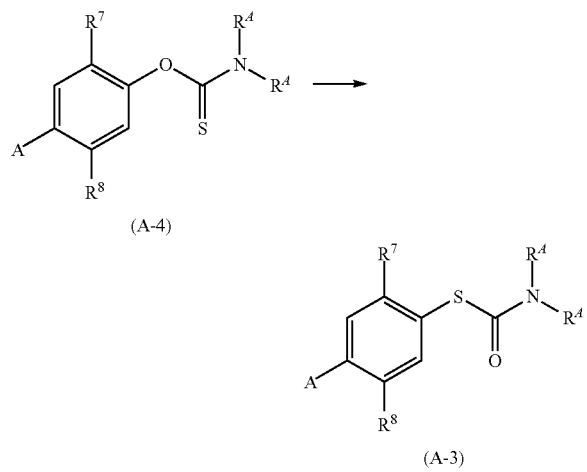

wherein symbols are the same as defined above.

The reaction is usually performed in a solvent.

Examples of the solvent to be used in the reaction include hydrocarbons such as toluene and xylene; ethers such as ethylene glycol dimethyl ether, anisole, and diphenyl ether; acid amides such as N,N-dimethylformamide, 1, 3-dimethyl-2-imidazolidinone, and N-methylpyrrolidone; sulfoxides such as dimethyl sulfoxide; nitriles such as acetonitrile; mixtures thereof, and mixtures of water and these solvents.

The reaction temperature of the reaction is usually within a range of 100 to 300° C. The reaction time of the reaction is usually within a range of 0.1 to 50 hours.

After completion of the reaction, the compound (A-3) can be isolated by performing post-treatment operations such as extraction of the reaction mixture with an organic solvent, and drying and concentration of the organic layer. The isolated compound (A-3) can also be purified by chromatography, recrystallization, and the like. The reaction mixture can also be directly purified by chromatography, recrystallization, and the like.

(Reference Production Process AC)

The compound (A-4) can be produced by reacting a compound represented by formula (A-5) (hereinafter referred to as the compound (A-5)) with a thiocarbamate compound in the presence of a base:

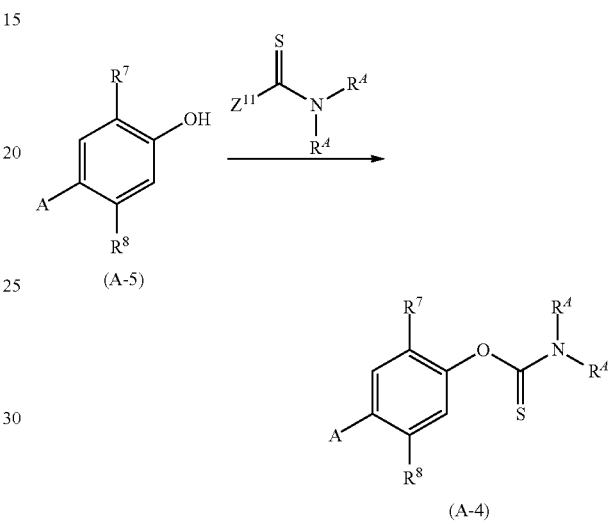

wherein symbols are the same as defined above.

The reaction is usually performed in a solvent.

Examples of the solvent include alcohols such as methanol, ethanol, isopropanol, and butanol; hydrocarbons such as toluene and xylene; ethers such as tetrahydrofuran, 1,4-dioxane, ethylene glycol dimethyl ether, and anisole; acid amides such as N,N-dimethylformamide, 1,3-dimethyl-2-imidazolidinone, and N-methylpyrrolidone; sulfoxides such as dimethyl sulfoxide; nitriles such as acetonitrile; mixtures thereof, and mixtures of water and these solvents.

Examples of the base to be used in the reaction include alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

Examples of thiocarbamates include commercially available dimethylthiocarbamoyl chloride and commercially available diethyl thiocarbamoyl chloride.

In the reaction, thiocarbamates are usually used in the proportion within a range of 1 to 10 mols, and the base is usually used in the proportion within a range of 1 to 10 mols, based on 1 mol of the compound (A-5).

The reaction temperature of the reaction is usually within a range of −90 to 150° C. The reaction time of the reaction is usually within a range of 0.1 to 24 hours.

After completion of the reaction, the compound (A-4) can be isolated by performing post-treatment operations such as extraction of the reaction mixture with an organic solvent, and drying and concentration of the organic layer. The isolated compound (A-4) can also be purified by chromatography, recrystallization, and the like.

(Reference Production Process BA)

A compound represented by formula (BB2) in which A is A1 (hereinafter referred to as the compound (BB2)) in the compound (A-5) can be produced by reacting a compound represented by formula (BB1) (hereinafter referred to as the compound (BB2)) with an acid:

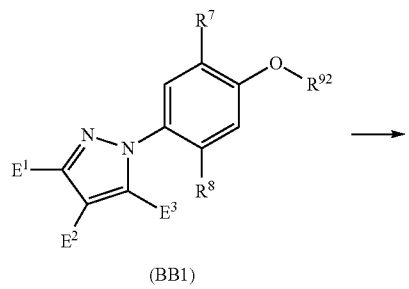

(BB1)

(BB2)

wherein $R^7$, $R^8$, $E^1$, $E^2$, and $E^3$ are the same as defined above, and $R^{92}$ represents a C1-C4 alkyl group.

The reaction is usually performed in a solvent.

Examples of the solvent to be used in the reaction include alcohols such as methanol, ethanol, propanol, and butanol; water, acetic acid, and mixtures thereof.

Examples of the acid to be used in the reaction include hydrochloric acid, hydrobromic acid, and the like, and aqueous solutions thereof can also be used as the solvent.

In the reaction, the acid is usually used in the proportion of large excess based on 1 mol of the compound (BB1).

The reaction temperature of the reaction is usually within a range of −20 to 150° C. The reaction time of the reaction is usually within a range of 0.1 to 100 hours.

After completion of the reaction, the compound (BB2) can be isolated by performing post-treatment operations such as extraction of the reaction mixture with an organic solvent, and drying and concentration of the organic layer, or the compound (BB2) can be isolated by performing post-operations such as concentration of the reaction mixture without being extracted. The isolated compound (BB2) can also be purified by chromatography, recrystallization, and the like.

(Reference Production Process BB)

The compound (BB1) can be produced by reacting a compound represented by formula (BB3) (hereinafter referred to as the compound (BB3)) with the compound (YD2) in the presence of a copper reagent and a base:

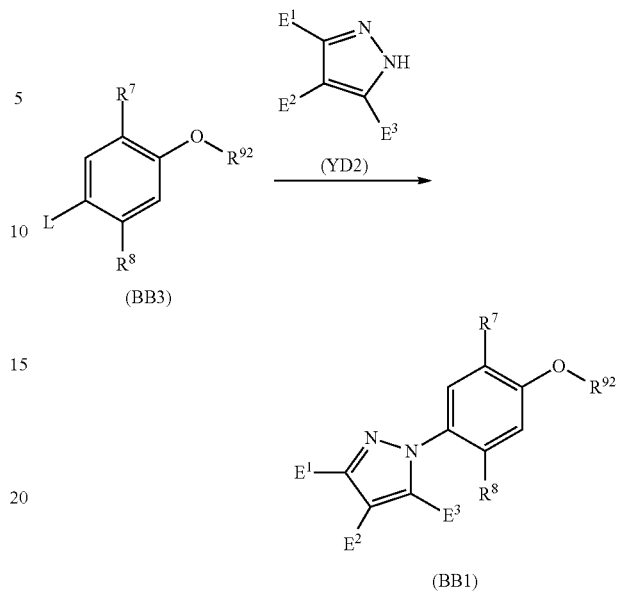

(BB3)

(BB1)

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; nitriles such as acetonitrile; alcohols such as methanol, ethanol, propanol, and butanol; mixtures thereof, and mixtures of water and these solvents.

It is possible to produce, as the compound (BB3) to be used in the reaction, a boronic acid ester derivative by reacting a compound (BB3-I) in which L is iodine in the compound (BB3) with butyllithium, followed by a reaction with a boric acid ester. It is possible to produce a boronic acid derivative by optionally hydrolyzing the boronic acid ester derivative obtained by the above-mentioned reaction. It is also possible to produce a trifluoroborate ($BF_3^-K^+$) by fluorinating the boronic acid ester derivative with potassium fluoride in accordance with a known method mentioned in Molander et al. Acc. Chem. Res., 2007, 40, 275.

Examples of the copper reagent to be used in the reaction include copper(II) acetate, copper(I) oxide, copper(I) iodide, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal fluorides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, usually, the compound (YD2) is used in the proportion within a range of 1 to 10 mols, the copper reagent is used in the proportion within a range of 1 to 10 mols, and the base is used in the proportion within a range of 1 to 10 mols, based on 1 mol of the compound (BB3).

In the reaction, a dehydrating agent such as a molecular sieve may be added, and the dehydrating agent is used in the proportion within a range of 100 to 500% by mass based on the mass of 1 mol of the compound (BB3).

The reaction temperature of the reaction is usually within a range of −20 to 150° C. The reaction time of the reaction is usually within a range of 0.1 to 120 hours.

After completion of the reaction, the compound (BB1) can be isolated by performing post-treatment operations such as extraction of the reaction mixture with an organic solvent, and drying and concentration of the organic layer. The isolated compound (BB1) can also be purified by chromatography, recrystallization, and the like.

(Reference Production Process CA)

A compound represented by formula (CC3) (hereinafter referred to as the compound (CC3)) can be produced by reacting a compound represented by formula (CC1) (hereinafter referred to as the compound (CC1)) with a compound represented by formula (CC2) (hereinafter referred to as the compound (CC2)):

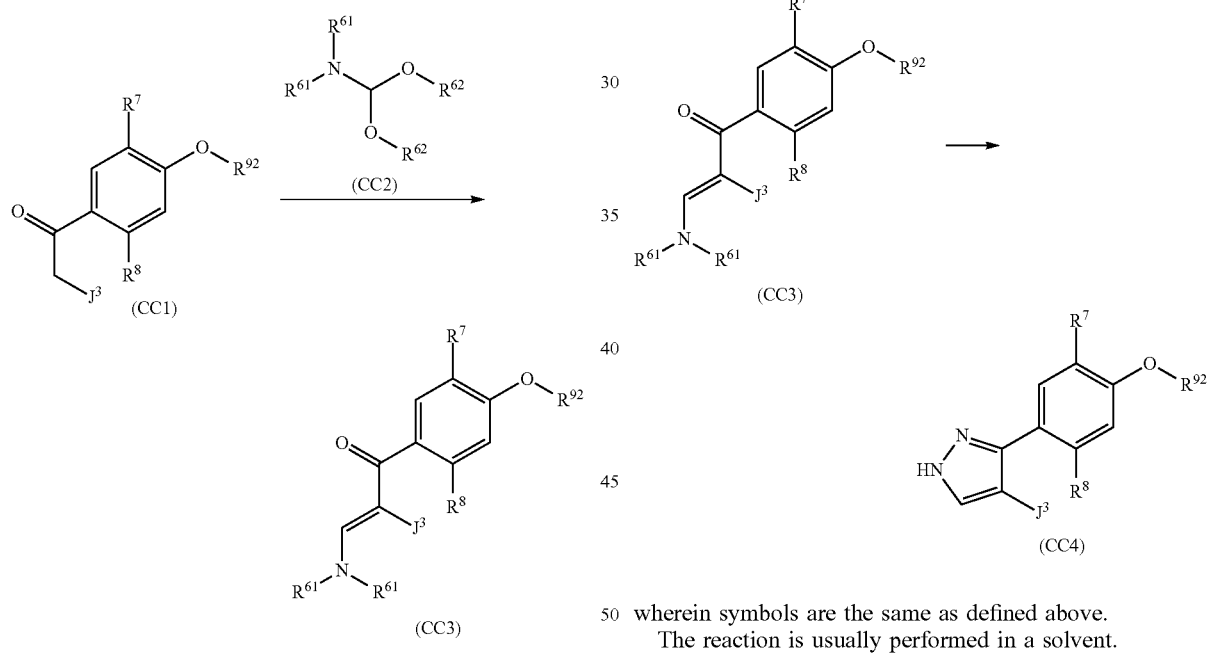

wherein $R^7$, $R^8$, $J^3$, $R^{61}$, and $R^{92}$ are the same as defined above, and $R^{62}$ represents a methyl group, an ethyl group, a propyl group, a butyl group, or a benzyl group.

The reaction is performed in a solvent or in the absence of a solvent.

Examples of the solvent to be used in the reaction include hydrocarbons such as heptane, hexane, cyclohexane, pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroetane, tetrachloroethane, and chlorobenzene; acid amides such as N,N-dimethylformamide, 1,3-dimethyl-2-imidazolidinone, and N-methylpyrrolidone; sulfoxides such as dimethyl sulfoxide; nitriles such as acetonitrile and propionitrile; alcohols such as methanol, ethanol, propanol, and butanol; mixtures thereof, and mixtures of water and these solvents.

Commercially available products are usually used as the compound (CC2).

In the reaction, the compound (CC2) is usually used in the proportion within a range of 1 to 10 mols based on 1 mol of the compound (CC1).

The reaction temperature of the reaction is usually within a range of −20 to 150° C. The reaction time of the reaction is usually within a range of 0.1 to 72 hours.

After completion of the reaction, the compound (CC3) can be isolated by performing post-treatment operations such as extraction of the reaction mixture with an organic solvent, and drying and concentration of the organic layer, or by performing post-treatment operations such as concentration of the reaction mixture without being extracted. The isolated compound (CC3) may also be purified by operations such as chromatography and recrystallization.

(Reference Production Process CB)

A compound represented by formula (CC4) (hereinafter referred to as the compound (CC4)) can be produced by reacting the compound (CC3) with a hydrazine compound:

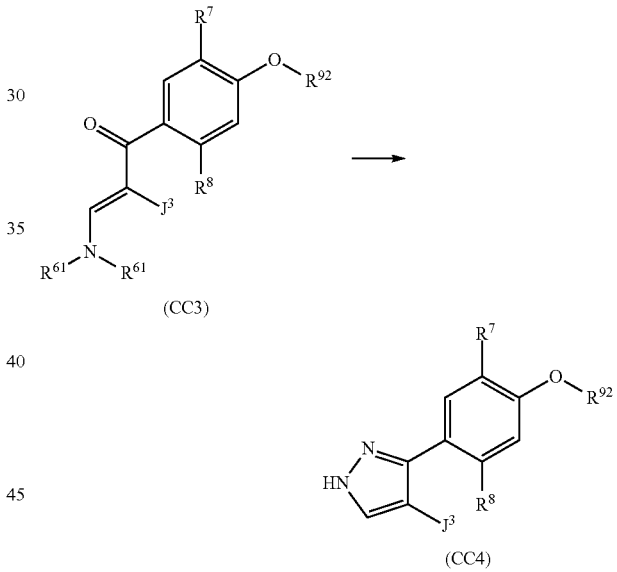

wherein symbols are the same as defined above.

The reaction is usually performed in a solvent.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as heptane, hexane, cyclohexane, pentane, toluene, and xylene; halogenated hydrocarbons such as carbon tetrachloride, chloroform, dichloromethane, 1,2-dichloroetane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; alcohols such as methanol, ethanol, propanol, and butanol; mixtures thereof, and mixtures of water and these solvents.

Examples of the hydrazine compound to be used in the reaction include hydrazine monohydrate, hydrazine hydrochloride, hydrazine sulfate, and anhydrous hydrazine.

In the reaction, the hydrazine compound is usually used in the proportion within a range of 1 to 100 mols based on 1 mol of the compound (CC3).

The reaction temperature of the reaction is usually within a range of −20 to 150° C. The reaction time of the reaction is usually within a range of 0.1 to 24 hours.

After completion of the reaction, the compound (CC4) can be isolated by performing post-treatment operations such as extraction of the reaction mixture with an organic solvent, and drying and concentration of the organic layer, or performing post-treatment operations such as concentration of the reaction mixture without being extracted. The isolated compound (CC4) may also be purified by operations such as chromatography and recrystallization.

(Reference Production Process CC)

A compound represented by formula (CC5) (hereinafter referred to as the compound (CC5)) can be produced by reacting the compound (CC4) with the compound (1-7):

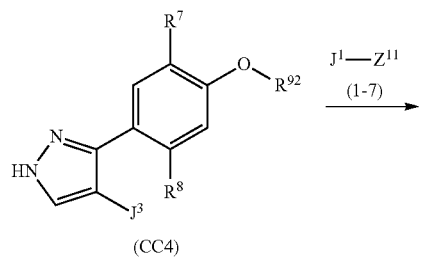

(CC4)

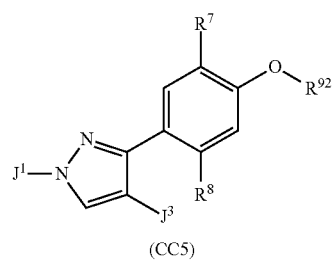

(CC5)

wherein symbols are the same as defined above.

The reaction can be carried out in accordance with the reaction mentioned in Production Process D.

(Reference Production Process CD)

A compound represented by formula (CC6) in which A is A2 and $J^2$ is a hydrogen atom (hereinafter referred to as the compound (CC6)) in the compound (A-5) can be produced by reacting the compound (CC4) with an acid:

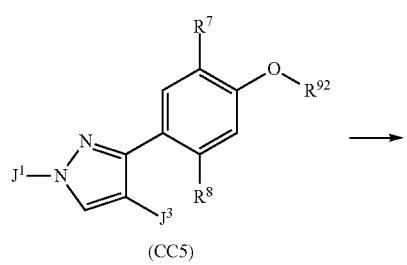

(CC5)

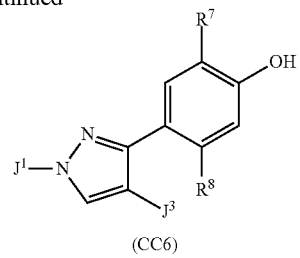

(CC6)

wherein symbols are the same as defined above.

The reaction can be carried out in accordance with the reaction mentioned in Reference Production Process BA.

(Reference Production Process DA)

A compound represented by formula (DD3) (hereinafter referred to as the compound (DD3)) can be produced by reacting a compound represented by formula (DD1) (hereinafter referred to as the compound (DD1)) with a compound represented by formula (DD2) (hereinafter referred to as the compound (DD2)) in the presence of a base:

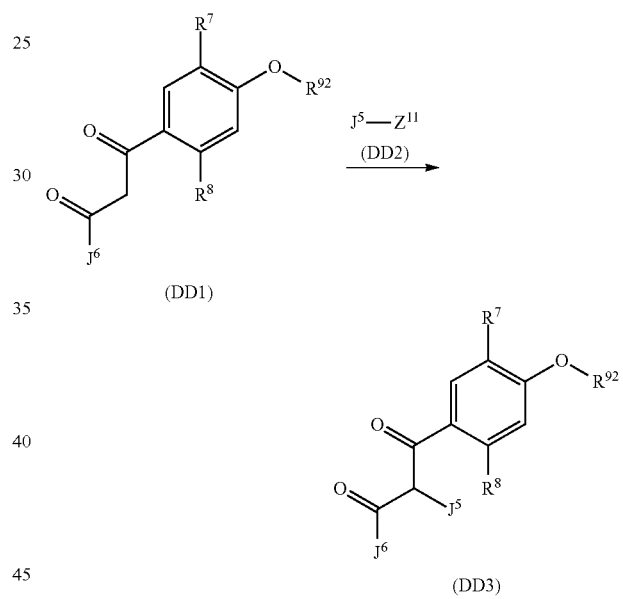

wherein $R^7$, $R^8$, $Z^{11}$, and $R^{92}$ are the same as defined above, $J^5$ represents a C1-C4 alkyl group optionally having one or more halogen atoms, or a C3-C4 cycloalkyl group optionally having one or more halogen atoms, and $J^6$ represents a hydrogen atom, an aldehyde group, a C1-C4 alkyl group optionally having one or more halogen atoms, or a C3-C4 cycloalkyl group optionally having one or more halogen atoms.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Commercially available products are usually used as the compound (DD2) to be used in the reaction.

Examples of the compound (DD2) include alkyl halides such as chlorodifluoromethane, methyl bromide, ethyl bromide, propyl bromide, methyl iodide, ethyl iodide, propyl bromide, cyclopropyl bromide, and 1,1-difluoro-2-iodoethane; dimethyl sulfate, methyl p-toluenesulfonate, ethyl p-toluenesulfonate, propyl p-toluenesulfonate, methyl methanesulfonate, ethyl methanesulfonate, propyl methanesulfonate, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; alkali metal hydrides such as lithium hydride, sodium hydride, and potassium hydride; and alkali metal alkoxides such as sodium tert-butoxide and potassium tert-butoxide.

In the reaction, if necessary, additives may be added, and examples thereof include tetrabutylammonium bromide and tetrabutylammonium fluoride.

In the reaction, the compound (DD2) is usually used in the proportion within a range of 1 to 10 mols, the base is usually used in the proportion within a range of 1 to 10 mols, and the additive is usually used in the proportion within a range of 0.01 to 1 mol, based on 1 mol of the compound (DD1).

The reaction temperature of the reaction is usually within a range of −20 to 150° C. The reaction time of the reaction is usually within a range of 0.1 to 24 hours.

After completion of the reaction, the compound (DD3) can be isolated by performing post-treatment operations such as extraction of the reaction mixture with an organic solvent, and drying and concentration of the organic layer. The isolated compound (DD3) can also be purified by chromatography, recrystallization, and the like.

(Reference Production Process DB)

A compound represented by formula (DD4) (hereinafter referred to as the compound (DD4)) can be produced by reacting the compound (DD3) with a hydrazine compound:

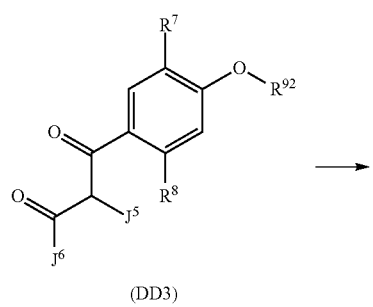

(DD3)

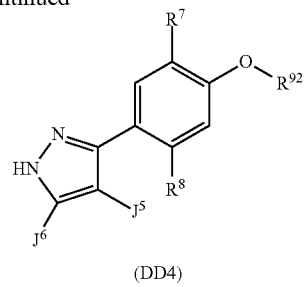

(DD4)

wherein $R^7$, $R^8$, $J^5$, $J^6$, and $R^{92}$ are the same as defined above.

The reaction is usually performed in a solvent.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as heptane, hexane, cyclohexane, pentane, toluene, and xylene; halogenated hydrocarbons such as carbon tetrachloride, chloroform, dichloromethane, 1,2-dichloroetane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; alcohols such as methanol, ethanol, propanol, and butanol; water and mixtures thereof.

Examples of the hydrazine compound to be used in the reaction include hydrazine monohydrate, hydrazine hydrochloride, hydrazine sulfate, anhydrous hydrazine, and the like.

In the reaction, the hydrazine compound is usually used in the proportion within a range of 1 to 100 mols based on 1 mol of the compound (DD3).

The reaction temperature of the reaction is usually within a range of −20 to 150° C. The reaction time of the reaction is usually within a range of 0.1 to 24 hours.

After completion of the reaction, the compound (DD4) can be isolated by performing post-treatment operations such as extraction of the reaction mixture with an organic solvent, and drying and concentration of the organic layer. The isolated compound (DD4) may also be purified by operations such as chromatography and recrystallization.

(Reference Production Process DC)

A compound represented by formula (DD6) (hereinafter referred to as the compound (DD6)) can be produced by reacting the compound (DD4) with a compound represented by formula (DD5) (hereinafter referred to as the compound (DD5) in the presence of a base:

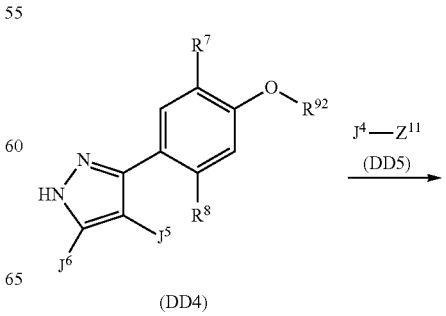

(DD4)

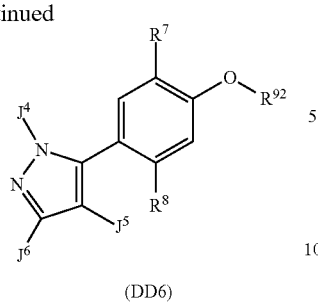

(DD6)

wherein symbols are the same as defined above.

The reaction can be carried out in accordance with Production Process D.

A compound represented by formula (DD8) (hereinafter referred to as the compound (DD8)) can be produced by reacting the compound (DD4) with the compound (D-1) in the presence of a base:

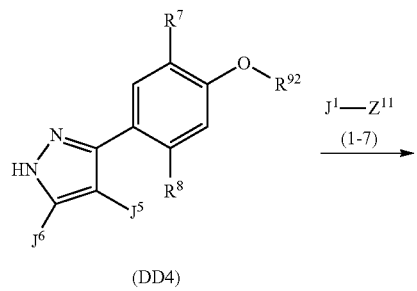

(DD4)

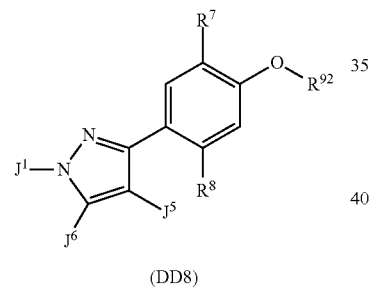

(DD8)

wherein symbols are the same as defined above.

The reaction can be carried out in accordance with the method mentioned in Production Process D.
(Reference Production Process DD)

A compound represented by formula (DD9) in which A is A2 (hereinafter referred to as the compound (DD9)) in the compound (A-5) can be produced by reacting a compound represented by formula (DD8) (hereinafter referred to as the compound (DD8)) with an acid:

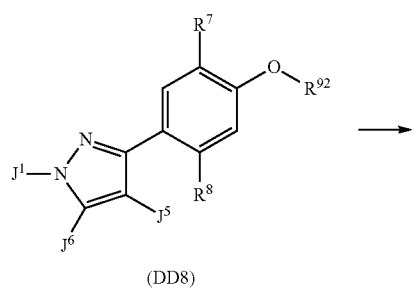

(DD8)

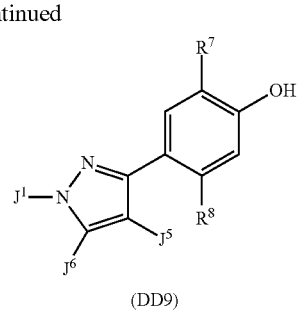

(DD9)

wherein symbols are the same as defined above.

The reaction can be carried out in accordance with the reaction mentioned in Reference Production Process BA.

A compound represented by formula (DD10) in which A is A3 (hereinafter referred to as the compound (DD10)) in the compound (A-5) can be produced by reacting the compound (DD6) with an acid:

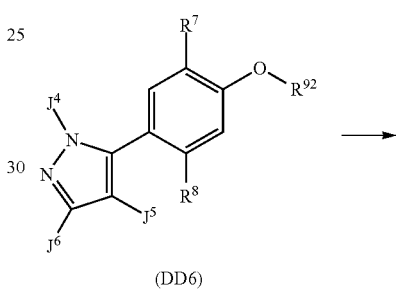

(DD6)

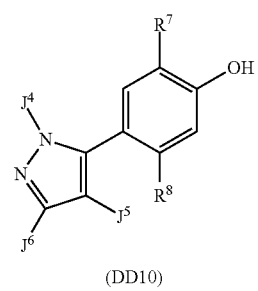

(DD10)

wherein symbols are the same as defined above.

The reaction can be carried out in accordance with the reaction mentioned in Reference Production Process BA.
(Reference Production Process EA)

A compound represented by formula (EE5) (hereinafter referred to as the compound (EE5)) can be produced by subjecting a compound represented by formula (EE4) (hereinafter referred to as the compound (EE4)) and a compound represented by formula (EE3) (hereinafter referred to as the compound (EE3)) to a coupling reaction in the presence of a base and a catalyst:

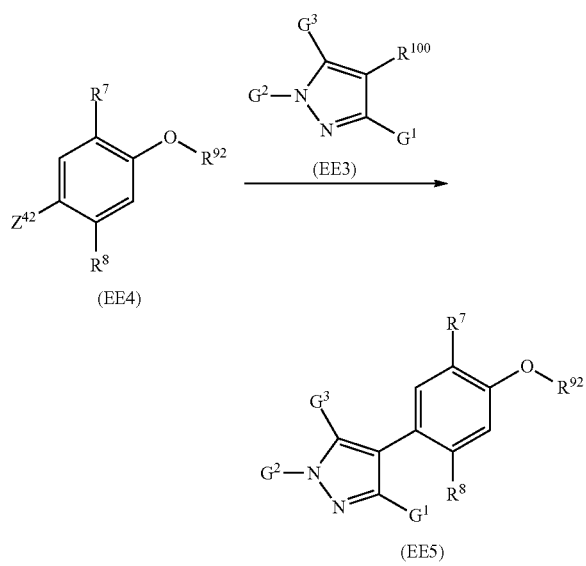

wherein symbols are the same as defined above, $R^{100}$ represents a chlorine atom, a bromine atom, or an iodine atom, and $Z^{42}$ represents $B(OH)_2$, a dialkoxyboranyl group, or trifluoroborate $BF_3^-K^+$.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; mixtures thereof, and mixtures of water and these solvents.

It is possible to usually use, as the compound (EE3) to be used in the reaction, commercially available compounds, or compounds produced by a known method mentioned in N. Miyaura and A. Suzuki, Chem. Rev., 1995, 95, 2457. It is possible to produce, as the compound (EE4) to be used in the reaction, a boronic acid ester derivative by reacting a compound (EE4-I) in which $Z^{22}$ is iodine in the compound (EE4) with butyllithium, followed by a reaction with a boric acid ester. It is possible to produce a boronic acid derivative by optionally hydrolyzing the boronic acid ester derivative obtained by the above-mentioned reaction. It is also possible to produce a trifluoroborate ($BF_3^-K^+$) by fluorinating the boronic acid ester derivative with potassium fluoride in accordance with a known method mentioned in Molander et al. Acc. Chem. Res., 2007, 40, 275.

Examples of the catalyst to be used in the reaction include palladium(II) acetate, dichlorobis(triphenylphosphine)palladium, tetrakis(triphenylphosphine)palladium(0), palladium (II) acetate/triscyclohexylphosphine, bis(diphenylphosphinoferrocenyl)palladium(II) dichloride, 1,3-bis(2,6-diisopropylphenyl)imidazol-2-ylidene(1,4-naphthoquinone)palladium dimer, allyl(chloro) (1,3-dimesityl-1,3-dihydro-2H-imidazol-2-ylidene) palladium or palladium(II) acetate/dicyclohexyl(2',4',6'-triisopropylbiphenyl-2-yl) phosppine, tris(dibenzylidineacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal fluorides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (B-2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B-1).

The reaction temperature of the reaction is usually within a range of 0 to 150° C. The reaction time of the reaction is usually within a range of 0.1 to 24 hours.

After completion of the reaction, the compound (EE5) can be isolated by performing post-treatment operations such as extraction of the reaction mixture with an organic solvent, and drying and concentration of the organic layer. The isolated compound (EE5) can also be purified by chromatography, recrystallization, and the like.

(Reference Production Process EB)

A compound represented by formula (EE6) in which A is A4 in the compound (A-5) (hereinafter referred to as the compound (EE6)) can be produced by reacting the compound (EE5) with an acid:

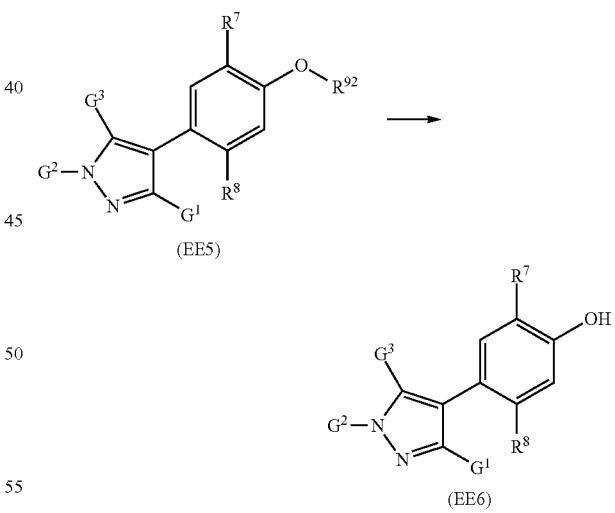

wherein symbols are the same as defined above.

The reaction can be carried out in accordance with the reaction mentioned in Reference Production Process BA.

(Reference Production Process F)

A compound represented by formula (FF0) in which A is A2 and $J^2$ is a chlorine atom in the compound (A-5) (hereinafter referred to as the compound (FF0)) can be produced by reacting a compound represented by formula (FF1) (hereinafter referred to as the compound (FF1)) with a chlorinating agent:

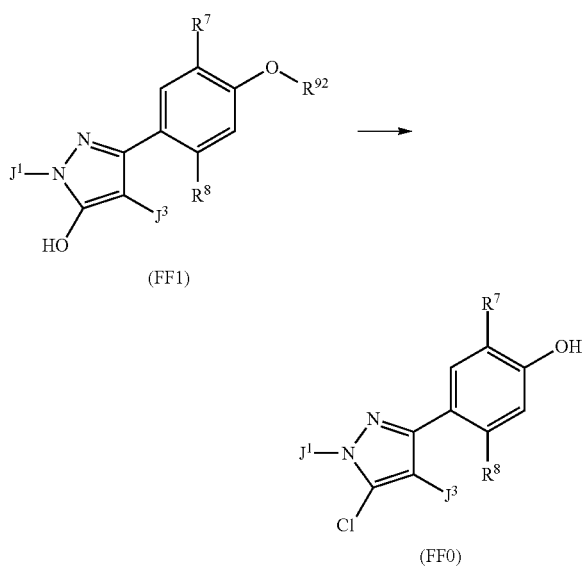

(FF1)

(FF0)

wherein symbols are the same as defined above.
(Reference Production Process FA)

A compound represented by formula (FF2) (hereinafter referred to as the compound (FF2)) can be produced by reacting the compound (FF1) with a chlorinating agent:

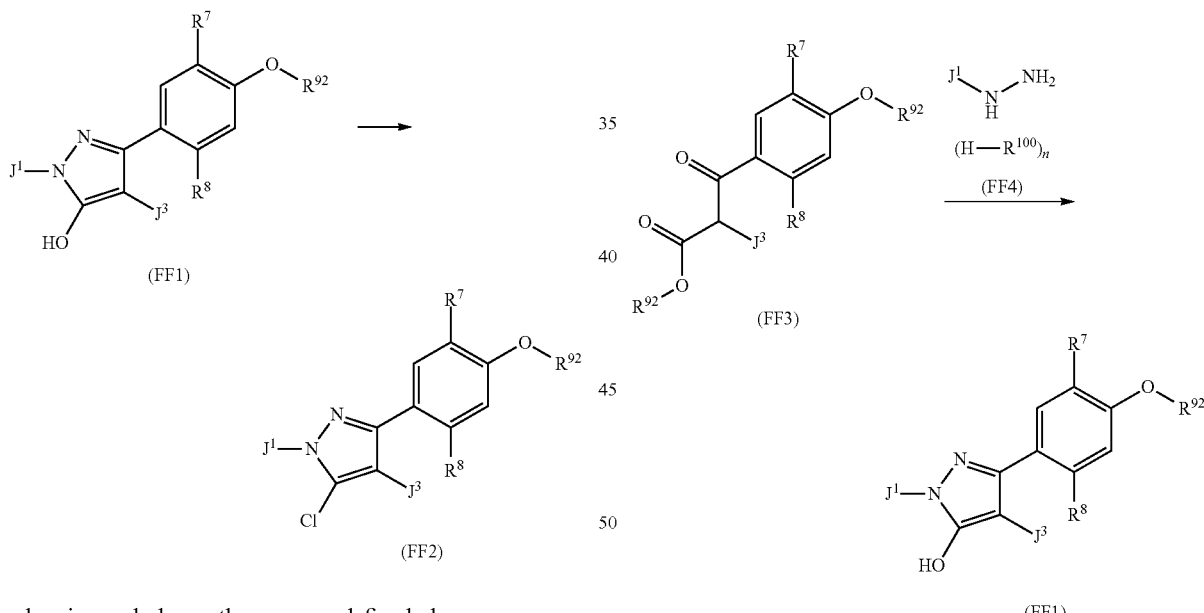

wherein symbols are the same as defined above.

The reaction is performed in a solvent or in the absence of a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Commercially available products are usually used as the chlorinating agent to be used in the reaction. Examples of the chlorinating agent include thionyl chloride, phosphorus oxychloride, phosphorus pentachloride, and mixtures thereof.

In the reaction, a base may be added, and examples of the base to be used in the reaction include organic bases such as triethylamine, pyridine, N-methylmorpholine, 4-dimethylaminopyridine, diisopropylethylamine, diazabicycloundecene, and the like.

In the reaction, the chlorinating agent is usually used in the proportion within a range of 1 mol to large excess, and the base is usually used in the proportion within a range of 1 to 10 mols, based on 1 mol of the compound (FF1).

The reaction temperature of the reaction is usually within a range of −20 to 150° C. The reaction time of the reaction is usually within a range of 0.1 to 72 hours.

After completion of the reaction, the compound (FF2) can be isolated by performing post-treatment operations such as concentration of the reaction mixture under reduced pressure, extraction of the reaction mixture with an organic solvent, and drying and concentration of the organic layer. The isolated compound (FF2) can also be purified by chromatography, recrystallization, and the like.
(Reference Production Process FB)

The compound (FF1) can be produced by reacting a compound represented by formula (FF3) (hereinafter referred to as the compound (FF3)) with a compound represented by formula (FF4) (hereinafter referred to as the compound (FF4)):

wherein $R^7$, $R^8$, $R^{92}$, $R^{100}$, $J^1$, and $J^3$ are the same as defined above, and n represents 0 or 1

The reaction is performed in a solvent or in the absence of a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; nitriles such as acetonitrile; water and mixtures thereof.

In the reaction, if necessary, an acid may be added, and examples of the acid to be used in the reaction include hydrochloric acid, sulfuric acid, acetic acid, hydrobromic acid, p-toluenesulphonic acid, and the like.

In the reaction, the compound (FF4) is usually used in the proportion within a range of 1 to 100 mols, and the acid is usually used in the proportion within a range of 1 to 10 mols, based on 1 mol of the compound (FF3).

The reaction temperature of the reaction is usually within a range of −20 to 150° C. The reaction time of the reaction is usually within a range of 0.1 to 24 hours.

After completion of the reaction, the compound (FF1) can be isolated by performing post-treatment operations such as concentration of the reaction mixture under reduced pressure, extraction of the reaction mixture with an organic solvent, and drying and concentration of the organic layer. The isolated present compound can also be purified by chromatography, recrystallization, and the like.

(Reference Production Process FC)

The compound (FF3) can be produced by reacting the compound (CC1) with a compound represented by formula (FF6) (hereinafter referred to as the compound (FF6)) in the presence of a base:

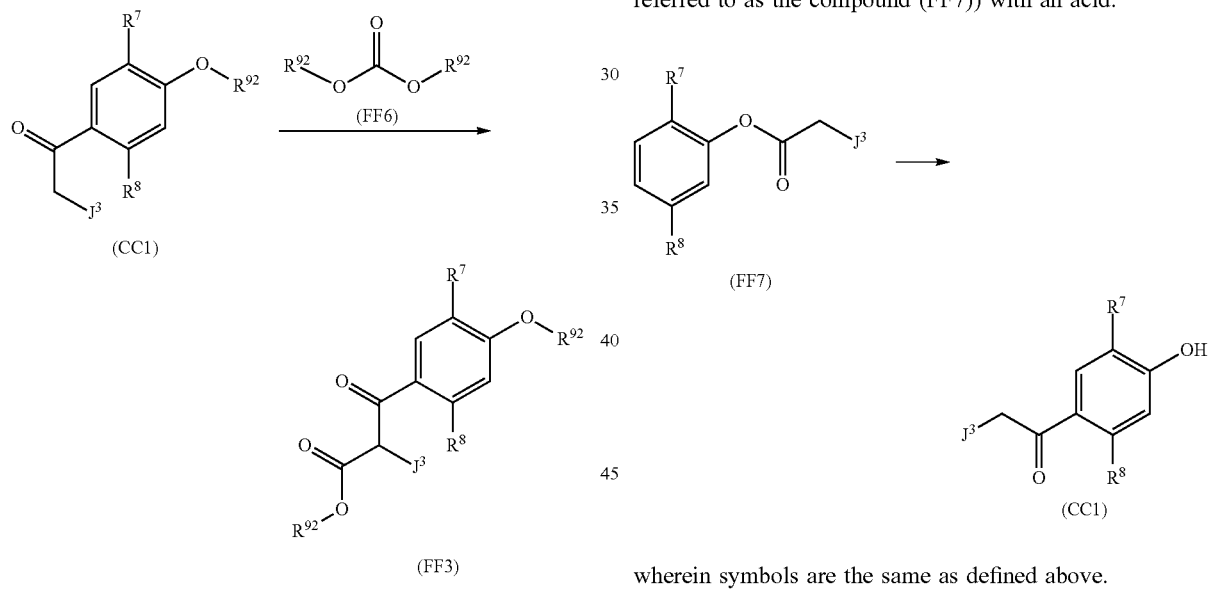

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether;

halogenated hydrocarbons such as chloroform, 1,2-dichloroetane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the base to be used in the reaction include alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

In the reaction, the compound (FF6) is usually used in the proportion within a range of 1 to 10 mols, and the base is usually used in the proportion within a range of 1 to 10 mols, based on 1 mol of the compound (CC1).

The reaction temperature of the reaction is usually within a range of −20 to 150° C. The reaction time of the reaction is usually within a range of 0.1 to 24 hours.

In the reaction, additives may be added, and examples of additives include 18-crown-6-ether and dibenzo-18-crown-6-ether. These additives are usually used in the proportion within a range of 0.001 to 1.2 mols based on 1 mol of the compound (CC1).

After completion of the reaction, the compound (FF3) can be isolated by performing post-treatment operations such as extraction of the reaction mixture with an organic solvent, and drying and concentration of the organic layer. The isolated compound (FF3) can also be purified by chromatography, recrystallization, and the like.

(Reference Production Process FD)

The compound (CC1) can be produced by mixing a compound represented by formula (FF7) (hereinafter referred to as the compound (FF7)) with an acid:

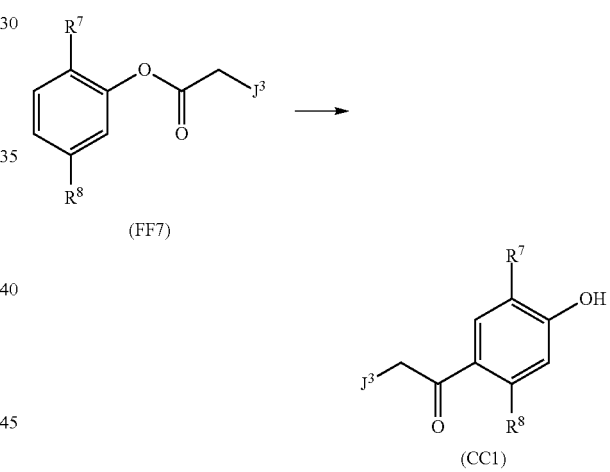

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; nitromethane, nitriles such as acetonitrile; and mixtures thereof.

Examples of the acid to be used in the reaction include aluminum trichloride, titanium tetrachloride, iron trichloride, hydrogen fluoride, hypochlorous acid, and polyphosphoric acid.

In the reaction, the acid is usually used in the proportion within a range of 1 to 10 mols based on 1 mol of the compound (FF7).

The reaction temperature of the reaction is usually within a range of −20 to 150° C. The reaction time of the reaction is usually within a range of 0.1 to 72 hours.

After completion of the reaction, the compound (CC1) can be isolated by performing post-treatment operations such as extraction of the reaction mixture with an organic solvent, and drying and concentration of the organic layer. The isolated compound (CC1) can also be purified by chromatography, recrystallization, and the like.

(Reference Production Process FE)

The compound (FF7) can be produced by reacting a compound represented by formula (FF8) (hereinafter referred to as the compound (FF8)) with a compound represented by formula (FF9) (hereinafter referred to as the compound (FF9)) in the presence of a base:

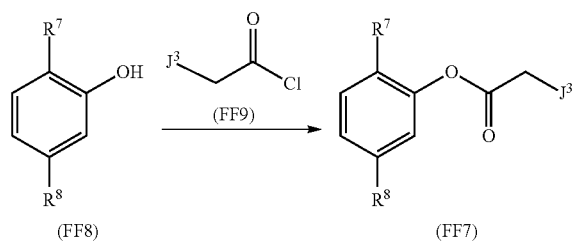

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; nitriles such as acetonitrile; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

In the reaction, the compound (FF9) is usually used in the proportion within a range of 1 to 10 mols, and the base is usually used in the proportion within a range of 1 to 10 mols, based on 1 mol of the compound (FF8).

The reaction temperature of the reaction is usually within a range of −78 to 150° C. The reaction time of the reaction is usually within a range of 0.1 to 72 hours.

After completion of the reaction, the compound (FF7) can be isolated by performing post-treatment operations such as extraction of the reaction mixture with an organic solvent, and drying and concentration of the organic layer. The isolated compound (FF7) can also be purified by chromatography, recrystallization, and the like.

Although a form used for the present compound may be the present compound as itself, the present compound is usually used after mixing with solid carriers, liquid carriers, surfactants, and the like, and optionally adding auxiliary agents for formulation, such as stickers, dispersers, and stabilizers to thereby formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexanone, and kerosene), esters (for example, ethyl acetate and butyl acetate), nitriles (for example, acetonitrile and isobutyronitrile), ethers (for example, 1,4-dioxane and diisopropylether), acid amides (for example, DMF and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyoxyethylene glycol ethers, polyhydric alcohol esters, and sugar alcohol derivatives.

Examples of other auxiliary agents for formulation include stickers and dispersers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof, and the like.

The method for applying the present control agent is not particularly limited, as long as the applying form is a form by which the present control agent can be applied substantially, and includes, for example, an application to plants such as a foliage application; an application to area for cultivating plants such as a submerged treatment; and an application to seeds such as seed disinfection.

The present control agent may be used as a mixture with various oils, such as mineral oils or vegetable oils, or surfactants. Specific examples of oils or surfactants, which can be used as a mixture with various oils or surfactants include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSprayN (registered trademark), BANOLE (registered trademark), and the like.

The present compound can also be used as a mixture with other fungicides, insecticides, acaricides, nematicides, and plant growth regulators, or simultaneously therewith.

The application dose of the present control agent varies depending on weather conditions, dosage forms, timing of application, methods of application, areas to be applied, target diseases, target plants, and the like, and the amount of the present compound in the present control agent is usually within a range of 1 to 500 g, and preferably 2 to 200 g, per 1,000 m$^2$ of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound in the present control agent is usually within a range of 0.001 to 100 g, and preferably 0.01 to 50 g, per 1 kg of the seeds.

Also, in another embodiment, for example, the present compound or the present control agent can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, or administration via injection subcutaneously, intramuscularly, or intravenously. Examples of a method of the external administration include transdermal administration. Also, the present compound can be ingested to a livestock animal so as to exterminate sanitary insects which occur in the excrement of the animal.

When the present compound or the present control agent is applied to the animals such as the livestock animal and pets on which pests are parasitic, the dose varies depending on the administration method etc., and it is desirable to administer the present compound so that a dose of the active ingredient (present compound) is generally within a range of 0.1 mg to 2,000 mg, and preferably 0.5 mg to 1,000 mg, per 1 kg of body weight of the animal.

The present compound or the present control agent can be used as an agent for controlling plant diseases in agricultural lands such as fields, paddy fields, lawns, and orchards. The present compound can control diseases occurred in the agricultural lands for cultivating the following plants.

Crops: corn, rice, wheat, barley, rye, oat, sorghum, cotton, soybean, peanut, buckwheat, beet, rapeseed, sunflower, sugar cane, tobacco, and the like; Vegetables: solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), umbelliferous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, and the like; Flowers; Ornamental foliage plants;

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, persimmon, olive, loquat, banana, coffee, date palm, coconuts, and the like;

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus* cuspidate); and the like.

Lawn: lawn grasses (zoysiagrass, Korean lawn grass, etc.), Bermuda glasses (*cynodon dactylon*, etc.), bentgrasses (redtop grass, creeping bentgrass, colonial bentgrass, etc.), bluegrasses (Kentucky bluegrass, rough bluegrass, etc.), fescue grasses (tall fescue, chewings fescue, creeping red fescue, etc.), perennial ryegrasses (Italian ryegrass, perennial flax, etc.), orchard grass, timothy, etc.

The above-mentioned "plants" include genetically modified crops.

The pests which can be controlled by the present compound include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium graminearum, F. avenaceum, F. culmorum, Microdochium nivale*), rust (*Puccinia striiformis, P. graminis, P. recondita*), snow mould (*Micronectriella nivale*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), damping-off by *Rhizoctonia* (*Rhizoctonia solani*), and take-all disease (*Gaeumannomyces graminis*); Barley diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), *Ramularia* leaf spot (*Ramularia collo-cygni*), and damping-off by *Rhizoctonia* (*Rhizoctonia solani*);

Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum graminicola*), gray leaf spot (*Cercospora zeae-maydis*), eyespot (*Kabatiella zeae*), and phaeosphaeria leaf spot (*Phaeosphaeria maydis*); Cotton diseases: anthracnose (*Colletotrichum gossypii*), grey mildew (*Ramularia areola*), and *alternaria* leaf spot (*Alternaria macrospora, A. gossypii*); Coffee diseases: rust (*Hemileia vastatrix*); Rape seed diseases: sclerotinia rot (*Sclerotinia sclerotiorum*), black spot (*Alternaria brassicae*), and black leg (*Phoma lingam*); Citrus diseases: melanose (*Diaporthe citri*), scab (*Elsinoe fawcetti*), and fruit rot (*Penicillium digitatum, P. italicum*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Glomerella cingulata*);

Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (Gloeosporium kaki) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), phytophthora rot (*Phytophthora* sp.), and damping-off (*Pythium* sp.);

Tomato diseases: early blight (*Alternaria solani*), leaf mold (*Cladosporium fulvum*), leaf mold (*Pseudocercospora fuligena*), and late blight (*Phytophthora infestans*); Eggplant diseases: brown spot (*Phomopsis vexans*) and powdery mildew (*Erysiphe cichoracearum*); Cruciferous vegetables diseases: alternaria leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), sphaceloma scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum* glycines, *C. truncatum*), Rhizoctonia aerial blight (*Rhizoctonia solani*), septoria brown spot (*Septoria glycines*), and frog eye leaf spot (*Cercosporasojina*); Kidneybean diseases: anthracnose (*Colletotrichum lindemuthianum*); Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*);

Potato diseases: early blight (*Alternaria solani*), late blight (*Phytophthora infestans*), and verticillium wilt (*Verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Sugar beet diseases: cercospora leaf spot (*Cercosporabeticola*), leaf blight (*Thanatephorus cucumeris*), root rot (*Thanatephorus cucumeris*), and aphanomyces root rot (*Aphanomyces cochlioides*);

Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: botrytis leaf blight (*Botrytiscinerea, B. byssoidea, B. squamosa*), gray-mold neck rot (*Botrytis alli*), and small sclerotial rot (*Botrytis squamosa*); various crops diseases: gray mold (*Botrytis cinerea*) and sclerotinia rot (*Sclerotinia sclerotiorum*); Japanese radish diseases: alternaria leaf spot (*Alternaria brassicicola*); Turfgrass diseases: dollar spot (*Sclerotinia homoeocarpa*) and brown patch and large patch (*Rhizoctonia solani*); and Banana diseases: Sigatoka disease (*Mycosphaerella fijiensis, Mycosphaerella musicola*).

Hemiptera: planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), and tarnished plant bug (*Lygus lineolaris*); whiteflies (Aleyrodidae) such as greenhouse whitefly (*Trialeurodes vaporariorum*) and silverleaf whitefly (*Bemisia argentifolii*); scales (Coccidae) such as California red scale (*Aonidiella aurantii*), San Jose scale (*Comstockaspis perniciosa*), citrus north scale (*Unaspis citri*), red wax scale (*Ceroplastes rubens*), and cottony cushion scale (*Icerya purchasi*); lace bugs (Tingidae); jumping plant lice (*Homoptera, Psylloidea*); and bed bugs (*Cimex lectularius*).

*Lepidoptera*: pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit *tortrix* (*Adoxophyesoranafasciata*), smaller tea *tortrix* (*Adoxophyes* sp.), oriental tea *tortrix* (*Homona magnanima*), apple *tortrix* (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); codling moths (Carposimidae) such as peach fruit moth (*Carposina niponensis*); lyonetiid moths (Lyonetiidae) such as *Lyonetia* spp.; tussock moths (Lymantriidae) such as *Lymantria* spp. and *Euproctis* spp.; yponomeutid moths (Yponomeutidae) such as diamondback (Plutellaxylostella); gelechildmoths (Gelechiidae) such as pink bollworm (*Pectinophora gossypiella*) and potato tubeworm (*Phthorimaea operculella*); tiger moths and allies (Arctiidae) such as fall webworm (*Hyphantria cunea*); and tineid moths (Tineidae) such as casemaking clothes moth (*Tinea translucens*), and webbing clothes moth (*Tineola bisselliella*).

*Thysanoptera*: yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), and tobacco thrips (*Frankliniella fusca*).

*Diptera*: houseflies (*Musca domestica*), common mosquito (*Culex pipiens pallens*), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Mediterranean fruit fly (*Ceratitis capitata*), and legume leafminer (*Liriomyza trifolii*).

Coleoptera: twenty-eight-spotted ladybirds (*Epilachna vigintioctopunctata*), cucurbit leaf beetle (*Aulacophora femoralis*), yellow striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*).

Orthoptera: asiatic locusts (*Locusta migratoria*), African mole cricket (*Gryllotalpa africana*), rice grasshopper (*Oxya yezoensis*), and rice grasshopper (*Oxya japonica*).

Hymenoptera: cabbage sawflies (*Athalia rosae*), leaf-cutting ant (*Acromyrmex* spp.), and fire ant (*Solenopsis* spp.).

Nematodes: white-tip nematode (*Aphelenchoides besseyi*), strawberry bud nematode (*Nothotylenchus acris*), soybean cyst nematode (*Heterodera glycines*), southern root-knot nematode (*Meloidogyne incognita*), cobb's root-lesion nematode (Pratylenchuspenetrans), and false root-knot nematode (*Nacobbus aberrans*).

Blattariae: German cockroach (*Blattella germanica*), smoky-brown cockroach (*Periplaneta fuliginosa*), American cockroach (*Periplaneta americana*), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus citri*), and *Oligonychus* spp.); Eriophyidae (for example, pink citrus rust mite (*Aculops pelekassi*)); Tarsonemidae (for example, broad mite (*Polyphagotarsonemus latus*)); Tenuipalpidae; Tuckerellidae; Tuckerellidae Acaridae (for example, common grain mite (*Tyrophagus putrescentiae*)); Pyroglyphidae (for example, Americal house dust mite (*Dermatophagoides farinae*) and house dust mite (*Dermatophagoides pteronyssinus*)); Cheyletidae (for example, cheyletid mite (*Cheyletus eruditus*), *Cheyletus malaccensis*, and *Cheyletus moorei*; and Dermanyssidae.

The formulation comprising the present compound can be used in the field relating to a treatment of livestock diseases or livestock industry, and can exterminate the living things or parasites which are parasitic on the inside and/or the outside of vertebrates such as human being, cow, sheep, goat, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *Dermacentor* spp., *Ornithodoros* spp. (for example, *Ornithodoros moubata*), red mite (*Dermanyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Aedes* spp. (for example, Asian tiger mosquito (*Aedes albopictus*)), *Anopheles* spp., *Culex* spp., *Culicoides* spp., *Musca* spp., *Hypoderma* spp., *Gasterophilus* spp., *Haematobia* spp., *Tabanus* spp., *Simulium* spp., *Triatoma* spp., lice (Phthiraptera) (for example, *Damalinia* spp.), *Linognathus* spp., *Haematopinus* spp., *Ctenocephalides* spp. (for example, cat flea (*Ctenocephalides felis*)) *Xenopsylla* spp., Pharaoh's ant (Monomoriumpharaonis) and nematodes [for example, hairworm (for example, *Nippostrongylus brasiliensis, Trichostrongylus axei, Trichostrongylus colubriformis*), *Trichinella* spp. (for example, *Trichinella spiralis*), barber pole worm (*Haemonchus contortus*), *Nematodirus* spp. (for example, *Nematodirus battus*), *Ostertagia circumcincta, Cooperia* spp., *Hymenolepis nana*, and the like.

The present control agent containing at least one selected from the group consisting of the above-mentioned known fungicides, insecticide, acaricides, nematicides, and plant growth regulators may be directly applied to a plant body to be protected from pests, or may be applied to soil for fix planting of the plant body, and seeds.

At least one selected from the group consisting of the above-mentioned known fungicides, insecticide, acaricides, nematicides, and plant growth regulators may be applied to the plant body, simultaneously or separately, when using together with the present control agent. When applying separately, an application date may be different and a different dosage form may be used.

It is possible to combine an application of the present control agent to seeds of the plant with an application of at least one selected from the group consisting of the above-mentioned known fungicides, insecticide, acaricides, nematicides, and plant growth regulators to the plant, or soil for fix planting of the plant. It is also possible to combine an application of at least one selected from the group consisting of the above-mentioned known fungicides, insecticide, acaricides, nematicides, and plant growth regulators to seeds of the plant with an application of the present control agent to the plant, or soil for fix planting of the plant. An application to the plant, or soil for fix planting of the plant may be performed before, on, or after fix planting.

This application method is preferably applied to cultivation of corn, wheat, and rice.

It is possible to combine an application of the present control agent to a plant body, or soil on which the plant body is cultivated or to be cultivated (for example, soil of paddy fields, crop fields, orchards, or non-cultivated lands) with an application of at least one selected from known herbicides to the soil. The pest control agent of the present invention and herbicides can be applied simultaneously or separately. When applying separately, the application may be performed on the same or different day.

Examples of the herbicide, which can be used together with the present control agent, include glyphosate, salts of glyphosate, glufosinate, salts of glyphosate, 2,4-D, salts of 2,4-D, dicamba, salts of dicamba, and flumioxazin.

EXAMPLES

The present invention will be described in more detail below by way of Production Examples, Formulation Examples, and Test Examples, but the present invention is not limited to these Examples.

First, Production Examples will be described.

Production Example 1

A mixture of 0.46 g of 1A mentioned in Reference Production Example 1, 0.56 g of 1-(2-bromomethyl-3-methylphenyl)-4-methyl-1,4-dihydrotetrazol-5-one, 0.75 g of potassium carbonate, and 5 ml of acetonitrile was stirred at 80° C. for 12 hours. After cooling to room temperature, the reaction mixture was filtered with Celite (registered trademark) and the filtrate was concentrated. The residue thus obtained was subjected to silica gel column chromatography to obtain 0.86 g of 1-{3-methyl-2-[2-methyl-4-(1,4-dimethyl-5-chloro-1H-pyrazol-3-yl)-phenylthiomethyl]-phenyl}-4-methyl-1,4-dihydrotetrazol-5-one (hereinafter referred to as the present compound 1).

Present Compound 1

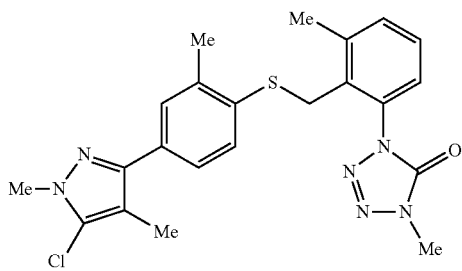 [SMILES: Cc1cc(-c2nn(C)c(Cl)c2C)ccc1SCc1c(C)cccc1-n1nnn(C)c1=O]

$^1$H-NMR (CDCl$_3$) δ: 7.45 (1H, br s), 7.36 (1H, dd, J=7.8, 1.9 Hz), 7.31 (2H, d, J=5.0 Hz), 7.28 (1H, s), 7.22-7.18 (1H, m), 4.14 (2H, s), 3.87 (3H, s), 3.63 (3H, s), 2.40 (3H, s), 2.30 (3H, s), 2.17 (3H, s).

Production Example 2

Using 2A Mentioned in Reference Production Example 2 in Place of 1A in Production Example 1, the Same Reaction was Performed to Obtain 1-{3-Methyl-2-[2-Methyl-4-(3,5-Dimethyl-Pyrazol-1-yl)-Phenylthiomethyl]-phenyl}-4-methyl-1,4-dihydrotetrazol-5-one (hereinafter referred to as the present compound 2).

Present Compound 2

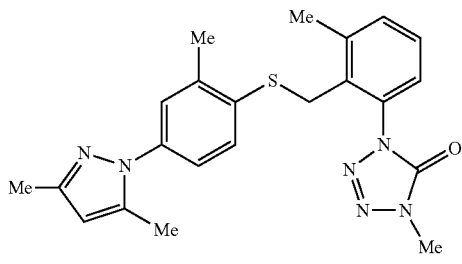 [SMILES: Cc1cc(C)n(-c2ccc(SCc3c(C)cccc3-n3nnn(C)c3=O)c(C)c2)n1]

$^1$H-NMR (CDCl$_3$) δ: 7.31-7.30 (2H, m), 7.27-7.25 (2H, m), 7.22-7.17 (1H, m), 7.13 (1H, dd, J=8.2, 2.3 Hz), 5.99 (1H, s), 4.12 (2H, s), 3.66 (3H, s), 2.39 (3H, s), 2.31 (3H, s), 2.30 (3H, s), 2.29 (3H, s).

Production Example 3

Using 3A mentioned in Reference Production Example 3 in place of 1A in Production Example 1, the same reaction was performed to obtain 1-{3-methyl-2-[2-chloro-4-(5-methyl-pyrazol-1-yl)-phenylthiomethyl]-phenyl}-4-methyl-1,4-dihydro tetrazol-5-one (hereinafter referred to as the present compound 3)

Present Compound 3

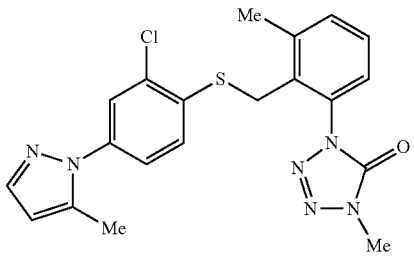 [SMILES: Cc1cccc(-n2nnn(C)c2=O)c1CSc1ccc(-n2nccc2C)cc1Cl]

$^1$H-NMR (CDCl$_3$) δ: 7.58 (1H, d, J=1.8 Hz), 7.54 (1H, d, J=2.3 Hz), 7.34-7.29 (3H, m), 7.24 (1H, dd, J=8.5, 2.3 Hz), 7.20-7.15 (1H, m), 6.20 (1H, dd, J=1.8, 0.8 Hz), 4.21 (2H, s), 3.68 (3H, s), 2.47 (3H, s), 2.39 (3H, s).

Production Example 4

Using 4A mentioned in Reference Production Example 4 in place of 1A in Production Example 1, the same reaction was performed to obtain 1-{3-methyl-2-[2-methyl-4-(3,4,5-trimethyl-pyrazol-1-yl)-phenylthiomethyl]-phenyl}-4-methyl-1,4-dihydrotetrazol-5-one (hereinafter referred to as the present compound 4).

Present Compound 4

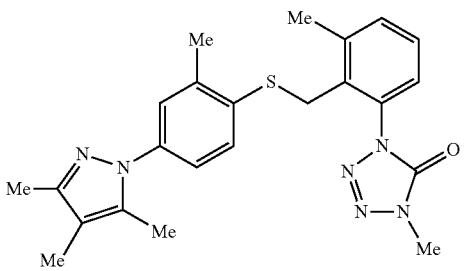 [SMILES: Cc1cc(-n2nc(C)c(C)c2C)ccc1SCc1c(C)cccc1-n1nnn(C)c1=O]

$^1$H-NMR (CDCl$_3$) δ: 7.34-7.30 (2H, m), 7.26-7.26 (2H, m), 7.22-7.17 (1H, m), 7.11 (1H, dd, J=8.3, 2.4 Hz), 4.11 (2H, s), 3.66 (3H, s), 2.39 (3H, s), 2.30 (3H, s), 2.24 (3H, s), 2.23 (3H, s), 1.97 (3H, s).

Production Example 5

Using 5A mentioned in Reference Production Example 5 in place of 1A in Production Example 1, the same reaction was performed to obtain 1-{3-methyl-2-[2-methyl-4-(3-t-butyl-pyrazol-1-yl)-phenylthio methyl]-phenyl}-4-methyl-1,4-dihydrotetrazol-5-one (hereinafter referred to as the present compound 5).

Present Compound 5

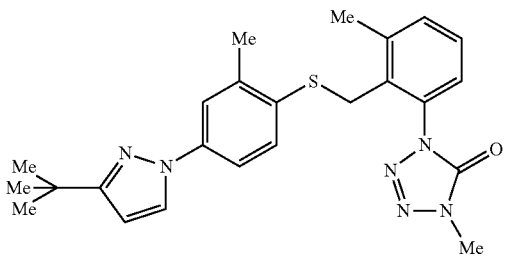 [SMILES: Cc1cc(-n2ccc(C(C)(C)C)n2)ccc1SCc1c(C)cccc1-n1nnn(C)c1=O]

¹H-NMR (CDCl₃) δ: 7.77 (1H, dd, J=2.5, 0.9 Hz), 7.50 (1H, d, J=2.5 Hz), 7.35 (1H, dd, J=8.4, 2.5 Hz), 7.30-7.29 (3H, m), 7.21-7.17 (1H, m), 6.31 (1H, dd, J=2.5, 0.7 Hz), 4.11 (2H, s), 3.60 (3H, s), 2.38 (3H, s), 2.31 (3H, s), 1.36 (9H, s).

Production Example 6

Using 6A mentioned in Reference Production Example 6 in place of 1A in Production Example 1, the same reaction was performed to obtain 1-{3-methyl-2-[2-methyl-4-(1,5-dimethyl-1H-pyrazol-3-yl)-phen ylthiomethyl]-phenyl}-4-methyl-1,4-dihydrotetrazol-5-one (hereinafter referred to as the present compound 6).
Present Compound 6

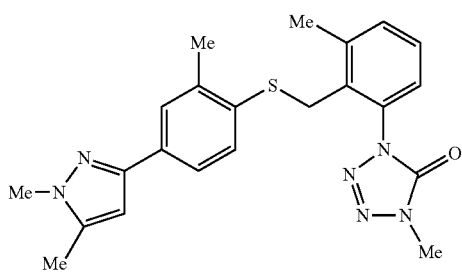 [SMILES: Cc1cc(-c2cc(C)n(C)n2)ccc1SCc1c(C)cccc1-n1nnn(C)c1=O]

¹H-NMR (CDCl₃) δ: 7.58 (1H, br s), 7.45 (1H, dd, J=8.0, 1.9 Hz), 7.30-7.29 (2H, m), 7.24 (1H, d, J=8.0 Hz), 7.19 (1H, t, J=4.6 Hz), 6.30 (1H, s), 4.13 (2H, s), 3.82 (3H, s), 3.61 (3H, s), 2.37 (3H, s), 2.31 (3H, s), 2.29 (3H, s).

Production Example 7

Using 7A mentioned in Reference Production Example 7 in place of 1A in Production Example 1, the same reaction was performed to obtain 1-{3-methyl-2-[2-methyl-4-(1-ethyl-1H-pyrazol-3-yl)-phenylthi omethyl]-phenyl}-4-methyl-1,4-dihydrotetrazol-5-one (hereinafter referred to as the present compound 7).
Present Compound 7

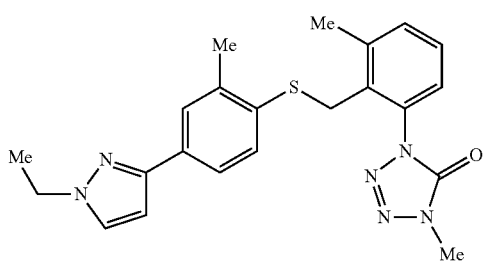 [SMILES: CCn1ccc(-c2ccc(SCc3c(C)cccc3-n3nnn(C)c3=O)c(C)c2)n1]

¹H-NMR (CDCl₃) δ: 7.62 (1H, d, J=1.4 Hz), 7.50 (1H, dd, J=8.1, 1.4 Hz), 7.41 (1H, d, J=2.3 Hz), 7.31-7.29 (2H, m), 7.25 (1H, d, J=6.9 Hz), 7.22-7.18 (1H, m), 6.51 (1H, d, J=2.3 Hz), 4.22 (2H, q, J=7.3 Hz), 4.13 (2H, s), 3.60 (3H, s), 2.38 (3H, s), 2.30 (3H, s), 1.53 (3H, t, J=7.3 Hz).

Production Example 8

Using 8A mentioned in Reference Production Example 8 in place of 1A in Production Example 1, the same reaction was performed to obtain 1-{3-methyl-2-[2-methyl-4-(1-iso-propyl-1H-pyrazol-4-yl)-phenylthiomethyl]-phenyl}-4-methyl-1,4-dihydrotetrazol-5-one (hereinafter referred to as the present compound 8).
Present Compound 8

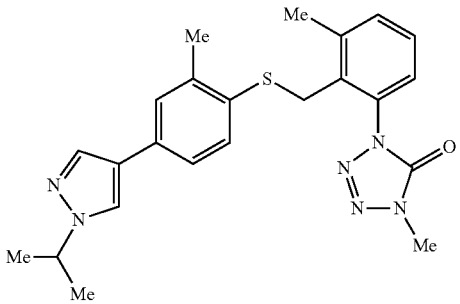 [SMILES: Cc1cc(-c2cnn(C(C)C)c2)ccc1SCc1c(C)cccc1-n1nnn(C)c1=O]

¹H-NMR (CDCl₃) δ: 7.76 (1H, s), 7.66 (1H, s), 7.30 (2H, d, J=5.3 Hz), 7.27 (1H, d, J=5.3 Hz), 7.21-7.18 (3H, m), 4.57-4.46 (1H, m), 4.11 (2H, s), 3.59 (3H, s), 2.39 (3H, s), 2.28 (3H, s), 1.55 (6H, d, J=6.6 Hz).

Production Example 9

Using 9A mentioned in Reference Production Example 9 in place of 1A in Production Example 1, the same reaction was performed to obtain 1-{3-methyl-2-[2-methyl-4-(1-ethyl-1H-pyrazol-4-yl)-phenylthi omethyl]-phenyl}-4-methyl-1,4-dihydrotetrazol-5-one (hereinafter referred to as the present compound 9).
Present Compound 9

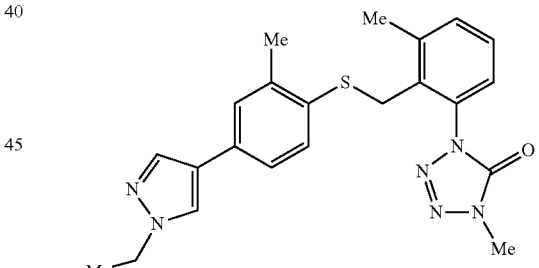

¹H-NMR (CDCl₃) δ: 7.76 (1H, s), 7.64 (1H, s), 7.31-7.17 (6H, m), 4.21 (2H, q, J=7.2 Hz), 4.12 (2H, s), 3.59 (3H, s), 2.39 (3H, s), 2.27 (3H, s), 1.53 (3H, t, J=7.2 Hz).

Production Example 10

Using 10A mentioned in Reference Production Example 10 in place of LA in Production Example 1, the same reaction was performed to obtain 1-{3-methyl-2-[2-methyl-4-(1-isobutyl-1H-pyrazol-4-yl)-phenyl thiomethyl]-phenyl}-4-methyl-1,4-dihydrotetrazol-5-one (hereinafter referred to as the present compound 10).

Present Compound 10

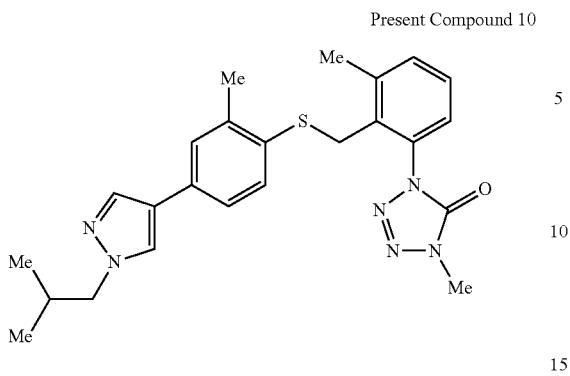

¹H-NMR (CDCl₃) δ: 7.76 (1H, s), 7.60 (1H, s), 7.31-7.18 (6H, m), 4.12 (2H, s), 3.93 (2H, d, J=7.2 Hz), 3.59 (3H, s), 2.40 (3H, s), 2.28 (3H, s), 2.18-2.29 (1H, m), 0.94 (6H, d, J=7.2 Hz).

Production Example 11

A mixture of 0.50 g of X1 mentioned in Reference Production Example 65, 0.15 g of pyrazole, 0.58 g of copper (II) acetate, 0.34 g of pyridine, 0.56 g of molecular sieves 4A, and 10 mL of acetonitrile was stirred at 80° C. for 24 hours. After cooling to room temperature, the reaction mixture was filtered with Celite (registered trademark) and the filtrate was concentrated. The residue thus obtained was subjected to silica gel column chromatography to obtain 0.10 g of 1-{3-methyl-2-[2-methyl-4-(pyrazol-1-yl)-phenyl-thiomethyl]-phenyl}-4-methyl-1,4-dihydrotetrazol-5-one (hereinafter referred to as the present compound 11).

Present Compound 11

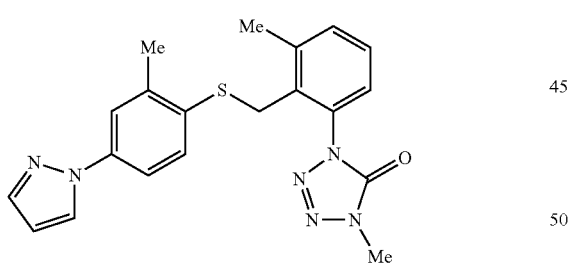

¹H-NMR (CDCl₃) δ: 7.90 (1H, d, J=2.5 Hz), 7.72 (1H, d, J=1.6 Hz), 7.54 (1H, d, J=2.3 Hz), 7.38 (1H, dd, J=8.6, 2.4 Hz), 7.32-7.29 (2H, m), 7.28-7.26 (1H, m), 7.21-7.17 (1H, m), 6.47 (1H, dd, J=2.5, 1.8 Hz), 4.13 (2H, s), 3.60 (3H, s), 2.38 (3H, s), 2.32 (3H, s).

Using commercially available compounds, the present compounds 14 to 19 were synthesized by the same reaction as in Production Example 11. Structures of the present compounds 14 to 19 and analysis values of ¹H-NMR thereof are shown below.

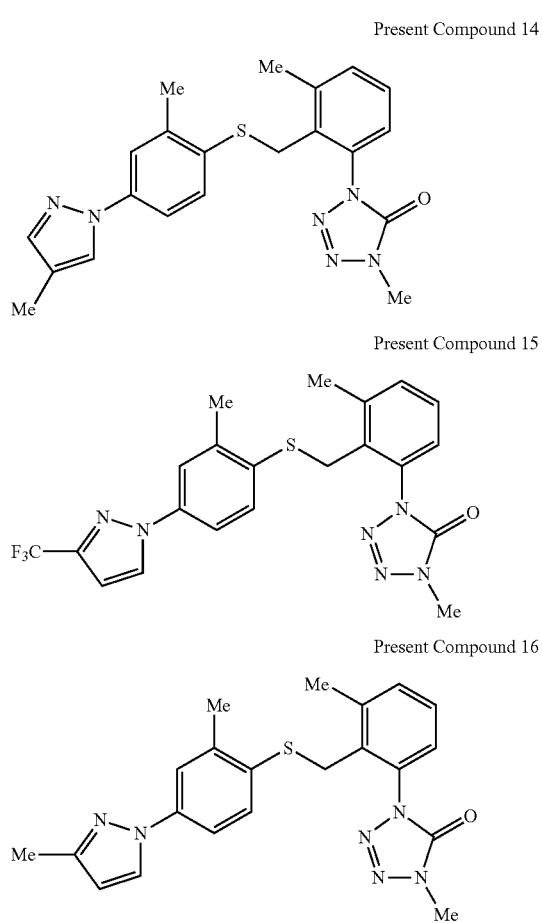

Present Compound 14

Present Compound 15

Present Compound 16

Present Compound 17

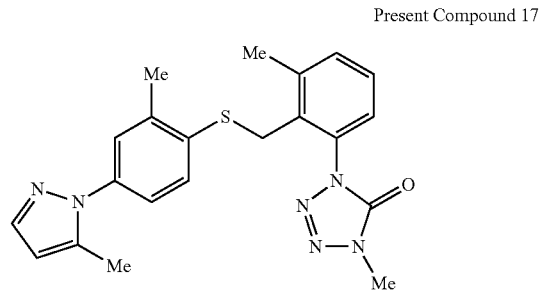 [SMILES: Cc1cc(-n2cccn2)ccc1SCc1c(C)cccc1-n1nnn(C)c1=O]

Present Compound 18

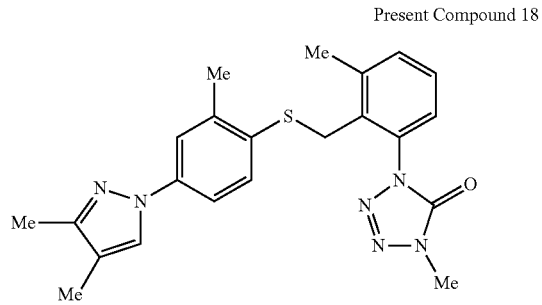

-continued

Present Compound 19

Present Compound 14
1H-NMR (CDCl$_3$) δ: 7.68 (1H, s), 7.52 (1H, s), 7.49 (1H, d, J=2.0 Hz), 7.31-7.28 (4H, m), 7.20-7.19 (1H, m), 4.11 (2H, s), 3.60 (3H, s), 2.37 (3H, s), 2.30 (3H, s), 2.15 (3H, s).
Present Compound 15
$^1$H-NMR (CDCl$_3$) δ: 7.92 (1H, d, J=1.6 Hz), 7.53 (1H, d, J=2.3 Hz), 7.39 (1H, dd, J=8.5, 2.6 Hz), 7.31 (3H, dd, J=11.1, 5.9 Hz), 7.20 (1H, td, J=8.8, 4.5 Hz), 6.72 (1H, d, J=2.5 Hz), 4.15 (2H, s), 3.62 (3H, s), 2.41 (3H, s), 2.32 (3H, s).
Present Compound 16
$^1$H-NMR (CDCl$_3$) δ: 7.78 (1H, s), 7.50 (1H, s), 7.33-7.25 (4H, m), 7.20-7.17 (1H, m), 6.24 (1H, s), 4.11 (2H, s), 3.61 (3H, s), 2.37 (3H, s), 2.36 (3H, s), 2.31 (3H, s).
Present Compound 17
$^1$H-NMR (CDCl$_3$) δ: 7.57 (1H, d, J=1.6 Hz), 7.32 (2H, d, J=5.2 Hz), 7.30-7.27 (2H, m), 7.20-7.16 (2H, m), 6.19 (1H, s), 4.14 (2H, s), 3.66 (3H, s), 2.41 (3H, s), 2.36 (3H, s), 2.31 (3H, s).
Present Compound 18
$^1$H-NMR (CDCl$_3$) δ: 7.61 (1H, s), 7.46 (1H, s), 7.28-7.24 (4H, m), 7.19-7.17 (1H, m), 4.09 (2H, s), 3.61 (3H, s), 2.34 (3H, s), 2.29 (3H, s), 2.28 (3H, s), 2.06 (3H, s).
Present Compound 19
$^1$H-NMR (CDCl$_3$) δ: 7.44 (1H, s), 7.33-7.30 (3H, m), 7.29-7.25 (1H, m), 7.21-7.17 (1H, m), 7.14 (1H, dd, J=8.3, 2.4 Hz), 4.13 (2H, s), 3.65 (3H, s), 2.40 (3H, s), 2.30 (3H, s), 2.25 (3H, s), 2.06 (3H, s).

Production Example 12

Using Y1 mentioned in Reference Production Example 66 in place of X1 in Production Example 11, the same reaction was performed to obtain 1-{3-methyl-2-[2,5-dimethyl-4-(pyrazol-1-yl)-phenylthiomethyl]-phenyl}-4-methyl-1,4-dihydrotetrazol-5-one (hereinafter referred to as the present compound 12).
Present Compound 12

Present Compound 12

$^1$H-NMR (CDCl$_3$) δ: 7.71 (1H, d, J=1.1 Hz), 7.61 (1H, dd, J=2.1, 0.7 Hz), 7.34-7.31 (2H, m), 7.19 (1H, dd, J=6.9, 2.1 Hz), 7.13 (2H, s), 6.43 (1H, t, J=2.1 Hz), 4.14 (2H, s), 3.65 (3H, s), 2.45 (3H, s), 2.22 (3H, s), 2.16 (3H, s).

Production Example 13

Using Y1 mentioned in Reference Production Example 66 in place of X1 in Production Example 11 and using 3,5-dimethylpyrazole in place of pyrazole, the same reaction was performed to obtain 1-{3-methyl-2-[2,5-dimethyl-4-(3,5-dimethyl-pyrazol-1-yl)-phe nylthiomethyl]-phenyl}-4-methyl-1,4-dihydrotetrazol-5-one (hereinafter referred to as the present compound 13).

Present Compound 13

$^1$H-NMR (CDCl3) δ: 7.33 (2H, d, J=5.3 Hz), 7.22-7.18 (1H, m), 7.11 (1H, s), 7.01 (1H, s), 5.95 (1H, s), 4.12 (2H, s), 3.69 (3H, s), 2.42 (3H, s), 2.28 (3H, s), 2.23 (3H, s), 2.06 (3H, s), 1.97 (3H, s).

With respect to the production of intermediates for the production of the above-mentioned present compounds, Reference Production Examples are shown below.

Reference Production Example 1

A mixture of 0.66 g of 1B mentioned in Reference Production Example 11, 9 ml of an aqueous 1N sodium hydroxide solution, and 9 ml of isopropanol was stirred at 60° C. for 24 hours. To the reaction mixture, an aqueous 10% hydrochloric acid solution was added, and the mixture was extracted with chloroform. The organic layer was washed with water, dried over anhydrous magnesium sulfate, and then concentrated under reduced pressure. The residue thus obtained was subjected to silica gel column chromatography to obtain 0.46 g of 1A represented by the following formula.

$^1$H-NMR (CDCl$_3$) δ: 7.46 (1H, s), 7.32-7.31 (2H, m), 3.86 (3H, s), 3.34 (1H, s), 2.37 (3H, s), 2.15 (3H, s).

Reference Production Example 2

Using 2B mentioned in Reference Production Example 12 in place of 1B in Reference Production Example 1, the same reaction was performed to obtain 2A represented by the following formula.

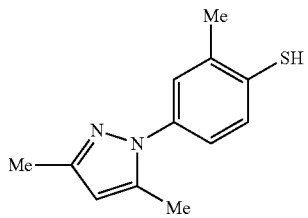

$^1$H-NMR (CDCl$_3$) δ: 7.32 (1H, d, J=8.2 Hz), 7.27 (1H, d, J=2.5 Hz), 7.10 (1H, dd, J=8.4, 2.5 Hz), 5.98 (1H, s), 3.37 (1H, s), 2.36 (3H, s), 2.29 (3H, s), 2.28 (3H, s).

Reference Production Example 3

Using 3B mentioned in Reference Production Example 13 in place of 1B in Reference Production Example 1, the same reaction was performed to obtain 3A represented by the following formula.

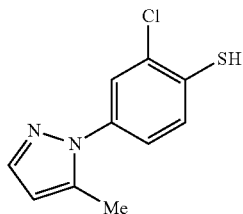 [SMILES: Cc1ccnn1-c1ccc(S)c(Cl)c1]

$^1$H-NMR (CDCl$_3$) δ: 7.57 (1H, d, J=1.8 Hz), 7.53 (1H, d, J=2.3 Hz), 7.43 (1H, d, J=8.5 Hz), 7.26 (1H, dd, J=8.5, 2.3 Hz), 6.20 (1H, s), 3.99 (1H, s), 2.36 (3H, s).

Reference Production Example 4

Using 4B mentioned in Reference Production Example 14 in place of 1B in Reference Production Example 1, the same reaction was performed to obtain 4A represented by the following formula.

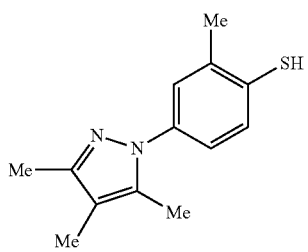

$^1$H-NMR (CDCl$_3$) δ: 7.31 (1H, d, J=8.4 Hz), 7.25 (1H, d, J=2.0 Hz), 7.08 (1H, dd, J=8.3, 2.4 Hz), 3.35 (1H, s), 2.36 (3H, s), 2.24 (3H, s), 2.20 (3H, s), 1.97 (3H, s).

Reference Production Example 5

Using 5B mentioned in Reference Production Example 15 in place of 1B in Reference Production Example 1, the same reaction was performed to obtain 5A represented by the following formula.

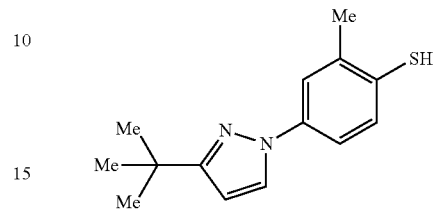

H-NMR (CDCl$_3$) δ: 7.77 (1H, d, J=2.5 Hz), 7.57 (1H, s), 7.47 (1H, d, J=8.5 Hz), 7.38 (1H, dd, J=8.5, 2.5 Hz), 6.31 (1H, d, J=2.5 Hz), 2.47 (3H, s), 1.36 (9H, s).

Reference Production Example 6

Using 6B mentioned in Reference Production Example 16 in place of 1B in Reference Production Example 1, the same reaction was performed to obtain 6A represented by the following formula.

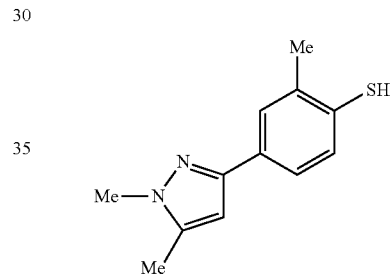

$^1$H-NMR (CDCl$_3$) δ: 7.59 (1H, d, J=1.1 Hz), 7.43 (1H, dd, J=8.0, 1.8 Hz), 7.27 (1H, d, J=8.0 Hz), 6.28 (1H, s), 3.81 (3H, s), 3.31 (1H, s), 2.36 (3H, s), 2.30 (3H, s).

Reference Production Example 7

Using 7B mentioned in Reference Production Example 17 in place of 1B in Reference Production Example 1, the same reaction was performed to obtain 7A represented by the following formula.

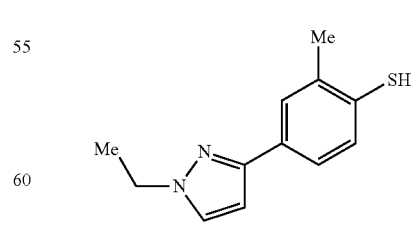

$^1$H-NMR (CDCl$_3$) δ: 7.63 (1H, s), 7.48 (1H, dd, J=8.2, 2.3 Hz), 7.40 (1H, d, J=2.3 Hz), 7.28 (1H, d, J=8.2 Hz), 6.49 (1H, d, J=2.3 Hz), 4.21 (2H, q, J=7.4 Hz), 3.32 (1H, s), 2.37 (3H, s), 1.52 (3H, t, J=7.4 Hz).

Reference Production Example 8

Using 8B mentioned in Reference Production Example 18 in place of 1B in Reference Production Example 1, the same reaction was performed to obtain 8A represented by the following formula.

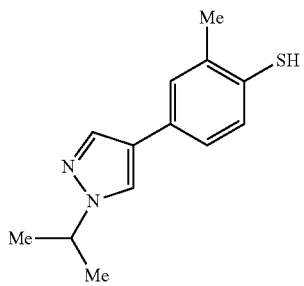 [SMILES: Cc1cc(-c2cnn(C(C)C)c2)ccc1S]

¹H-NMR (CDCl₃) δ: 7.74 (1H, d, J=0.9 Hz), 7.63 (1H, d, J=0.7 Hz), 7.29 (1H, d, J=1.8 Hz), 7.26 (1H, d, J=7.9 Hz), 7.19 (1H, dd, J=7.9, 1.8 Hz), 4.57-4.47 (1H, m), 3.29 (1H, s), 2.36 (3H, s), 1.54 (6H, d, J=6.6 Hz).

Reference Production Example 9

Using 9B mentioned in Reference Production Example 19 in place of 1B in Reference Production Example 1, the same reaction was performed to obtain 9A represented by the following formula.

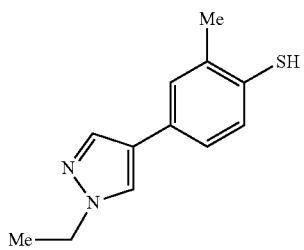 [SMILES: CCn1cc(-c2ccc(S)c(C)c2)cn1]

¹H-NMR (CDCl₃) δ: 7.73 (1H, s), 7.61 (1H, s), 7.29-7.25 (2H, m), 7.18 (1H, dd, J=7.9, 1.9 Hz), 4.20 (2H, q, J=7.3 Hz), 3.29 (1H, s), 2.36 (3H, s), 1.53 (3H, t, J=7.3 Hz).

Reference Production Example 10

Using 10B mentioned in Reference Production Example 20 in place of 1B in Reference Production Example 1, the same reaction was performed to obtain 10A represented by the following formula.

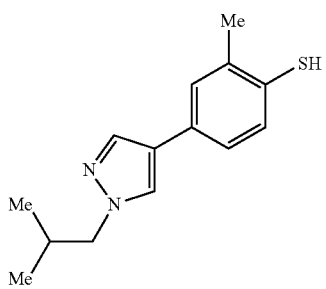 [SMILES: Cc1cc(-c2cnn(CC(C)C)c2)ccc1S]

¹H-NMR (CDCl₃) δ: 7.74 (1H, s), 7.57 (1H, s), 7.29 (1H, s), 7.26 (1H, d, J=8.0 Hz), 7.19 (1H, d, J=8.0 Hz), 3.92 (2H, d, J=7.3 Hz), 3.29 (1H, s), 2.36 (3H, s), 2.28-2.18 (1H, m), 0.94 (6H, d, J=6.6 Hz).

Reference Production Example 11

A mixture of 1.02 g of 1C mentioned in Reference Production Example 21, and 20 ml of diphenyl ether was stirred at 230° C. for 24 hours, and this solution was subjected to silica gel column chromatography to obtain 0.66 g of 1B represented by the following formula.

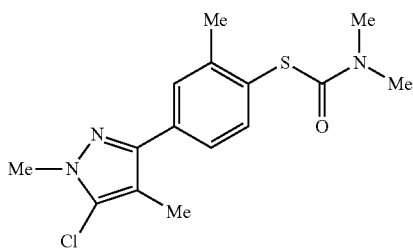 [SMILES: Cc1cc(-c2nn(C)c(Cl)c2C)ccc1SC(=O)N(C)C]

¹H-NMR (CDCl₃) δ: 7.60 (1H, d, J=1.8 Hz), 7.52 (1H, d, J=8.0 Hz), 7.45 (1H, dd, J=8.0, 1.8 Hz), 3.87 (3H, s), 3.14 (3H, br s), 3.03 (3H, br s), 2.45 (3H, s), 2.18 (3H, s).

Reference Production Example 12

Using 2C mentioned in Reference Production Example 22 in place of 1C in Reference Production Example 11, the same reaction was performed to obtain 2B represented by the following formula.

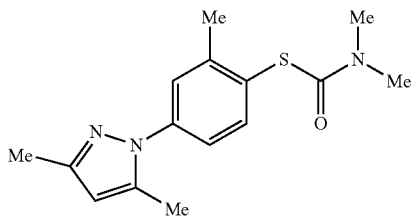 [SMILES: Cc1cc(C)n(-c2ccc(SC(=O)N(C)C)c(C)c2)n1]

¹H-NMR (CDCl₃) δ: 7.54 (1H, d, J=8.2 Hz), 7.43 (1H, d, J=2.1 Hz), 7.24 (1H, dd, J=8.2, 2.1 Hz), 5.99 (1H, s), 3.14 (3H, br s), 3.04 (3H, br s), 2.45 (3H, s), 2.34 (3H, s), 2.29 (3H, s).

Reference Production Example 13

Using 3C mentioned in Reference Production Example 23 in place of 1C in Reference Production Example 11, the same reaction was performed to obtain 3B represented by the following formula.

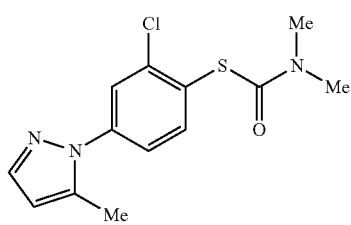 [SMILES: Cc1ccnn1-c1ccc(SC(=O)N(C)C)c(Cl)c1]

$^1$H-NMR (CDCl$_3$) δ: 7.70-7.68 (2H, m), 7.59 (1H, d, J=1.6 Hz), 7.41 (1H, dd, J=8.5, 2.3 Hz), 6.21 (1H, s), 3.16 (3H, br s), 3.06 (3H, br s), 2.42 (3H, s).

Reference Production Example 14

Using 4C mentioned in Reference Production Example 24 in place of 1C in Reference Production Example 11, the same reaction was performed to obtain 4B represented by the following formula.

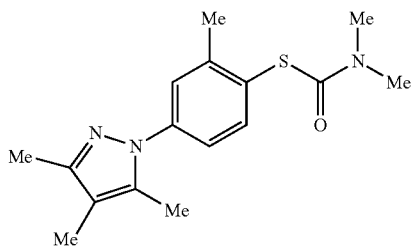 [SMILES: Cc1cc(-n2nc(C)c(C)c2C)ccc1SC(=O)N(C)C]

$^1$H-NMR (CDCl$_3$) δ: 7.52 (1H, d, J=8.2 Hz), 7.41 (1H, d, J=2.3 Hz), 7.22 (1H, dd, J=8.2, 2.3 Hz), 3.14 (3H, br s), 3.03 (3H, br s), 2.44 (3H, s), 2.26 (3H, s), 2.24 (3H, s), 1.97 (3H, s).

Reference Production Example 15

Using 5C mentioned in Reference Production Example 25 in place of 1C in Reference Production Example 11, the same reaction was performed to obtain 5B represented by the following formula.

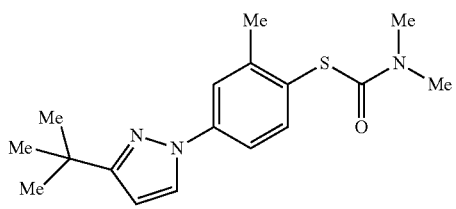 [SMILES: Cc1cc(-n2ccc(C(C)(C)C)n2)ccc1SC(=O)N(C)C]

$^1$H-NMR (CDCl$_3$) δ: 7.79 (1H, d, J=2.5 Hz), 7.65 (1H, d, J=2.3 Hz), 7.50 (1H, d, J=8.5 Hz), 7.47 (1H, dd, J=8.5, 2.3 Hz), 6.31 (1H, d, J=2.5 Hz), 3.14 (3H, br s), 3.03 (3H, br s), 2.46 (3H, s), 1.36 (9H, s).

Reference Production Example 16

Using 6C mentioned in Reference Production Example 26 in place of 1C in Reference Production Example 11, the same reaction was performed to obtain 6B represented by the following formula.

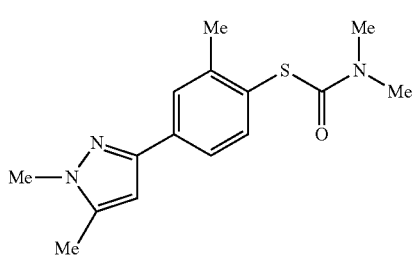

$^1$H-NMR (CDCl$_3$) δ: 7.71 (1H, s), 7.55 (1H, dd, J=8.0, 1.6 Hz), 7.46 (1H, d, J=8.0 Hz), 6.32 (1H, s), 3.82 (3H, s), 3.13 (3H, br s), 3.02 (3H, br s), 2.44 (3H, s), 2.30 (3H, s).

Reference Production Example 17

Using 7C mentioned in Reference Production Example 27 in place of 1C in Reference Production Example 11, the same reaction was performed to obtain 7B represented by the following formula.

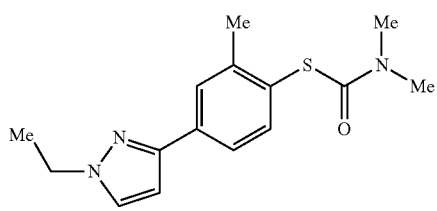 [SMILES: CCn1ccc(-c2ccc(SC(=O)N(C)C)c(C)c2)n1]

$^1$H-NMR (CDCl$_3$) δ: 7.76 (1H, s), 7.59 (1H, d, J=7.9 Hz), 7.48 (1H, d, J=7.9 Hz), 7.41 (1H, dd, J=2.3, 1.1 Hz), 6.53 (1H, dd, J=2.3, 1.1 Hz), 4.22 (2H, dq, J=1.1, 7.4 Hz), 3.13 (3H, br s), 3.03 (3H, br s), 2.45 (3H, s), 1.52 (3H, td, J=7.4, 1.1 Hz).

Reference Production Example 18

Using 8C mentioned in Reference Production Example 28 in place of 1C in Reference Production Example 11, the same reaction was performed to obtain 8B represented by the following formula.

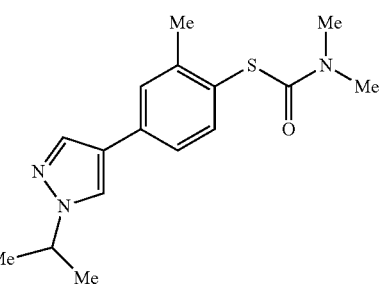

$^1$H-NMR (CDCl$_3$) δ: 7.76 (1H, s), 7.66 (1H, s), 7.44 (1H, d, J=8.2 Hz), 7.41 (1H, d, J=1.6 Hz), 7.30 (1H, dd, J=8.2, 1.6 Hz), 4.57-4.47 (1H, m), 3.13 (3H, br s), 3.03 (3H, br s), 2.43 (3H, s), 1.55 (6H, d, J=6.6 Hz).

Reference Production Example 19

Using 9C mentioned in Reference Production Example 29 in place of 1C in Reference Production Example 11, the same reaction was performed to obtain 9B represented by the following formula.

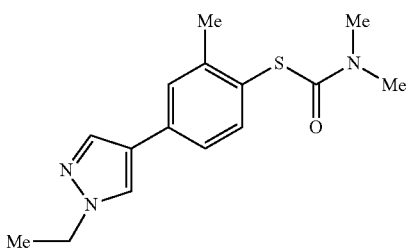 [SMILES: CCn1cc(-c2ccc(SC(=O)N(C)C)c(C)c2)cn1]

$^1$H-NMR (CDCl$_3$) δ: 7.76 (1H, s), 7.65 (1H, s), 7.45 (1H, d, J=8.0 Hz), 7.41 (1H, d, J=2.1 Hz), 7.30 (1H, dd, J=8.0, 1.9 Hz), 4.21 (2H, q, J=7.3 Hz), 3.14 (3H, br s), 3.03 (3H, br s), 2.43 (3H, s), 1.53 (3H, t, J=7.3 Hz).

Reference Production Example 20

Using 10C mentioned in Reference Production Example 30 in place of 1C in Reference Production Example 11, the same reaction was performed to obtain 10B represented by the following formula.

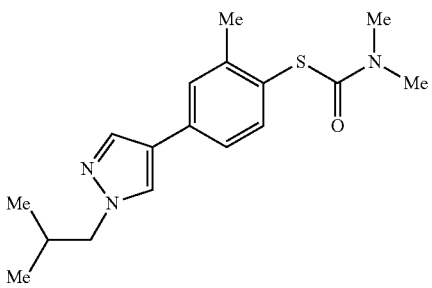 [SMILES: Cc1cc(-c2cnn(CC(C)C)c2)ccc1SC(=O)N(C)C]

$^1$H-NMR (CDCl$_3$) δ: 7.77 (1H, s), 7.61 (1H, s), 7.47-7.39 (2H, m), 7.31 (1H, d, J=7.3 Hz), 3.94 (2H, dd, J=7.2, 3.5 Hz), 3.14 (3H, br s), 3.03 (3H, br s), 2.43 (3H, s), 2.29-2.18 (1H, m), 0.94 (6H, d, J=6.6 Hz).

Reference Production Example 21

To a mixture of 1.0 g of 1Z mentioned in Reference Production Example 64 and 10 ml of dimethylformamide, 0.218 g of 55% sodium hydride was added at 0° C., followed by stirring for 0.5 hour, addition of 0.618 g of dimethylthiocarbamoyl chloride, and further stirring for 8 hours. To the reaction mixture, an aqueous ammonium chloride solution was added and the mixture was extracted with ethyl acetate. The organic layer was washed with water, dried over anhydrous magnesium sulfate, and then concentrated under reduced pressure. The residue thus obtained was subjected to silica gel column chromatography to obtain 1.02 g of 1C represented by the following formula.

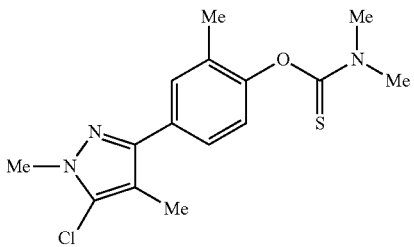

$^1$H-NMR (CDCl$_3$) δ: 7.55 (1H, d, J=1.8 Hz), 7.48 (1H, dd, J=8.2, 1.8 Hz), 7.04 (1H, d, J=8.2 Hz), 3.87 (3H, s), 3.48 (3H, s), 3.38 (3H, s), 2.24 (3H, s), 2.19 (3H, s).

Reference Production Example 22

Using 2Z mentioned in Reference Production Example 43 in place of 1Z in Reference Production Example 21, the same reaction was performed to obtain 2C represented by the following formula.

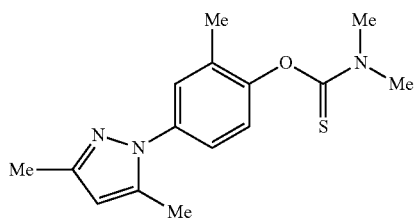 [SMILES: Cc1cc(C)n(-c2ccc(OC(=S)N(C)C)c(C)c2)n1]

$^1$H-NMR (CDCl$_3$) δ: 7.35 (1H, d, J=2.3 Hz), 7.24 (1H, dd, J=8.5, 2.1 Hz), 7.04 (1H, d, J=8.7 Hz), 5.98 (1H, s), 3.48 (3H, s), 3.38 (3H, s), 2.33 (3H, s), 2.29 (3H, s), 2.23 (3H, s).

Reference Production Example 23

Using 3Z mentioned in Reference Production Example 39 in place of 1Z in Reference Production Example 21, the same reaction was performed to obtain 3C represented by the following formula.

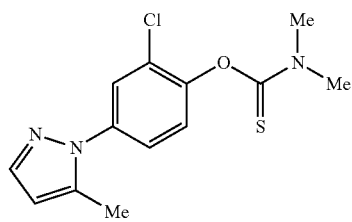 [SMILES: Cc1ccnn1-c1ccc(OC(=S)N(C)C)c(Cl)c1]

$^1$H-NMR (CDCl$_3$) δ: 7.60 (1H, d, J=2.5 Hz), 7.58 (1H, d, J=1.6 Hz), 7.41 (1H, dd, J=8.6, 2.5 Hz), 7.25 (1H, d, J=8.6 Hz), 6.20 (1H, s), 3.49 (3H, s), 3.42 (3H, s), 2.41 (3H, s).

Reference Production Example 24

Using 4Z mentioned in Reference Production Example 33 in place of 1Z in Reference Production Example 21, the same reaction was performed to obtain 4C represented by the following formula.

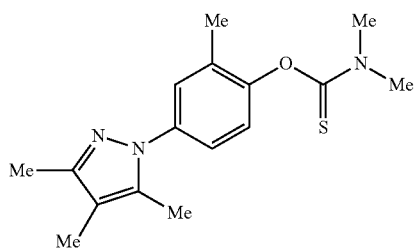 [SMILES: Cc1cc(-n2nc(C)c(C)c2C)ccc1OC(=S)N(C)C]

¹H-NMR (CDCl₃) δ: 7.32 (1H, d, J=2.5 Hz), 7.22 (1H, dd, J=8.5, 2.5 Hz), 7.03 (1H, d, J=8.5 Hz), 3.48 (3H, s), 3.38 (3H, s), 2.25 (3H, s), 2.24 (3H, s), 2.22 (3H, s), 1.97 (3H, s).

Reference Production Example 25

Using 5Z mentioned in Reference Production Example 41 in place of 1Z in Reference Production Example 21, the same reaction was performed to obtain 5C represented by the following formula.

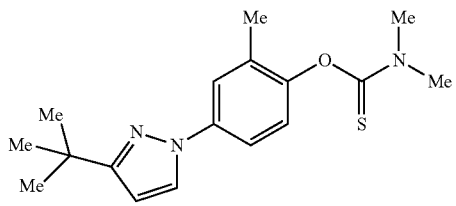 [SMILES: Cc1cc(-n2ccc(C(C)(C)C)n2)ccc1OC(=S)N(C)C]

¹H-NMR (CDCl₃) δ: 7.76 (1H, d, J=2.5 Hz), 7.58 (1H, s), 7.48 (1H, ddd, J=8.7, 2.5, 0.5 Hz), 7.02 (1H, d, J=8.7 Hz), 6.29 (1H, d, J=2.5 Hz), 3.48 (3H, s), 3.38 (3H, s), 2.24 (3H, s), 1.36 (9H, s).

Reference Production Example 26

Using 6Z mentioned in Reference Production Example 48 in place of 1Z in Reference Production Example 21, the same reaction was performed to obtain 6C represented by the following formula.

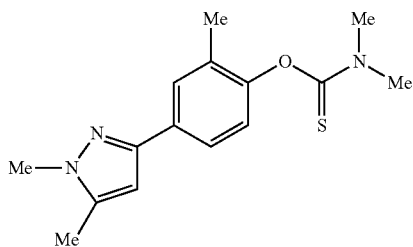 [SMILES: Cc1cc(-c2cc(C)n(C)n2)ccc1OC(=S)N(C)C]

¹H-NMR (CDCl₃) δ: 7.65 (1H, s), 7.56 (1H, d, J=7.6 Hz), 6.99 (1H, d, J=7.6 Hz), 6.28 (1H, s), 3.81 (3H, s), 3.48 (3H, s), 3.37 (3H, s), 2.30 (3H, s), 2.22 (3H, s).

Reference Production Example 27

Using 7Z mentioned in Reference Production Example 58 in place of 1Z in Reference Production Example 21, the same reaction was performed to obtain 7C represented by the following formula.

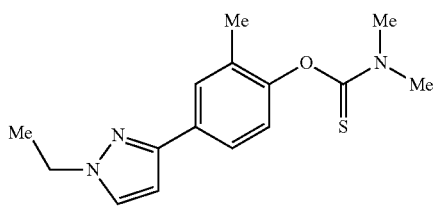 [SMILES: CCn1ccc(-c2ccc(OC(=S)N(C)C)c(C)c2)n1]

¹H-NMR (CDCl₃) δ: 7.70 (1H, d, J=1.8 Hz), 7.62 (1H, ddd, J=8.3, 2.3, 0.6 Hz), 7.40 (1H, d, J=2.3 Hz), 7.01 (1H, d, J=8.3 Hz), 6.50 (1H, d, J=2.3 Hz), 4.21 (2H, q, J=7.3 Hz), 3.48 (3H, s), 3.38 (3H, s), 2.23 (3H, s), 1.52 (3H, t, J=7.3 Hz).

Reference Production Example 28

Using 8Z mentioned in Reference Production Example 54 in place of 1Z in Reference Production Example 21, the same reaction was performed to obtain 8C represented by the following formula.

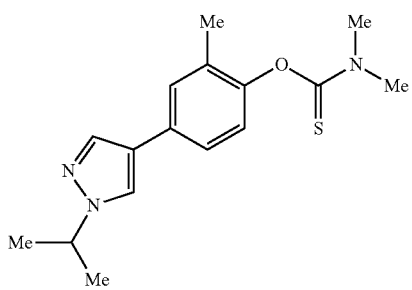 [SMILES: Cc1cc(-c2cnn(C(C)C)c2)ccc1OC(=S)N(C)C]

¹H-NMR (CDCl₃) δ: 7.74 (1H, s), 7.63 (1H, s), 7.36-7.30 (2H, m), 6.98 (1H, d, J=8.0 Hz), 4.58-4.46 (1H, m), 3.48 (3H, s), 3.37 (3H, s), 2.22 (3H, s), 1.54 (6H, d, J=6.9 Hz).

Reference Production Example 29

Using 9Z mentioned in Reference Production Example 37 in place of 1Z in Reference Production Example 21, the same reaction was performed to obtain 9C represented by the following formula.

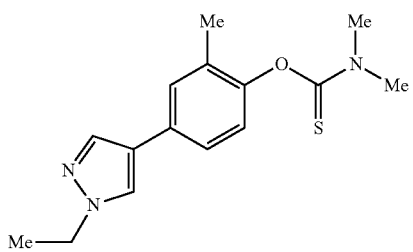

¹H-NMR (CDCl₃) δ: 7.67 (1H, s), 7.54 (1H, s), 7.28-7.23 (2H, m), 6.91 (1H, d, J=8.0 Hz), 4.13 (2H, d, J=7.3 Hz), 3.41 (3H, s), 3.31 (3H, s), 2.15 (3H, s), 1.46 (3H, t, J=7.3 Hz).

Reference Production Example 30

Using 10Z mentioned in Reference Production Example 51 in place of 1Z in Reference Production Example 21, the same reaction was performed to obtain 10C represented by the following formula.

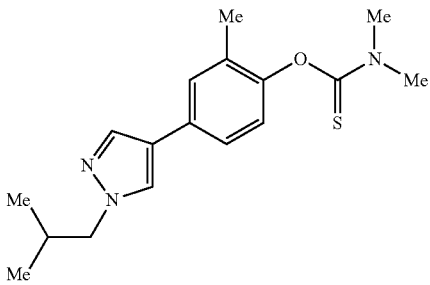 [SMILES: Cc1cc(-c2cnn(CC(C)C)c2)ccc1OC(=S)N(C)C]

$^1$H-NMR (CDCl$_3$) δ: 7.74 (1H, s), 7.57 (1H, s), 7.34-7.32 (2H, m), 6.98 (1H, d, J=8.0 Hz), 3.93 (3H, d, J=7.3 Hz), 3.48 (3H, s), 3.38 (3H, s), 3.30 (1H, d, J=8.2 Hz), 2.22 (2H, s), 0.93 (6H, d, J=6.6 Hz).

Reference Production Example 32

A mixture of 10 g of 4-methoxy-3-methyl-phenylboronic acid, 7.3 g of 3, 4, 5-trimethyl-1H-pyrazole (4X), 18.4 g of copper (II) acetate, 10.0 g of pyridine, 20.0 g of molecular sieves 4A, and 300 ml of acetonitrile was stirred with heating under reflux for 30 hours. The reaction mixture was filtered with Celite (registered trademark) and the filtrate was concentrated under reduced pressure, and then the residue was subjected to column chromatography to obtain 7.3 g of 4Y represented by the following formula.

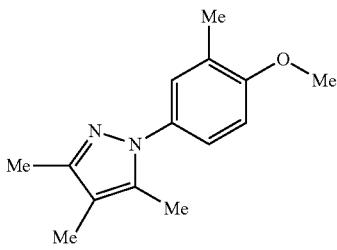 [SMILES: COc1ccc(-n2nc(C)c(C)c2C)cc1C]

$^1$H-NMR (CDCl$_3$) δ: 7.19-7.17 (1H, m), 7.14 (1H, dd, J=8.5, 2.7 Hz), 6.84 (1H, d, J=8.5 Hz), 3.86 (3H, s), 2.24 (6H, s), 2.16 (3H, s), 1.97 (3H, s).

Reference Production Example 33

A mixture of 7.3 g of 4Y mentioned in Reference Production Example 32, 50 ml of 47% hydrobromic acid, and 50 ml of acetic acid was stirred with heating under reflux for 30 hours. Hydrobromic acid and acetic acid were distilled off and 400 ml of ethyl acetate was added to the residue, followed by stirring at room temperature for 1 hour. The precipitate formed by stirring was filtered, and the solid thus obtained was washed with hexane and then dried under reduced pressure to obtain 6.1 g of 4Z represented by the following formula.

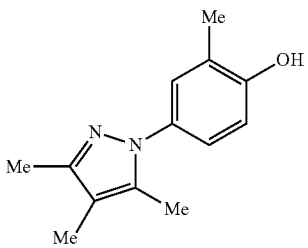 [SMILES: Cc1cc(-n2nc(C)c(C)c2C)ccc1O]

$^1$H-NMR (DMSO-D$_6$) δ: 7.22 (1H, d, J=2.2 Hz), 7.14 (1H, dd, J=8.4, 2.3 Hz), 6.91 (1H, d, J=8.3 Hz), 2.22 (3H, s), 2.17 (3H, s), 2.16 (3H, s), 1.97 (3H, s).

Reference Production Example 36

In a nitrogen atmosphere, a mixture of 1.62 g of 4-methoxy-3-methyl-phenylboronic acid, 1.57 g of 4-bromo-1-ethyl-1H-pyrazole (9X), 0.79 g of a 1,1'-bis (diphenylphosphino)ferrocene-palladium(II) dichloride-dichloromethane complex, 3.51 g of sodium carbonate, 100 ml of 1, 4-dioxane, and 30 ml of water was stirred with heating under reflux for 4 hours. The reaction mixture was extracted with ethyl acetate, and the organic layer was washed with water, dried over anhydrous magnesium sulfate, and then concentrated under reduced pressure. The residue thus obtained was subjected to silica gel column chromatography to obtain 1.3 g of 9Y represented by the following formula.

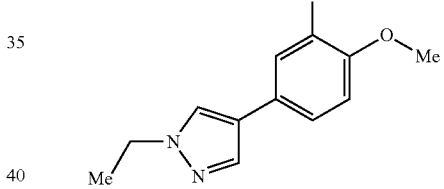

$^1$H-NMR (CDCl$_3$) δ: 7.70 (1H, s), 7.56 (1H, s), 7.28-7.24 (2H, m), 6.82 (1H, d, J=8.5 Hz), 4.19 (2H, q, J=7.3 Hz), 3.84 (3H, s), 2.24 (3H, s), 1.52 (3H, t, J=7.3 Hz).

Reference Production Example 37

Using 9Y mentioned in Reference Production Example 32 in place of 4Y in Reference Production Example 33, the same reaction was performed to obtain 9Z represented by the following formula.

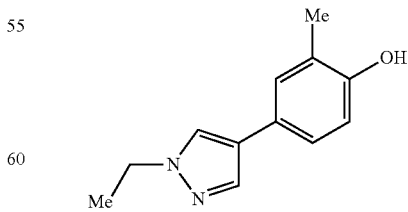

$^1$H-NMR (DMSO-D$_6$) δ: 7.99 (1H, s), 7.70 (1H, s), 7.26 (1H, d, J=1.2 Hz), 7.17 (1H, dd, J=8.2, 2.4 Hz), 6.74 (1H, d, J=8.2 Hz), 4.11 (2H, q, J=7.2 Hz), 2.13 (3H, s), 1.38 (3H, dd, J=7.8, 6.9 Hz).

Reference Production Example 38

Using 3-chloro-4-methoxy-phenylboronic acid in place of 4-methoxy-3-methyl-phenylboronic acid and using 3-methyl-1H-pyrazole in place of 4X in Reference Production Example 32, the same reaction was performed to obtain 3Y and 3Y' represented by the following formulas.

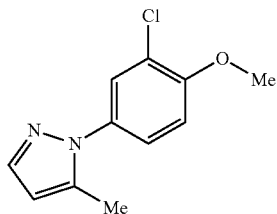

3Y $^1$H-NMR (CDCl$_3$) δ: 7.55 (1H, d, J=1.7 Hz), 7.49 (1H, d, J=2.6 Hz), 7.31 (1H, dd, J=8.8, 2.6 Hz), 7.00 (1H, d, J=8.8 Hz), 6.18-6.17 (1H, m), 3.95 (3H, s), 2.32 (3H, s).

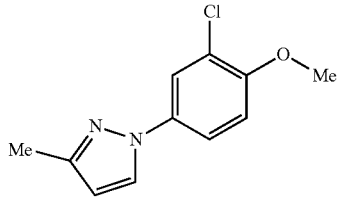

3Y'

$^1$H-NMR (CDCl$_3$) δ: 7.70 (2H, t, J=2.3 Hz), 7.49 (1H, dd, J=9.0, 2.7 Hz), 6.96 (1H, d, J=9.0 Hz), 6.23 (1H, d, J=2.3 Hz), 3.93 (3H, s), 2.37 (3H, s)

Reference Production Example 39

Using 3Y mentioned in Reference Production Example 38 in place of 4Y in Reference Production Example 33, the same reaction was performed to obtain 3Z represented by the following formula.

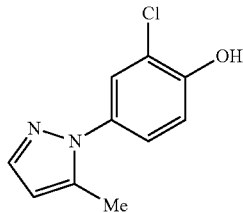 [SMILES: Cc1ccnn1-c1ccc(O)c(Cl)c1]

$^1$H-NMR (DMSO-D$_6$) δ: 10.54 (1H, s), 7.50-7.49 (1H, m), 7.48-7.47 (1H, m), 7.28 (1H, ddd, J=8.7, 2.6, 0.7 Hz), 7.06 (1H, d, J=8.5 Hz), 6.22 (1H, dd, J=1.7, 0.7 Hz), 2.27 (3H, s).

Reference Production Example 40

Using 3-tert-butyl-1H-pyrazole in place of 4XY in Reference Production Example 32, the same reaction was performed to obtain 5Y represented by the following formula.

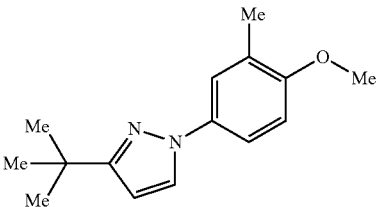 [SMILES: COc1ccc(-n2ccc(C(C)(C)C)n2)cc1C]

$^1$H-NMR (CDCl$_3$) δ: 7.68 (1H, d, J=2.4 Hz), 7.44 (1H, d, J=2.2 Hz), 7.38 (1H, dd, J=8.5, 2.7 Hz), 6.85-6.81 (1H, m), 6.27 (1H, d, J=2.4 Hz), 3.84 (3H, s), 2.26 (3H, s), 1.37 (9H, s).

Reference Production Example 41

Using 5Y mentioned in Reference Production Example 40 in place of 4Y in Reference Production Example 33, the same reaction was performed to obtain 5Z represented by the following formula.

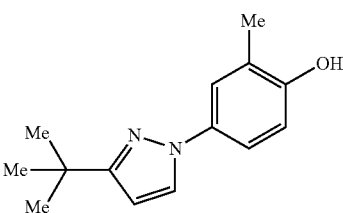 [SMILES: Cc1cc(-n2ccc(C(C)(C)C)n2)ccc1O]

$^1$H-NMR (DMSO-D$_6$) δ: 8.11 (1H, d, J=2.4 Hz), 7.46 (1H, d, J=2.7 Hz), 7.36 (1H, dd, J=8.5, 2.7 Hz), 6.82 (1H, d, J=8.5 Hz), 6.33 (1H, d, J=2.2 Hz), 2.17 (3H, s), 1.29 (9H, s).

Reference Production Example 42

Using 3,5-dimethyl-1H-pyrazole in place of 4X in Reference Production Example 32, the same reaction was performed to obtain 2Y represented by the following formula.

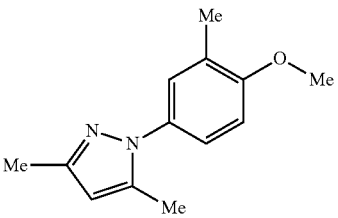 [SMILES: COc1ccc(-n2nc(C)cc2C)cc1C]

$^1$H-NMR (CDCl$_3$) δ: 7.20 (1H, d, J=2.0 Hz), 7.16 (1H, dd, J=8.5, 2.7 Hz), 6.84 (1H, d, J=8.5 Hz), 5.95 (1H, s), 3.86 (3H, s), 2.29 (3H, s), 2.24 (3H, s), 2.24 (3H, s).

Reference Production Example 43

Using 2Y mentioned in Reference Production Example 42 in place of 4Y in Reference Production Example 33, the same reaction was performed to obtain 2Z represented by the following formula.

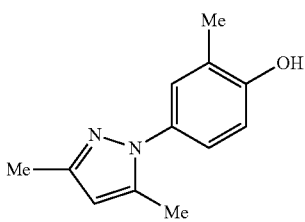 [SMILES: Cc1cc(C)n(-c2ccc(O)c(C)c2)n1]

$^1$H-NMR (DMSO-D$_6$) δ: 9.68 (1H, br s), 7.19 (1H, s), 7.10 (1H, dd, J=8.8, 2.3 Hz), 6.87 (1H, d, J=8.8 Hz), 6.13 (1H, s), 2.20 (6H, s), 2.16 (3H, s).

Reference Production Example 44

A mixture of 5.0 g of 1-(4-hydroxy-3-methylphenyl)-ethanone, 5.70 g of methyl iodide, 20.0 g of potassium carbonate, and 200 ml of acetone was stirred with heating under reflux for 6 hours. The reaction mixture was filtered and extracted with ethyl acetate. The organic layer was washed with water, dried over anhydrous magnesium sulfate, and then concentrated under reduced pressure to obtain 5.3 g of 1P represented by the following formula.

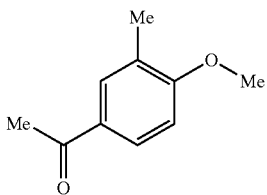 [SMILES: COc1ccc(C(C)=O)cc1C]

$^1$H-NMR (CDCl$_3$) δ: 7.82 (1H, dd, J=8.5, 1.7 Hz), 7.79-7.76 (1H, m), 6.85 (1H, d, J=8.5 Hz), 3.90 (3H, s), 2.55 (3H, s), 2.25 (3H, s).

Reference Production Example 45

To 50 ml of tetrahydrofuran, 3.07 g of 55% sodium hydride and 5.90 g of ethyl acetate were added at room temperature, followed by stirring for 0.5 hour. Next, 5.50 g of 1P mentioned in Reference Production Example 44, 0.024 g of dibenzo-18-crown-6, and 1 ml of ethanol were added, followed by stirring with heating under reflux for 6 hours. To the reaction mixture, water was added. Subsequently, the mixture was acidified with 10% hydrochloric acid and extracted with ethyl acetate. The organic layer was washed with water, dried over anhydrous magnesium sulfate, and then concentrated under reduced pressure. The residue thus obtained was subjected to silica gel column chromatography to obtain 6.50 g of 6Q represented by the following formula.

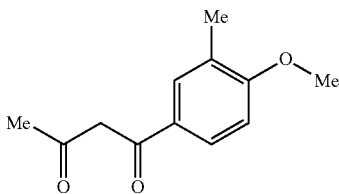 [SMILES: COc1ccc(C(=O)CC(C)=O)cc1C]

$^1$H-NMR (CDCl$_3$: 23° C.) δ: 7.76 (1H, dd, J=8.6, 2.3 Hz), 7.69 (1H, d, J=1.4 Hz), 6.85 (1H, d, J=8.5 Hz), 6.12 (1H, s), 3.89 (3H, s), 2.25 (3H, s), 2.17 (3H, s).

Reference Production Example 46

To a mixture of 7.69 g of 6Q mentioned in Reference Production Example 45 and 100 ml of ethanol, 9.8 ml of hydrazine monohydrate was added at room temperature, followed by stirring for 24 hours. After concentration under reduced pressure until the amount of ethanol in the reaction mixture became about 10 ml, the residue thus obtained was subjected to silica gel column chromatography to obtain 5.4 g of 6R represented by the following formula.

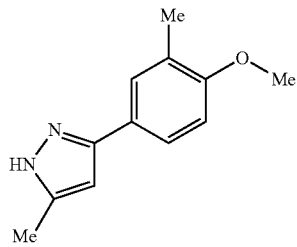 [SMILES: COc1ccc(-c2cc(C)[nH]n2)cc1C]

$^1$H-NMR (CDCl$_3$) δ: 7.49-7.46 (2H, m), 6.83-6.80 (1H, m), 6.26 (1H, s), 3.84 (3H, s), 2.31 (3H, s), 2.23 (3H, s).

Reference Production Example 47

To a mixture of 5.38 g of 6R mentioned in Reference Production Example 45 and 100 ml of N,N-dimethylformamide, 1.5 g of 55% sodium hydride was added at room temperature, followed by stirring for 0.5 hour and further addition of 7.9 g of methyl iodide. After stirring for 12 hours, water was added to the reaction mixture and the mixture was extracted with ethyl acetate. The organic layer was washed with water, dried over anhydrous magnesium sulfate, and then concentrated under reduced pressure. The residue thus obtained was subjected to silica gel column chromatography to obtain 2.9 g of 6Y represented by the following formula and 1.0 g of 6Y' represented by the following formula.

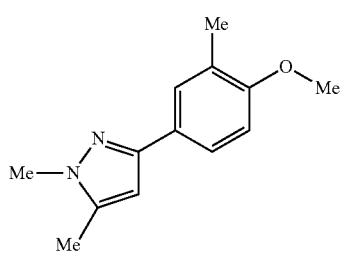

6Y $^1$H-NMR (CDCl$_3$) δ: 7.56-7.55 (1H, m), 7.53-7.50 (1H, m), 6.82 (1H, d, J=8.5 Hz), 6.24 (1H, d, J=0.7 Hz), 3.84 (3H, s), 3.80 (3H, s), 2.29 (3H, s), 2.25 (3H, s).

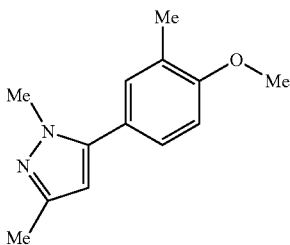

6Y'

¹H-NMR (CDCl₃) δ: 7.20-7.17 (2H, m), 6.88 (1H, d, J=8.2 Hz), 6.02 (1H, s), 3.87 (3H, s), 3.79 (3H, s), 2.29 (3H, s), 2.26 (3H, s).

Reference Production Example 48

Using 6Y mentioned in Reference Production Example 47 in place of 4Y in Reference Production Example 33, the same reaction was performed to obtain 6Z represented by the following formula.

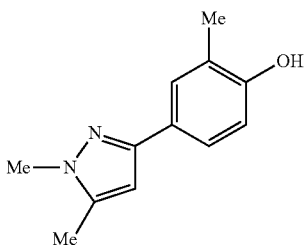 [SMILES: Cc1cc(-c2cc(C)n(C)n2)ccc1O]

¹H-NMR (DMSO-D₆) δ: 9.31 (1H, br s), 7.43 (1H, d, J=1.7 Hz), 7.33 (1H, dd, J=8.2, 2.2 Hz), 6.75 (1H, d, J=8.2 Hz), 6.29 (1H, s), 3.71 (3H, s), 2.24 (3H, s), 2.13 (3H, s).

Reference Production Example 50

Using 4-bromo-1-isopropyl-1H-pyrazole in place of 9X in Reference Production Example 36, the same reaction was performed to obtain 10Y represented by the following formula.

Reference Production Example 51

Using 10Y mentioned in Reference Production Example 50 in place of 4Y in Reference Production Example 33, the same reaction was performed to obtain 10Z represented by the following formula.

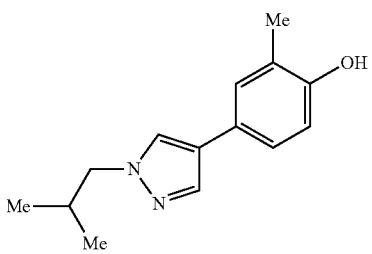 [SMILES: Cc1cc(-c2cnn(CC(C)C)c2)ccc1O]

¹H-NMR (DMSO-D₆) δ: 9.17 (1H, s), 7.94 (1H, s), 7.69 (1H, s), 7.26 (1H, s), 7.16 (1H, d, J=8.2 Hz), 6.73 (1H, d, J=8.2 Hz), 3.88 (2H, d, J=7.0 Hz), 2.12 (3H, s), 0.84 (6H, d, J=6.5 Hz).

Reference Production Example 53

Using 4-bromo-1-isopropyl-1H-pyrazole in place of 9X in Reference Production Example 36, the same reaction was performed to obtain 8Y represented by the following formula.

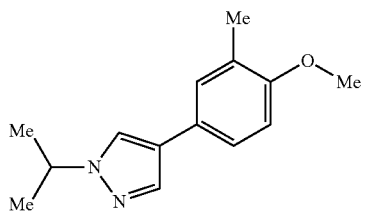 [SMILES: COc1ccc(-c2cnn(C(C)C)c2)cc1C]

¹H-NMR (CDCl₃) δ: 7.71 (1H, s), 7.59 (1H, s), 7.29-7.26 (2H, m), 6.82 (1H, d, J=8.7 Hz), 4.57-4.46 (1H, m), 3.84 (3H, s), 2.25 (3H, s), 1.54 (6H, d, J=6.5 Hz).

Reference Production Example 54

Using 8Y mentioned in Reference Production Example 53 in place of 4Y in Reference Production Example 33, the same reaction was performed to obtain 8Z represented by the following formula.

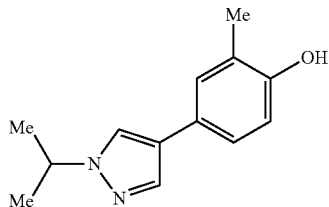 [SMILES: Cc1cc(-c2cnn(C(C)C)c2)ccc1O]

¹H-NMR (DMSO-D₆) δ: 8.03 (1H, d, J=1.5 Hz), 7.70 (1H, d, J=1.7 Hz), 7.27 (1H, s), 7.17 (1H, d, J=8.3 Hz), 6.75-6.72 (1H, m), 4.46 (1H, dt, J=14.0, 6.0 Hz), 2.13 (3H, s), 1.43 (3H, d, J=2.4 Hz), 1.41 (3H, d, J=2.4 Hz).

Reference Production Example 55

A mixture of 5.76 g of 1P mentioned in Reference Production Example 44 and 7.46 ml of N,N-dimethylformamide diethyl acetal was stirred with heating under reflux for 24 hours. After concentration under reduced pressure, 4.78 g of 7W represented by the following formula was obtained.

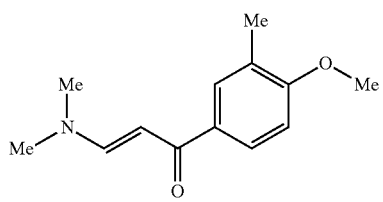 [SMILES: COc1ccc(C(=O)/C=C/N(C)C)cc1C]

$^1$H-NMR (DMSO-D$_6$) δ: 7.76 (1H, dd, J=8.5, 2.2 Hz), 7.72 (1H, s), 7.64 (1H, d, J=12.4 Hz), 6.95 (1H, d, J=8.5 Hz), 5.80 (1H, d, J=12.4 Hz), 3.83 (3H, s), 3.11 (3H, br s), 2.90 (3H, br s), 2.18 (3H, s).

Reference Production Example 56

To a mixture of 7.69 g of 7W mentioned in Reference Production Example 55 and 100 ml of ethanol, 9.8 ml of hydrazine monohydrate was added at room temperature, followed by stirring for 24 hours. After concentration under reduced pressure until the amount of ethanol in the reaction mixture became about 10 ml, the residue thus obtained was subjected to silica gel column chromatography to obtain 5.4 g of 7X represented by the following formula.

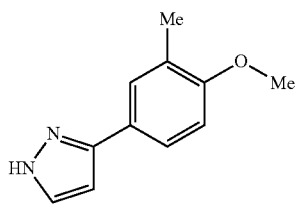 [SMILES: COc1ccc(-c2cc[nH]n2)cc1C]

$^1$H-NMR (CDCl$_3$) δ: 11.91 (1H, br s), 7.58 (1H, d, J=2.2 Hz), 7.54-7.50 (2H, m), 6.84-6.80 (1H, m), 6.51 (1H, d, J=2.0 Hz), 3.85 (3H, s), 2.24 (3H, s).

Reference Production Example 57

To a mixture of 5.38 g of 7X mentioned in Reference Production Example 56 and 100 ml of N,N-dimethylformamide, 1.5 g of 55% sodium hydride was added at room temperature, followed by stirring for 0.5 hour and further addition of 10.0 g of ethyl iodide. After stirring for 12 hours, water was added to the reaction mixture and the mixture was extracted with ethyl acetate. The organic layer was washed with water, dried over anhydrous magnesium sulfate, and then concentrated under reduced pressure. The residue thus obtained was subjected to silica gel column chromatography to obtain 2.9 g of 7Y represented by the following formula.

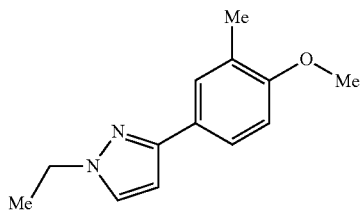 [SMILES: CCn1ccc(-c2ccc(OC)c(C)c2)n1]

$^1$H-NMR (CDCl$_3$) δ: 7.60 (1H, s), 7.57 (1H, dd, J=8.5, 2.2 Hz), 7.38 (1H, d, J=2.4 Hz), 6.84 (1H, d, J=8.2 Hz), 6.45 (1H, d, J=2.2 Hz), 4.20 (2H, q, J=7.3 Hz), 3.85 (3H, s), 2.26 (3H, s), 1.52 (3H, t, J=7.4 Hz).

Reference Production Example 58

Using 7Y mentioned in Reference Production Example 57 in place of 4Y in Reference Production Example 33, the same reaction was performed to obtain 7Z represented by the following formula.

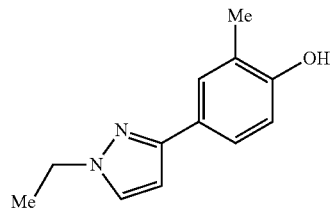 [SMILES: CCn1ccc(-c2ccc(O)c(C)c2)n1]

$^1$H-NMR (DMSO-D$_6$) δ: 9.30 (1H, br s), 7.68 (1H, d, J=2.2 Hz), 7.48 (1H, d, J=2.2 Hz), 7.39 (1H, dd, J=8.3, 2.2 Hz), 6.76 (1H, d, J=8.3 Hz), 6.49 (1H, d, J=2.2 Hz), 4.12 (2H, q, J=6.2 Hz), 2.14 (3H, s), 1.38 (3H, t, J=7.2 Hz).

Reference Production Example 59

To a mixture of 5.0 g of 4-methoxy-3-methyl-benzoic acid and 100 ml of tetrahydrofuran, 4.0 g of oxalyl chloride and 0.2 ml of dimethylformamide were added at room temperature, followed by stirring for 2.5 hours and further concentration under reduced pressure. To this mixture, 150 ml of chloroform, 3.5 g of N,O-dimethylhydroxylamine hydrochloride, and 9.3 g of N,N-diisopropylethylamine were added at room temperature, followed by stirring for 4 hours. To the reaction mixture, water was added and the mixture was extracted with chloroform. The organic layer was washed with water, dried over anhydrous magnesium sulfate, and then concentrated under reduced pressure. The residue was subjected to column chromatography to obtain 6.1 g of 1U represented by the following formula.

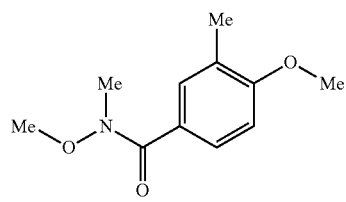 [SMILES: COc1ccc(C(=O)N(C)OC)cc1C]

$^1$H-NMR (CDCl$_3$) δ: 7.61-7.58 (1H, m), 7.54 (1H, dd, J=2.1, 0.6 Hz), 6.81 (1H, d, J=8.5 Hz), 3.87 (3H, s), 3.57 (3H, s), 3.35 (3H, s), 2.23 (3H, s).

Reference Production Example 61

A mixture of 5.2 g of 1-(4-methoxy-3-methylphenyl)-propan-1-one, 100 ml of tetrahydrofuran, 4.1 g of potassium tert-butoxide, and 3.6 g of diethyl carbonate was stirred with heating under reflux for 5.5 hours. To the reaction mixture, 20 ml of 20% hydrochloric acid was added at room temperature and the mixture was extracted with ethyl acetate. The organic layer was washed with water, dried over anhydrous magnesium sulfate, and then concentrated under reduced pressure. The residue was subjected to column chromatography to obtain 3.5 g of 1W represented by the following formula.

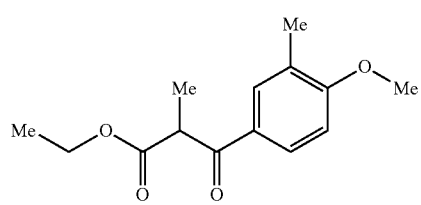 [SMILES: CCOC(=O)C(C)C(=O)c1ccc(OC)c(C)c1]

$^1$H-NMR (CDCl$_3$) δ: 7.86 (1H, dd, J=8.6, 2.3 Hz), 7.80 (1H, d, J=2.2 Hz), 6.86 (1H, d, J=8.7 Hz), 4.19-4.10 (3H, m), 3.90 (3H, s), 2.25 (3H, s), 1.47 (3H, d, J=7.2 Hz), 1.19 (3H, t, J=7.1 Hz).

Reference Production Example 62

A mixture of 3.5 g of 1W mentioned in Reference Production Example 61, 100 ml of toluene, and 7.4 g of methylhydrazine was stirred with heating under reflux for 18 hours. Toluene was distilled off and 10% hydrochloric acid was added, and then the precipitate thus formed was filtrated and the solid thus obtained was washed with hexane to obtain 1.4 g of 1X represented by the following formula.

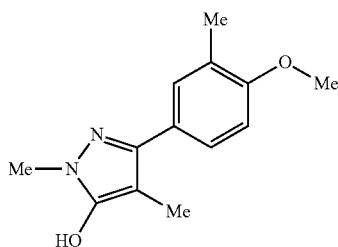 [SMILES: COc1ccc(-c2nn(C)c(O)c2C)cc1C]

$^1$H-NMR (DMSO-D$_6$) δ: 7.47-7.44 (2H, m), 7.07 (1H, d, J=8.2 Hz), 3.84 (3H, s), 3.66 (3H, s), 2.20 (3H, s), 2.05 (3H, s).

Reference Production Example 63

A mixture of 1.4 g of 1X mentioned in Reference Production Example 62 and 31.8 g of phosphorus oxychloride was stirred at 100° C. for 11 hours. The reaction mixture was concentrated under reduced pressure and extracted with ethyl acetate. The organic layer was washed with water, dried over anhydrous magnesium sulfate, and then concentrated under reduced pressure. The residue was subjected to column chromatography to obtain 0.4 g of 1Y represented by the following formula.

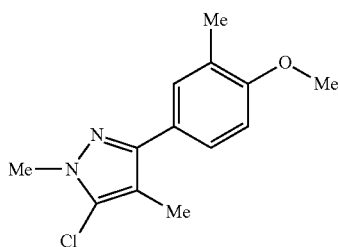 [SMILES: COc1ccc(-c2nn(C)c(Cl)c2C)cc1C]

$^1$H-NMR (DMSO-D$_6$) δ: 7.42-7.40 (2H, m), 6.98 (1H, d, J=9.2 Hz), 3.81 (3H, s), 3.80 (3H, s), 2.19 (3H, s), 2.11 (3H, s).

Reference Production Example 64

A mixture of 0.4 g of 1Y of Reference Production Example 63, 3 ml of 47% hydrobromic acid, and 3 ml of acetic acid was stirred with heating under reflux for 15 hours. Hydrobromic acid and acetic acid were distilled off and 20 ml of ethyl acetate was added to the residue, followed by stirring at room temperature for 1 hour. The precipitate formed by stirring was filtered, and the solid thus obtained was washed with hexane and dried under reduced pressure to obtain 0.3 g of 1Z represented by the following formula.

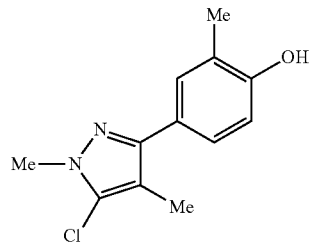 [SMILES: Cc1cc(-c2nn(C)c(Cl)c2C)ccc1O]

$^1$H-NMR (DMSO-D$_6$) δ: 7.33 (1H, s), 7.24 (1H, d, J=8.2 Hz), 6.83 (1H, d, J=8.2 Hz), 3.78 (3H, s), 2.15 (3H, s), 2.09 (3H, s).

Reference Production Example 65

A mixture of 2 g of X2 mentioned in Reference Production Example 67, 0.74 g of a [1,1'-bis(diphenylphosphino) ferrocene] palladium (II) dichloride dichloromethane adduct, 2.2 g of potassium acetate, 2.1 g of bis(pinacolato) diboron, and 30 mL of dimethyl sulfoxide was stirred at 90° C. for 12 hours. After cooling to room temperature, a saturated saline solution was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 2.5 g of X1 represented by the following formula.

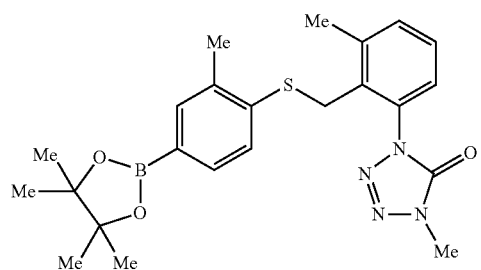 [SMILES: Cc1cc(B2OC(C)(C)C(C)(C)O2)ccc1SCc1c(C)cccc1-n1nnn(C)c1=O]

$^1$H-NMR (CDCl$_3$) δ: 7.56 (2H, d, J=6.3 Hz), 7.34-7.30 (2H, m), 7.22-7.19 (2H, m), 4.16 (2H, s), 3.63 (3H, s), 2.43 (3H, s), 2.24 (3H, s), 1.34 (12H, s).

Reference Production Example 66

Using Y2 mentioned in Reference Production Example 68 in place of X2 in Reference Production Example 65, the same reaction was performed to obtain Y1 represented by the following formula.

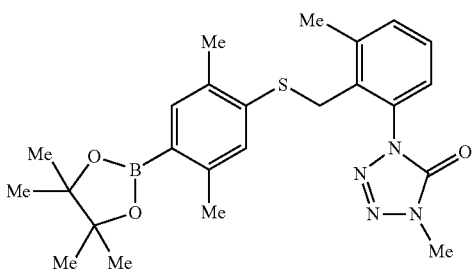 [SMILES: Cc1cc(B2OC(C)(C)C(C)(C)O2)c(C)cc1SCc1c(C)cccc1-n1nnn(C)c1=O]

¹H-NMR (CDCl₃) δ: 7.50 (1H, s), 7.34-7.31 (2H, m), 7.20 (1H, dd, J=6.5, 3.1 Hz), 7.00 (1H, s), 4.14 (2H, s), 3.63 (3H, s), 2.47 (3H, s), 2.44 (3H, s), 2.20 (3H, s), 1.33 (12(12H, s)H, s).

Reference Production Example 67

A mixture of 4 g of 1-(2-bromomethyl-3-methylphenyl)-4-methyl-1,4-dihydrotetrazol-5-one, 4.1 g of 11A mentioned in Reference Production Example 69, 7.6 g of potassium carbonate, and 20 ml of acetonitrile was stirred at 80° C. for 7 hours. The reaction mixture was concentrated under reduced pressure. The residue thus obtained was subjected to silica gel column chromatography to obtain 6.42 g of X2 represented by the following formula.

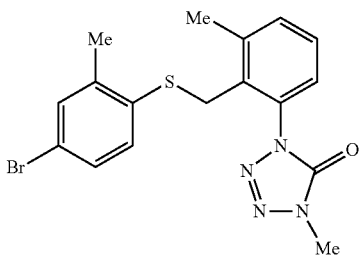 [SMILES: Cc1cc(Br)ccc1SCc1c(C)cccc1-n1nnn(C)c1=O]

¹H-NMR (CDCl₃) δ: 7.33-7.29 (3H, m), 7.22-7.18 (2H, m), 7.07 (1H, d, J=8.2 Hz), 4.10 (2H, s), 3.64 (3H, s), 2.39 (3H, s), 2.22 (3H, s).

Reference Production Example 68

Using 12A mentioned in Reference Production Example 70 in place of 11A in Reference Production Example 67, the same reaction was performed to obtain Y2 represented by the following formula.

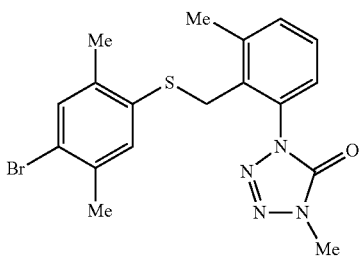 [SMILES: Cc1cc(SCc2c(C)cccc2-n2nnn(C)c2=O)c(C)cc1Br]

¹H-NMR (CDCl₃) δ: 7.32-7.30 (3H, m), 7.20-7.16 (1H, m), 7.05 (1H, s), 4.09 (2H, s), 3.63 (3H, s), 2.40 (3H, s), 2.29 (3H, s), 2.18 (3H, s).

Reference Production Example 69

A mixture of 13 g of 11C mentioned in Reference Production Example 72 and 50 ml of diphenyl ether was stirred at 230° C. for 24 hours, and then this solution was subjected to silica gel column chromatography to obtain 10 g of 2-methyl-4-bromo-phenyl-S-phenyl-N,N-dimethylthio-carbamate (referred to as 11B).

A mixture of 10 g of 11B, 50 ml of an aqueous 20% sodium hydroxide solution, and 50 ml of isopropanol was stirred at 80° C. for 24 hours. To the reaction mixture, 10% hydrochloric acid was added and the mixture was extracted with chloroform. The organic layer was washed with water, dried over anhydrous magnesium sulfate, and then concentrated under reduced pressure. The residue thus obtained was subjected to silica gel column chromatography to obtain 8.2 g of 11A represented by the following formula.

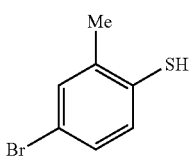

¹H-NMR (CDCl₃) δ: 7.30 (1H, d, J=2.1 Hz), 7.19 (1H, dd, J=8.2, 2.1 Hz), 7.13 (1H, d, J=8.2 Hz), 3.28 (1H, s), 2.30 (3H, s).

Reference Production Example 70

Using 12B mentioned in Reference Production Example 71 in place of 11B in Reference Production Example 69, the same reaction was performed to obtain 12A represented by the following formula.

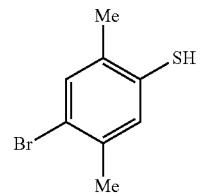

¹H-NMR (CDCl₃) δ: 7.32 (1H, s), 7.14 (1H, s), 3.24 (1H, s), 2.30 (3H, s), 2.26 (3H, s).

Reference Production Example 71

Using 12C mentioned in Reference Production Example 73 in place of 11C in Reference Production Example 69, the same reaction was performed to obtain 12B represented by the following formula.

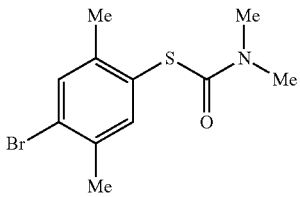 [SMILES: Cc1cc(SC(=O)N(C)C)c(C)cc1Br]

¹H-NMR (CDCl₃) δ: 7.47 (1H, s), 7.33 (1H, s), 3.12 (3H, br s), 3.01 (3H, br s), 2.34 (6H, s).

Reference Production Example 72

To a mixture of 10.3 g of commercially available 2-methyl-4-bromo-phenol and 100 ml of dimethylformamide, 2.64 g of 55% sodium hydride was added at 0° C. and the temperature was raised to room temperature, followed by stirring at room temperature for 0.5 hour and further cooling to 0° C. After adding 7.5 g of dimethylthiocarbamoyl chloride at 0° C., the temperature was raised to room temperature, followed by stirring at room temperature for 5 hours. To the reaction mixture, water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 13 g of 11C represented by the following formula.

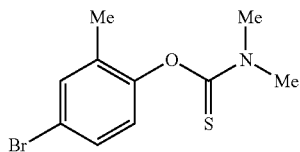 [SMILES: Cc1cc(Br)ccc1OC(=S)N(C)C]

¹H-NMR (CDCl₃) δ: 7.38 (1H, d, J=2.3 Hz), 7.33 (1H, dd, J=8.7, 2.3 Hz), 6.86 (1H, d, J=8.7 Hz), 3.46 (3H, s), 3.36 (3H, s), 2.17 (3H, s).

Reference Production Example 73

Using commercially available 2,5-dimethyl-4-bromophenol in place of 2-methyl-4-bromo-phenol in Reference Production Example 72, the same reaction was performed to obtain 12C represented by the following formula.

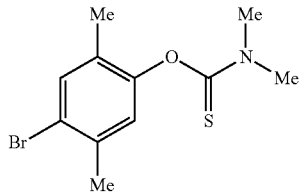 [SMILES: Cc1cc(OC(=S)N(C)C)c(C)cc1Br]

¹H-NMR (CDCl₃) δ: 7.40 (1H, s), 6.86 (1H, s), 3.46 (3H, s), 3.35 (3H, s), 2.35 (3H, s), 2.14 (3H, s).

In accordance with the process mentioned above, it is possible to obtain compounds HA1001-0001 to 101012-1272.

The above-mentioned compounds HA1001-0001 to 101012-1272 (hereinafter referred to as the compound A) are aromatic compounds shown below [wherein A represents any one of the below-mentioned substituent numbers 1 to 1272]. In the following [substituent number; A], F represents fluoro, Cl represents chloro, Br represents bromo, CN represents cyano, Me represents methyl, Et represents ethyl, CF3 represents trifluoromethyl, CHF2 represents difluoromethyl, OMe represents methoxy, OEt represents ethoxy, OCF3 represents trifluoromethoxy, OCHF2 represents difluoromethoxy, PYR1 represents a pyrazol-1-yl group, PYR2 represents a pyrazol-2-yl group, PYR3 represents a pyrazol-3-yl group, and PYR4 represents a pyrazol-4-yl group.

(HA1001)

(HA1002)

(HA1003)

(HA1004)

(HA1005)

(HA1006)
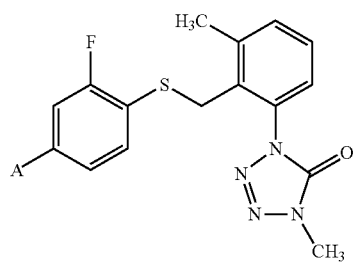
(HA1007)
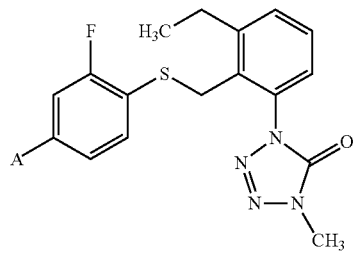
(HA1008)
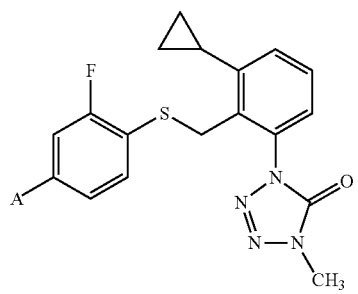
(HA1009)
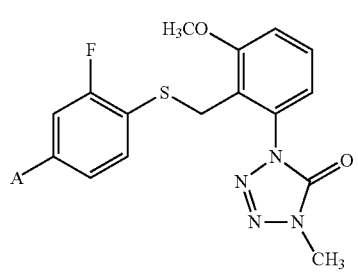
(HA1010)
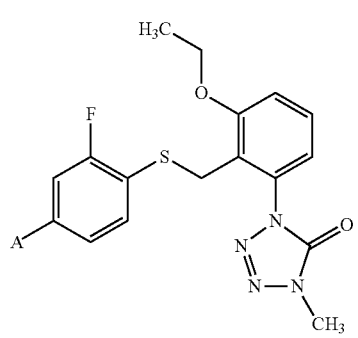
(HA1011)
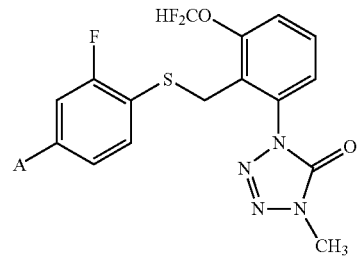
(HA1012)
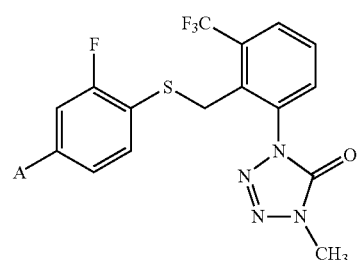
(HB1001)
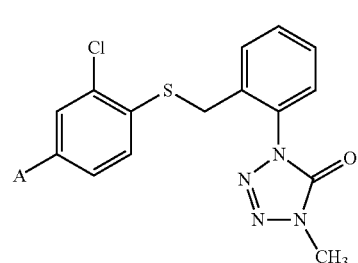
(HB1002)
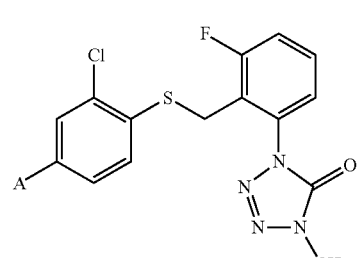
(HB1003)
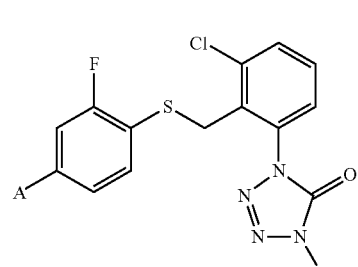
(HB1004)
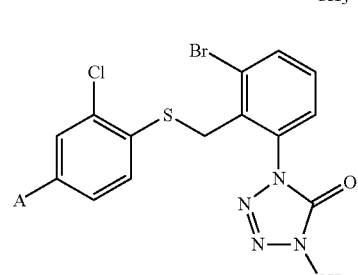

77
-continued
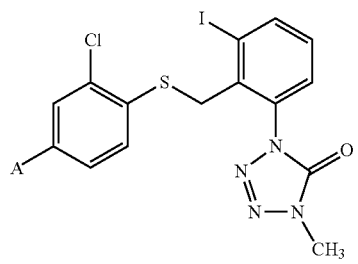
(HB1005)
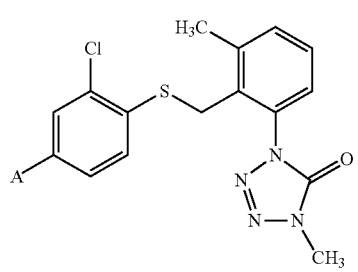
(HB1006)
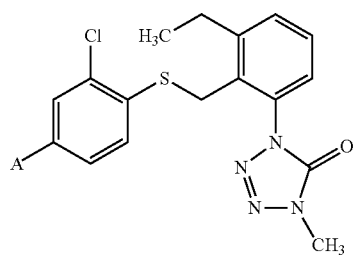
(HB1007)
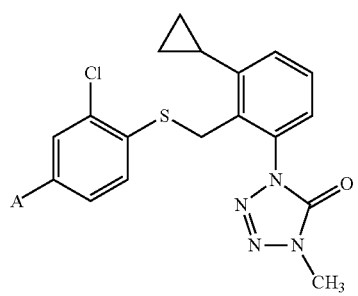
(HB1008)
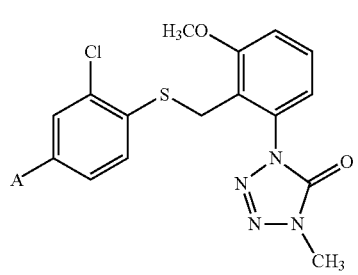
(HB1009)
78
-continued
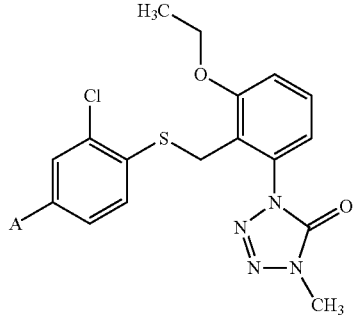
(HB1010)
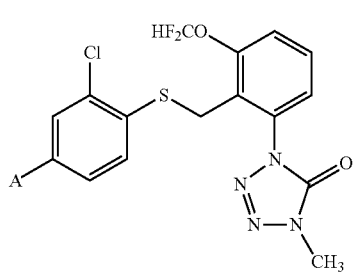
(HB1011)
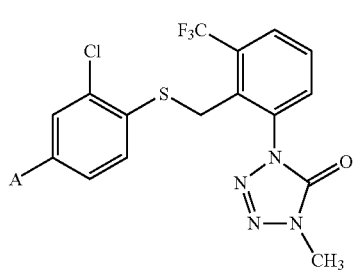
(HB1012)
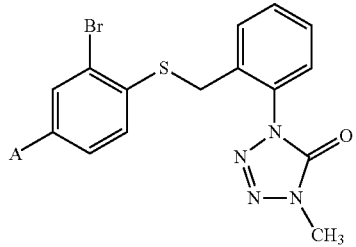
(HC1001)
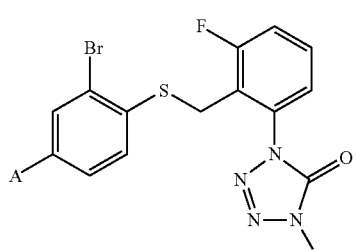
(HC1002)
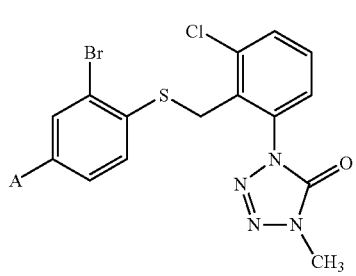
(HC1003)

(HC1004)
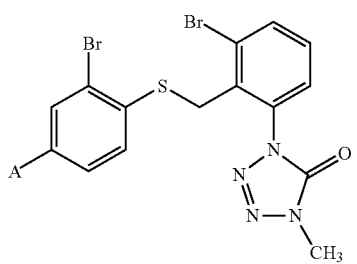
(HC1005)
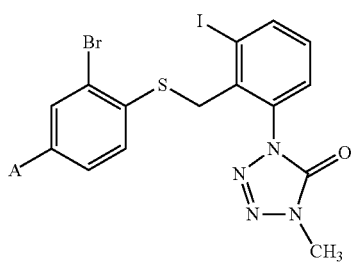
(HC1006)
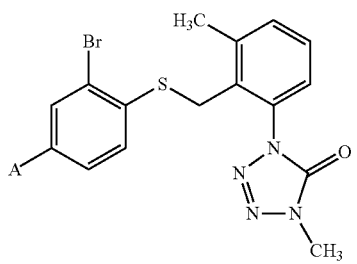
(HC1007)
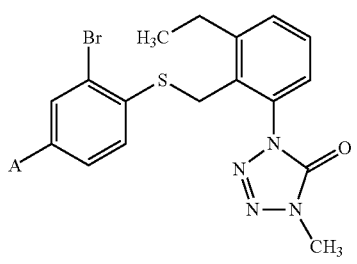
(HC1008)
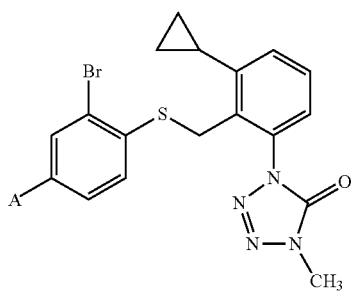
(HC1009)
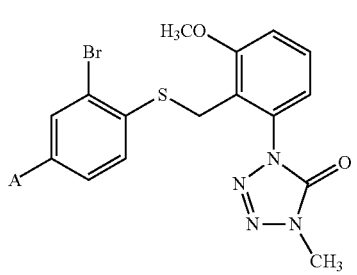
(HC1010)
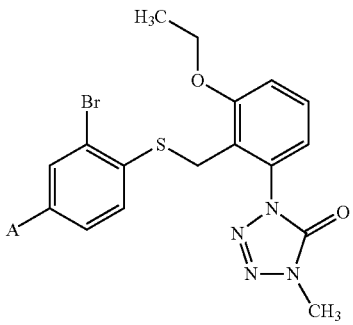
(HC1011)
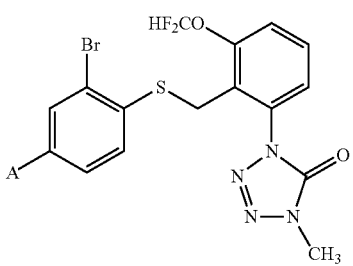
(HC1012)
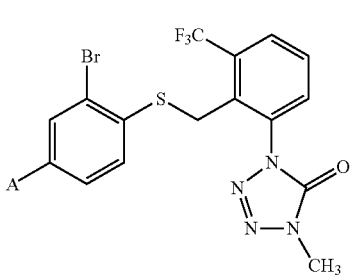
(HD1001)
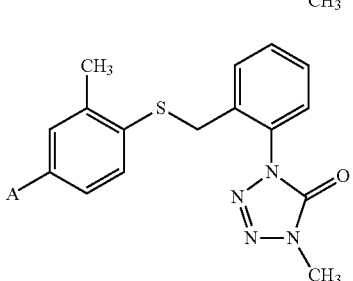
(HD1002)
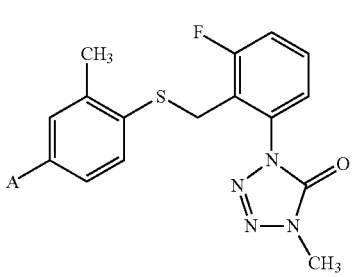
(HD1003)
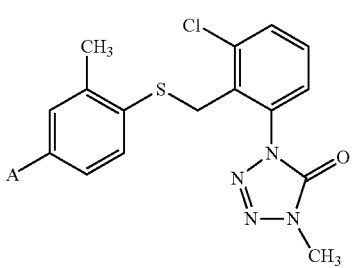

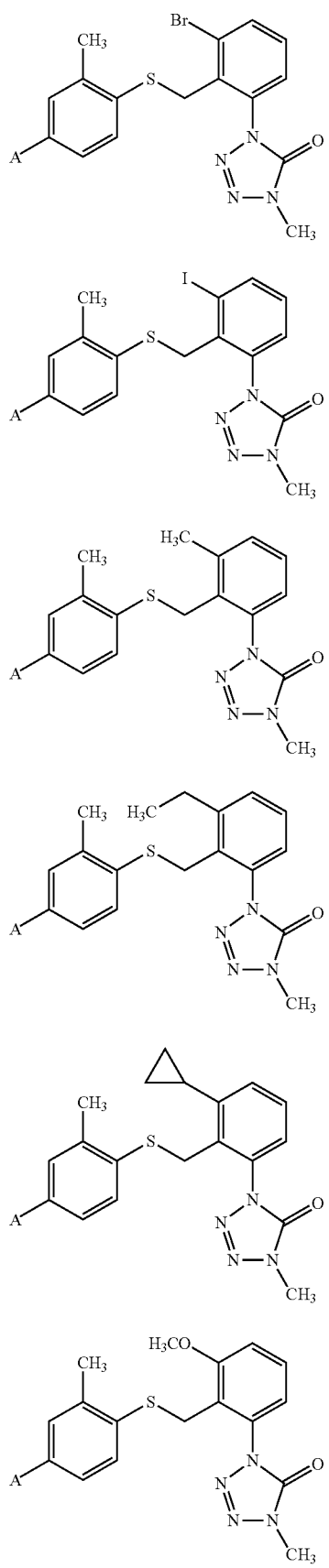
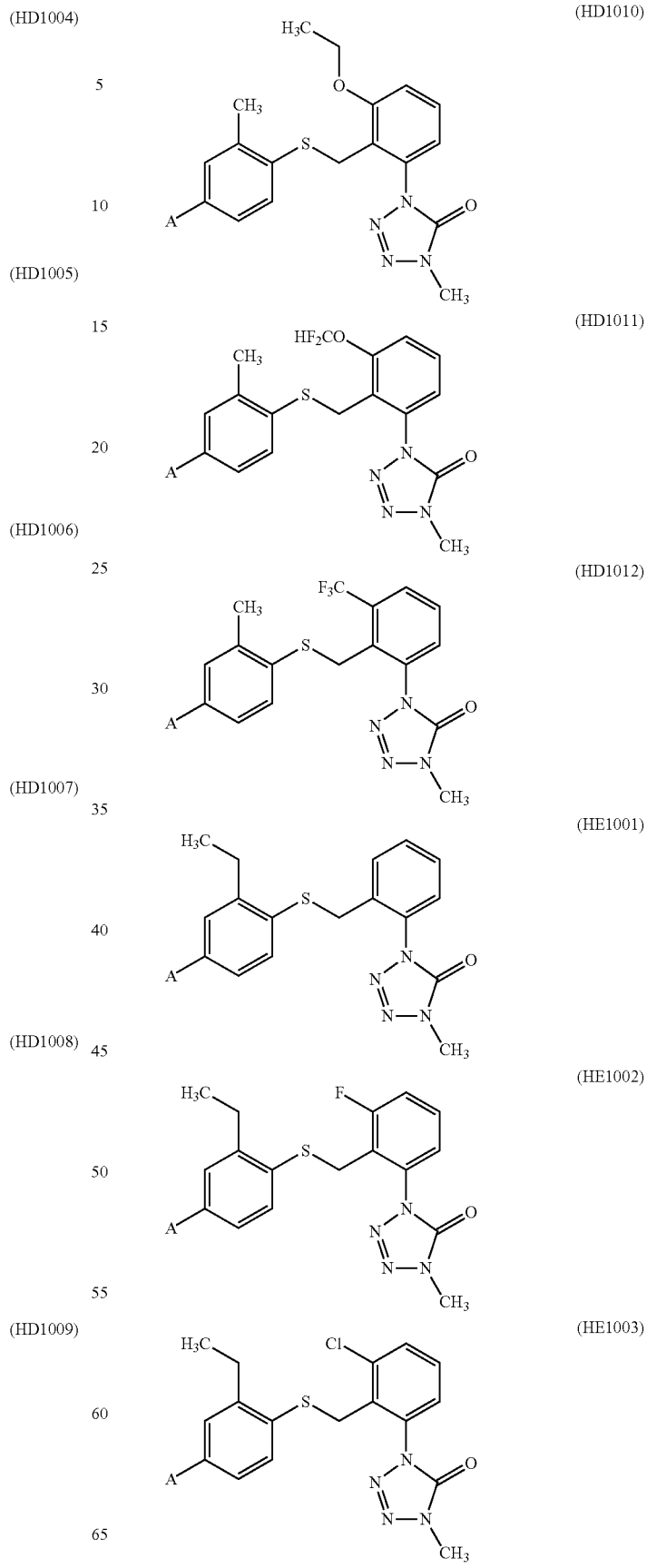

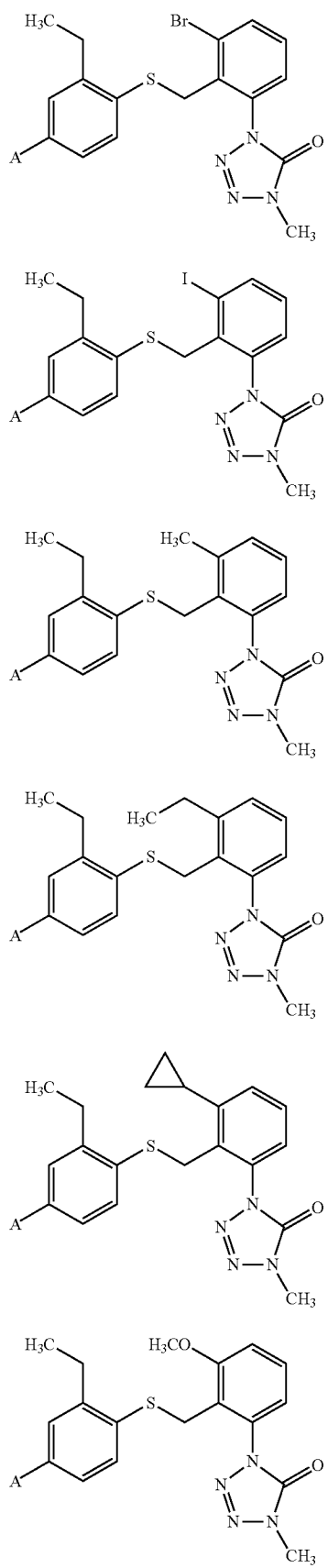
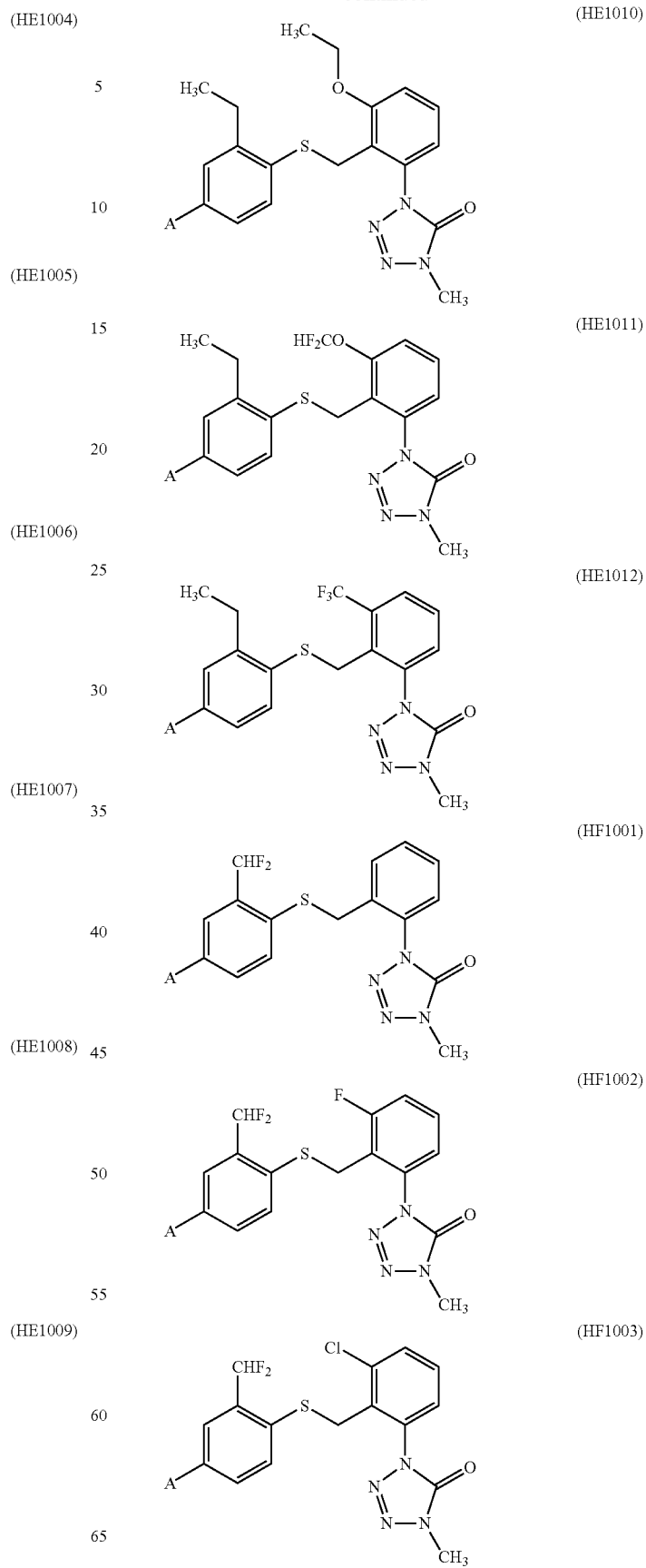

-continued
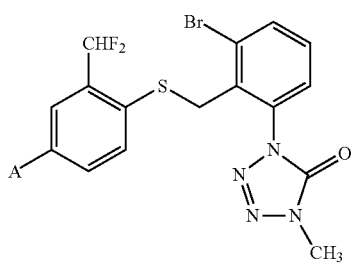 (HF1004)
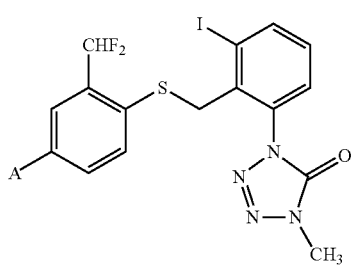 (HF1005)
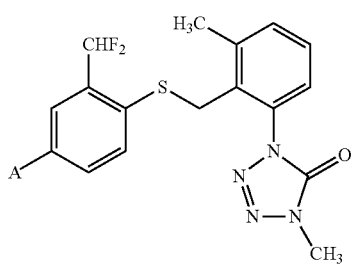 (HF1006)
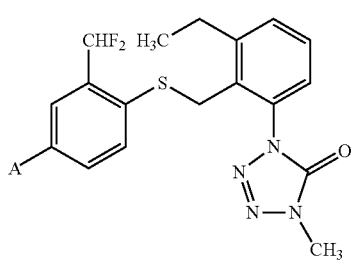 (HF1007)
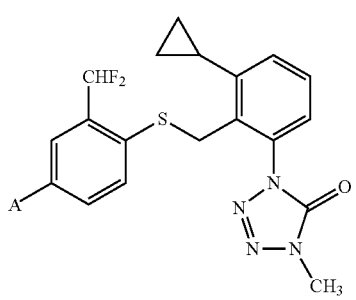 (HF1008)
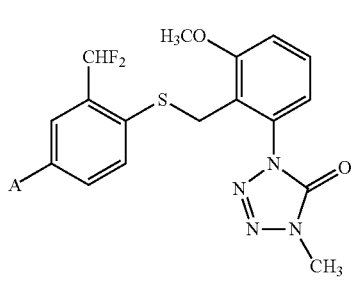 (HF1009)
-continued
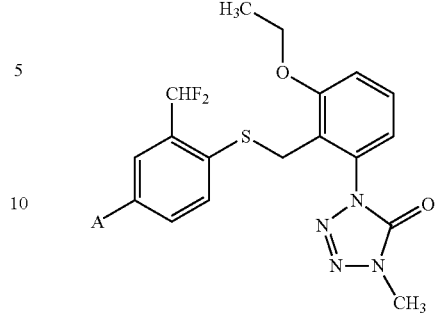 (HF1010)
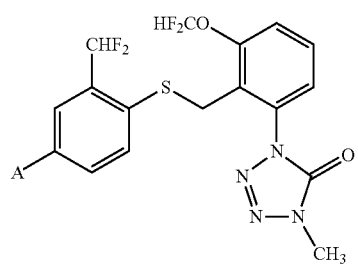 (HF1011)
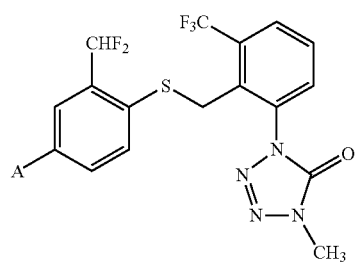 (HF1012)
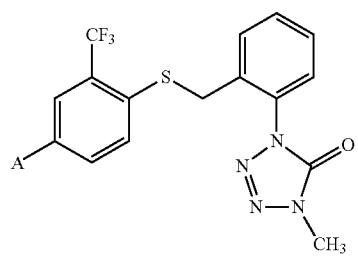 (HG1001)
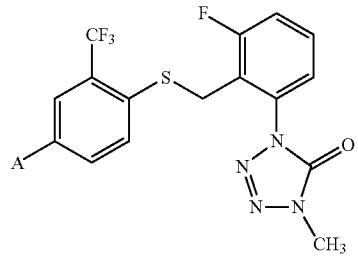 (HG1002)
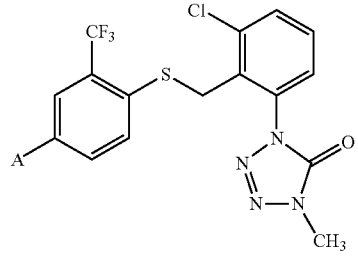 (HG1003)

87
-continued
(HG1004)
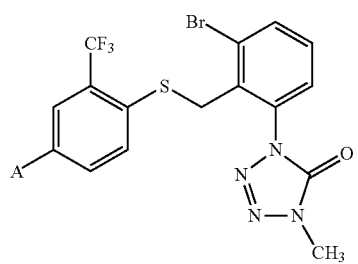
(HG1005)
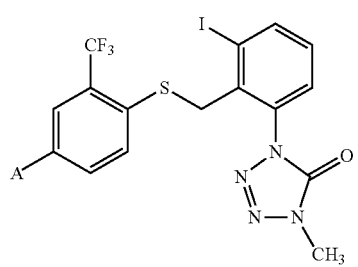
(HG1006)
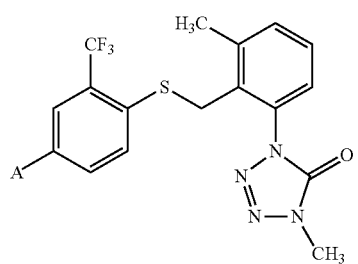
(HG1007)
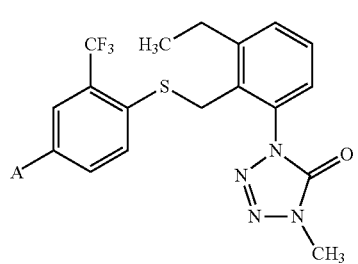
(HG1008)
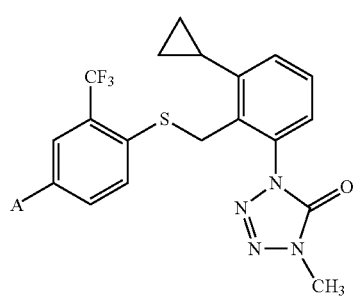
(HG1009)
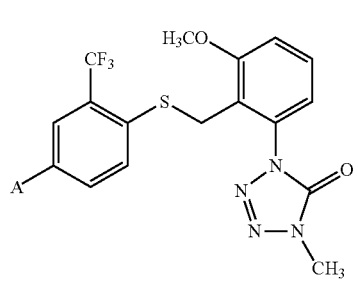
88
-continued
(HG1010)
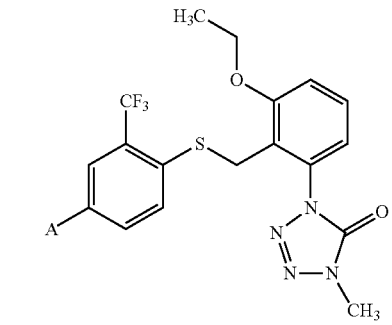
(HG1011)
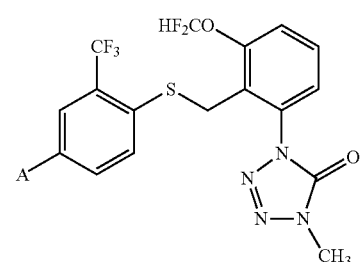
(HG1012)
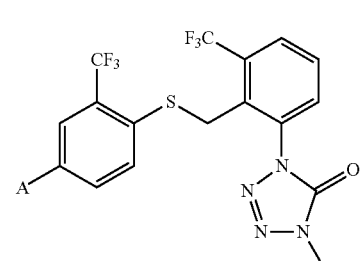
(HH1001)
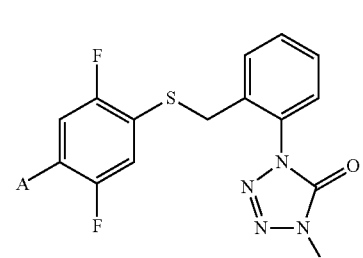
(HH1002)
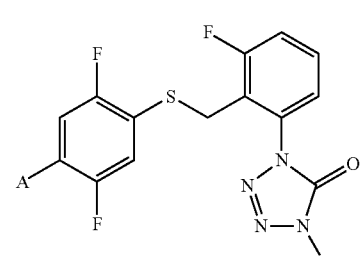
(HH1003)
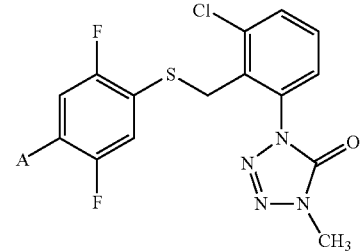

(HH1004)
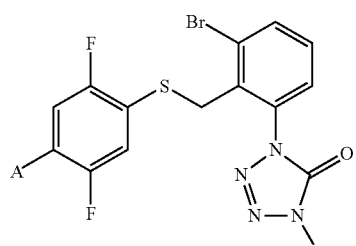
(HH1005)
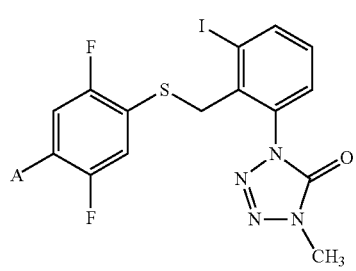
(HH1006)
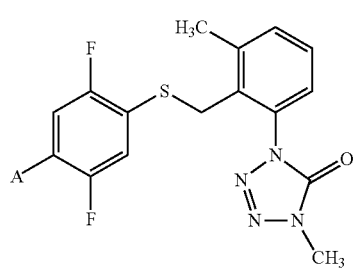
(HH1007)
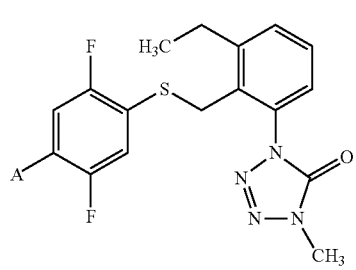
(HH1008)
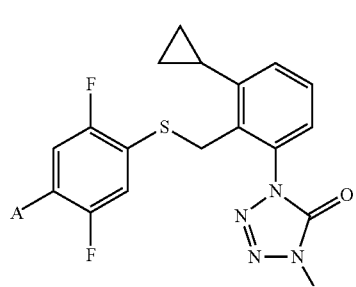
(HH1009)
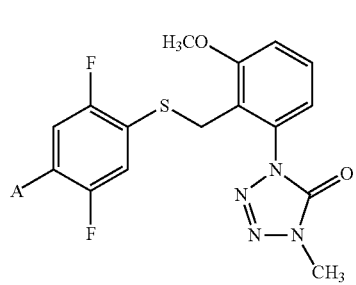
(HH1010)
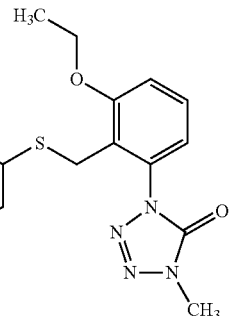
(HH1011)
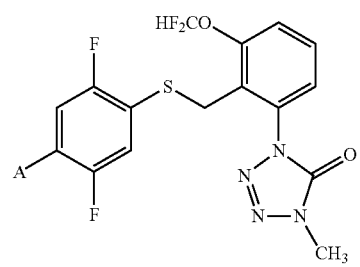
(HH1012)
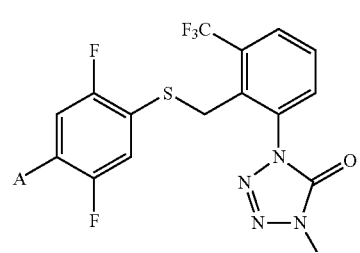
(HI1001)
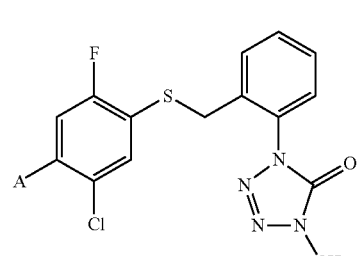
(HI1002)
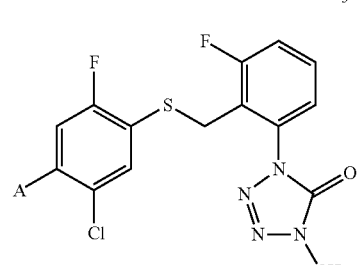
(HI1003)
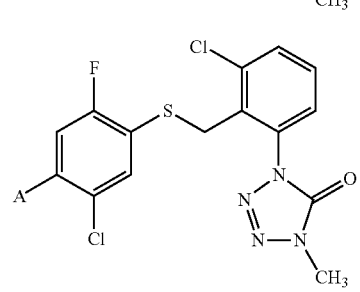

(HI1004) 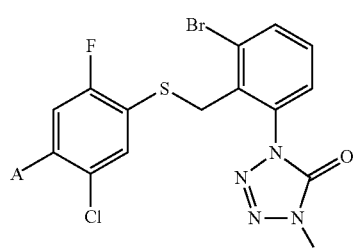
(HI1005) 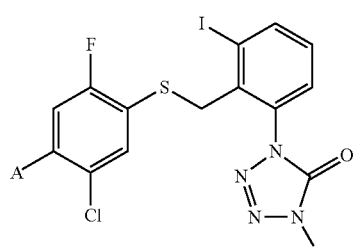
(HI1006) 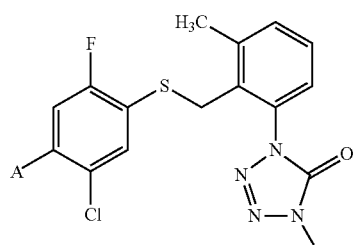
(HI1007) 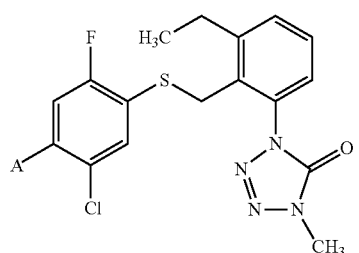
(HI1008) 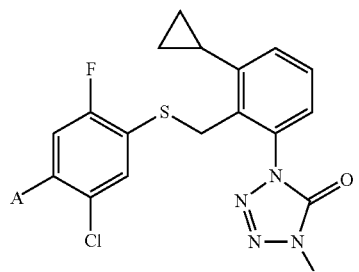
(HI1009) 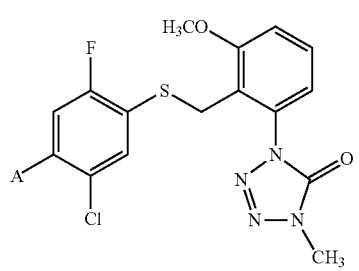
(HI1010) 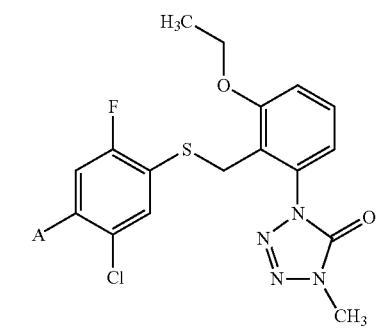
(HI1011) 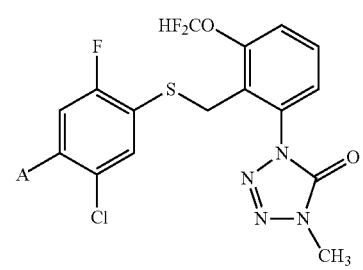
(HI1012) 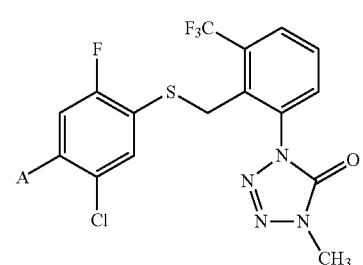
(HJ1001) 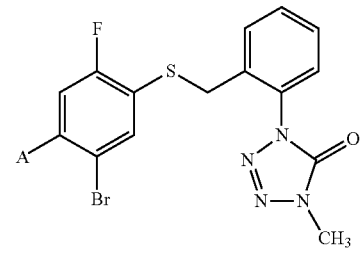
(HJ1002) 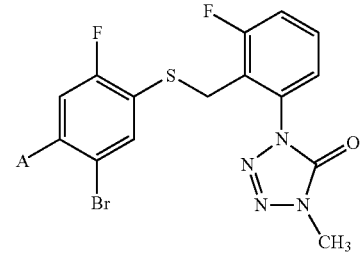
(HJ1003) 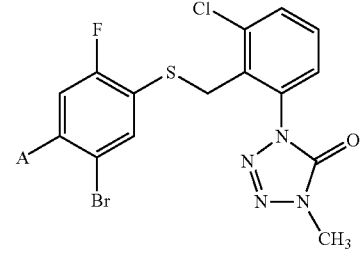

(HJ1004)
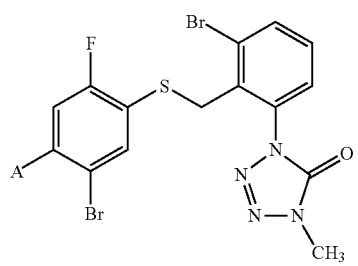
(HJ1005)
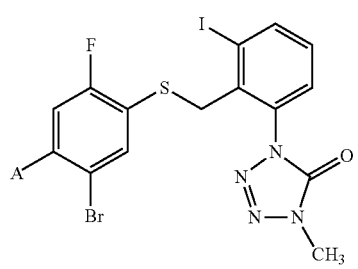
(HJ1006)
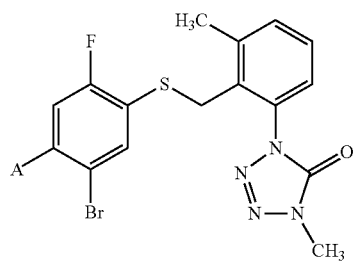
(HJ1007)
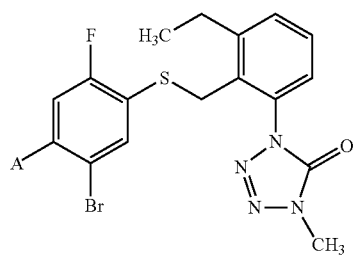
(HJ1008)
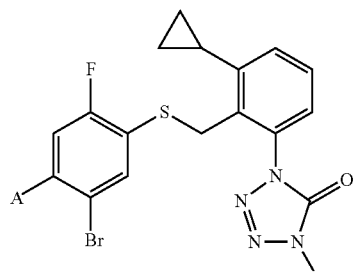
(HJ1009)
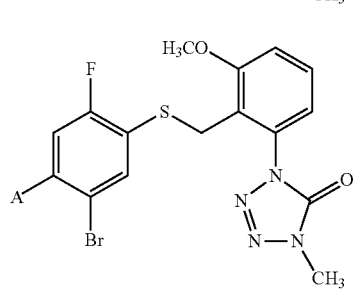
(HJ1010)
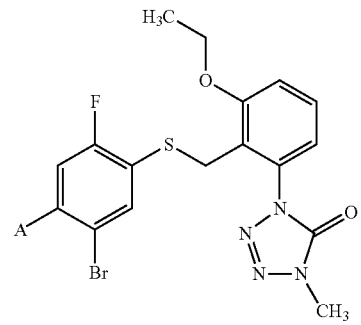
(HJ1011)
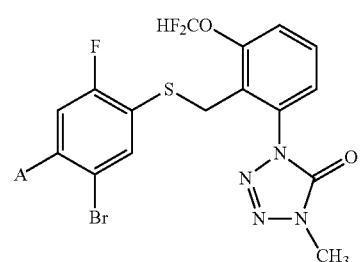
(HJ1012)
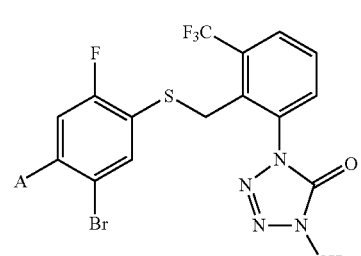
(HK1001)
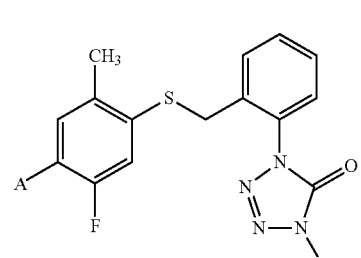
(HK1002)
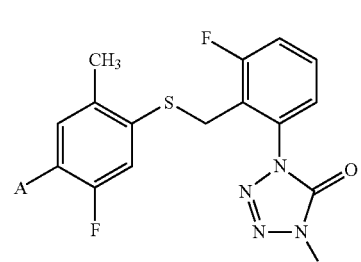
(HK1003)
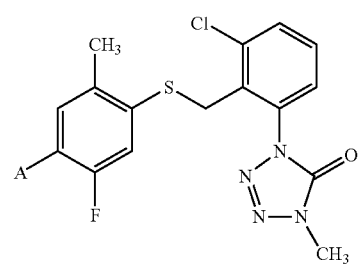

95
-continued
(HK1004)
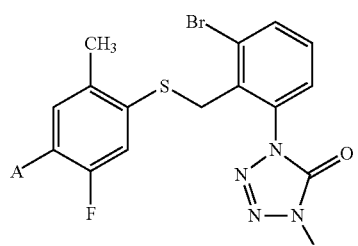
(HK1005)
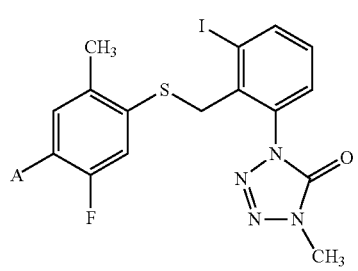
(HK1006)
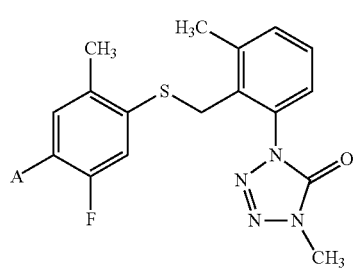
(HK1007)
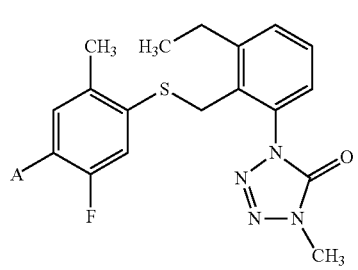
(HK1008)
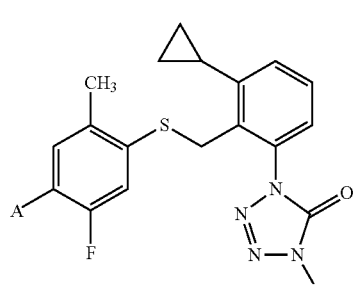
(HK1009)
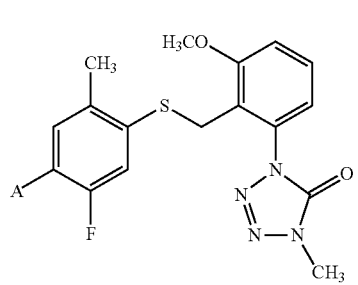
96
-continued
(HK1010)
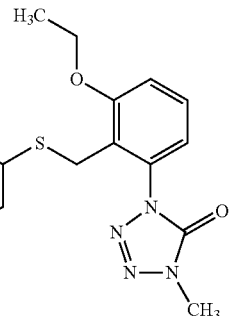
(HK1011)
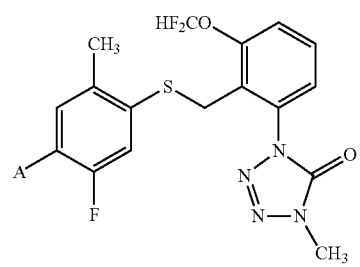
(HK1012)
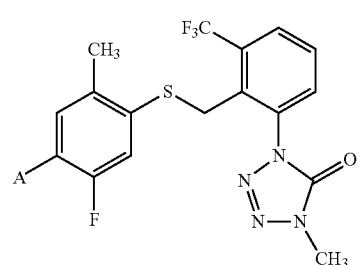
(HL1001)
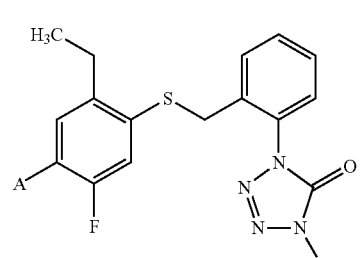
(HL1002)
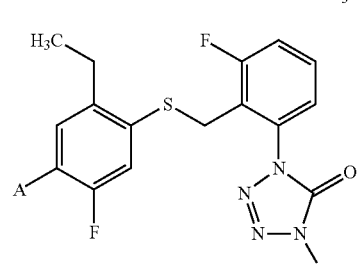
(HL1003)
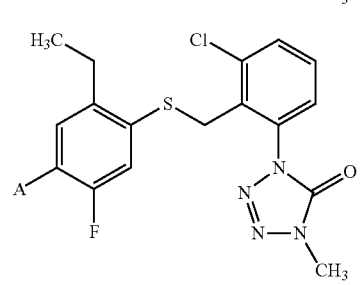

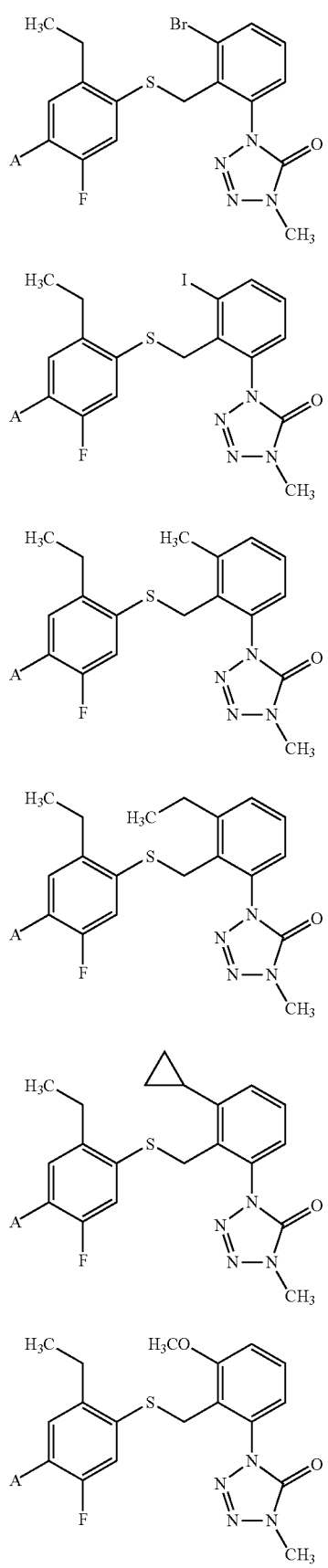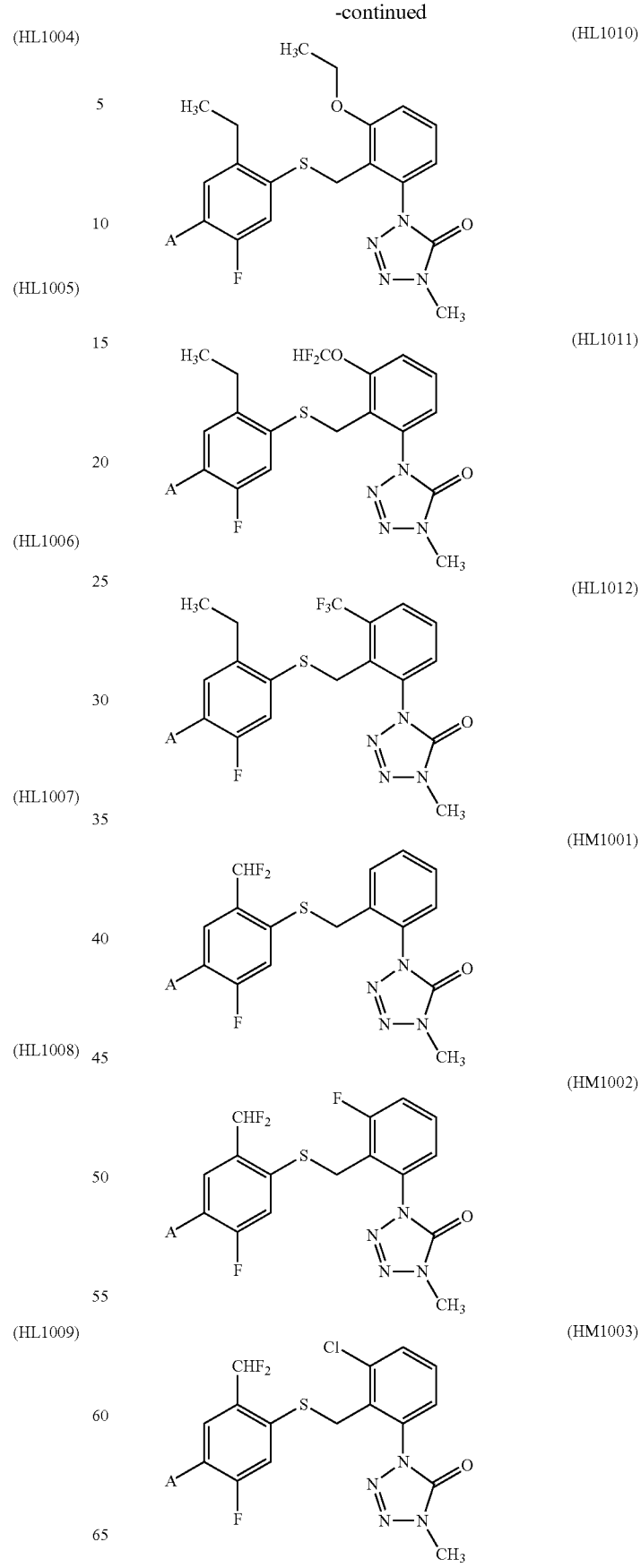

(HM1004)
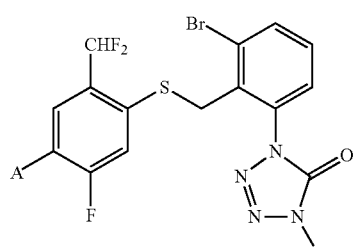
(HM1005)
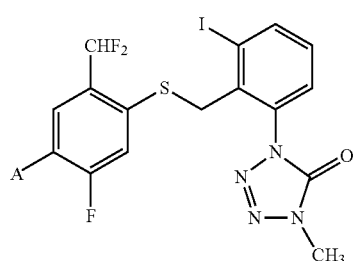
(HM1006)
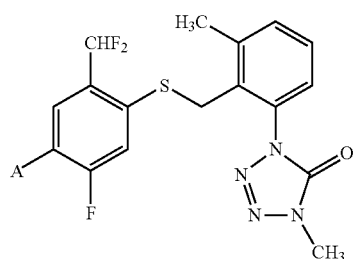
(HM1007)
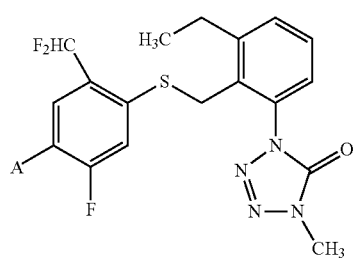
(HM1008)
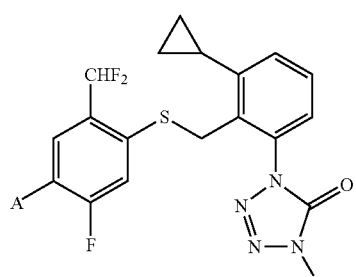
(HM1009)
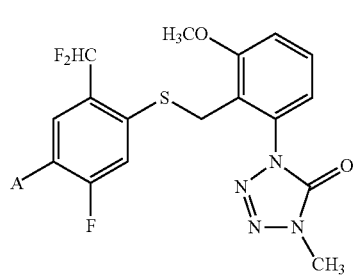
(HM1010)
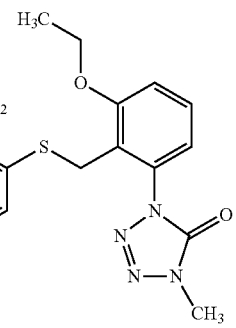
(HM1011)
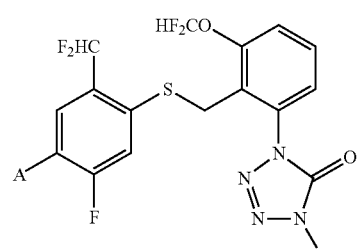
(HM1012)
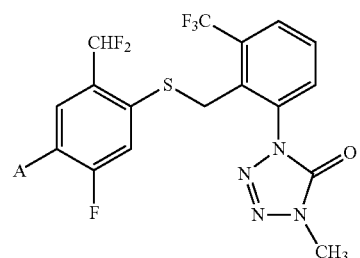
(HN1001)
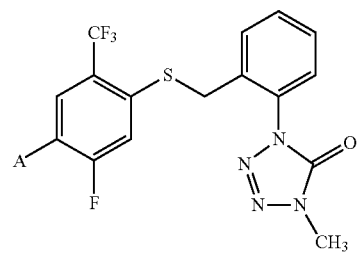
(HN1002)
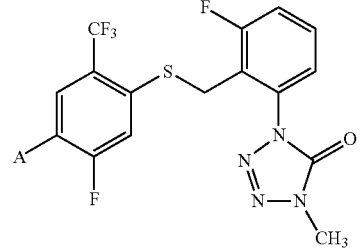
(HN1003)
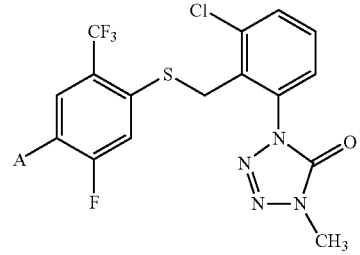

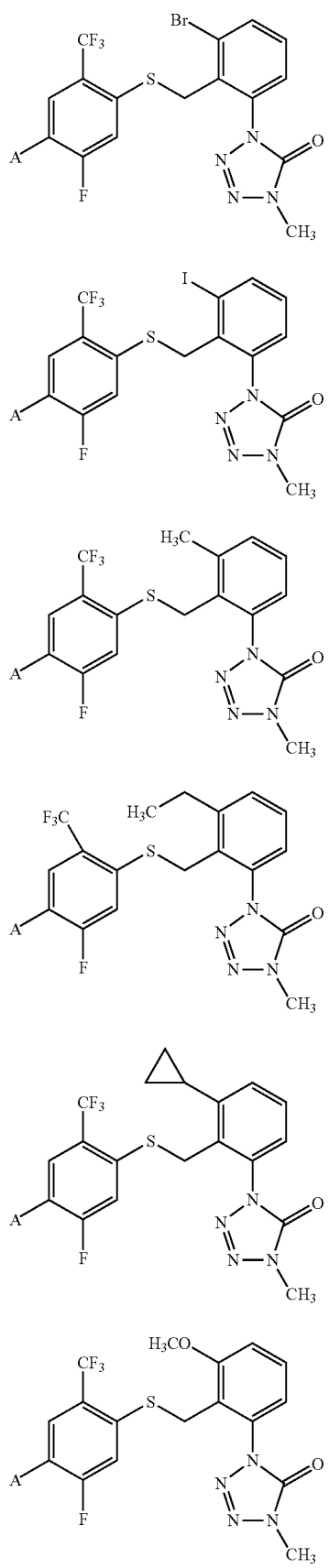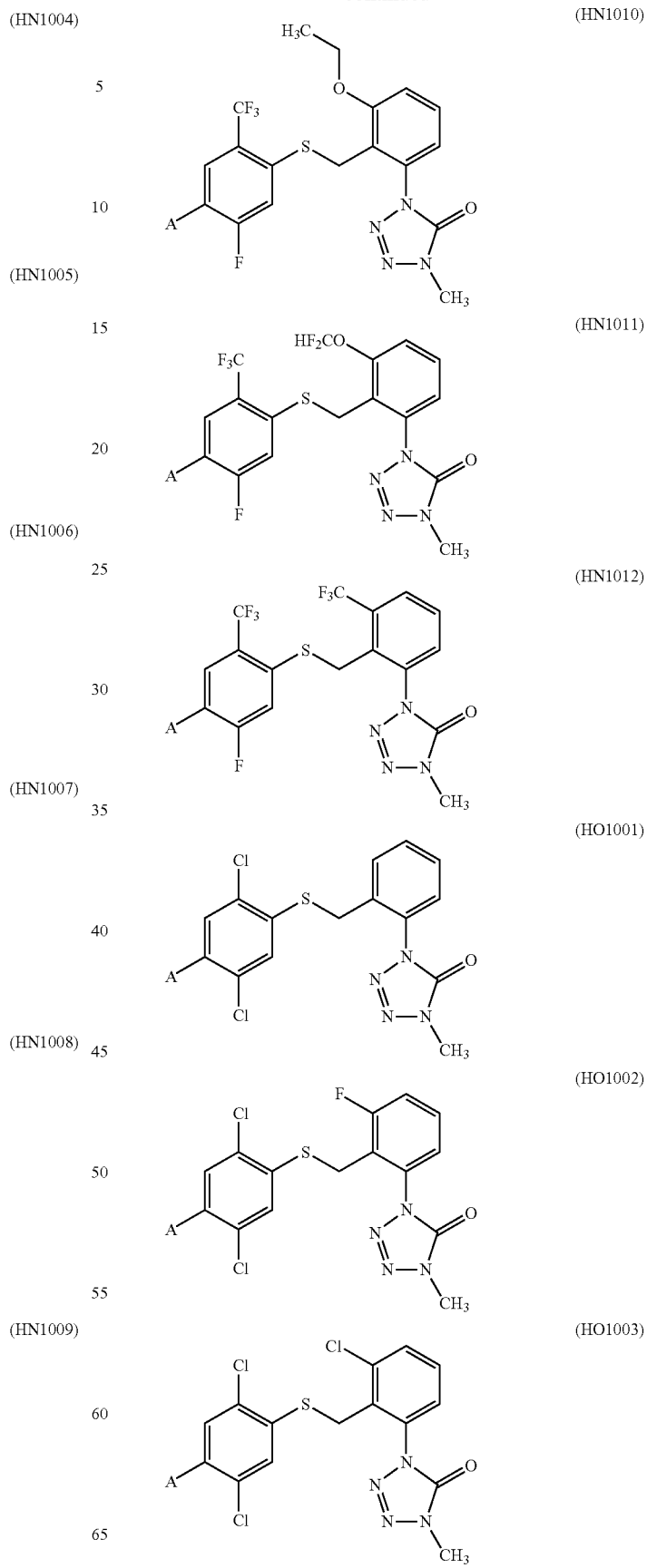

103
-continued
(HO1004)
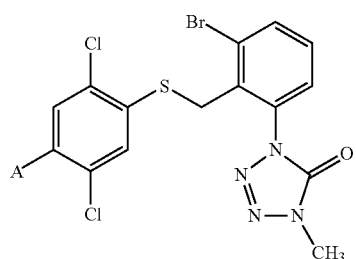
(HO1005)
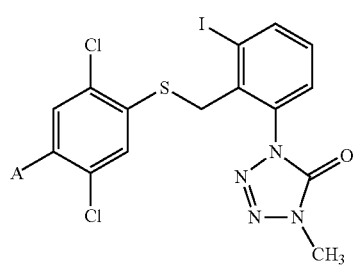
(HO1006)
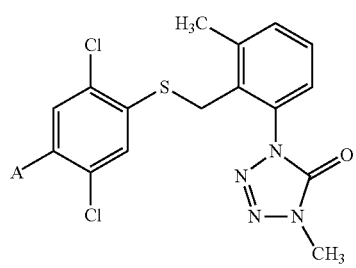
(HO1007)
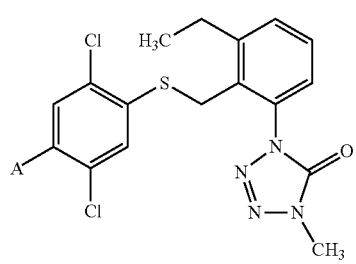
(HO1008)
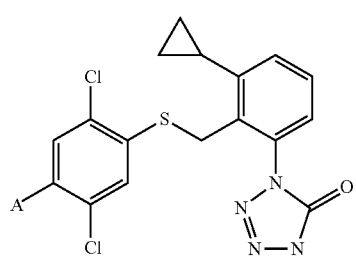
(HO1009)
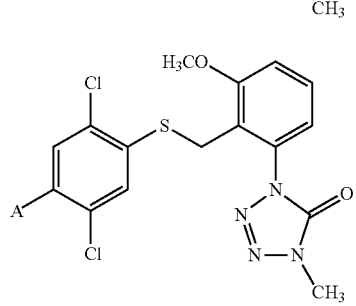
104
-continued
(HO1010)
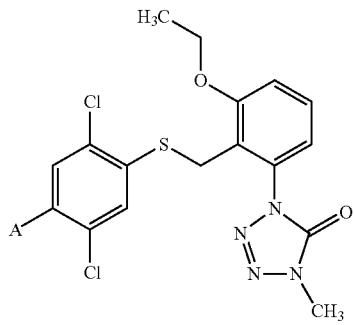
(HO1011)
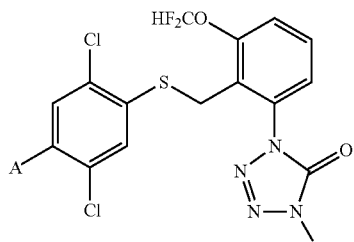
(HO1012)
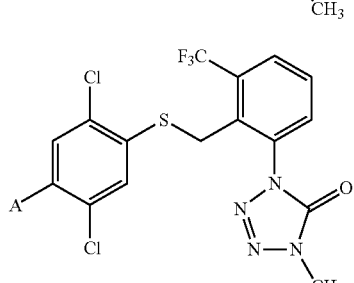
(HP1001)
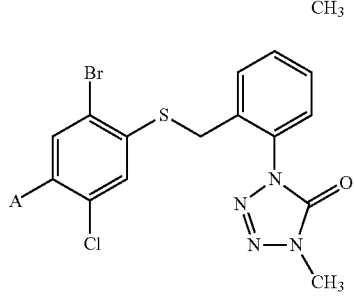
(HP1002)
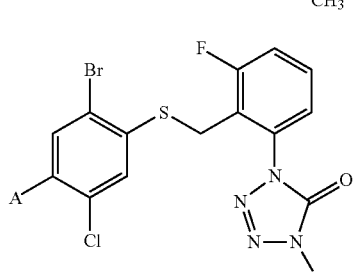
(HP1003)
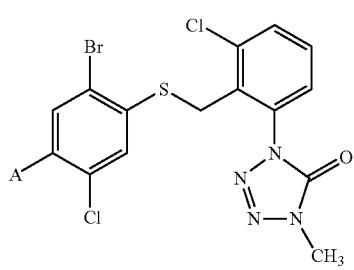

-continued
(HP1004)
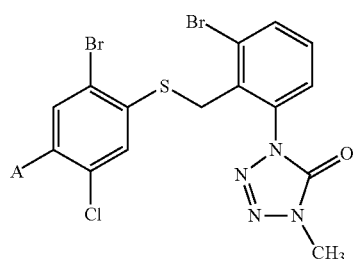
(HP1005)
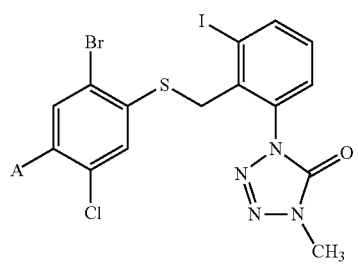
(HP1006)
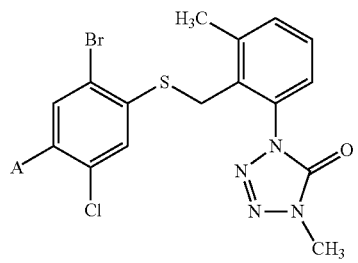
(HP1007)
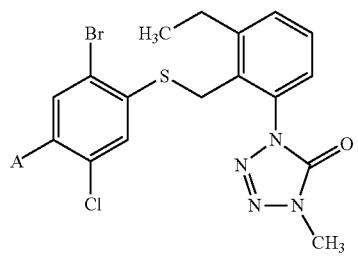
(HP1008)
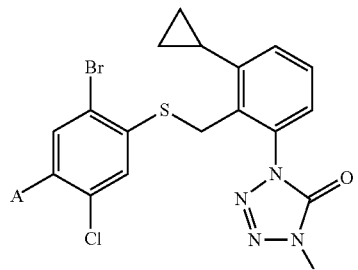
(HP1009)
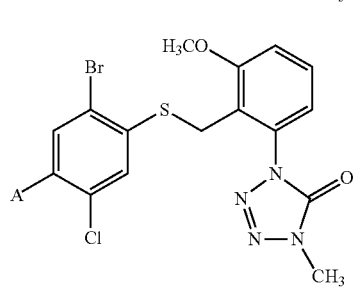
-continued
(HP1010)
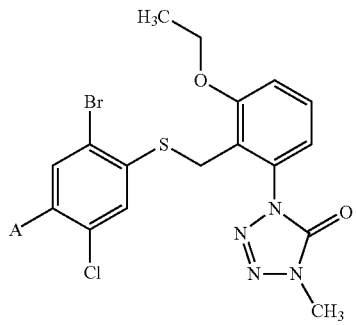
(HP1011)
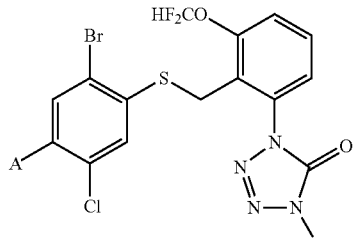
(HP1012)
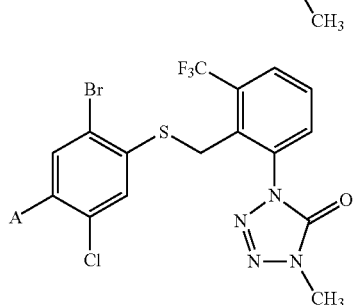
(HQ1001)
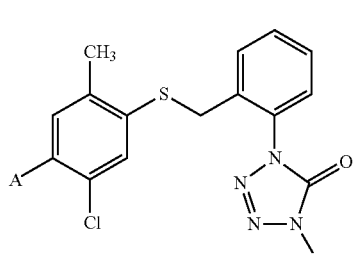
(HQ1002)
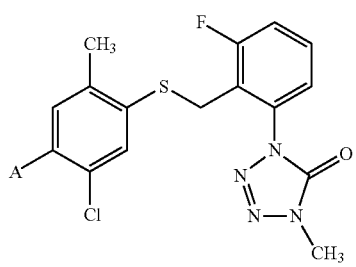
(HQ1003)
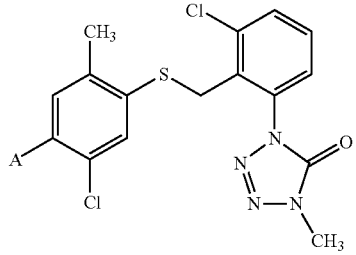

(HQ1004)
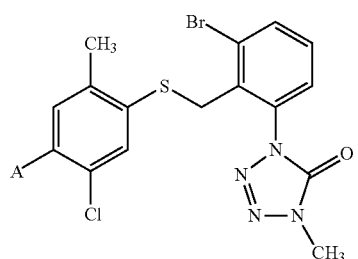
(HQ1005)
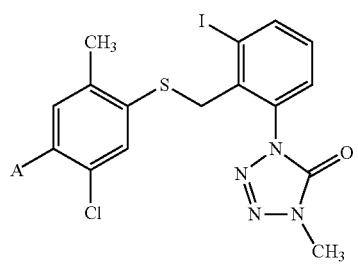
(HQ1006)
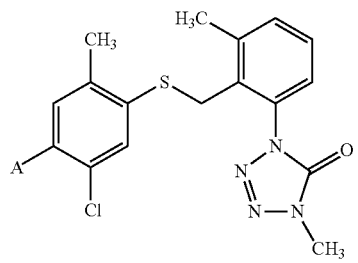
(HQ1007)
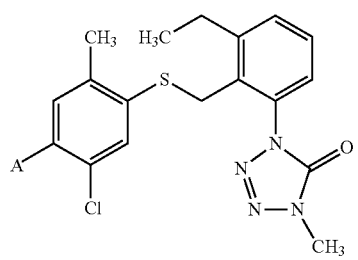
(HQ1008)
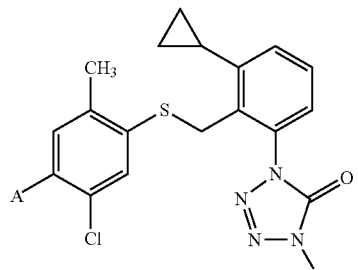
(HQ1009)
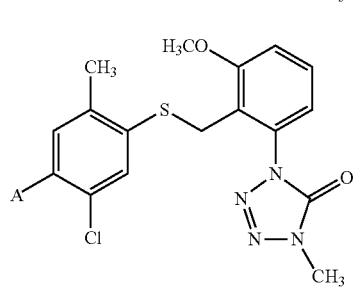
(HQ1010)
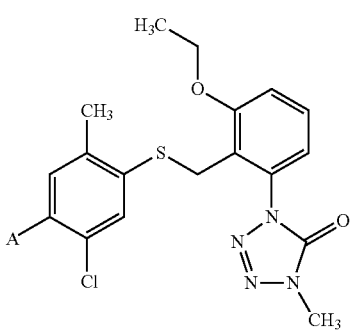
(HQ1011)
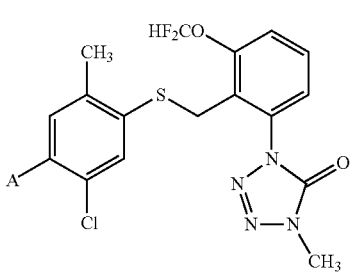
(HQ1012)
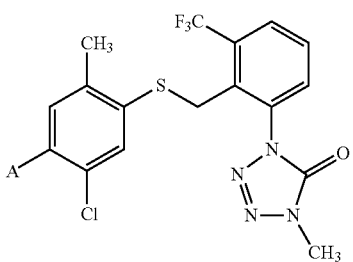
(HR1001)
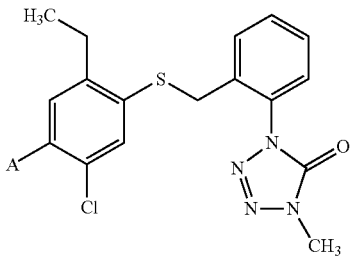
(HR1002)
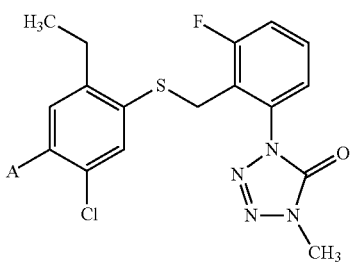

-continued
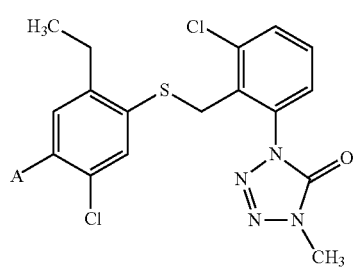 (HR1003)
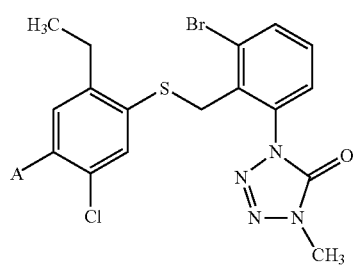 (HR1004)
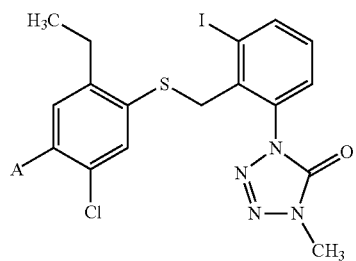 (HR1005)
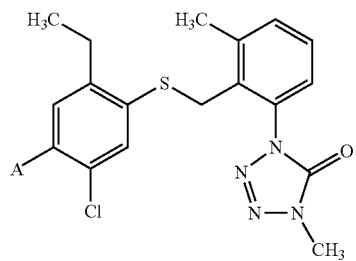 (HR1006)
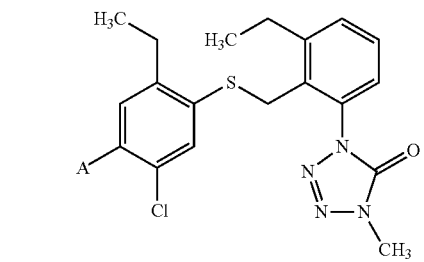 (HR1007)
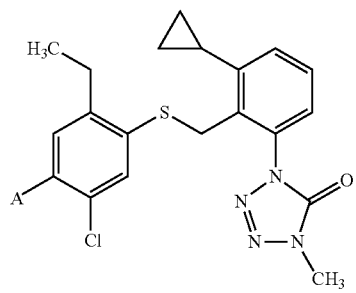 (HR1008)
-continued
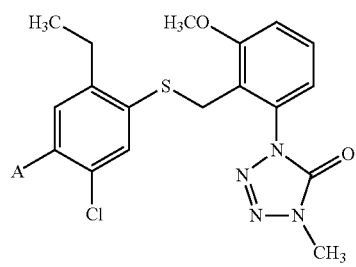 (HR1009)
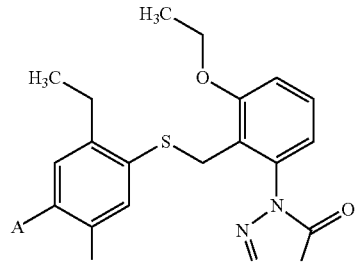 (HR1010)
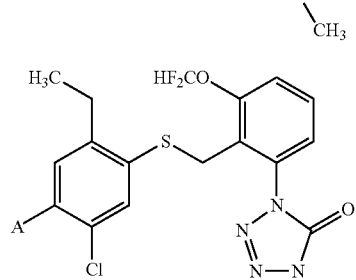 (HR1011)
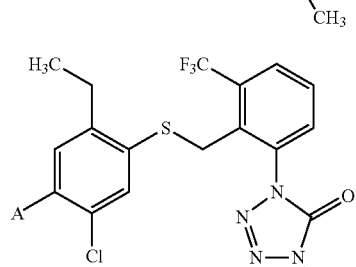 (HR1012)
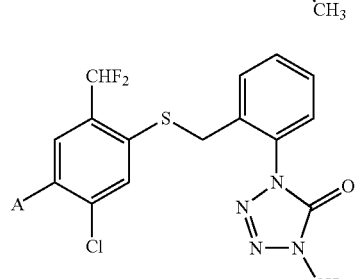 (HS1001)
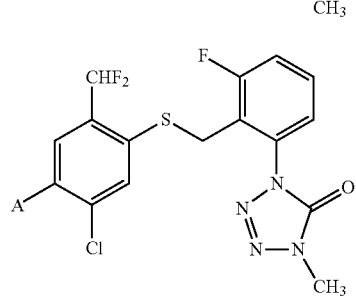 (HS1002)

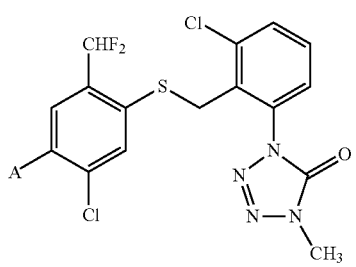
(HS1003)
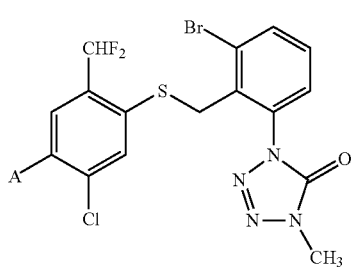
(HS1004)
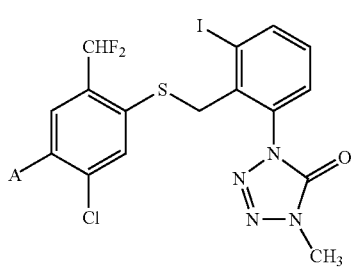
(HS1005)
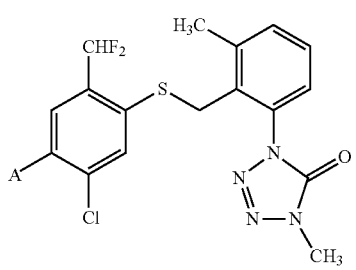
(HS1006)
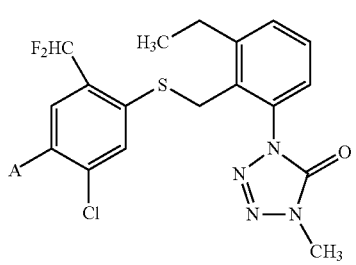
(HS1007)
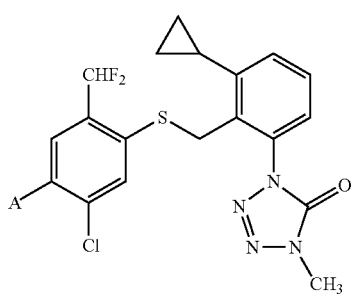
(HS1008)
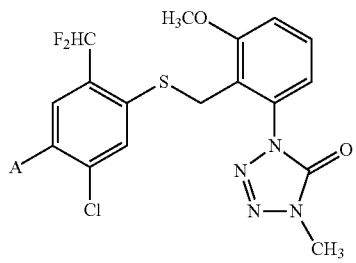
(HS1009)
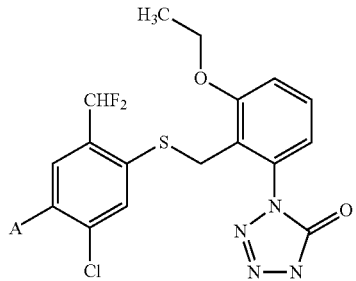
(HS1010)
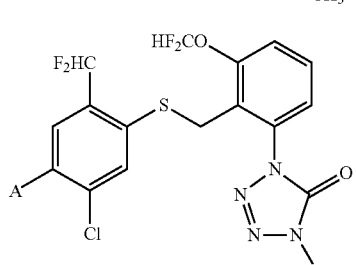
(HS1011)
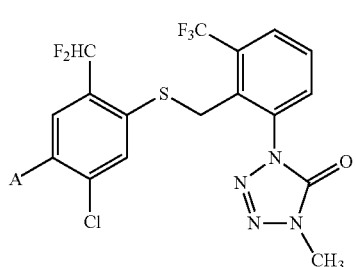
(HS1012)
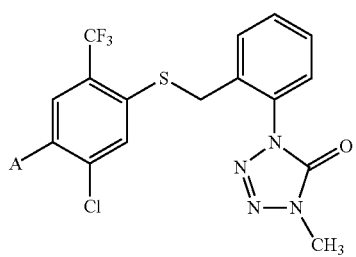
(HT1001)
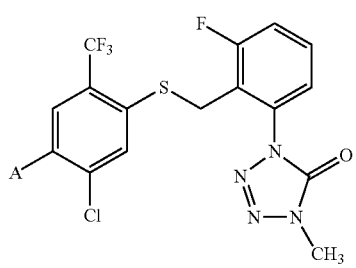
(HT1002)

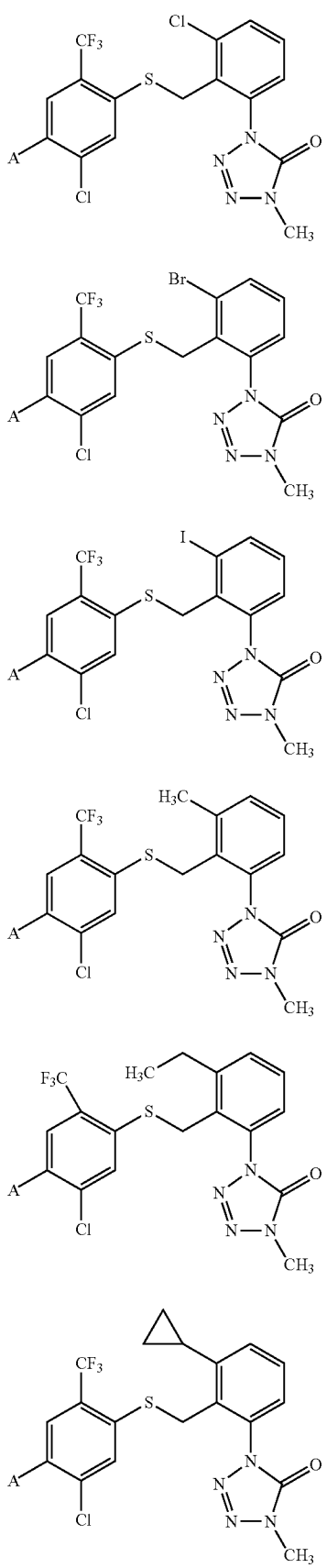
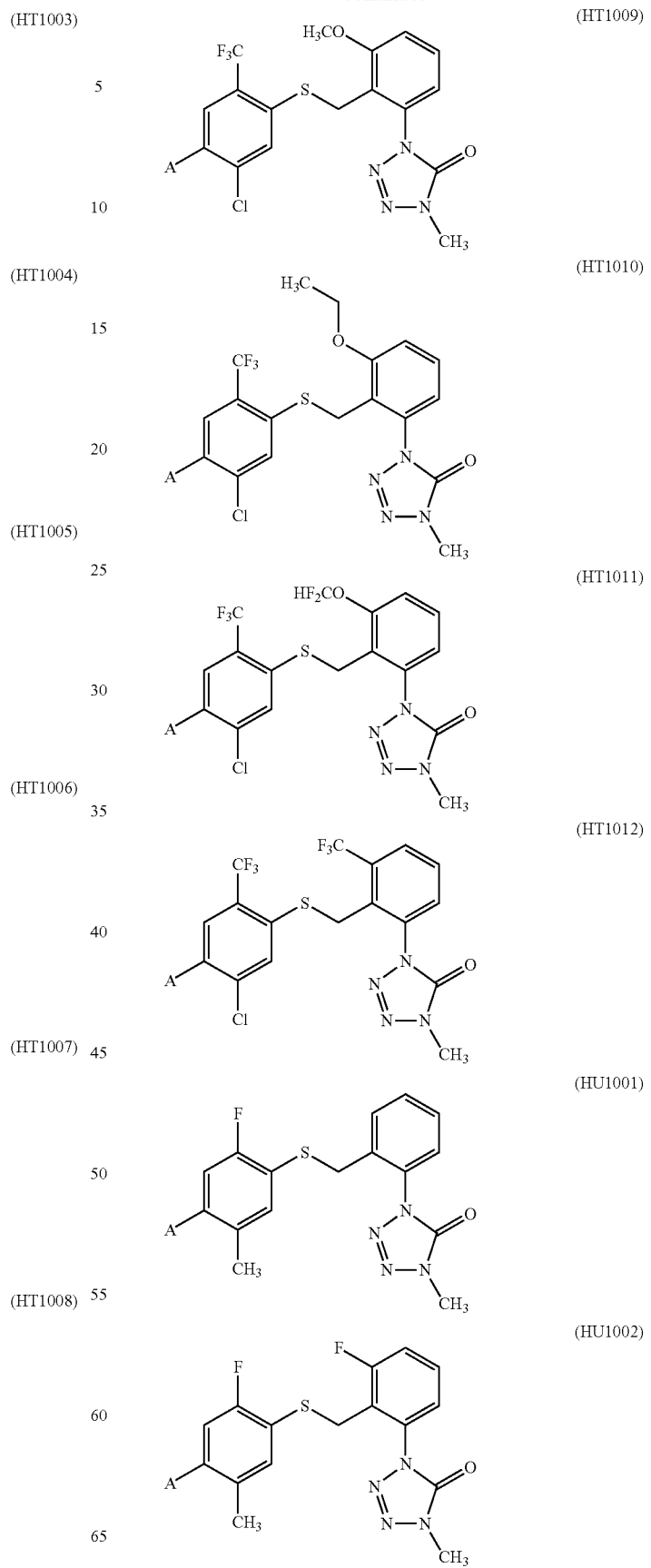

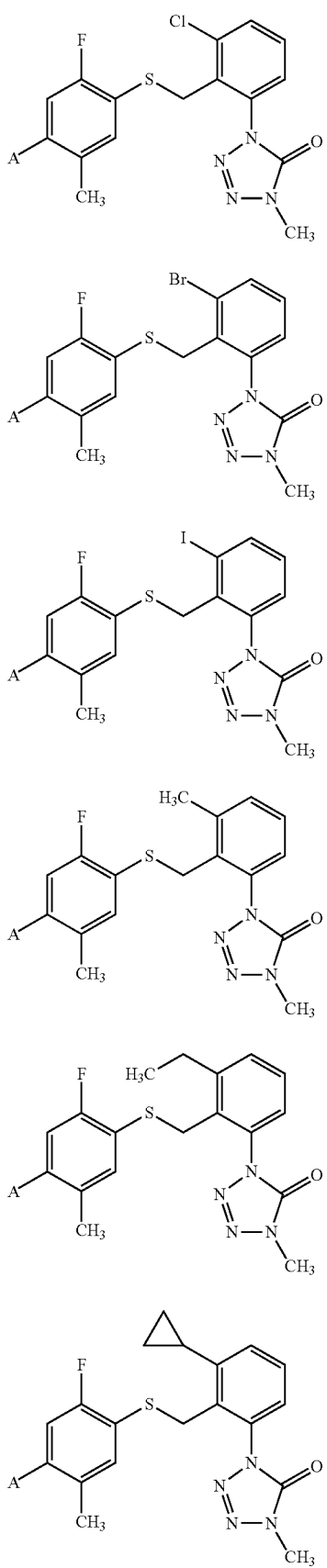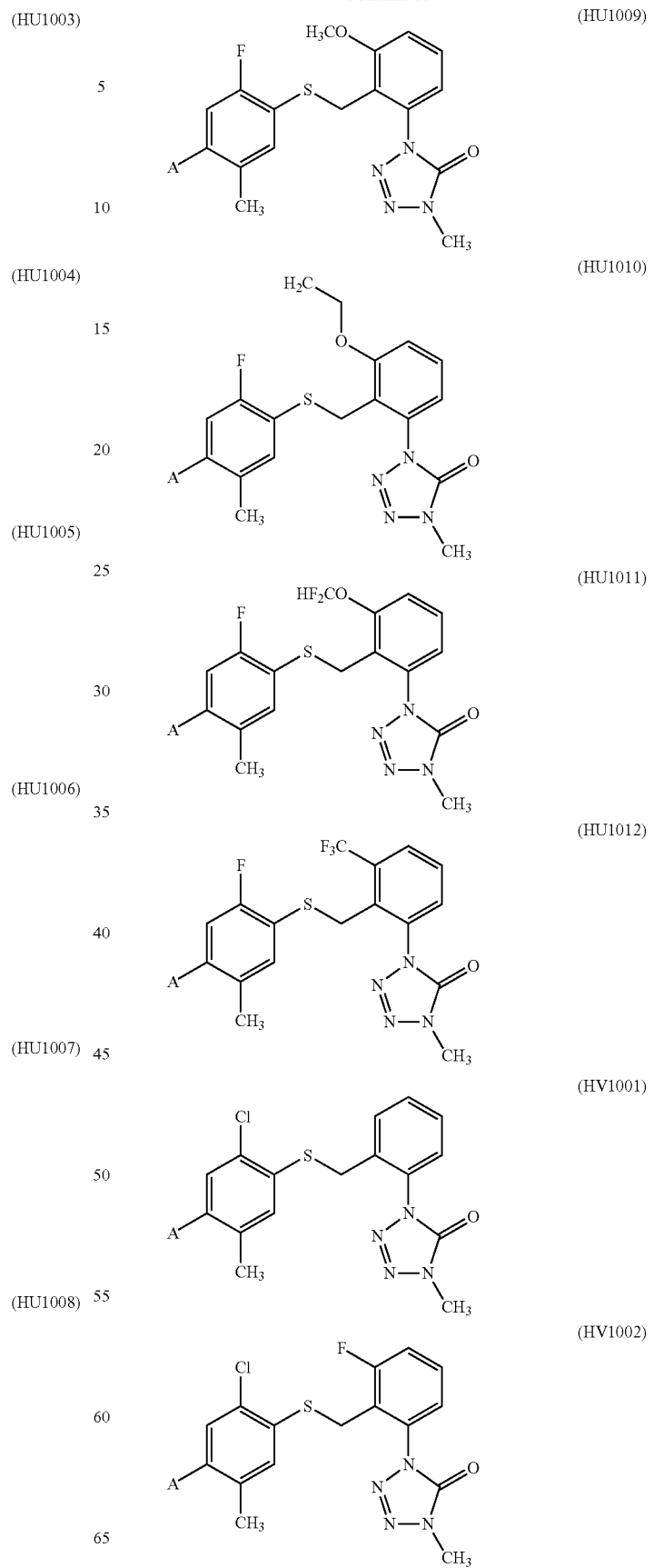

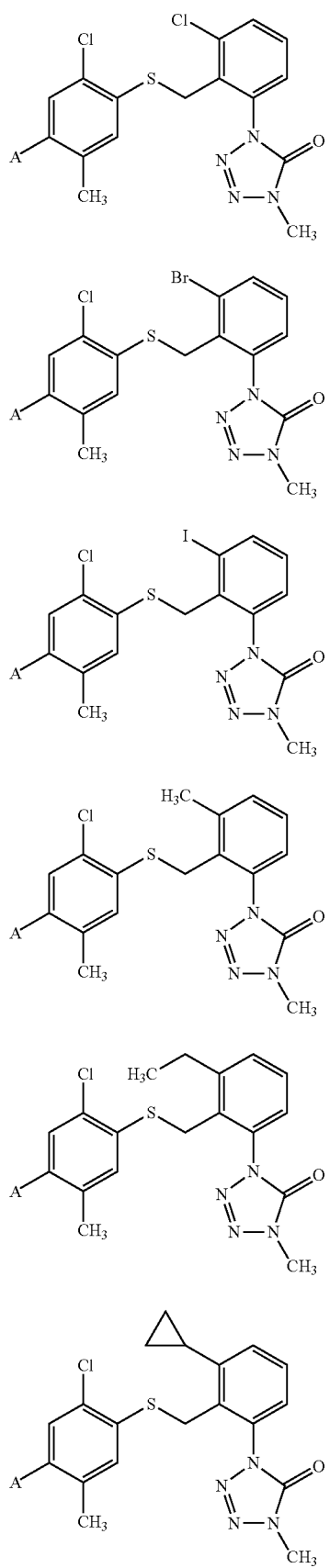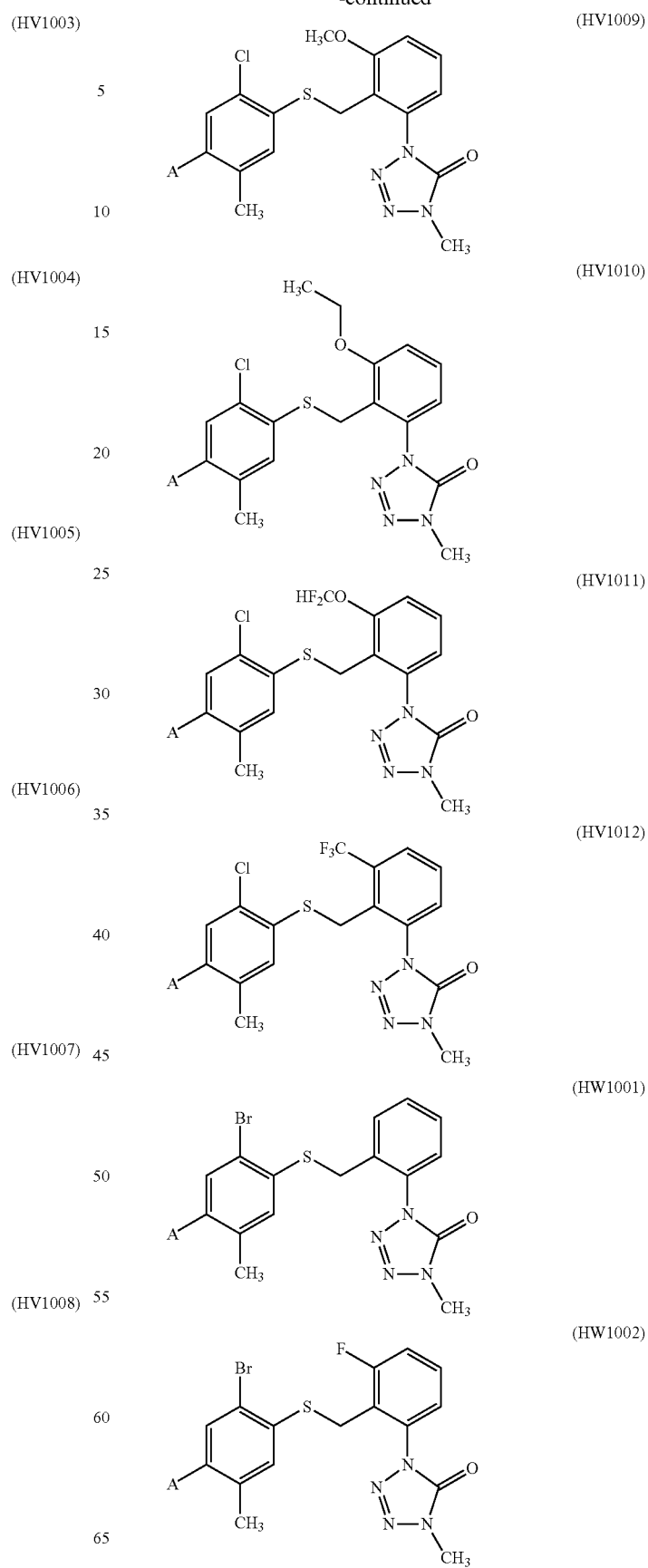

(HW1003) 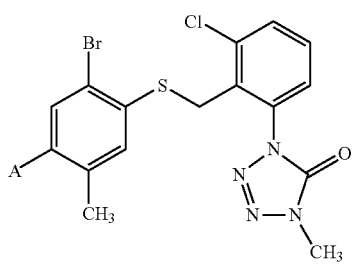
(HW1004) 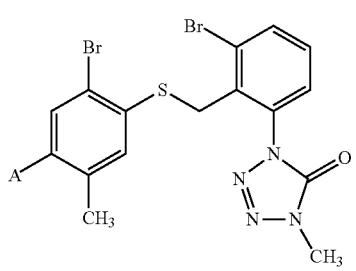
(HW1005) 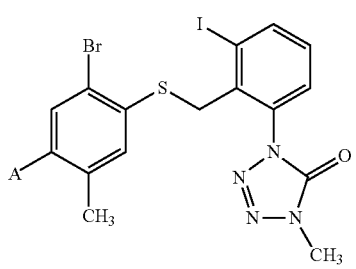
(HW1006) 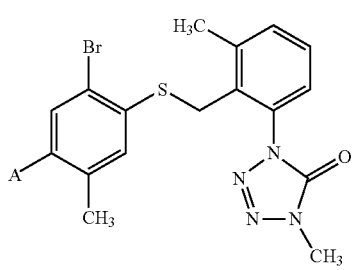
(HW1007) 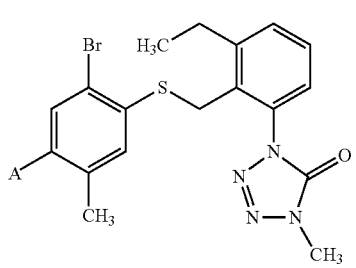
(HW1008) 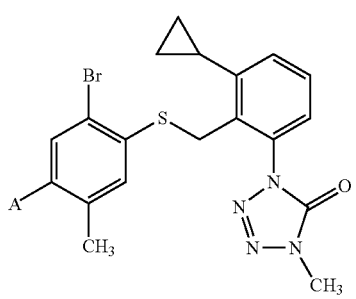
(HW1009) 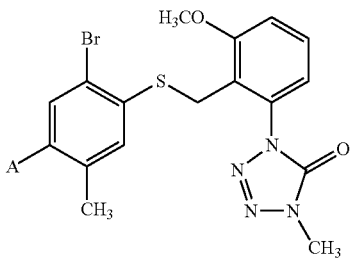
(HW1010) 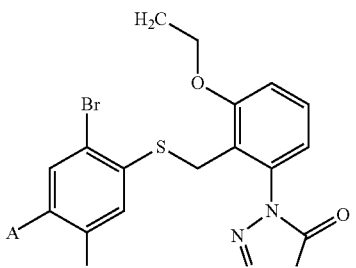
(HW1011) 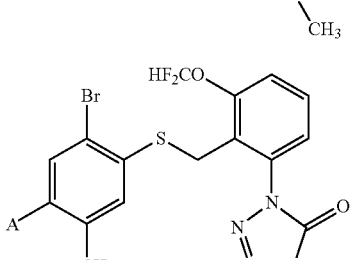
(HW1012) 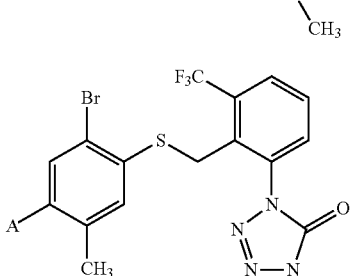
(HX1001) 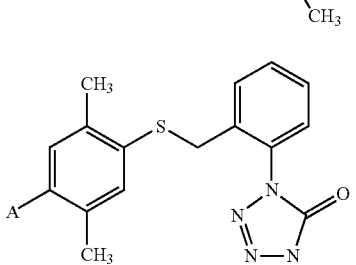
(HX1002) 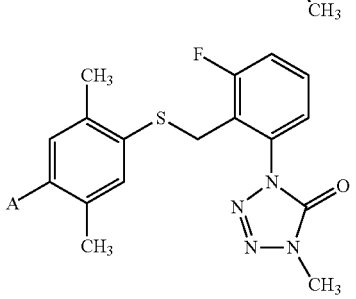

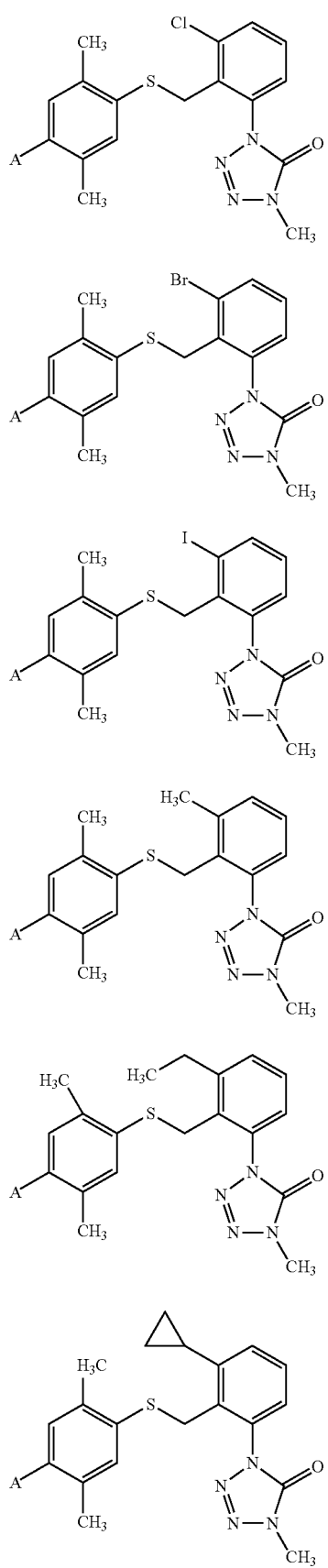
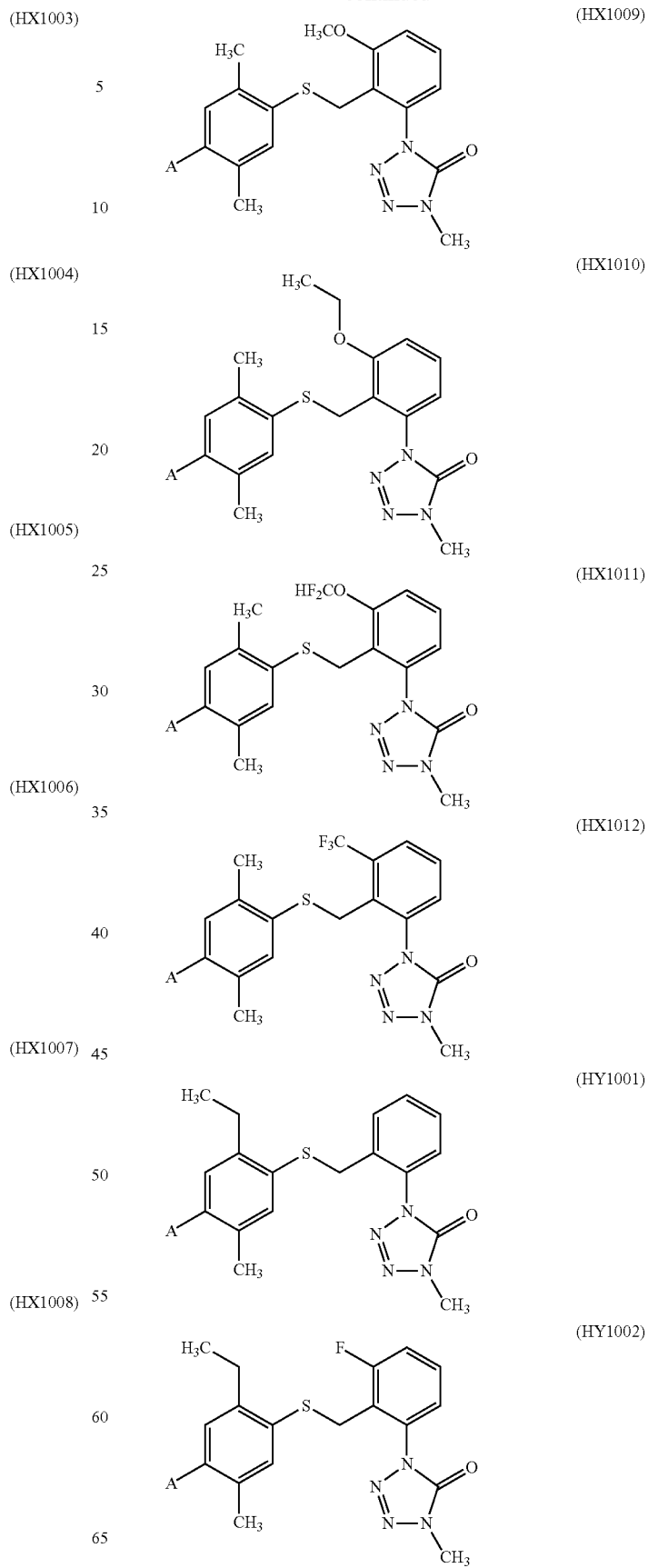

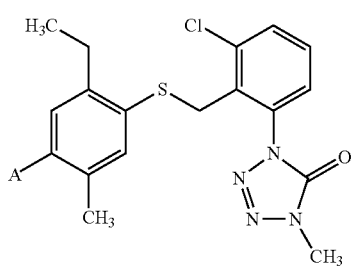
(HY1003)
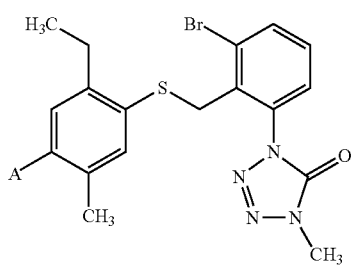
(HY1004)
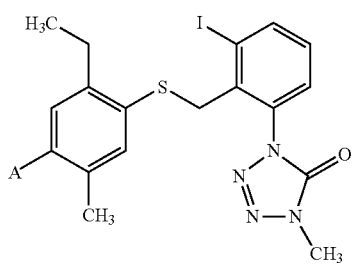
(HY1005)
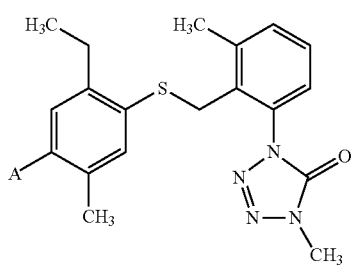
(HY1006)
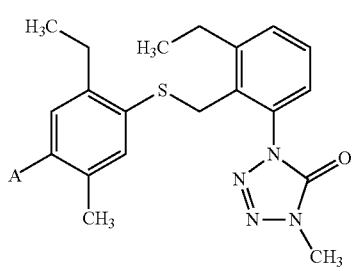
(HY1007)
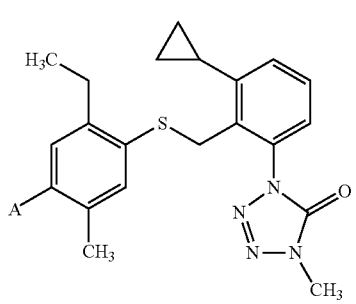
(HY1008)
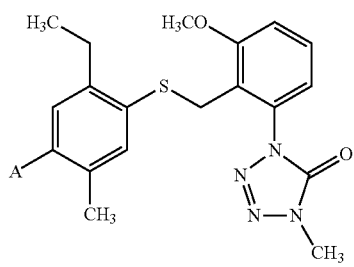
(HY1009)
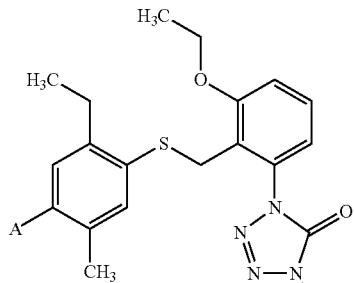
(HY1010)
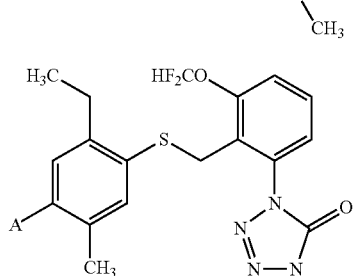
(HY1011)
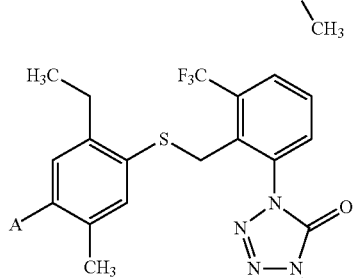
(HY1012)
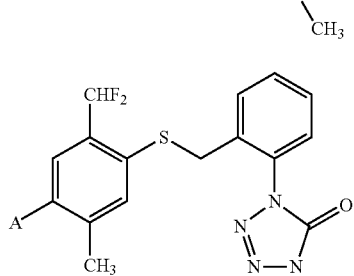
(HZ1001)
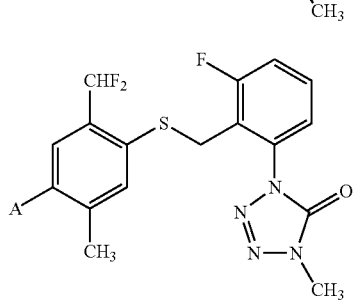
(HZ1002)

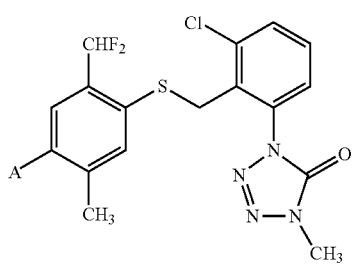 (HZ1003)
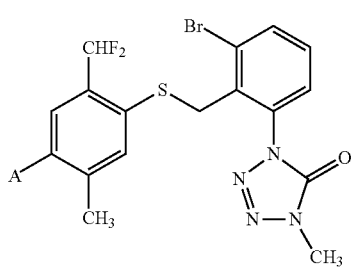 (HZ1004)
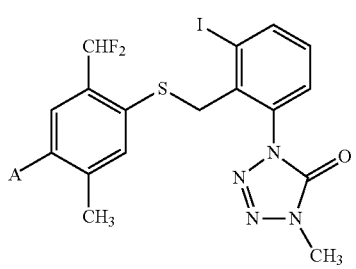 (HZ1005)
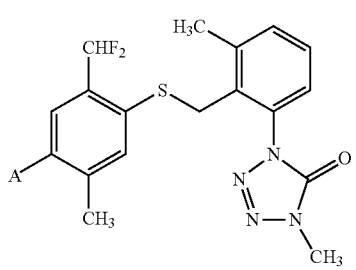 (HZ1006)
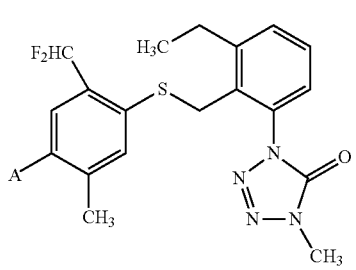 (HZ1007)
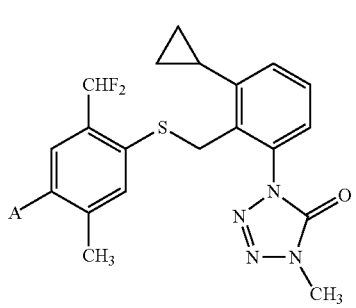 (HZ1008)
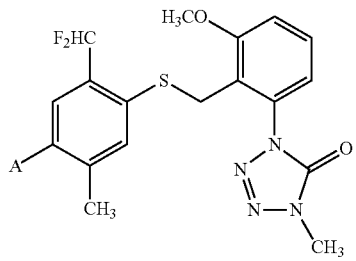 (HZ1009)
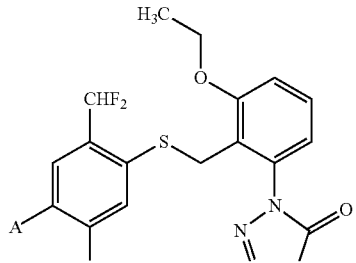 (HZ1010)
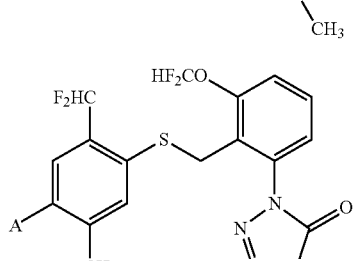 (HZ1011)
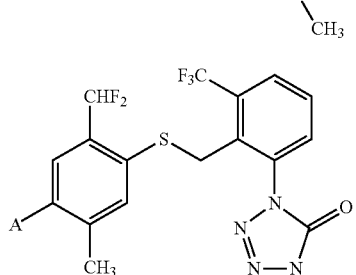 (HZ1012)
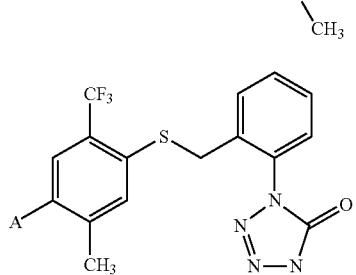 (IA1001)
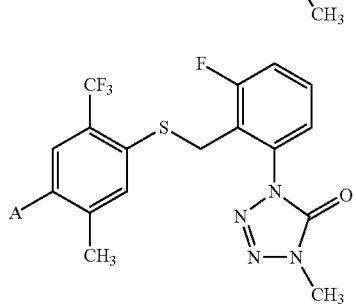 (IA1002)

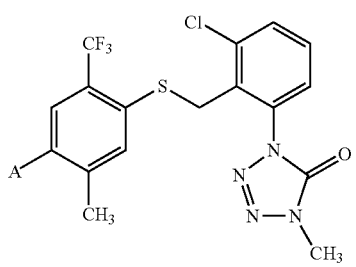 (IA1003)
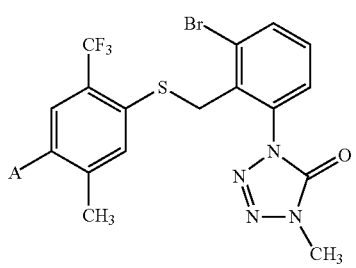 (IA1004)
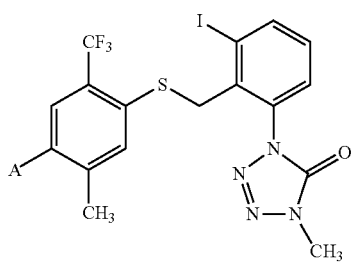 (IA1005)
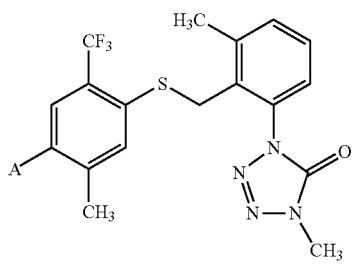 (IA1006)
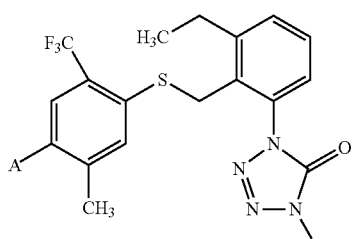 (IA1007)
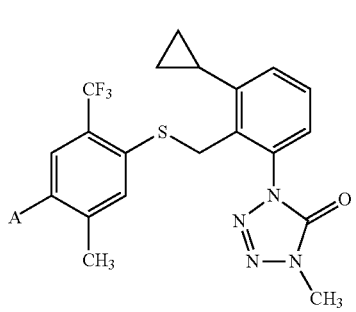 (IA1008)
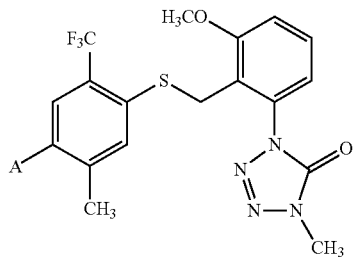 (IA1009)
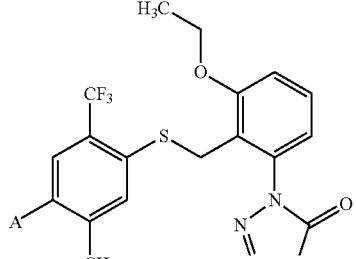 (IA1010)
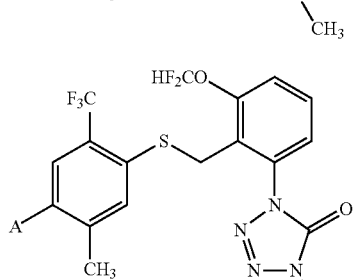 (IA1011)
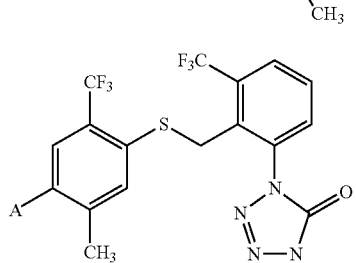 (IA1012)
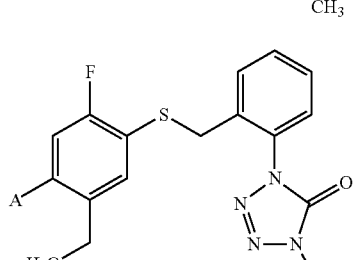 (IB1001)
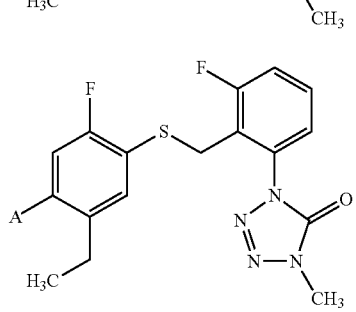 (IB1002)

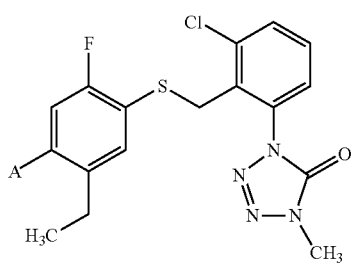
(IB1003)
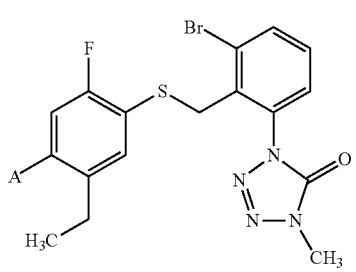
(IB1004)
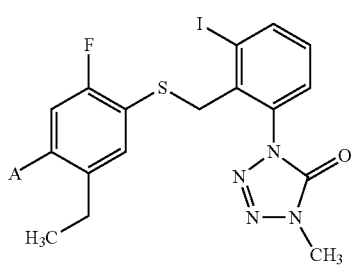
(IB1005)
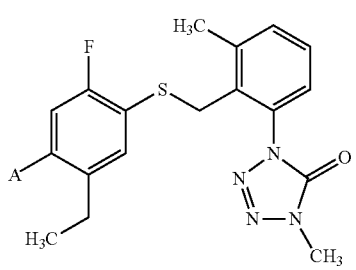
(IB1006)
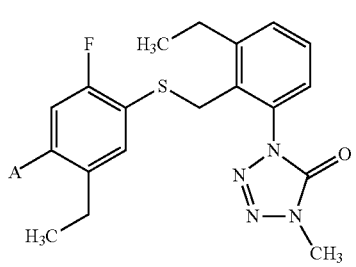
(IB1007)
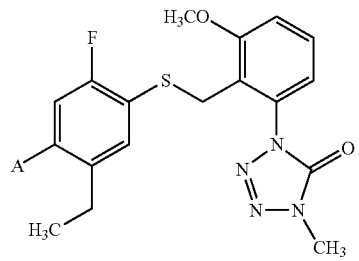
(IB1008)
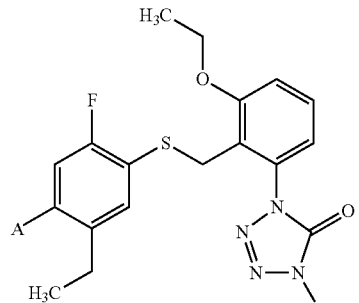
(IB1009)
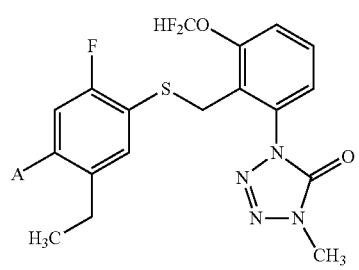
(IB1010)
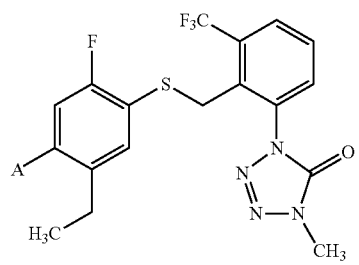
(IB1011)
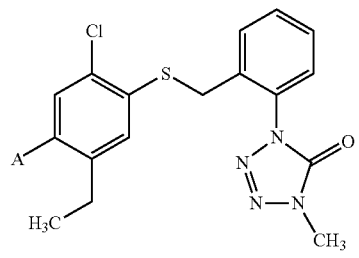
(IB1012)
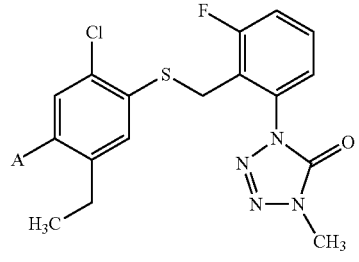
(IC1001)
(IC1002)

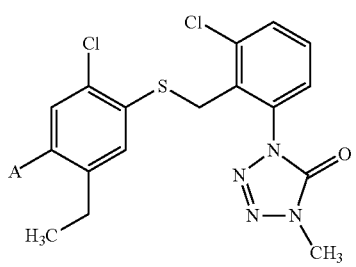 (IC1003)
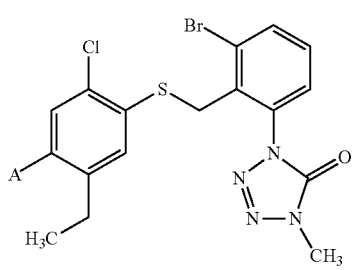 (IC1004)
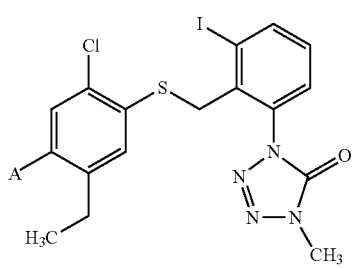 (IC1005)
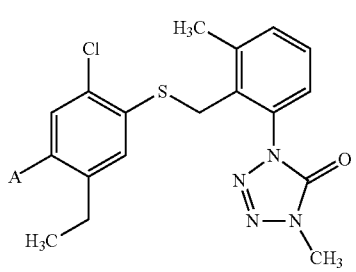 (IC1006)
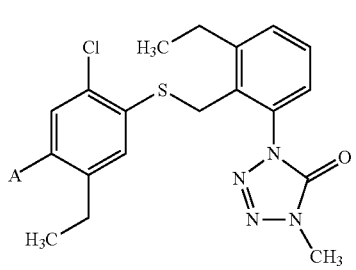 (IC1007)
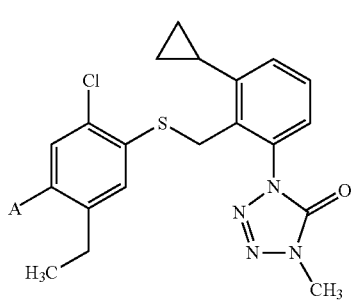 (IC1008)
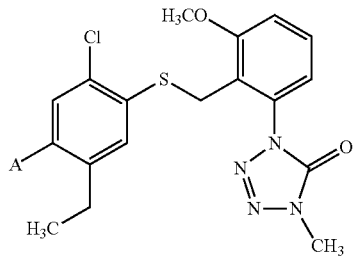 (IC1009)
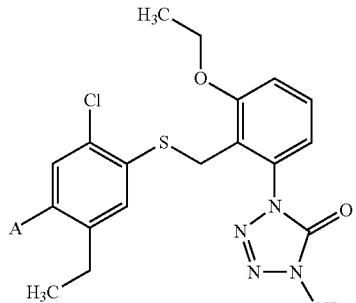 (IC1010)
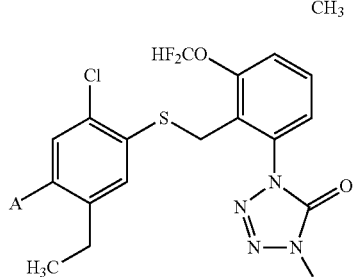 (IC1011)
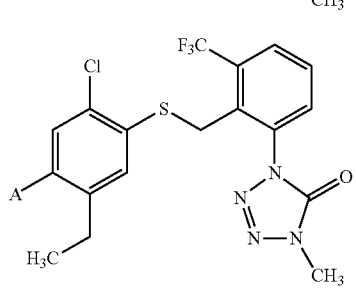 (IC1012)
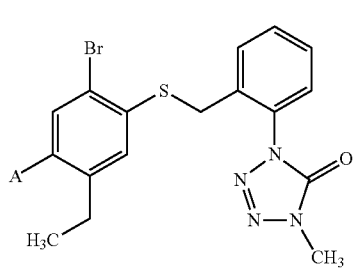 (ID1001)
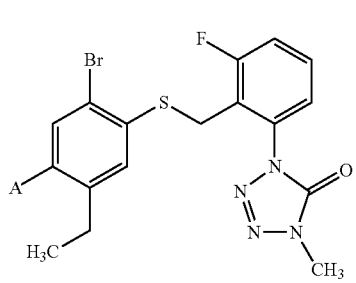 (ID1002)

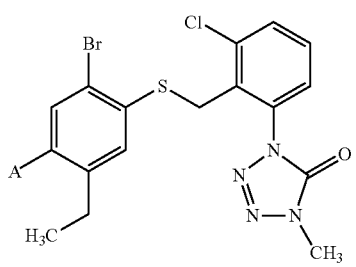
(ID1003)
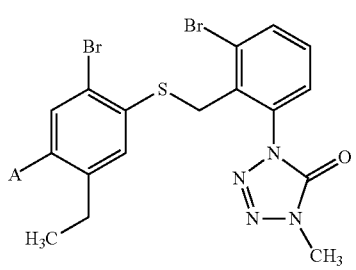
(ID1004)
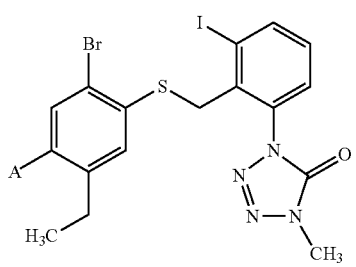
(ID1005)
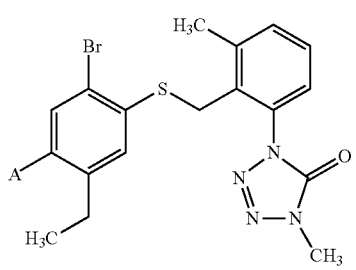
(ID1006)
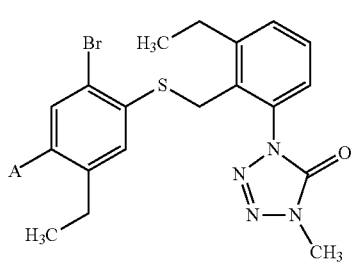
(ID1007)
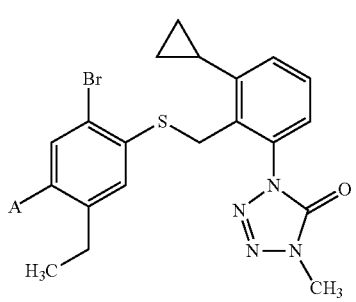
(ID1008)
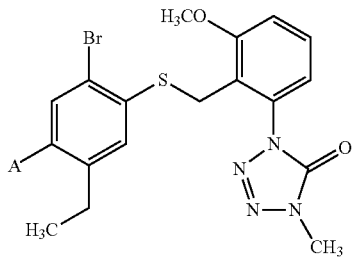
(ID1009)
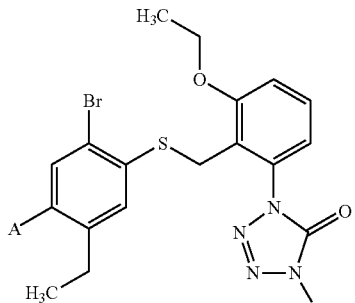
(ID1010)
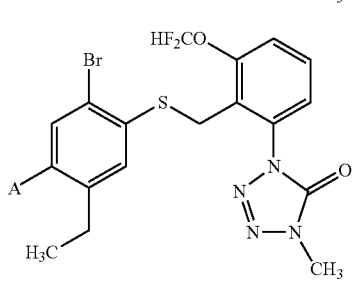
(ID1011)
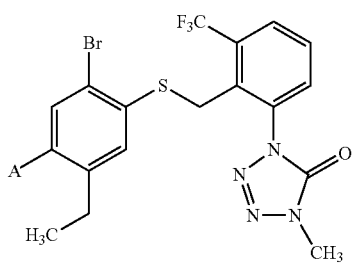
(ID1012)
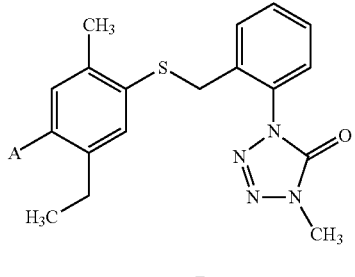
(IE1001)
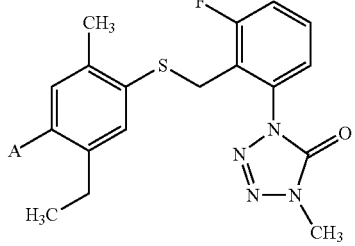
(IE1002)

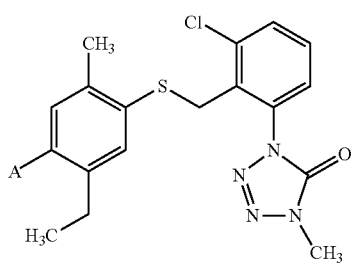 (IE1003)
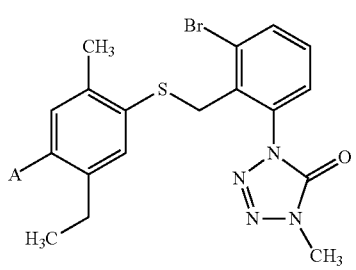 (IE1004)
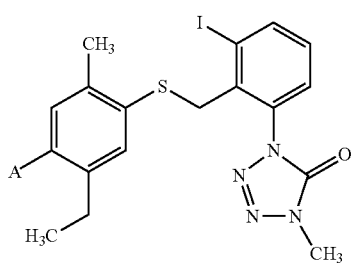 (IE1005)
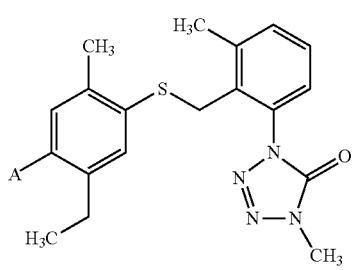 (IE1006)
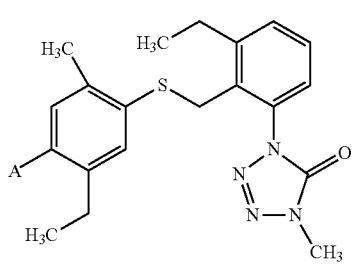 (IE1007)
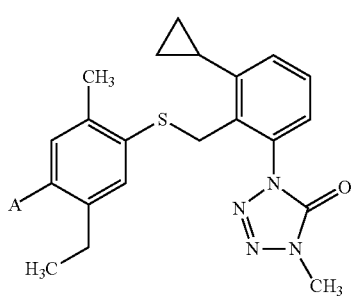 (IE1008)
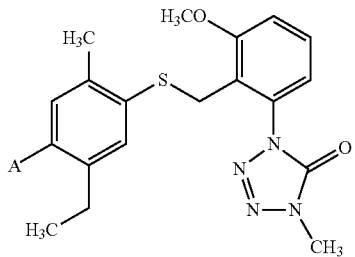 (IE1009)
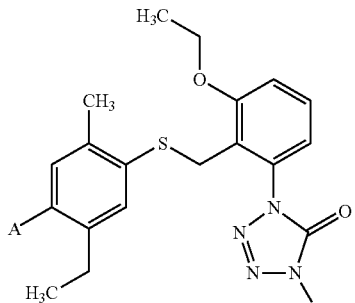 (IE1010)
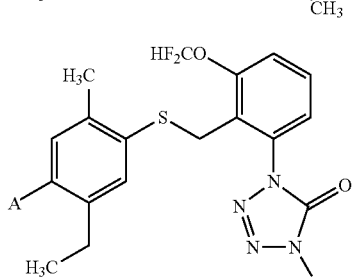 (IE1011)
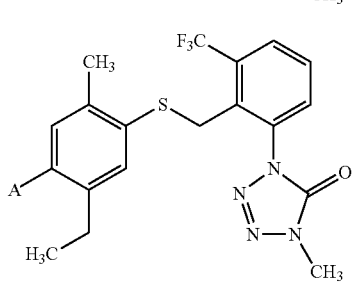 (IE1012)
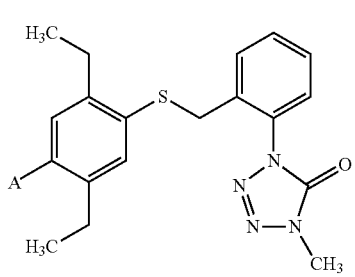 (IF1001)
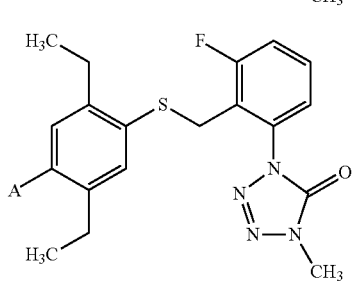 (IF1002)

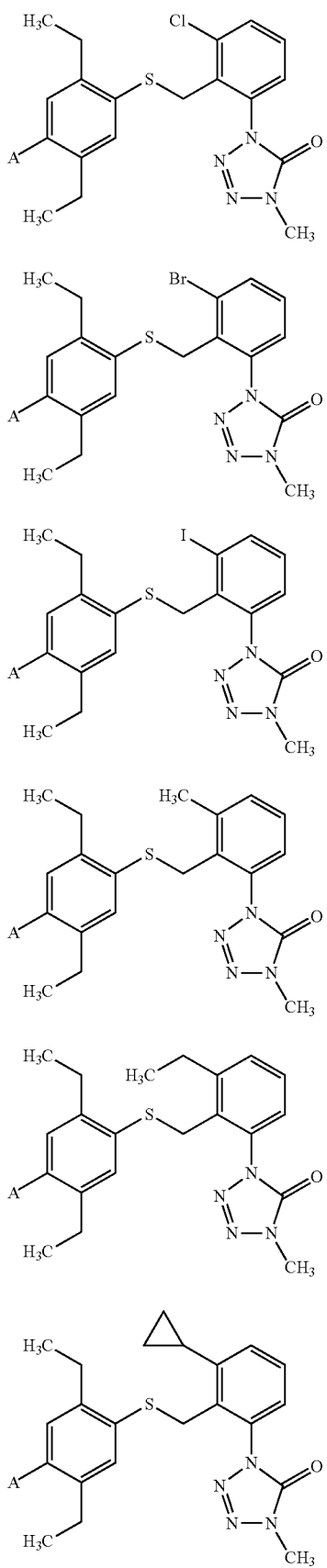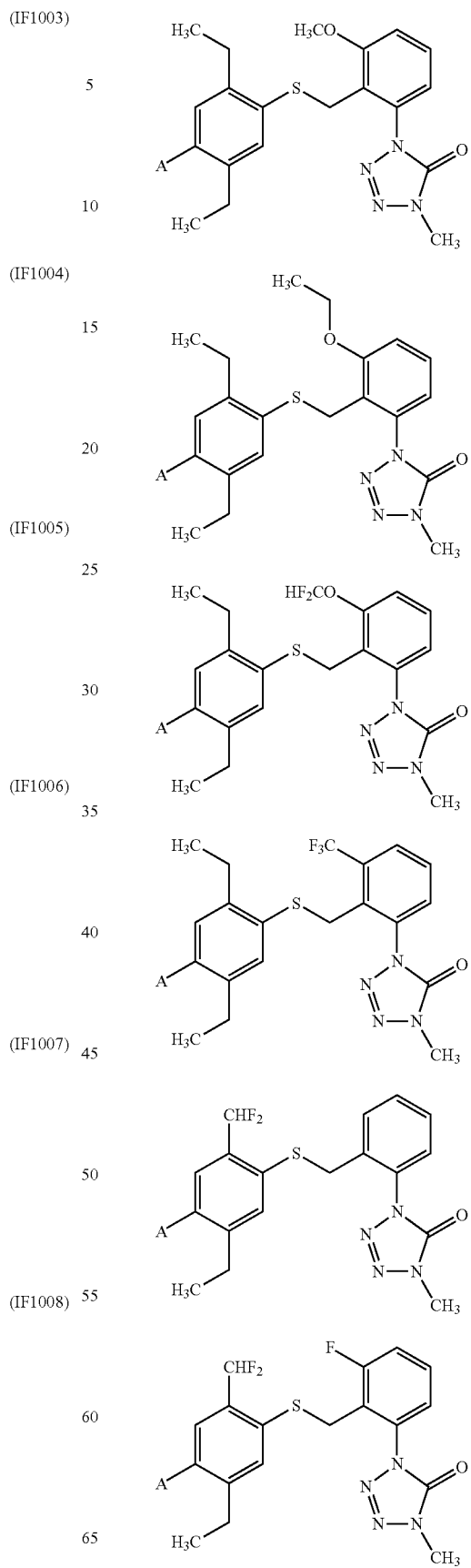

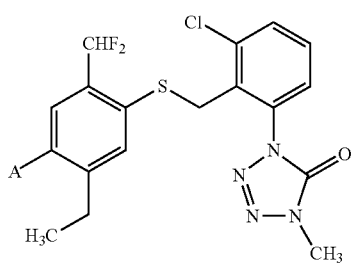
(IG1003)
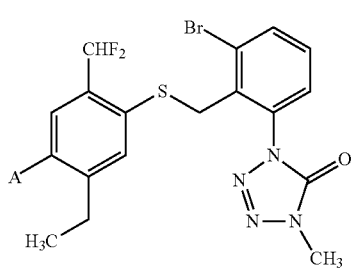
(IG1004)
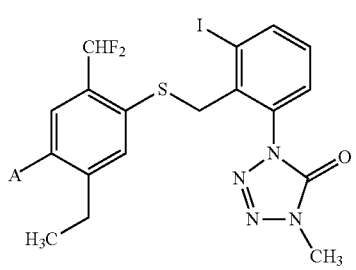
(IG1005)
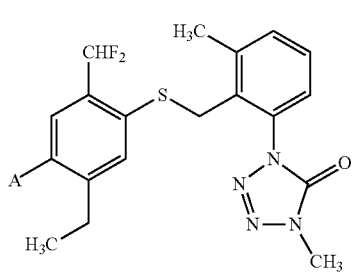
(IG1006)
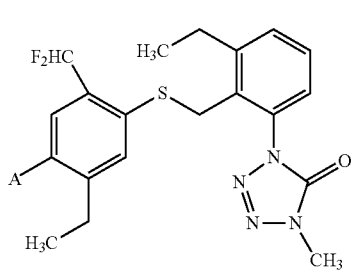
(IG1007)
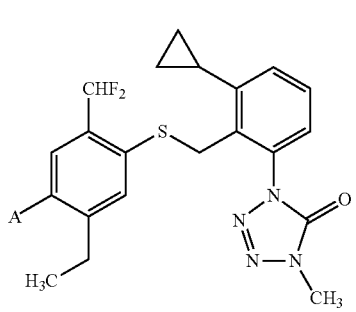
(IG1008)
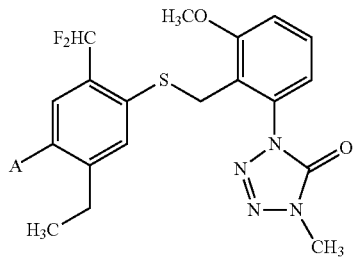
(IG1009)
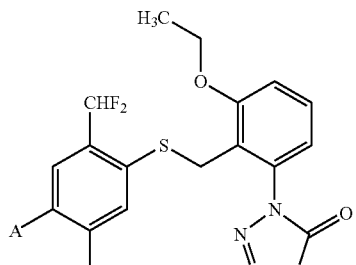
(IG1010)
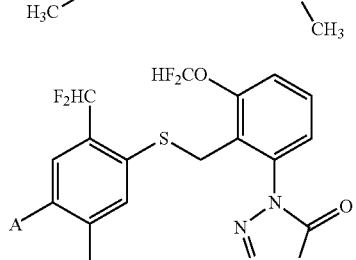
(IG1011)
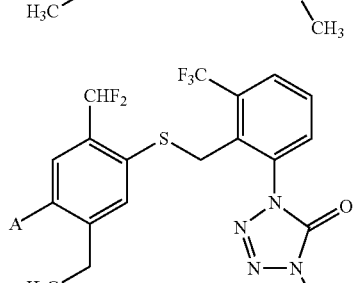
(IG1012)
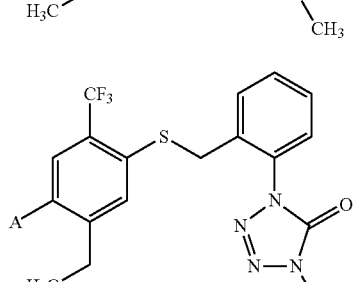
(IH1001)
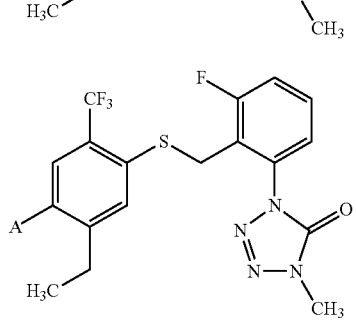
(IH1002)

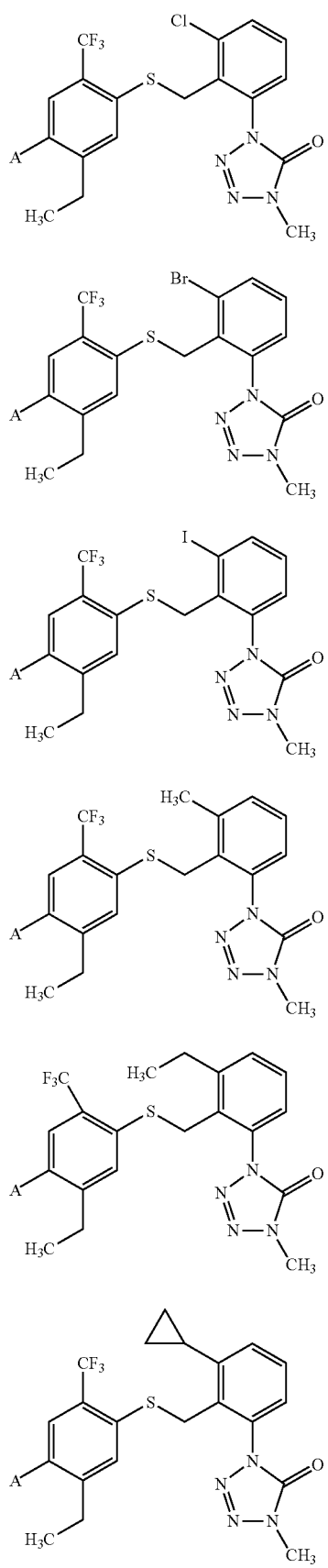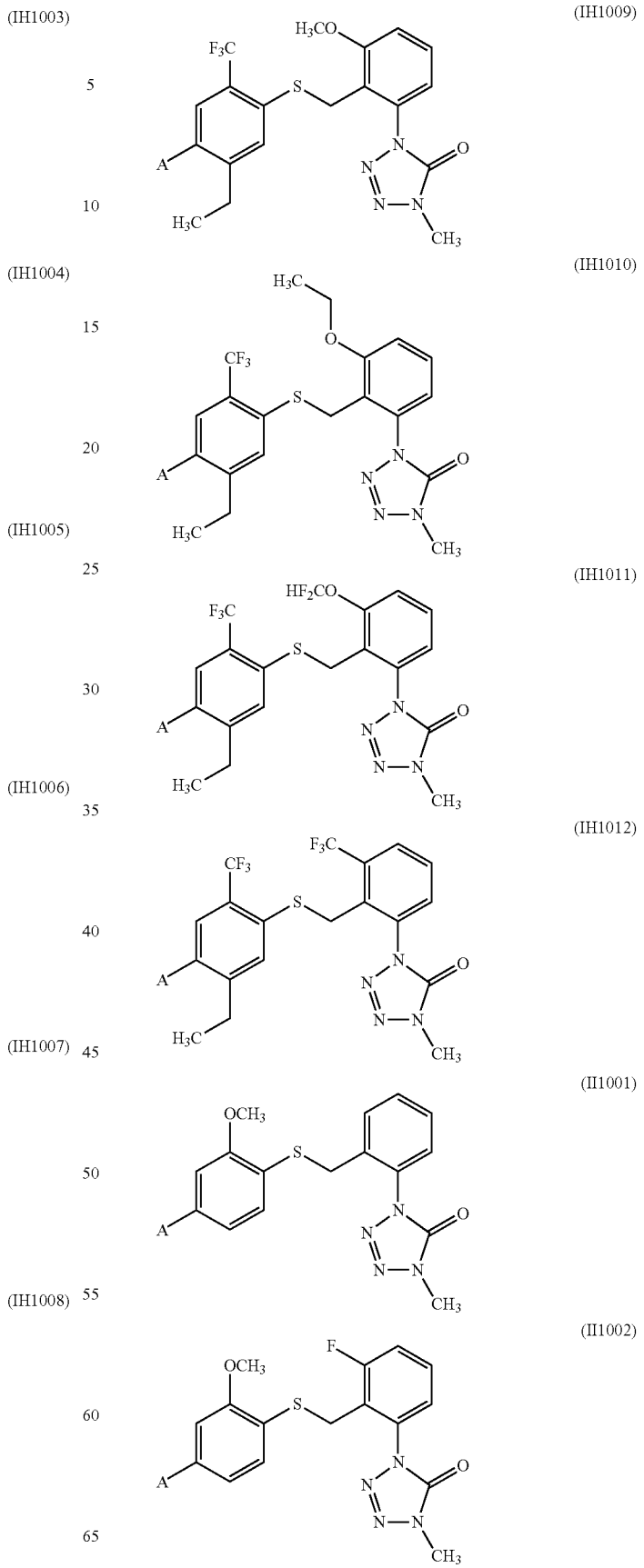

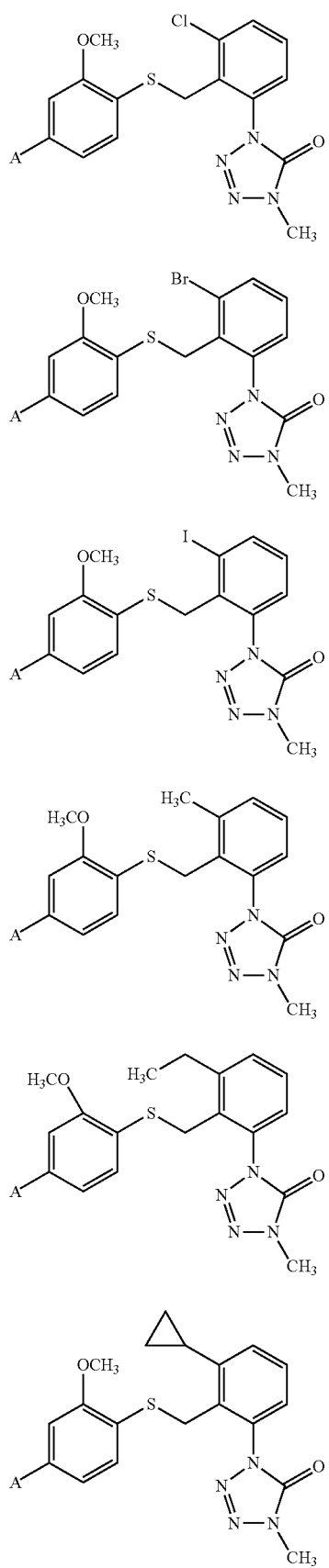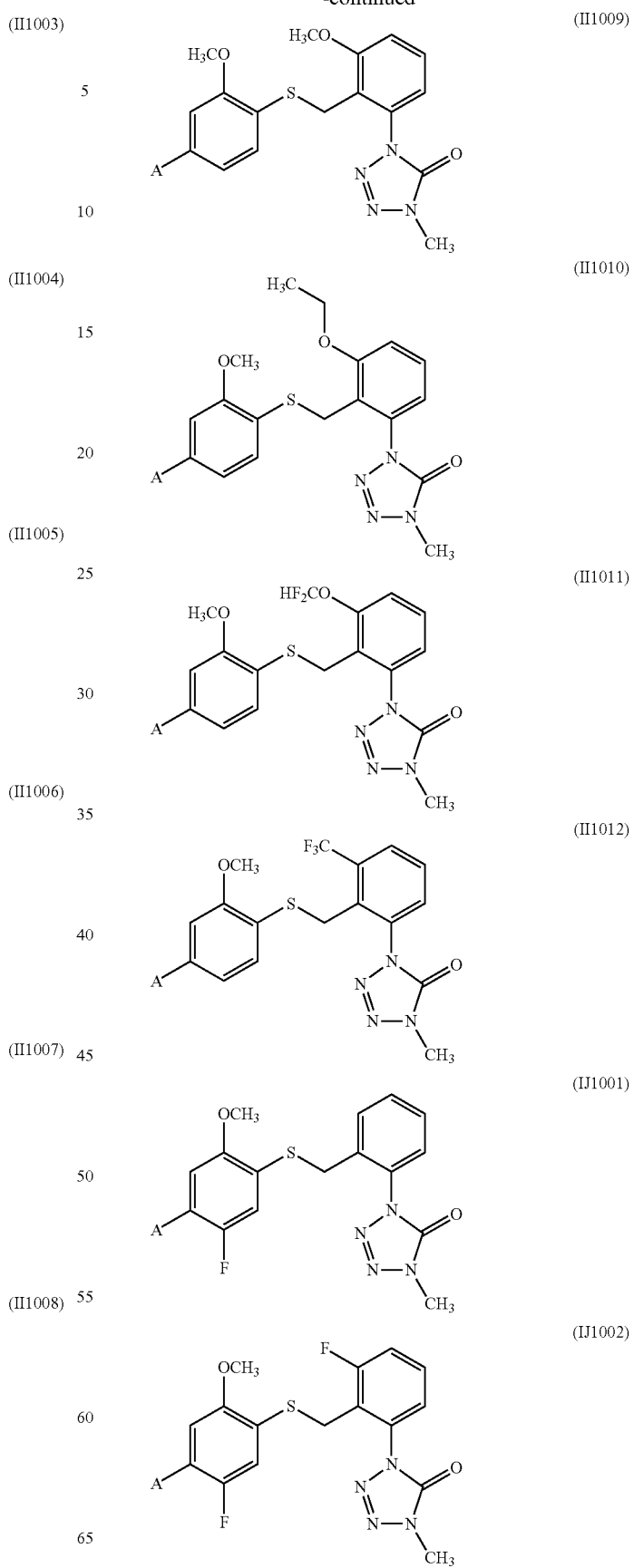

-continued
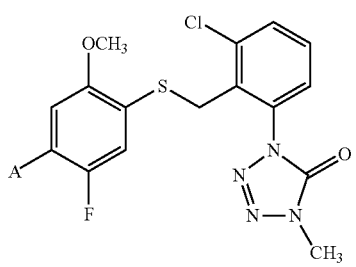 (IJ1003)
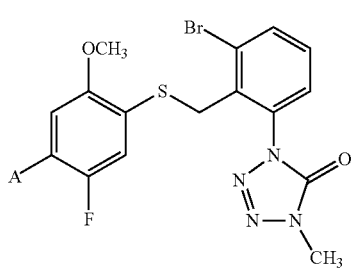 (IJ1004)
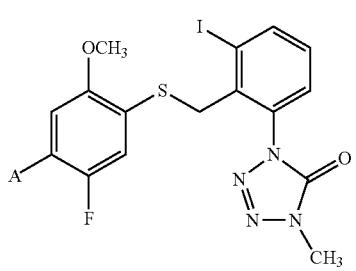 (IJ1005)
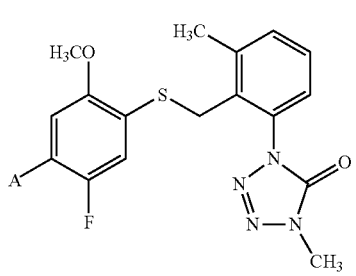 (IJ1006)
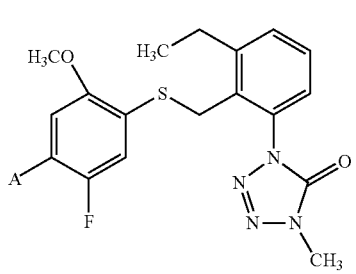 (IJ1007)
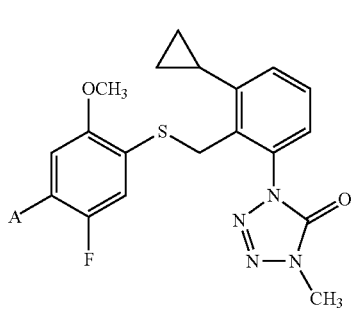 (IJ1008)
-continued
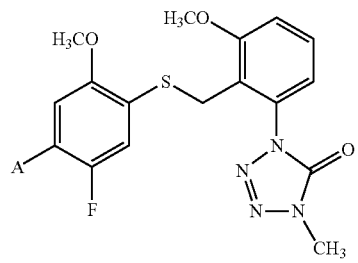 (IJ1009)
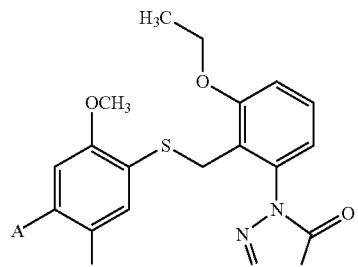 (IJ1010)
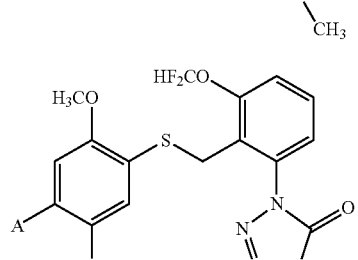 (IJ1011)
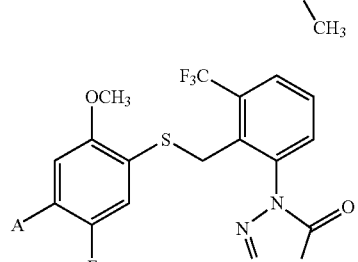 (IJ1012)
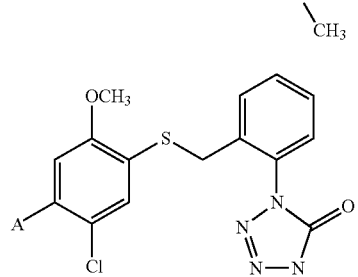 (IK1001)
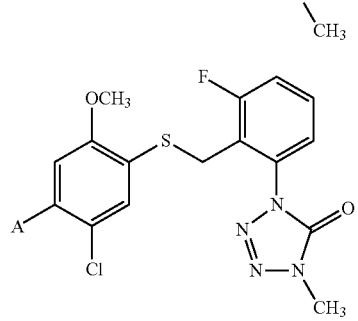 (IK1002)

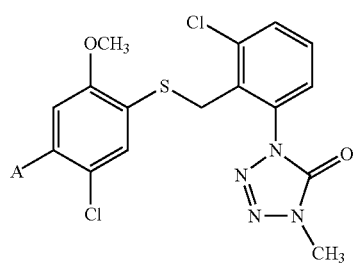
(IK1003)
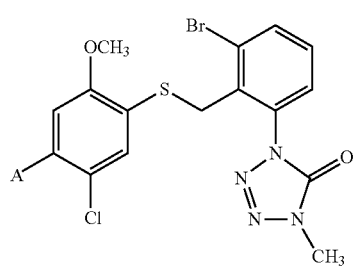
(IK1004)
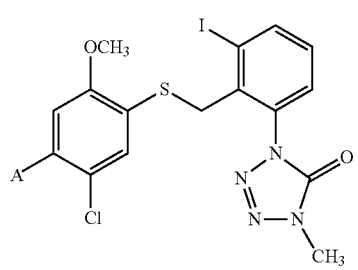
(IK1005)
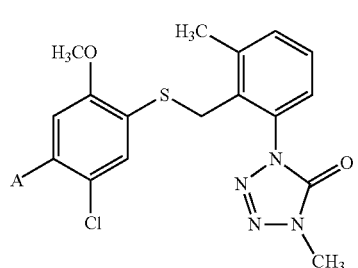
(IK1006)
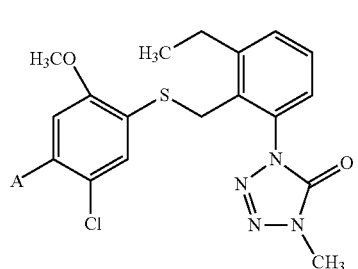
(IK1007)
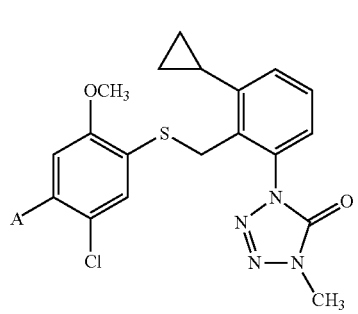
(IK1008)
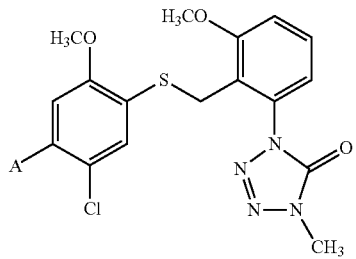
(IK1009)
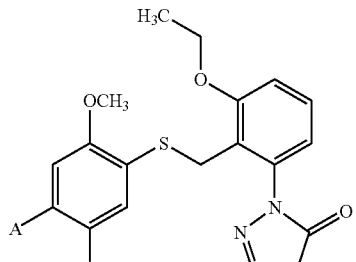
(IK1010)
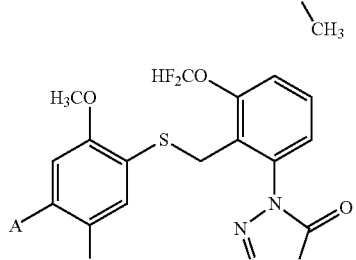
(IK1011)
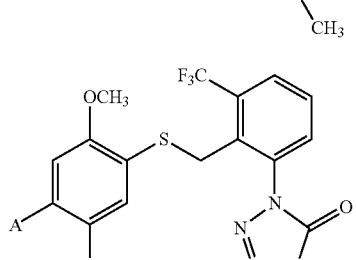
(IK1012)
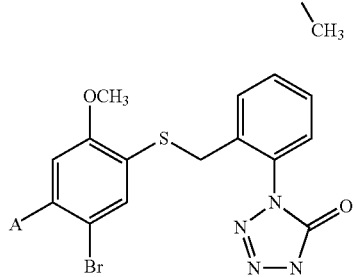
(IL1001)
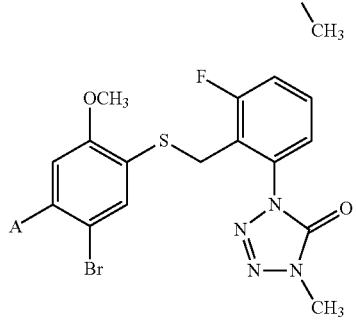
(IL1002)

-continued
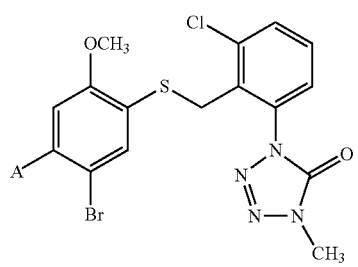 (IL1003)
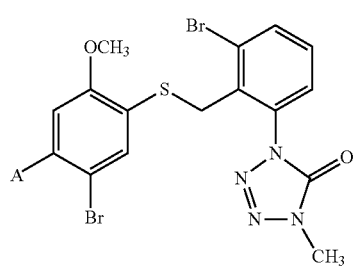 (IL1004)
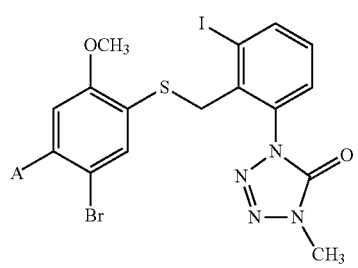 (IL1005)
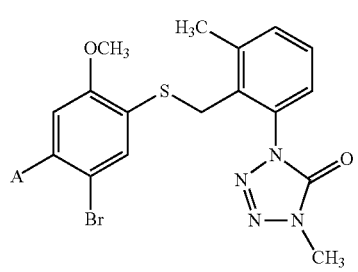 (IL1006)
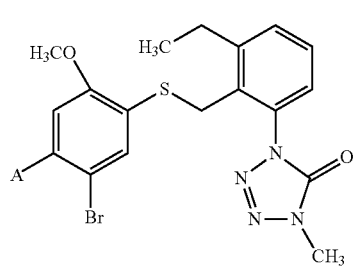 (IL1007)
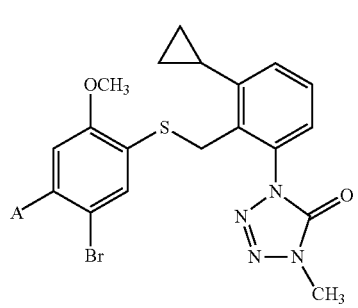 (IL1008)
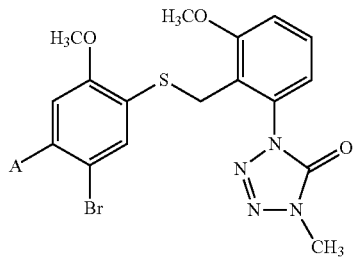 (IL1009)
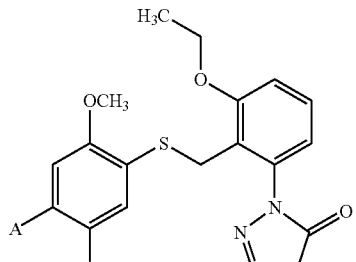 (IL1010)
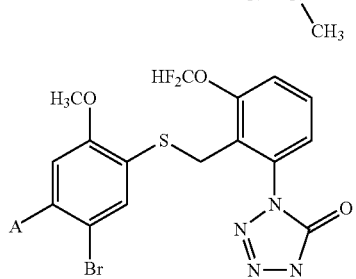 (IL1011)
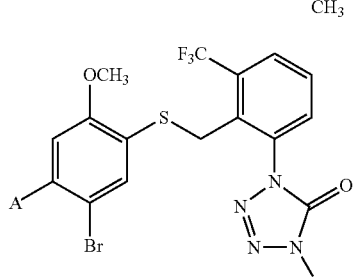 (IL1012)
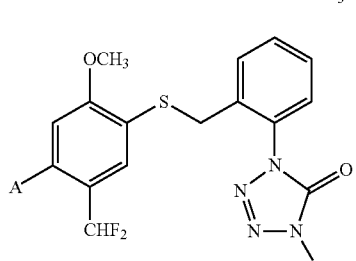 (IM1001)
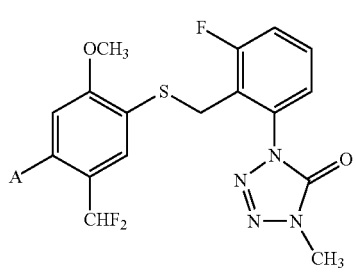 (IM1002)

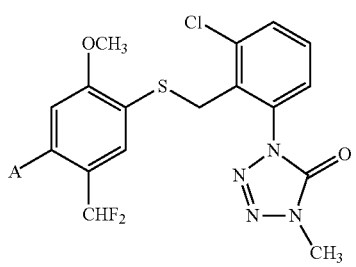
(IM1003)
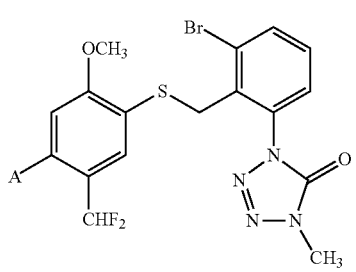
(IM1004)
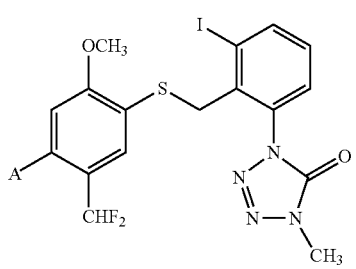
(IM1005)
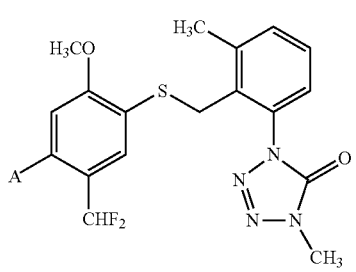
(IM1006)
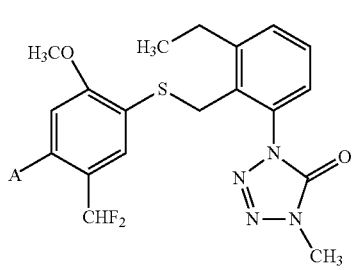
(IM1007)
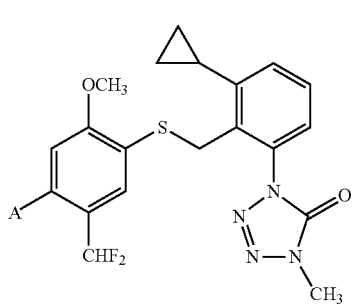
(IM1008)
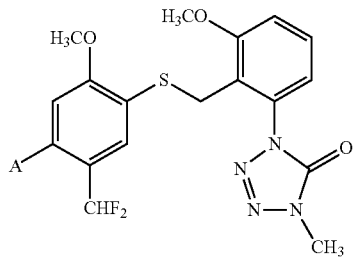
(IM1009)
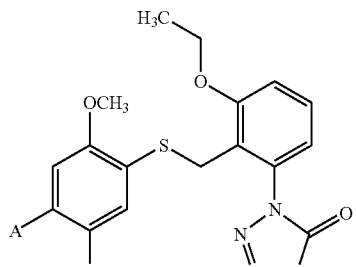
(IM1010)
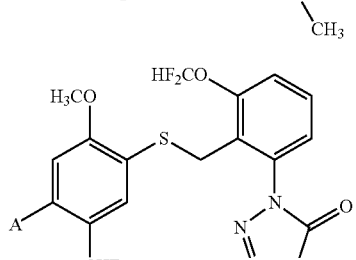
(IM1011)
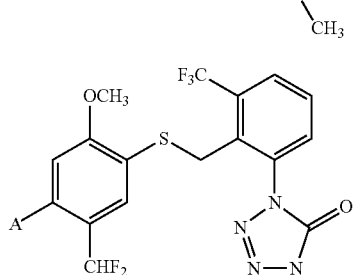
(IM1012)
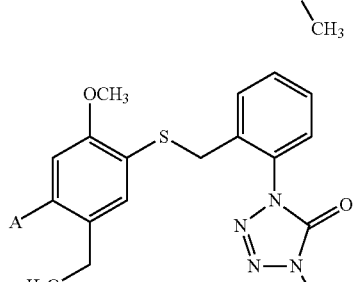
(IN1001)
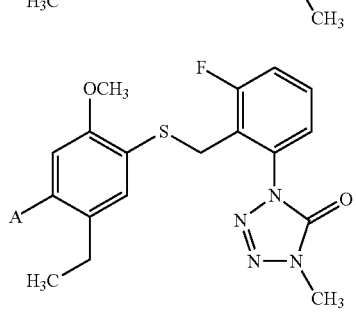
(IN1002)

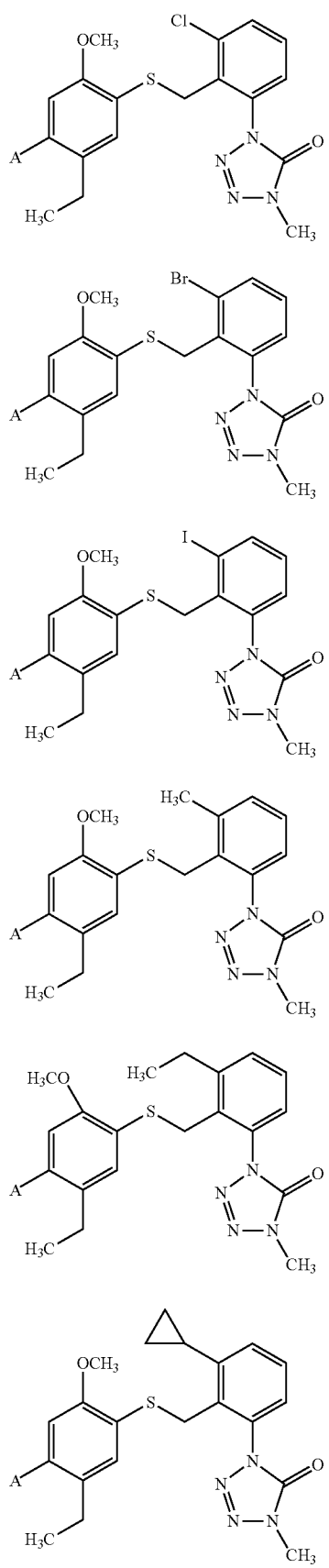
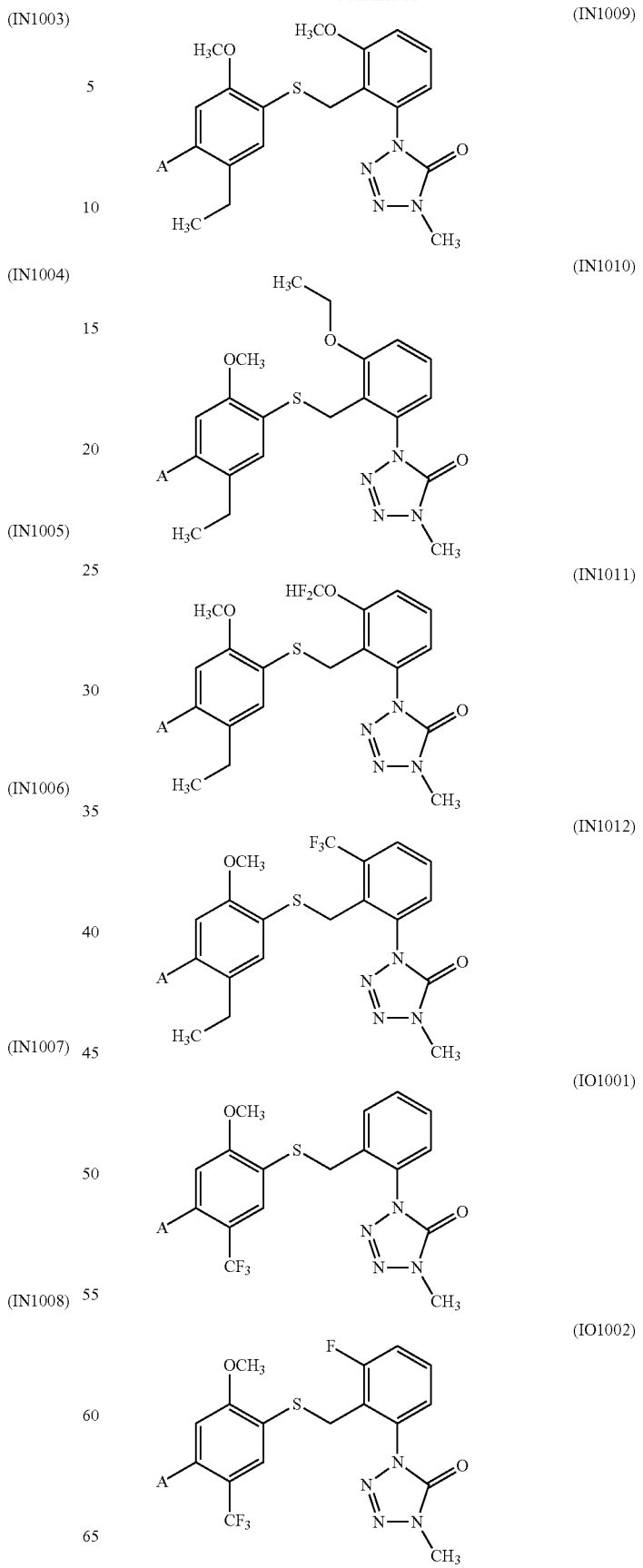

(IO1003) 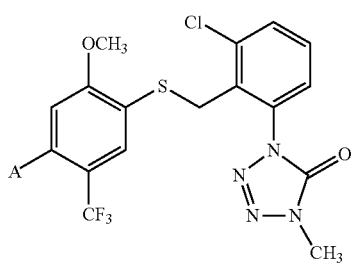

(IO1004) 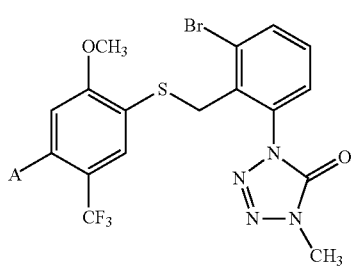

(IO1005) 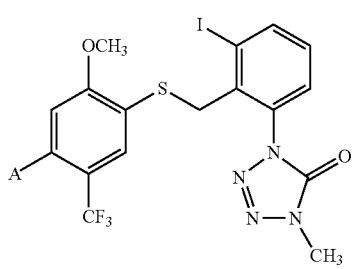

(IO1006) 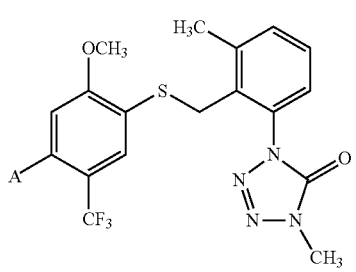

(IO1007) 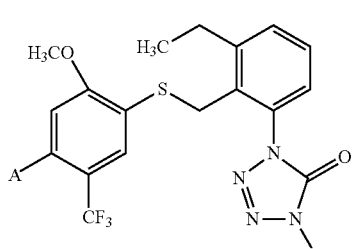

(IO1008) 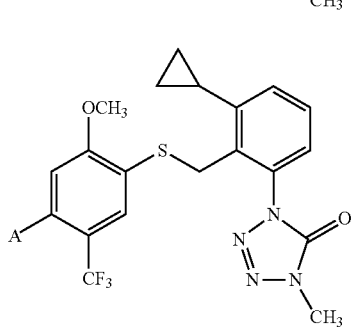

(IO1009) 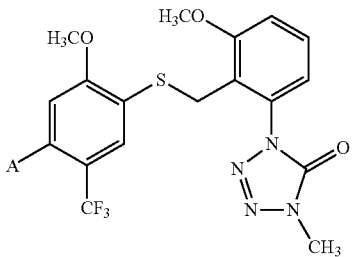

(IO1010) 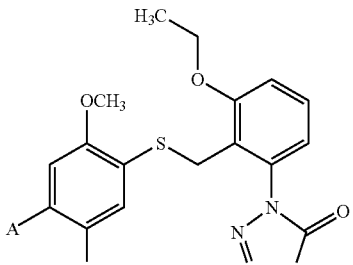

(IO1011) 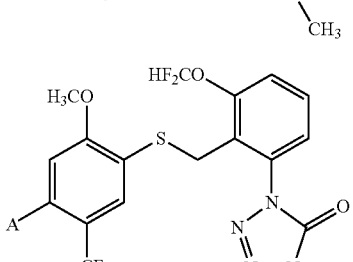

(IO1012) 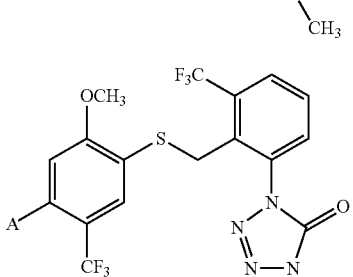

[substituent number; A]; [0001; 3-Me-PYR1], [0002; 3-Me-4-F-PYR1], [0003; 3-Me-4-Cl-PYR1], [0004; 3-Me-4-Br-PYR1], [0005; 3-Me-4-Me-PYR1], [0006; 3-Me-4-Et-PYR1], [0007; 3-Me-4-OMe-PYR1], [0008; 3-Me-4-OEt-PYR1], [0009; 3-Me-4-CN-PYR1], [0010; 3-Me-4-CHF2-PYR1], [0011; 3-Me-4-CF3-PYR1], [0012; 3-Me-4-OCHF2-PYR1], [0013; 3-Me-4-OCF3-PYR1], [0014; 3-Me-5-F-PYR1], [0015; 3-Me-5-Cl-PYR1], [0016; 3-Me-5-Br-PYR1], [0017; 3-Me-5-Me-PYR1], [0018; 3-Me-5-Et-PYR1], [0019; 3-Me-5-OMe-PYR1], [0020; 3-Me-5-OEt-PYR1], [0021; 3-Me-5-CN-PYR1], [0022; 3-Me-5-CHF2-PYR1], [0023; 3-Me-5-CF3-PYR1], [0024; 3-Me-5-OCHF2-PYR1], [0025; 3-Me-5-OCF3-PYR1], [0026; 3-Me-4-F-5-F-PYR1], [0027; 3-Me-4-F-5-Cl-PYR1], [0028; 3-Me-4-F-5-Br-PYR1], [0029; 3-Me-4-F-5-Me-PYR1], [0030; 3-Me-4-F-5-Et-PYR1], [0031; 3-Me-4-F-5-OMe-PYR1], [0032; 3-Me-4-F-5-OEt-PYR1], [0033; 3-Me-4-F-5-CN-PYR1], [0034; 3-Me-4-F-5-CHF2-PYR1], [0035; 3-Me-4-F-5-CF3-PYR1], [0036; 3-Me-4-F-5-OCHF2-PYR1], [0037; 3-Me-4-F-5-OCF3-PYR1], [0038; 3-Me-4-

Cl-5-F-PYR1], [0039; 3-Me-4-Cl-5-Cl-PYR1], [0040; 3-Me-4-Cl-5-Br-PYR1], [0041; 3-Me-4-Cl-5-Me-PYR1], [0042; 3-Me-4-Cl-5-Et-PYR1], [0043; 3-Me-4-Cl-5-OMe-PYR1], [0044; 3-Me-4-Cl-5-OEt-PYR1], [0045; 3-Me-4-Cl-5-CN-PYR1], [0046; 3-Me-4-Cl-5-CHF2-PYR1], [0047; 3-Me-4-Cl-5-CF3-PYR1], [0048; 3-Me-4-Cl-5-OCHF2-PYR1], [0049; 3-Me-4-Cl-5-OCF3-PYR1], [0050; 3-Me-4-Br-5-F-PYR1], [0051; 3-Me-4-Br-5-Cl-PYR1], [0052; 3-Me-4-Br-5-Br-PYR1], [0053; 3-Me-4-Br-5-Me-PYR1], [0054; 3-Me-4-Br-5-Et-PYR1], [0055; 3-Me-4-Br-5-OMe-PYR1], [0056; 3-Me-4-Br-5-OEt-PYR1], [0057; 3-Me-4-Br-5-CN-PYR1], [0058; 3-Me-4-Br-5-CHF2-PYR1], [0059; 3-Me-4-Br-5-CF3-PYR1], [0060; 3-Me-4-Br-5-OCHF2-PYR1], [0061; 3-Me-4-Br-5-OCF3-PYR1], [0062; 3-Me-4-Me-5-F-PYR1], [0063; 3-Me-4-Me-5-Cl-PYR1], [0064; 3-Me-4-Me-5-Br-PYR1], [0065; 3-Me-4-Me-5-Me-PYR1], [0066; 3-Me-4-Me-5-Et-PYR1], [0067; 3-Me-4-Me-5-OMe-PYR1], [0068; 3-Me-4-Me-5-OEt-PYR1], [0069; 3-Me-4-Me-5-CN-PYR1], [0070; 3-Me-4-Me-5-CHF2-PYR1], [0071; 3-Me-4-Me-5-CF3-PYR1], [0072; 3-Me-4-Me-5-OCHF2-PYR1], [0073; 3-Me-4-Me-5-OCF3-PYR1], [0074; 3-Me-4-Et-5-F-PYR1], [0075; 3-Me-4-Et-5-Cl-PYR1], [0076; 3-Me-4-Et-5-Br-PYR1], [0077; 3-Me-4-Et-5-Me-PYR1], [0078; 3-Me-4-Et-5-Et-PYR1], [0079; 3-Me-4-Et-5-OMe-PYR1], [0080; 3-Me-4-Et-5-OEt-PYR1], [0081; 3-Me-4-Et-5-CN-PYR1], [0082; 3-Me-4-Et-5-CHF2-PYR1], [0083; 3-Me-4-Et-5-CF3-PYR1], [0084; 3-Me-4-Et-5-OCHF2-PYR1], [0085; 3-Me-4-Et-5-OCF3-PYR1], [0086; 3-Me-4-OMe-5-F-PYR1], [0087; 3-Me-4-OMe-5-Cl-PYR1], [0088; 3-Me-4-OMe-5-Br-PYR1], [0089; 3-Me-4-OMe-5-Me-PYR1], [0090; 3-Me-4-OMe-5-Et-PYR1], [0091; 3-Me-4-OMe-5-OMe-PYR1], [0092; 3-Me-4-OMe-5-OEt-PYR1], [0093; 3-Me-4-OMe-5-CN-PYR1], [0094; 3-Me-4-OMe-5-CHF2-PYR1], [0095; 3-Me-4-OMe-5-CF3-PYR1], [0096; 3-Me-4-OMe-5-OCHF2-PYR1], [0097; 3-Me-4-OMe-5-OCF3-PYR1], [0098; 3-Me-4-OEt-5-F-PYR1], [0099; 3-Me-4-OEt-5-Cl-PYR1], [0100; 3-Me-4-OEt-5-Br-PYR1],

[0101; 3-Me-4-OEt-5-Me-PYR1], [0102; 3-Me-4-OEt-5-Et-PYR1], [0103; 3-Me-4-OEt-5-OMe-PYR1], [0104; 3-Me-4-OEt-5-OEt-PYR1], [0105; 3-Me-4-OEt-5-CN-PYR1], [0106; 3-Me-4-OEt-5-CHF2-PYR1], [0107; 3-Me-4-OEt-5-CF3-PYR1], [0108; 3-Me-4-OEt-5-OCHF2-PYR1], [0109; 3-Me-4-OEt-5-OCF3-PYR1], [0110; 3-Me-4-CN-5-F-PYR1], [0111; 3-Me-4-CN-5-Cl-PYR1], [0112; 3-Me-4-CN-5-Br-PYR1], [0113; 3-Me-4-CN-5-Me-PYR1], [0114; 3-Me-4-CN-5-Et-PYR1], [0115; 3-Me-4-CN-5-OMe-PYR1], [0116; 3-Me-4-CN-5-OEt-PYR1], [0117; 3-Me-4-CN-5-CN-PYR1], [0118; 3-Me-4-CN-5-CHF2-PYR1], [0119; 3-Me-4-CN-5-CF3-PYR1], [0120; 3-Me-4-CN-5-OCHF2-PYR1], [0121; 3-Me-4-CN-5-OCF3-PYR1], [0122; 3-Me-4-CHF2-5-F-PYR1], [0123; 3-Me-4-CHF2-5-Cl-PYR1], [0124; 3-Me-4-CHF2-5-Br-PYR1], [0125; 3-Me-4-CHF2-5-Me-PYR1], [0126; 3-Me-4-CHF2-5-Et-PYR1], [0127; 3-Me-4-CHF2-5-OMe-PYR1], [0128; 3-Me-4-CHF2-5-OEt-PYR1], [0129; 3-Me-4-CHF2-5-CN-PYR1], [0130; 3-Me-4-CHF2-5-CHF2-PYR1], [0131; 3-Me-4-CHF2-5-CF3-PYR1], [0132; 3-Me-4-CHF2-5-OCHF2-PYR1], [0133; 3-Me-4-CHF2-5-OCF3-PYR1], [0134; 3-Me-4-CF3-5-F-PYR1], [0135; 3-Me-4-CF3-5-Cl-PYR1], [0136; 3-Me-4-CF3-5-Br-PYR1], [0137; 3-Me-4-CF3-5-Me-PYR1], [0138; 3-Me-4-CF3-5-Et-PYR1], [0139; 3-Me-4-CF3-5-OMe-PYR1], [0140; 3-Me-4-CF3-5-OEt-PYR1], [0141; 3-Me-4-CF3-5-CN-PYR1], [0142; 3-Me-4-CF3-5-CHF2-PYR1], [0143; 3-Me-4-CF3-5-CF3-PYR1], [0144; 3-Me-4-CF3-5-OCHF2-PYR1], [0145; 3-Me-4-CF3-5-OCF3-PYR1], [0146; 3-Me-4-OCHF2-5-F-PYR1], [0147; 3-Me-4-OCHF2-5-Cl-PYR1], [0148; 3-Me-4-OCHF2-5-Br-PYR1], [0149; 3-Me-4-OCHF2-5-Me-PYR1], [0150; 3-Me-4-OCHF2-5-Et-PYR1], [0151; 3-Me-4-OCHF2-5-OMe-PYR1], [0152; 3-Me-4-OCHF2-5-OEt-PYR1], [0153; 3-Me-4-OCHF2-5-CN-PYR1], [0154; 3-Me-4-OCHF2-5-CHF2-PYR1], [0155; 3-Me-4-OCHF2-5-CF3-PYR1], [0156; 3-Me-4-OCHF2-5-OCHF2-PYR1], [0157; 3-Me-4-OCHF2-5-OCF3-PYR1], [0158; 3-Me-4-OCF3-5-F-PYR1], [0159; 3-Me-4-OCF3-5-Cl-PYR1], [0160; 3-Me-4-OCF3-5-Br-PYR1], [0161; 3-Me-4-OCF3-5-Me-PYR1], [0162; 3-Me-4-OCF3-5-Et-PYR1], [0163; 3-Me-4-OCF3-5-OMe-PYR1], [0164; 3-Me-4-OCF3-5-OEt-PYR1], [0165; 3-Me-4-OCF3-5-CN-PYR1], [0166; 3-Me-4-OCF3-5-CHF2-PYR1], [0167; 3-Me-4-OCF3-5-CF3-PYR1], [0168; 3-Me-4-OCF3-5-OCHF2-PYR1], [0169; 3-Me-4-OCF3-5-OCF3-PYR1], [0170; PYR1], [0171; 1-Me-PYR3], [0172; 1-Me-4-F-PYR3], [0173; 1-Me-4-Cl-PYR3], [0174; 1-Me-4-Br-PYR3], [0175; 1-Me-4-Me-PYR3], [0176; 1-Me-4-Et-PYR3], [0177; 1-Me-4-OMe-PYR3], [0178; 1-Me-4-OEt-PYR3], [0179; 1-Me-4-CN-PYR3], [0180; 1-Me-4-CHF2-PYR3], [0181; 1-Me-4-CF3-PYR3], [0182; 1-Me-4-OCHF2-PYR3], [0183; 1-Me-4-OCF3-PYR3], [0184; 1-Me-5-F-PYR3], [0185; 1-Me-5-Cl-PYR3], [0186; 1-Me-5-Br-PYR3], [0187; 1-Me-5-Me-PYR3], [0188; 1-Me-5-Et-PYR3], [0189; 1-Me-5-OMe-PYR3], [0190; 1-Me-5-OEt-PYR3], [0191; 1-Me-5-CN-PYR3], [0192; 1-Me-5-CHF2-PYR3], [0193; 1-Me-5-CF3-PYR3], [0194; 1-Me-5-OCHF2-PYR3], [0195; 1-Me-5-OCF3-PYR3], [0196; 1-Me-4-F-5-F-PYR3], [0197; 1-Me-4-F-5-Cl-PYR3], [0198; 1-Me-4-F-5-Br-PYR3], [0199; 1-Me-4-F-5-Me-PYR3], [0200; 1-Me-4-F-5-Et-PYR3],

[0201; 1-Me-4-F-5-OMe-PYR3], [0202; 1-Me-4-F-5-OEt-PYR3], [0203; 1-Me-4-F-5-CN-PYR3], [0204; 1-Me-4-F-5-CHF2-PYR3], [0205; 1-Me-4-F-5-CF3-PYR3], [0206; 1-Me-4-F-5-OCHF2-PYR3], [0207; 1-Me-4-F-5-OCF3-PYR3], [0208; 1-Me-4-Cl-5-F-PYR3], [0209; 1-Me-4-Cl-5-Cl-PYR3], [0210; 1-Me-4-Cl-5-Br-PYR3], [0211; 1-Me-4-Cl-5-Me-PYR3], [0212; 1-Me-4-Cl-5-Et-PYR3], [0213; 1-Me-4-Cl-5-OMe-PYR3], [0214; 1-Me-4-Cl-5-OEt-PYR3], [0215; 1-Me-4-Cl-5-CN-PYR3], [0216; 1-Me-4-Cl-5-CHF2-PYR3], [0217; 1-Me-4-Cl-5-CF3-PYR3], [0218; 1-Me-4-Cl-5-OCHF2-PYR3], [0219; 1-Me-4-Cl-5-OCF3-PYR3], [0220; 1-Me-4-Br-5-F-PYR3], [0221; 1-Me-4-Br-5-Cl-PYR3], [0222; 1-Me-4-Br-5-Br-PYR3], [0223; 1-Me-4-Br-5-Me-PYR3], [0224; 1-Me-4-Br-5-Et-PYR3], [0225; 1-Me-4-Br-5-OMe-PYR3], [0226; 1-Me-4-Br-5-OEt-PYR3], [0227; 1-Me-4-Br-5-CN-PYR3], [0228; 1-Me-4-Br-5-CHF2-PYR3], [0229; 1-Me-4-Br-5-CF3-PYR3], [0230; 1-Me-4-Br-5-OCHF2-PYR3], [0231; 1-Me-4-Br-5-OCF3-PYR3], [0232; 1-Me-4-Me-5-F-PYR3], [0233; 1-Me-4-Me-5-Cl-PYR3], [0234; 1-Me-4-Me-5-Br-PYR3], [0235; 1-Me-4-Me-5-Me-PYR3], [0236; 1-Me-4-Me-5-Et-PYR3], [0237; 1-Me-4-Me-5-OMe-PYR3], [0238; 1-Me-4-Me-5-OEt-PYR3], [0239; 1-Me-4-Me-5-CN-PYR3], [0240; 1-Me-4-Me-5-CHF2-PYR3], [0241; 1-Me-4-Me-5-CF3-PYR3], [0242; 1-Me-4-Me-5-OCHF2-PYR3], [0243; 1-Me-4-Me-5-OCF3-PYR3], [0244; 1-Me-4-Et-5-F-PYR3], [0245; 1-Me-4-Et-5-Cl-PYR3], [0246; 1-Me-4-Et-5-Br-PYR3], [0247; 1-Me-4-Et-5-Me-PYR3], [0248; 1-Me-4-Et-5-Et-PYR3], [0249; 1-Me-4-Et-5-OMe-PYR3], [0250; 1-Me-4-Et-5-OEt-PYR3], [0251; 1-Me-4-Et-5-CN-PYR3], [0252; 1-Me-4-Et-5-CHF2-PYR3], [0253; 1-Me-4-Et-5-CF3-PYR3], [0254; 1-Me-4-Et-5-OCHF2-PYR3], [0255; 1-Me-4-Et-5-OCF3-PYR3], [0256; 1-Me-4-OMe-5-F-PYR3], [0257; 1-Me-4-OMe-5-Cl-PYR3], [0258; 1-Me-4-OMe-5-Br-PYR3], [0259; 1-Me-4-OMe-5-Me-PYR3], [0260; 1-Me-4-OMe-5-Et-PYR3], [0261; 1-Me-4-OMe-5-

OMe-PYR3], [0262; 1-Me-4-OMe-5-OEt-PYR3], [0263; 1-Me-4-OMe-5-CN-PYR3], [0264; 1-Me-4-OMe-5-CHF2-PYR3], [0265; 1-Me-4-OMe-5-CF3-PYR3], [0266; 1-Me-4-OMe-5-OCHF2-PYR3], [0267; 1-Me-4-OMe-5-OCF3-PYR3], [0268; 1-Me-4-OEt-5-F-PYR3], [0269; 1-Me-4-OEt-5-Cl-PYR3], [0270; 1-Me-4-OEt-5-Br-PYR3], [0271; 1-Me-4-OEt-5-Me-PYR3], [0272; 1-Me-4-OEt-5-Et-PYR3], [0273; 1-Me-4-OEt-5-OMe-PYR3], [0274; 1-Me-4-OEt-5-OEt-PYR3], [0275; 1-Me-4-OEt-5-CN-PYR3], [0276; 1-Me-4-OEt-5-CHF2-PYR3], [0277; 1-Me-4-OEt-5-CF3-PYR3], [0278; 1-Me-4-OEt-5-OCHF2-PYR3], [0279; 1-Me-4-OEt-5-OCF3-PYR3], [0280; 1-Me-4-CN-5-F-PYR3], [0281; 1-Me-4-CN-5-Cl-PYR3], [0282; 1-Me-4-CN-5-Br-PYR3], [0283; 1-Me-4-CN-5-Me-PYR3], [0284; 1-Me-4-CN-5-Et-PYR3], [0285; 1-Me-4-CN-5-OMe-PYR3], [0286; 1-Me-4-CN-5-OEt-PYR3], [0287; 1-Me-4-CN-5-CN-PYR3], [0288; 1-Me-4-CN-5-CHF2-PYR3], [0289; 1-Me-4-CN-5-CF3-PYR3], [0290; 1-Me-4-CN-5-OCHF2-PYR3], [0292; 1-Me-4-CN-5-OCF3-PYR3], [0293; 1-Me-4-CHF2-5-F-PYR3], [0294; 1-Me-4-CHF2-5-Cl-PYR3], [0295; 1-Me-4-CHF2-5-Br-PYR3], [0296; 1-Me-4-CHF2-5-Me-PYR3], [0297; 1-Me-4-CHF2-5-Et-PYR3], [0298; 1-Me-4-CHF2-5-OMe-PYR3], [0299; 1-Me-4-CHF2-5-OEt-PYR3], [0300; 1-Me-4-CHF2-5-CN-PYR3],

[0301; 1-Me-4-CHF2-5-CHF2-PYR3], [0302; 1-Me-4-CHF2-5-CF3-PYR3], [0303; 1-Me-4-CHF2-5-OCHF2-PYR3], [0304; 1-Me-4-CHF2-5-OCF3-PYR3], [0305; 1-Me-4-CF3-5-F-PYR3], [0306; 1-Me-4-CF3-5-Cl-PYR3], [0307; 1-Me-4-CF3-5-Br-PYR3], [0308; 1-Me-4-CF3-5-Me-PYR3], [0309; 1-Me-4-CF3-5-Et-PYR3], [0310; 1-Me-4-CF3-5-OMe-PYR3], [0311; 1-Me-4-CF3-5-OEt-PYR3], [0312; 1-Me-4-CF3-5-CN-PYR3], [0313; 1-Me-4-CF3-5-CHF2-PYR3], [0314; 1-Me-4-CF3-5-CF3-PYR3], [0315; 1-Me-4-CF3-5-OCHF2-PYR3], [0316; 1-Me-4-CF3-5-OCF3-PYR3], [0317; 1-Me-4-OCHF2-5-F-PYR3], [0318; 1-Me-4-OCHF2-5-Cl-PYR3], [0319; 1-Me-4-OCHF2-5-Br-PYR3], [0320; 1-Me-4-OCHF2-5-Me-PYR3], [0321; 1-Me-4-OCHF2-5-Et-PYR3], [0322; 1-Me-4-OCHF2-5-OMe-PYR3], [0323; 1-Me-4-OCHF2-5-OEt-PYR3], [0324; 1-Me-4-OCHF2-5-CN-PYR3], [0325; 1-Me-4-OCHF2-5-CHF2-PYR3], [0326; 1-Me-4-OCHF2-5-CF3-PYR3], [0327; 1-Me-4-OCHF2-5-OCHF2-PYR3], [0328; 1-Me-4-OCHF2-5-OCF3-PYR3], [0329; 1-Me-4-OCF3-5-F-PYR3], [0330; 1-Me-4-OCF3-5-Cl-PYR3], [0331; 1-Me-4-OCF3-5-Br-PYR3], [0332; 1-Me-4-OCF3-5-Me-PYR3], [0333; 1-Me-4-OCF3-5-Et-PYR3], [0334; 1-Me-4-OCF3-5-OMe-PYR3], [0335; 1-Me-4-OCF3-5-OEt-PYR3], [0336; 1-Me-4-OCF3-5-CN-PYR3], [0337; 1-Me-4-OCF3-5-CHF2-PYR3], [0338; 1-Me-4-OCF3-5-CF3-PYR3], [0339; 1-Me-4-OCF3-5-OCHF2-PYR3], [0340; 1-Me-4-OCF3-5-OCF3-PYR3], [0341; 2-Me-PYR3], [0342; 2-Me-4-F-PYR3], [0343; 2-Me-4-Cl-PYR3], [0344; 2-Me-4-Br-PYR3], [0345; 2-Me-4-Me-PYR3], [0346; 2-Me-4-Et-PYR3], [0347; 2-Me-4-OMe-PYR3], [0348; 2-Me-4-OEt-PYR3], [0349; 2-Me-4-CN-PYR3], [0350; 2-Me-4-CHF2-PYR3], [0351; 2-Me-4-CF3-PYR3], [0352; 2-Me-4-OCHF2-PYR3], [0353; 2-Me-4-OCF3-PYR3], [0354; 2-Me-5-F-PYR3], [0355; 2-Me-5-Cl-PYR3], [0356; 2-Me-5-Br-PYR3], [0357; 2-Me-5-Me-PYR3], [0358; 2-Me-5-Et-PYR3], [0359; 2-Me-5-OMe-PYR3], [0360; 2-Me-5-OEt-PYR3], [0361; 2-Me-5-CN-PYR3], [0362; 2-Me-5-CHF2-PYR3], [0363; 2-Me-5-CF3-PYR3], [0364; 2-Me-5-OCHF2-PYR3], [0365; 2-Me-5-OCF3-PYR3], [0366; 2-Me-4-F-5-F-PYR3], [0367; 2-Me-4-F-5-Cl-PYR3], [0368; 2-Me-4-F-5-Br-PYR3], [0369; 2-Me-4-F-5-Me-PYR3], [0370; 2-Me-4-F-5-Et-PYR3], [0371; 2-Me-4-F-5-OMe-PYR3], [0372; 2-Me-4-F-5-OEt-PYR3], [0373; 2-Me-4-F-5-CN-PYR3], [0374; 2-Me-4-F-5-CHF2-PYR3], [0375; 2-Me-4-F-5-CF3-PYR3], [0376; 2-Me-4-F-5-OCHF2-PYR3], [0377; 2-Me-4-F-5-OCF3-PYR3], [0378; 2-Me-4-Cl-5-F-PYR3], [0379; 2-Me-4-Cl-5-Cl-PYR3], [0380; 2-Me-4-Cl-5-Br-PYR3], [0381; 2-Me-4-Cl-5-Me-PYR3], [0382; 2-Me-4-Cl-5-Et-PYR3], [0383; 2-Me-4-Cl-5-OMe-PYR3], [0384; 2-Me-4-Cl-5-OEt-PYR3], [0385; 2-Me-4-Cl-5-CN-PYR3], [0386; 2-Me-4-Cl-5-CHF2-PYR3], [0387; 2-Me-4-Cl-5-CF3-PYR3], [0388; 2-Me-4-Cl-5-OCHF2-PYR3], [0389; 2-Me-4-Cl-5-OCF3-PYR3], [0390; 2-Me-4-Br-5-F-PYR3], [0391; 2-Me-4-Br-5-Cl-PYR3], [0392; 2-Me-4-Br-5-Br-PYR3], [0393; 2-Me-4-Br-5-Me-PYR3], [0394; 2-Me-4-Br-5-Et-PYR3], [0395; 2-Me-4-Br-5-OMe-PYR3], [0396; 2-Me-4-Br-5-OEt-PYR3], [0397; 2-Me-4-Br-5-CN-PYR3], [0398; 2-Me-4-Br-5-CHF2-PYR3], [0399; 2-Me-4-Br-5-CF3-PYR3], [0400; 2-Me-4-Br-5-OCHF2-PYR3],

[0401; 2-Me-4-Br-5-OCF3-PYR3], [0402; 2-Me-4-Me-5-F-PYR3], [0403; 2-Me-4-Me-5-Cl-PYR3], [0404; 2-Me-4-Me-5-Br-PYR3], [0405; 2-Me-4-Me-5-Me-PYR3], [0406; 2-Me-4-Me-5-Et-PYR3], [0407; 2-Me-4-Me-5-OMe-PYR3], [0408; 2-Me-4-Me-5-OEt-PYR3], [0409; 2-Me-4-Me-5-CN-PYR3], [0410; 2-Me-4-Me-5-CHF2-PYR3], [0411; 2-Me-4-Me-5-CF3-PYR3], [0412; 2-Me-4-Me-5-OCHF2-PYR3], [0413; 2-Me-4-Me-5-OCF3-PYR3], [0414; 2-Me-4-Et-5-F-PYR3], [0415; 2-Me-4-Et-5-Cl-PYR3], [0416; 2-Me-4-Et-5-Br-PYR3], [0417; 2-Me-4-Et-5-Me-PYR3], [0418; 2-Me-4-Et-5-Et-PYR3], [0419; 2-Me-4-Et-5-OMe-PYR3], [0420; 2-Me-4-Et-5-OEt-PYR3], [0421; 2-Me-4-Et-5-CN-PYR3], [0422; 2-Me-4-Et-5-CHF2-PYR3], [0423; 2-Me-4-Et-5-CF3-PYR3], [0424; 2-Me-4-Et-5-OCHF2-PYR3], [0425; 2-Me-4-Et-5-OCF3-PYR3], [0426; 2-Me-4-OMe-5-F-PYR3], [0427; 2-Me-4-OMe-5-Cl-PYR3], [0428; 2-Me-4-OMe-5-Br-PYR3], [0429; 2-Me-4-OMe-5-Me-PYR3], [0430; 2-Me-4-OMe-5-Et-PYR3], [0431; 2-Me-4-OMe-5-OMe-PYR3], [0432; 2-Me-4-OMe-5-OEt-PYR3], [0433; 2-Me-4-OMe-5-CN-PYR3], [0434; 2-Me-4-OMe-5-CHF2-PYR3], [0435; 2-Me-4-OMe-5-CF3-PYR3], [0436; 2-Me-4-OMe-5-OCHF2-PYR3], [0437; 2-Me-4-OMe-5-OCF3-PYR3], [0438; 2-Me-4-OEt-5-F-PYR3], [0439; 2-Me-4-OEt-5-Cl-PYR3], [0440; 2-Me-4-OEt-5-Br-PYR3], [0441; 2-Me-4-OEt-5-Me-PYR3], [0442; 2-Me-4-OEt-5-Et-PYR3], [0443; 2-Me-4-OEt-5-OMe-PYR3], [0444; 2-Me-4-OEt-5-OEt-PYR3], [0445; 2-Me-4-OEt-5-CN-PYR3], [0446; 2-Me-4-OEt-5-CHF2-PYR3], [0447; 2-Me-4-OEt-5-CF3-PYR3], [0448; 2-Me-4-OEt-5-OCHF2-PYR3], [0449; 2-Me-4-OEt-5-OCF3-PYR3], [0450; 2-Me-4-CN-5-F-PYR3], [0451; 2-Me-4-CN-5-Cl-PYR3], [0452; 2-Me-4-CN-5-Br-PYR3], [0453; 2-Me-4-CN-5-Me-PYR3], [0454; 2-Me-4-CN-5-Et-PYR3], [0455; 2-Me-4-CN-5-OMe-PYR3], [0456; 2-Me-4-CN-5-OEt-PYR3], [0457; 2-Me-4-CN-5-CN-PYR3], [0458; 2-Me-4-CN-5-CHF2-PYR3], [0459; 2-Me-4-CN-5-CF3-PYR3], [0460; 2-Me-4-CN-5-OCHF2-PYR3], [0461; 2-Me-4-CN-5-OCF3-PYR3], [0462; 2-Me-4-CHF2-5-F-PYR3], [0463; 2-Me-4-CHF2-5-Cl-PYR3], [0464; 2-Me-4-CHF2-5-Br-PYR3], [0465; 2-Me-4-CHF2-5-Me-PYR3], [0466; 2-Me-4-CHF2-5-Et-PYR3], [0467; 2-Me-4-CHF2-5-OMe-PYR3], [0468; 2-Me-4-CHF2-5-OEt-PYR3], [0469; 2-Me-4-CHF2-5-CN-PYR3], [0470; 2-Me-4-CHF2-5-CHF2-PYR3], [0471; 2-Me-4-CHF2-5-CF3-PYR3], [0472; 2-Me-4-CHF2-5-OCHF2-PYR3], [0473; 2-Me-4-CHF2-5-OCF3-PYR3], [0474; 2-Me-4-CF3-5-F-PYR3], [0475; 2-Me-4-CF3-5-Cl-PYR3], [0476; 2-Me-4-CF3-5-Br-PYR3], [0477; 2-Me-4-CF3-5-Me-PYR3], [0478; 2-Me-4-CF3-5-Et-PYR3], [0479; 2-Me-4-CF3-5-OMe-PYR3], [0480; 2-Me-

4-CF3-5-OEt-PYR3], [0481; 2-Me-4-CF3-5-CN-PYR3], [0482; 2-Me-4-CF3-5-CHF2-PYR3], [0483; 2-Me-4-CF3-5-CF3-PYR3], [0484; 2-Me-4-CF3-5-OCHF2-PYR3], [0485; 2-Me-4-CF3-5-OCF3-PYR3], [0486; 2-Me-4-OCHF2-5-F-PYR3], [0487; 2-Me-4-OCHF2-5-Cl-PYR3], [0488; 2-Me-4-OCHF2-5-Br-PYR3], [0489; 2-Me-4-OCHF2-5-Me-PYR3], [0490; 2-Me-4-OCHF2-5-Et-PYR3], [0491; 2-Me-4-OCHF2-5-OMe-PYR3], [0492; 2-Me-4-OCHF2-5-OEt-PYR3], [0493; 2-Me-4-OCHF2-5-CN-PYR3], [0494; 2-Me-4-OCHF2-5-CHF2-PYR3], [0495; 2-Me-4-OCHF2-5-CF3-PYR3], [0496; 2-Me-4-OCHF2-5-OCHF2-PYR3], [0497; 2-Me-4-OCHF2-5-OCF3-PYR3], [0498; 2-Me-4-OCF3-5-F-PYR3], [0499; 2-Me-4-OCF3-5-Cl-PYR3], [0500; 2-Me-4-OCF3-5-Br-PYR3],

[0501; 2-Me-4-OCF3-5-Me-PYR3], [0502; 2-Me-4-OCF3-5-Et-PYR3], [0503; 2-Me-4-OCF3-5-OMe-PYR3], [0504; 2-Me-4-OCF3-5-OEt-PYR3], [0505; 2-Me-4-OCF3-5-CN-PYR3], [0506; 2-Me-4-OCF3-5-CHF2-PYR3], [0507; 2-Me-4-OCF3-5-CF3-PYR3], [0508; 2-Me-4-OCF3-5-OCHF2-PYR3], [0509; 2-Me-4-OCF3-5-OCF3-PYR3], [0510; 1-Me-PYR4], [0511; 1-Me-3-F-PYR4], [0512; 1-Me-3-Cl-PYR4], [0513; 1-Me-3-Br-PYR4], [0514; 1-Me-3-Me-PYR4], [0515; 1-Me-3-Et-PYR4], [0516; 1-Me-3-OMe-PYR4], [0517; 1-Me-3-OEt-PYR4], [0518; 1-Me-3-CN-PYR4], [0519; 1-Me-3-CHF2-PYR4], [0520; 1-Me-3-CF3-PYR4], [0521; 1-Me-3-OCHF2-PYR4], [0522; 1-Me-3-OCF3-PYR4], [0523; 1-Me-5-F-PYR4], [0524; 1-Me-5-Cl-PYR4], [0525; 1-Me-5-Br-PYR4], [0526; 1-Me-5-Me-PYR4], [0527; 1-Me-5-Et-PYR4], [0528; 1-Me-5-OMe-PYR4], [0529; 1-Me-5-OEt-PYR4], [0530; 1-Me-5-CN-PYR4], [0531; 1-Me-5-CHF2-PYR4], [0532; 1-Me-5-CF3-PYR4], [0533; 1-Me-5-OCHF2-PYR4], [0534; 1-Me-5-OCF3-PYR4], [0535; 1-Me-3-F-5-F-PYR4], [0536; 1-Me-3-F-5-Cl-PYR4], [0537; 1-Me-3-F-5-Br-PYR4], [0538; 1-Me-3-F-5-Me-PYR4], [0539; 1-Me-3-F-5-Et-PYR4], [0540; 1-Me-3-F-5-OMe-PYR4], [0541; 1-Me-3-F-5-OEt-PYR4], [0542; 1-Me-3-F-5-CN-PYR4], [0543; 1-Me-3-F-5-CHF2-PYR4], [0544; 1-Me-3-F-5-CF3-PYR4], [0545; 1-Me-3-F-5-OCHF2-PYR4], [0546; 1-Me-3-F-5-OCF3-PYR4], [0547; 1-Me-3-Cl-5-F-PYR4], [0548; 1-Me-3-Cl-5-Cl-PYR4], [0549; 1-Me-3-Cl-5-Br-PYR4], [0550; 1-Me-3-Cl-5-Me-PYR4], [0551; 1-Me-3-Cl-5-Et-PYR4], [0552; 1-Me-3-Cl-5-OMe-PYR4], [0553; 1-Me-3-Cl-5-OEt-PYR4], [0554; 1-Me-3-Cl-5-CN-PYR4], [0555; 1-Me-3-Cl-5-CHF2-PYR4], [0556; 1-Me-3-Cl-5-CF3-PYR4], [0557; 1-Me-3-Cl-5-OCHF2-PYR4], [0558; 1-Me-3-Cl-5-OCF3-PYR4], [0559; 1-Me-3-Br-5-F-PYR4], [0560; 1-Me-3-Br-5-Cl-PYR4], [0561; 1-Me-3-Br-5-Br-PYR4], [0562; 1-Me-3-Br-5-Me-PYR4], [0563; 1-Me-3-Br-5-Et-PYR4], [0564; 1-Me-3-Br-5-OMe-PYR4], [0565; 1-Me-3-Br-5-OEt-PYR4], [0566; 1-Me-3-Br-5-CN-PYR4], [0567; 1-Me-3-Br-5-CHF2-PYR4], [0568; 1-Me-3-Br-5-CF3-PYR4], [0569; 1-Me-3-Br-5-OCHF2-PYR4], [0570; 1-Me-3-Br-5-OCF3-PYR4], [0571; 1-Me-3-Me-5-F-PYR4], [0572; 1-Me-3-Me-5-Cl-PYR4], [0573; 1-Me-3-Me-5-Br-PYR4], [0574; 1-Me-3-Me-5-Me-PYR4], [0575; 1-Me-3-Me-5-Et-PYR4], [0576; 1-Me-3-Me-5-OMe-PYR4], [0577; 1-Me-3-Me-5-OEt-PYR4], [0578; 1-Me-3-Me-5-CN-PYR4], [0579; 1-Me-3-Me-5-CHF2-PYR4], [0580; 1-Me-3-Me-5-CF3-PYR4], [0581; 1-Me-3-Me-5-OCHF2-PYR4], [0582; 1-Me-3-Me-5-OCF3-PYR4], [0583; 1-Me-3-Et-5-F-PYR4], [0584; 1-Me-3-Et-5-Cl-PYR4], [0585; 1-Me-3-Et-5-Br-PYR4], [0586; 1-Me-3-Et-5-Me-PYR4], [0587; 1-Me-3-Et-5-Et-PYR4], [0588; 1-Me-3-Et-5-OMe-PYR4], [0589; 1-Me-3-Et-5-OEt-PYR4], [0590; 1-Me-3-Et-5-CN-PYR4], [0591; 1-Me-3-Et-5-CHF2-PYR4], [0592; 1-Me-3-Et-5-CF3-PYR4], [0593; 1-Me-3-Et-5-OCHF2-PYR4], [0594; 1-Me-3-Et-5-OCF3-PYR4], [0595; 1-Me-3-OMe-5-F-PYR4], [0596; 1-Me-3-OMe-5-Cl-PYR4], [0597; 1-Me-3-OMe-5-Br-PYR4], [0598; 1-Me-3-OMe-5-Me-PYR4], [0599; 1-Me-3-OMe-5-Et-PYR4], [0600; 1-Me-3-OMe-5-OMe-PYR4],

[0601; 1-Me-3-OMe-5-OEt-PYR4], [0602; 1-Me-3-OMe-5-CN-PYR4], [0603; 1-Me-3-OMe-5-CHF2-PYR4], [0604; 1-Me-3-OMe-5-CF3-PYR4], [0605; 1-Me-3-OMe-5-OCHF2-PYR4], [0606; 1-Me-3-OMe-5-OCF3-PYR4], [0607; 1-Me-3-OEt-5-F-PYR4], [0608; 1-Me-3-OEt-5-Cl-PYR4], [0609; 1-Me-3-OEt-5-Br-PYR4], [0610; 1-Me-3-OEt-5-Me-PYR4], [0611; 1-Me-3-OEt-5-Et-PYR4], [0612; 1-Me-3-OEt-5-OMe-PYR4], [0613; 1-Me-3-OEt-5-OEt-PYR4], [0614; 1-Me-3-OEt-5-CN-PYR4], [0615; 1-Me-3-OEt-5-CHF2-PYR4], [0616; 1-Me-3-OEt-5-CF3-PYR4], [0617; 1-Me-3-OEt-5-OCHF2-PYR4], [0618; 1-Me-3-OEt-5-OCF3-PYR4], [0619; 1-Me-3-CN-5-F-PYR4], [0620; 1-Me-3-CN-5-Cl-PYR4], [0621; 1-Me-3-CN-5-Br-PYR4], [0622; 1-Me-3-CN-5-Me-PYR4], [0623; 1-Me-3-CN-5-Et-PYR4], [0624; 1-Me-3-CN-5-OMe-PYR4], [0625; 1-Me-3-CN-5-OEt-PYR4], [0626; 1-Me-3-CN-5-CN-PYR4], [0627; 1-Me-3-CN-5-CHF2-PYR4], [0628; 1-Me-3-CN-5-CF3-PYR4], [0629; 1-Me-3-CN-5-OCHF2-PYR4], [0630; 1-Me-3-CN-5-OCF3-PYR4], [0631; 1-Me-3-CHF2-5-F-PYR4], [0632; 1-Me-3-CHF2-5-Cl-PYR4], [0633; 1-Me-3-CHF2-5-Br-PYR4], [0634; 1-Me-3-CHF2-5-Me-PYR4], [0635; 1-Me-3-CHF2-5-Et-PYR4], [0636; 1-Me-3-CHF2-5-OMe-PYR4], [0637; 1-Me-3-CHF2-5-OEt-PYR4], [0638; 1-Me-3-CHF2-5-CN-PYR4], [0639; 1-Me-3-CHF2-5-CHF2-PYR4], [0640; 1-Me-3-CHF2-5-CF3-PYR4], [0641; 1-Me-3-CHF2-5-OCHF2-PYR4], [0642; 1-Me-3-CHF2-5-OCF3-PYR4], [0643; 1-Me-3-CF3-5-F-PYR4], [0644; 1-Me-3-CF3-5-Cl-PYR4], [0645; 1-Me-3-CF3-5-Br-PYR4], [0646; 1-Me-3-CF3-5-Me-PYR4], [0647; 1-Me-3-CF3-5-Et-PYR4], [0648; 1-Me-3-CF3-5-OMe-PYR4], [0649; 1-Me-3-CF3-5-OEt-PYR4], [0650; 1-Me-3-CF3-5-CN-PYR4], [0651; 1-Me-3-CF3-5-CHF2-PYR4], [0652; 1-Me-3-CF3-5-CF3-PYR4], [0653; 1-Me-3-CF3-5-OCHF2-PYR4], [0654; 1-Me-3-CF3-5-OCF3-PYR4], [0655; 1-Me-3-OCHF2-5-F-PYR4], [0656; 1-Me-3-OCHF2-5-Cl-PYR4], [0657; 1-Me-3-OCHF2-5-Br-PYR4], [0658; 1-Me-3-OCHF2-5-Me-PYR4], [0659; 1-Me-3-OCHF2-5-Et-PYR4], [0660; 1-Me-3-OCHF2-5-OMe-PYR4], [0661; 1-Me-3-OCHF2-5-OEt-PYR4], [0662; 1-Me-3-OCHF2-5-CN-PYR4], [0663; 1-Me-3-OCHF2-5-CHF2-PYR4], [0664; 1-Me-3-OCHF2-5-CF3-PYR4], [0665; 1-Me-3-OCHF2-5-OCHF2-PYR4], [0666; 1-Me-3-OCHF2-5-OCF3-PYR4], [0667; 1-Me-3-OCF3-5-F-PYR4], [0668; 1-Me-3-OCF3-5-Cl-PYR4], [0669; 1-Me-3-OCF3-5-Br-PYR4], [0670; 1-Me-3-OCF3-5-Me-PYR4], [0671; 1-Me-3-OCF3-5-Et-PYR4], [0672; 1-Me-3-OCF3-5-OMe-PYR4], [0673; 1-Me-3-OCF3-5-OEt-PYR4], [0674; 1-Me-3-OCF3-5-CN-PYR4], [0675; 1-Me-3-OCF3-5-CHF2-PYR4], [0676; 1-Me-3-OCF3-5-CF3-PYR4], [0677; 1-Me-3-OCF3-5-OCHF2-PYR4], [0678; 1-Me-3-OCF3-5-OCF3-PYR4], [0679; 2-Me-PYR4], [0680; 2-Me-3-F-PYR4], [0681; 2-Me-3-Cl-PYR4], [0682; 2-Me-3-Br-PYR4], [0683; 2-Me-3-Me-PYR4], [0684; 2-Me-3-Et-PYR4], [0685; 2-Me-3-OMe-PYR4], [0686; 2-Me-3-OEt-PYR4], [0687; 2-Me-3-CN-PYR4], [0688; 2-Me-3-CHF2-PYR4], [0689; 2-Me-3-CF3-PYR4], [0690; 2-Me-3-OCHF2-PYR4], [0691; 2-Me-3-OCF3-PYR4], [0692; 2-Me-5-F-PYR4], [0693; 2-Me-5-Cl-PYR4], [0694; 2-Me-5-Br-PYR4], [0695; 2-Me-5-Me-PYR4], [0696; 2-Me-5-Et-PYR4], [0697; 2-Me-5-OMe-PYR4], [0698; 2-Me-5-OEt-PYR4], [0699; 2-Me-5-CN-PYR4], [0700; 2-Me-5-CHF2-PYR4],

[0701; 2-Me-5-CF3-PYR4], [0702; 2-Me-5-OCHF2-PYR4], [0703; 2-Me-5-OCF3-PYR4], [0705; 2-Me-3-F-5-F-PYR4], [0706; 2-Me-3-F-5-Cl-PYR4], [0707; 2-Me-3-F-5-Br-PYR4], [0708; 2-Me-3-F-5-Me-PYR4], [0709; 2-Me-3-F-5-Et-PYR4], [0710; 2-Me-3-F-5-OMe-PYR4], [0711; 2-Me-3-F-5-OEt-PYR4], [0712; 2-Me-3-F-5-CN-PYR4], [0713; 2-Me-3-F-5-CHF2-PYR4], [0714; 2-Me-3-F-5-CF3-PYR4], [0715; 2-Me-3-F-5-OCHF2-PYR4], [0716; 2-Me-3-F-5-OCF3-PYR4], [0717; 2-Me-3-Cl-5-F-PYR4], [0718; 2-Me-3-Cl-5-Cl-PYR4], [0719; 2-Me-3-Cl-5-Br-PYR4], [0720; 2-Me-3-Cl-5-Me-PYR4], [0721; 2-Me-3-Cl-5-Et-PYR4], [0722; 2-Me-3-Cl-5-OMe-PYR4], [0723; 2-Me-3-Cl-5-OEt-PYR4], [0724; 2-Me-3-Cl-5-CN-PYR4], [0725; 2-Me-3-Cl-5-CHF2-PYR4], [0726; 2-Me-3-Cl-5-CF3-PYR4], [0727; 2-Me-3-Cl-5-OCHF2-PYR4], [0728; 2-Me-3-Cl-5-OCF3-PYR4], [0729; 2-Me34-Br-5-F-PYR4], [0730; 2-Me-3-Br-5-Cl-PYR4], [0731; 2-Me-3-Br-5-Br-PYR4], [0732; 2-Me-3-Br-5-Me-PYR4], [0733; 2-Me-3-Br-5-Et-PYR4], [0734; 2-Me-3-Br-5-OMe-PYR4], [0735; 2-Me-3-Br-5-OEt-PYR4], [0736; 2-Me-3-Br-5-CN-PYR4], [0737; 2-Me-3-Br-5-CHF2-PYR4], [0738; 2-Me-3-Br-5-CF3-PYR4], [0739; 2-Me-3-Br-5-OCHF2-PYR4], [0740; 2-Me-3-Br-5-OCF3-PYR4], [0741; 2-Me-3-Me-5-F-PYR4], [0742; 2-Me-3-Me-5-Cl-PYR4], [0743; 2-Me-3-Me-5-Br-PYR4], [0744; 2-Me-3-Me-5-Me-PYR4], [0745; 2-Me-3-Me-5-Et-PYR4], [0746; 2-Me-3-Me-5-OMe-PYR4], [0747; 2-Me-3-Me-5-OEt-PYR4], [0748; 2-Me-3-Me-5-CN-PYR4], [0749; 2-Me-3-Me-5-CHF2-PYR4], [0750; 2-Me-3-Me-5-CF3-PYR4], [0751; 2-Me-3-Me-5-OCHF2-PYR4], [0752; 2-Me-3-Me-5-OCF3-PYR4], [0753; 2-Me-3-Et-5-F-PYR4], [0754; 2-Me-3-Et-5-Cl-PYR4], [0755; 2-Me-3-Et-5-Br-PYR4], [0756; 2-Me-3-Et-5-Me-PYR4], [0757; 2-Me-3-Et-5-Et-PYR4], [0758; 2-Me-3-Et-5-OMe-PYR4], [0759; 2-Me-3-Et-5-OEt-PYR4], [0760; 2-Me-3-Et-5-CN-PYR4], [0761; 2-Me-3-Et-5-CHF2-PYR4], [0762; 2-Me-3-Et-5-CF3-PYR4], [0763; 2-Me-3-Et-5-OCHF2-PYR4], [0764; 2-Me-3-Et-5-OCF3-PYR4], [0765; 2-Me-3-OMe-5-F-PYR4], [0766; 2-Me-3-OMe-5-Cl-PYR4], [0767; 2-Me-3-OMe-5-Br-PYR4], [0768; 2-Me-3-OMe-5-Me-PYR4], [0769; 2-Me-3-OMe-5-Et-PYR4], [0770; 2-Me-3-OMe-5-OMe-PYR3], [0771; 2-Me-3-OMe-5-OEt-PYR4], [0772; 2-Me-3-OMe-5-CN-PYR4], [0773; 2-Me-3-OMe-5-CHF2-PYR4], [0774; 2-Me-3-OMe-5-CF3-PYR4], [0775; 2-Me-3-OMe-5-OCHF2-PYR4], [0776; 2-Me-3-OMe-5-OCF3-PYR4], [0777; 2-Me-3-OEt-5-F-PYR4], [0778; 2-Me-3-OEt-5-Cl-PYR4], [0779; 2-Me-3-OEt-5-Br-PYR4], [0780; 2-Me-3-OEt-5-Me-PYR4], [0781; 2-Me-3-OEt-5-Et-PYR4], [0782; 2-Me-3-OEt-5-OMe-PYR4], [0783; 2-Me-3-OEt-5-OEt-PYR4], [0784; 2-Me-3-OEt-5-CN-PYR4], [0785; 2-Me-3-OEt-5-CHF2-PYR4], [0786; 2-Me-3-OEt-5-CF3-PYR4], [0787; 2-Me-3-OEt-5-OCHF2-PYR4], [0788; 2-Me-3-OEt-5-OCF3-PYR4], [0789; 2-Me-3-CN-5-F-PYR4], [0790; 2-Me-3-CN-5-Cl-PYR4], [0791; 2-Me-3-CN-5-Br-PYR4], [0792; 2-Me-3-CN-5-Me-PYR4], [0793; 2-Me-3-CN-5-Et-PYR4], [0794; 2-Me-3-CN-5-OMe-PYR4], [0795; 2-Me-3-CN-5-OEt-PYR4], [0796; 2-Me-3-CN-5-CN-PYR4], [0797; 2-Me-3-CN-5-CHF2-PYR4], [0798; 2-Me-3-CN-5-CF3-PYR4], [0799; 2-Me-3-CN-5-OCHF2-PYR4], [0800; 2-Me-3-CN-5-OCF3-PYR4],

[0801; 2-Me-3-CHF2-5-F-PYR4], [0802; 2-Me-3-CHF2-5-Cl-PYR4], [0803; 2-Me-3-CHF2-5-Br-PYR4], [0804; 2-Me-3-CHF2-5-Me-PYR4], [0805; 2-Me-3-CHF2-5-Et-PYR4], [0806; 2-Me-3-CHF2-5-OMe-PYR4], [0807; 2-Me-3-CHF2-5-OEt-PYR4], [0808; 2-Me-3-CHF2-5-CN-PYR4], [0809; 2-Me-3-CHF2-5-CHF2-PYR4], [0810; 2-Me-3-CHF2-5-CF3-PYR4], [0811; 2-Me-3-CHF2-5-OCHF2-PYR4], [0812; 2-Me-3-CHF2-5-OCF3-PYR4], [0813; 2-Me-3-CF3-5-F-PYR4], [0814; 2-Me-3-CF3-5-Cl-PYR4], [0815; 2-Me-3-CF3-5-Br-PYR4], [0816; 2-Me-3-CF3-5-Me-PYR4], [0817; 2-Me-3-CF3-5-Et-PYR4], [0818; 2-Me-3-CF3-5-OMe-PYR4], [0819; 2-Me-3-CF3-5-OEt-PYR4], [0820; 2-Me-3-CF3-5-CN-PYR4], [0821; 2-Me-3-CF3-5-CHF2-PYR4], [0822; 2-Me-3-CF3-5-CF3-PYR4], [0823; 2-Me-3-CF3-5-OCHF2-PYR4], [0824; 2-Me-3-CF3-5-OCF3-PYR4], [0825; 2-Me-3-OCHF2-5-F-PYR4], [0826; 2-Me-3-OCHF2-5-Cl-PYR4], [0827; 2-Me-3-OCHF2-5-Br-PYR4], [0828; 2-Me-3-OCHF2-5-Me-PYR4], [0829; 2-Me-3-OCHF2-5-Et-PYR4], [0830; 2-Me-3-OCHF2-5-OMe-PYR4], [0831; 2-Me-3-OCHF2-5-OEt-PYR4], [0832; 2-Me-3-OCHF2-5-CN-PYR4], [0833; 2-Me-3-OCHF2-5-CHF2-PYR4], [0834; 2-Me-3-OCHF2-5-CF3-PYR4], [0835; 2-Me-3-OCHF2-5-OCHF2-PYR4], [0836; 2-Me-3-OCHF2-5-OCF3-PYR4], [0837; 2-Me-3-OCF3-5-F-PYR4], [0838; 2-Me-3-OCF3-5-Cl-PYR4], [0839; 2-Me-3-OCF3-5-Br-PYR4], [0840; 2-Me-3-OCF3-5-Me-PYR4], [0841; 2-Me-3-OCF3-5-Et-PYR4], [0842; 2-Me-3-OCF3-5-OMe-PYR4], [0843; 2-Me-3-OCF3-5-OEt-PYR4], [0844; 2-Me-3-OCF3-5-CN-PYR4], [0845; 2-Me-3-OCF3-5-CHF2-PYR4], [0846; 2-Me-3-OCF3-5-CF3-PYR4], [0847; 2-Me-3-OCF3-5-OCHF2-PYR4], [0848; 2-Me-3-OCF3-5-OCF3-PYR4]

For example, HA1012-0111 is a compound in which substituent number is 0111 in a compound represented by formula (HA1012), and is represented by the following structure.

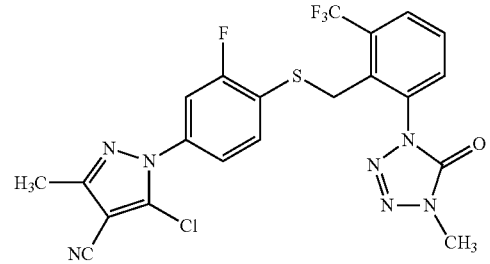 [SMILES: Cc1nn(-c2ccc(SCc3c(-n4nnn(C)c4=O)cccc3C(F)(F)F)c(F)c2)c(Cl)c1C#N]

Examples of the present control agent will be shown below.

Formulation Example 1

Fifty parts (50 parts) of any one of the present compounds A, 3 parts of calcium ligninsulfonate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds A and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds A, 88 parts of kaolin clay, and 10 parts of talc are thoroughly ground and mixed to obtain each formulation.

Formulation Example 4

Five parts (5 parts) of any one of the present compounds A, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds A, 1 part of synthetic hydrated silicon oxide, 2 parts of calcium ligninsulfonate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds A, 35 parts of white carbon containing 50 parts of a polyoxyethylene alkyl ether sulfate ammonium salt, and 55 parts of water are finely ground by a wet grinding method to obtain each formulation.

Next, Test Examples will be shown.

The control effect was evaluated by visually observing the area of lesion spots on each of test plants at the time of investigation, and comparing the area of lesion spots on a plant treated with the present compound with that on an untreated plant.

Test Example 1

Each of plastic pots was filled with soil and barley (cultivar: NISHINOHOSHI) was sowed and grown in a greenhouse for 7 days. Then, each water dilution prepared by adjusting so as to contain a predetermined concentration (200 ppm) of any one compound of the present compounds 1, 2, 3, 4, 5, 6, 7, 8, 9, 10, 11, 12, 13, 14, 15, 16, 17, 18, and 19 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with the present compound 1, 2, 3, 4, 5, 6, 7, 8, 9, 10, 11, 12, 13, 14, 15, 16, 17, 18, or 19 was 30% or less of that on an untreated plant.

Test Example 2

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of any one compound of the present compounds 1, 2, 3, 4, 5, 6, 7, 8, 9, 10, 11, 12, 13, 17, 18, and 19 was sprayed over stems and leaves of the cucumber so that it sufficiently adhered to the surface of the leaves of the cucumber. After spraying, the plant was air-dried. After 1 day, an aqueous suspension containing spores of cucumber target leaf spot fungus (*Corynespora cassiicola*) was sprayed to inoculate the spores. After the inoculation, the plant was cultivated at 24° C. in the daytime and 20° C. at night under high humidity condition for 7 days, and then the area of lesion was investigated. As a result, the area of lesion on the plant treated with the present compound 1, 2, 6, 7, 8, 9, or 10 was 30% or less of that on an untreated plant.

Test Example 3

Each of plastic pots was filled with soil and cucumber (cultivar: SAGAMI HANJIRO) was sowed and grown in a greenhouse for 12 days. Then, each water dilution prepared by adjusting so as to contain a predetermined concentration (200 ppm) of any one compound of the present compounds 1, 2, 4, 5, 7, 11, 13, 15, and 19 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion was investigated. As a result, the area of lesion on the plant treated with the present compound 1, 2, 4, 5, 7, 11, 13, 15, or 19 was 30% or less of that on an untreated plant.

Test Example 4

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of any one compound of the present compounds 1, 2, 3, 4, 5, 6, 7, 8, 9, 11, 12, 13, 14, 15, 16, and 19 was sprayed over stems and leaves of the cucumber so that it sufficiently adhered to the surface of the leaves of the cucumber. After spraying, the plant was air-dried. After 1 day, an aqueous suspension containing spores of cucumber anthracnose fungus (*Colletotrichum lagenarium*) was sprayed to inoculate the spores. After the inoculation, the plant was placed at 23° C. for one day under high humidity condition, and then cultivated in a greenhouse at 24° C. in the daytime and 20° C. at night for 6 days, and then the area of lesion was investigated.

As a result, the area of lesion on the plant treated with the present compound 1, 2, 3, 4, 5, 6, 7, 8, 9, 11, 12, 13, 14, 15, 16, or 19 was 30% or less of that on an untreated plant.

Test Example 5

Each of plastic pots was filled with soil and soybean (cultivar: KUROSENGOKU) was sowed and grown in a greenhouse for 13 days. Then, each water dilution prepared by adjusting so as to contain a predetermined concentration (200 ppm) of any one compound of the present compounds 1, 2, 4, 7, 11, 13, and 19 was sprayed over stems and leaves of the soybean so that it sufficiently adhered to the surface of the leaves of the soybean. After spraying, the plant was air-dried. After 2 days, an aqueous suspension containing spores of soybean rust fungus (*Phakopsora pachyrhizi*) was sprayed to inoculate the spores. After completion of the inoculation, the plant was placed for 3 days in a greenhouse at 23° C. in the daytime and 20° C. at night under high humidity condition and cultivated in a greenhouse for 14 days, and then the area of lesion was investigated. As a result, the area of lesion on the plant treated with the present compound 1, 2, 4, 7, 11, 13, or 19 was 30% or less of that on an untreated plant.

Test Example 6

Each of plastic pots was filled with soil and barley (cultivar: NISHINOHOSHI) was sowed and grown in a greenhouse for 7 days. Then, each water dilution prepared by adjusting so as to contain a predetermined concentration (200 ppm) of any one compound of the present compounds 1, 2, 3, 4, 5, 7, 8, 10, 11, 12, 13, 14, 15, 16, 17, 18, and 19 was sprayed over stems and leaves of the barley so that it sufficiently adhered to the surface of the leaves of the barley. After spraying, the plant was air-dried. After 2 days, an aqueous suspension containing spores of barley leaf blotch fungus (*Rhynchosporium secalis*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with the present compound 1, 2, 3, 4, 5, 7, 8, 10, 11, 12, 13, 14, 15, 16, 17, 18, or 19 was 30% or less of that on an untreated plant.

Test Example 7

Each of plastic pots was filled with soil and wheat (cultivar: APOGEE) was sowed and grown in a greenhouse for 10 days. Then, each water dilution prepared by adjusting so as to contain a predetermined concentration (200 ppm) of any one compound of the present compounds 1, 2, 3, 4, 5, 6, 7, 8, 9, 10, 11, 12, 13, 14, 15, 16, 17, 18, and 19 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed over the wheat to inoculate the spores. After completion of the inoculation, the plant was placed at 18° C. under high humidity condition for 3 days and then placed under illumination for 14 to 18 days, and then the area of lesion was investigated. As a result, the area of lesion on the plant treated with the present compound 1, 2, 3, 4, 5, 6, 7, 8, 9, 10, 11, 12, 13, 14, 15, 16, 17, 18, or 19 was 30% or less of that on an untreated plant.

Test Example 8

Each of plastic pots was filled with soil and rice (cultivar: NIHONBARE) was sowed and grown in a greenhouse for 20 days. Then, each water dilution prepared by adjusting so as to contain a predetermined concentration (200 ppm) of any one compound of the present compounds 1, 2, 4, 5, 11, 17, and 19 was sprayed over stems and leaves so that it sufficiently adhered to the surface of the leaves of the rice. After spraying, the plant was air-dried and placed for 6 days at 24° C. in the daytime and 20° C. at night under high humidity condition, while being in contact with the rice seedling (cultivar: NIHONBARE) infected by the rice blast fungus (*Magnaporthe grisea*), and then the area of lesion was investigated.

As a result, the lesion areas on the plant treated with the present compound 1, 2, 4, 5, 11, 17, or 19 were 30% or less with respect to the lesion area on the non-treated plant.

Test Example 9

Each of plastic pots was filled with soil and wheat (cultivar: SHIROGANE) was sowed and grown in a greenhouse for 9 days. Then, each water dilution prepared by adjusting so as to contain a predetermined concentration (200 ppm) of any one compound of the present compounds 1, 2, 3, 4, 6, 7, 8, 9, 11, 12, 13, 14, 15, 16, 17, and 19 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was placed at 23° C. for one day under dark and high humidity condition, and cultivated under illumination at 20° C. for 8 days, and then the area of lesion was investigated.

As a result, the area of lesion on the plant treated with the present compound 1, 2, 3, 4, 6, 7, 8, 9, 11, 12, 13, 14, 15, 16, 17, or 19 was 30% or less of that on an untreated plant.

Test Example 10

Each of compounds 8, 18, and 19 obtained in Formulation Example 6 was diluted with water so as to adjust the concentration of each compound to 500 ppm to obtain a dilution.

About 30 heads of cotton aphid (*Aphis gossypii*) (including all stages) were inoculated on cucumber seedlings (first true-leaf stage) planted in each of plastic pots and, after being placed for 1 day, 20 mL of the dilution was sprayed over the seedlings.

After 6 days, the number of surviving cotton aphid parasitizing to the leaves of the cucumber was counted and the control value was calculated by the following equation.

$$\text{Control value (\%)} = \{1 - (Cb \times Tai)/(Cai \times Tb)\} \times 100$$

wherein symbols in the equation represent the followings:

Cb: Number of insects before treatment in untreated area;

Cai: Number of surviving parasites in untreated area during observation;

Tb: Number of insects before treatment in treated area; and

Tai: Number of surviving parasites in treated area during observation.

As used herein, the untreated area means an area where a solution prepared by diluting a formulation containing no present compound with the same amount of water as in the treated area in Formulation Example 6 was sprayed.

As a result, all treated areas using the test chemical solution of the present compound 8, 18, or 19 showed 60% or more of the control value.

The present compound has control activity against pests and is useful as an active ingredient of a pest control agent.

The invention claimed is:
1. A tetrazolinone compound represented by formula (1):

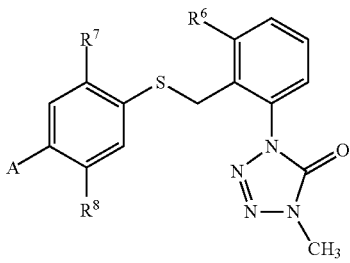

wherein A represents the following group A2, A3, or A4;
A;

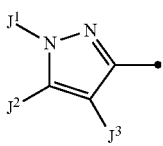
A2

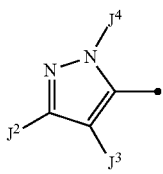
A3

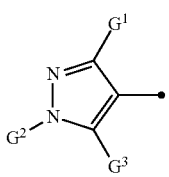
A4 in which $R^6$ represents a hydrogen atom, a halogen atom, a C1-C4 alkyl group optionally substituted with one or more halogen atoms, a C3-C4 cycloalkyl group optionally substituted with one or more halogen atoms, or a C1-C4 alkoxy group optionally substituted with one or more halogen atoms, $R^7$ and $R^8$ each represents a hydrogen atom, a halogen atom, a C1-C4 alkyl group optionally substituted with one or more halogen atoms, or a C1-C4 alkoxy group optionally substituted with one or more halogen atoms, $G^1$ and $G^3$ each represents a hydrogen atom, a halogen atom, a C1-C4 alkoxy group optionally substituted with one or more halogen atoms, or a C1-C4 alkyl group optionally substituted with one or more halogen atoms, $G^2$, $J^1$, and $J^4$ each represents a hydrogen atom, a C1-C4 alkyl group optionally substituted with one or more halogen atoms, or a C3-C4 cycloalkyl group optionally substituted with one or more halogen atoms, and $J^2$, and $J^3$ each represents a hydrogen atom, a halogen atom, a cyano group, an aldehyde group, a C1-C4 alkoxy group optionally substituted with one or more halogen atoms, a C1-C4 alkyl group optionally substituted with one or more halogen atoms, or a C3-C4 cycloalkyl group optionally substituted with one or more halogen atoms.

2. The tetrazolinone compound according to claim 1, wherein A is A2.

3. The tetrazolinone compound according to claim 1, wherein A is A3.

4. The tetrazolinone compound according to claim 1, wherein A is A4.

5. A pest control agent comprising the tetrazolinone compound according to claim 1.

6. A method for control pests, which comprises applying an effective amount of the tetrazolinone compound according to claim 1 to plants or soil.

* * * * *